United States Patent
Martinez Botella et al.

(10) Patent No.: US 10,577,390 B2
(45) Date of Patent: Mar. 3, 2020

(54) COMPOSITIONS AND METHODS FOR TREATING CNS DISORDERS

(71) Applicant: Sage Therapeutics, Inc., Cambridge, MA (US)

(72) Inventors: Gabriel Martinez Botella, Wayland, MA (US); Francesco G. Salituro, Marlborough, MA (US); Albert J. Robichaud, Cambridge, MA (US); Boyd L. Harrison, Princeton Junction, NJ (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/519,480

(22) PCT Filed: Oct. 16, 2015

(86) PCT No.: PCT/US2015/056054
§ 371 (c)(1),
(2) Date: Apr. 14, 2017

(87) PCT Pub. No.: WO2016/061527
PCT Pub. Date: Apr. 21, 2016

(65) Prior Publication Data
US 2017/0240589 A1     Aug. 24, 2017

Related U.S. Application Data

(60) Provisional application No. 62/064,961, filed on Oct. 16, 2014.

(51) Int. Cl.
| | | |
|---|---|---|
| *C07J 43/00* | (2006.01) | |
| *A61K 45/06* | (2006.01) | |
| *C07J 9/00* | (2006.01) | |
| *A61K 31/575* | (2006.01) | |
| *A61K 31/58* | (2006.01) | |

(Continued)

(52) U.S. Cl.
CPC .......... *C07J 43/003* (2013.01); *A61K 31/575* (2013.01); *A61K 31/58* (2013.01); *A61K 45/06* (2013.01); *C07J 9/00* (2013.01); *C07J 1/0011* (2013.01); *C07J 1/0022* (2013.01); *C07J 3/005* (2013.01); *C07J 5/0053* (2013.01); *C07J 7/002* (2013.01); *C07J 7/007* (2013.01); *C07J 7/008* (2013.01); *C07J 11/00* (2013.01); *C07J 13/007* (2013.01); *C07J 21/00* (2013.01); *C07J 31/006* (2013.01);

(Continued)

(58) Field of Classification Search
CPC .......... C07J 43/003; C07J 9/00; A61K 31/58; A61K 31/575; A61K 45/06
See application file for complete search history.

(56) References Cited

U.S. PATENT DOCUMENTS

| 2,856,415 A | 10/1958 | Mihina |
| 3,169,134 A | 2/1965 | Klimstra et al. |

(Continued)

FOREIGN PATENT DOCUMENTS

| CA | 2831054 A1 | 12/2013 |
| CN | 1190404 A | 8/1998 |

(Continued)

OTHER PUBLICATIONS

Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs," Bioorganic & Medicinal Chemistry Letters 20:6680-6684 (2010).

Botella et al., "Neuroactive Steroid& 1. Positive Allosteric Modulators of the (g-Aminobutyric Acid)A Receptor: Structure-Activity Relationships of Heterocyclic Substitution at C-21" Journal of Medical Chemistry, 2015, 58 pp. 3500-3511.

Botella et al., "Neuroactive Steroids. 2. 3a-Hydroxy-3b-methyl-21-(4-cyano-1H-pyrazol-1-yl)-19-nor-5b-pregnan-20-(SAGE-217): A Clinical Next Generation Neuroactive Steroid Positive Allosteric Modulator of the (g-Aminobutyric Acid)A Receptor" Journal of Medical Chemistry, 2017, 10 pp. A-J.

(Continued)

*Primary Examiner* — Angela C Brown-Pettigrew
(74) *Attorney, Agent, or Firm* — Catherine M. McCarty; Christopher K. Haley; Goodwin Procter LLP

(57) ABSTRACT

Described herein are neuroactive steroids of the Formula (I): or a pharmaceutically acceptable salt thereof; wherein (II), A, $R^1$, $R^2$, $R^{3a}$, $R^{4a}$, $R^{4b}$, $R^5$, $R^{7a}$, and $R^{7b}$ are as defined herein. Such compounds are envisioned, in certain embodiments, to behave as GABA modulators. The present invention also provides pharmaceutical compositions comprising a compound of the present invention and methods of use and treatment, e.g., such for inducing sedation and/or anesthesia.

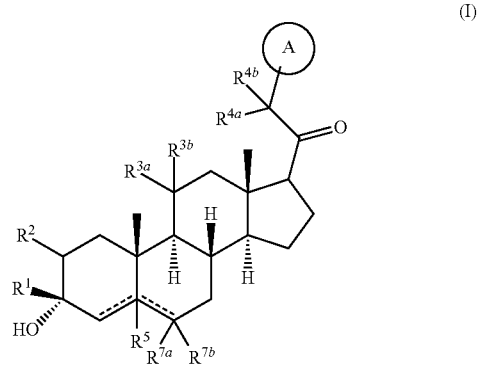

3 Claims, No Drawings

(51) Int. Cl.

| | | |
|---|---|---|
| C07J 1/00 | (2006.01) | |
| C07J 3/00 | (2006.01) | |
| C07J 5/00 | (2006.01) | |
| C07J 7/00 | (2006.01) | |
| C07J 11/00 | (2006.01) | |
| C07J 13/00 | (2006.01) | |
| C07J 21/00 | (2006.01) | |
| C07J 31/00 | (2006.01) | |
| C07J 41/00 | (2006.01) | |
| C07J 51/00 | (2006.01) | |
| C07J 71/00 | (2006.01) | |

(52) U.S. Cl.
CPC ............ *C07J 41/0066* (2013.01); *C07J 51/00* (2013.01); *C07J 71/001* (2013.01)

(56) References Cited

U.S. PATENT DOCUMENTS

| | | | |
|---|---|---|---|
| 3,206,459 A | 9/1965 | Cross | |
| 3,580,937 A | 5/1971 | Campbell et al. | |
| 3,943,124 A | 3/1976 | Phillipps et al. | |
| 3,983,111 A | 9/1976 | Phillipps et al. | |
| 3,998,829 A | 12/1976 | Phillips et al. | |
| 4,029,777 A | 6/1977 | Engelfried et al. | |
| 4,071,625 A | 1/1978 | Grunwell et al. | |
| 4,179,336 A | 12/1979 | Weber et al. | |
| 4,192,871 A | 3/1980 | Phillipps et al. | |
| 4,389,345 A | 6/1983 | Lenz | |
| 5,593,983 A | 1/1997 | Campbell | |
| 5,721,227 A | 2/1998 | Melloni et al. | |
| 5,925,630 A | 7/1999 | Upasani et al. | |
| 5,935,545 A | 8/1999 | Leary et al. | |
| 5,939,545 A | 8/1999 | Upasani et al. | |
| 6,133,280 A | 10/2000 | Brodie et al. | |
| 6,143,736 A | 11/2000 | Upasani et al. | |
| 6,277,838 B1 | 8/2001 | Upasani et al. | |
| 6,717,002 B2 | 4/2004 | Yano et al. | |
| 6,844,456 B2 | 1/2005 | Covey | |
| 7,064,116 B2 | 6/2006 | Calogeropoulou et al. | |
| 7,781,421 B2 | 8/2010 | Covey et al. | |
| 8,759,330 B2 | 6/2014 | Covey et al. | |
| 8,939,545 B2 | 1/2015 | Tunmore et al. | |
| 9,156,876 B2 | 10/2015 | Covey | |
| 9,365,611 B2 | 6/2016 | Martinez Botella et al. | |
| 9,512,165 B2 | 12/2016 | Martinez Botella et al. | |
| 9,630,986 B2 | 4/2017 | Covey et al. | |
| 9,725,481 B2 | 8/2017 | Martinez Botella et al. | |
| 9,765,110 B2 | 9/2017 | Covey | |
| 10,246,482 B2 | 4/2019 | Harrison et al. | |
| 2002/0091112 A1 | 7/2002 | Menzenbach et al. | |
| 2005/0176976 A1 | 8/2005 | Calogeropoulou et al. | |
| 2006/0094696 A1 | 5/2006 | Leese et al. | |
| 2007/0014719 A1 | 1/2007 | Reading et al. | |
| 2008/0269183 A1 | 10/2008 | Mellon et al. | |
| 2009/0048218 A1 | 2/2009 | Kuhnke | |
| 2010/0152840 A1 | 6/2010 | Seguin et al. | |
| 2010/0234335 A1 | 9/2010 | Gravanis et al. | |
| 2010/0317638 A1 | 12/2010 | Covey et al. | |
| 2011/0152840 A1 | 6/2011 | Lee et al. | |
| 2011/0172242 A1 | 7/2011 | Helton et al. | |
| 2014/0017675 A1 | 1/2014 | Ito | |
| 2014/0050789 A1 | 2/2014 | Rogawski et al. | |
| 2014/0094619 A1 | 4/2014 | Runyon et al. | |
| 2014/0148412 A1 | 5/2014 | Hogenkamp | |
| 2014/0235600 A1 | 8/2014 | Covey | |
| 2014/0249120 A1 | 9/2014 | Covey et al. | |
| 2014/0275241 A1 | 9/2014 | Covey | |
| 2015/0291654 A1 | 10/2015 | Upasani et al. | |
| 2015/0315230 A1 | 11/2015 | Covey et al. | |
| 2016/0068563 A1 | 3/2016 | Martinez Botella et al. | |
| 2016/0083418 A1 | 3/2016 | Martinez Botella et al. | |
| 2016/0108080 A1 | 4/2016 | Martinez Botella et al. | |
| 2016/0229887 A1 | 8/2016 | Martinez Botella et al. | |
| 2017/0233433 A1 | 8/2017 | Martinez Botella et al. | |
| 2017/0246191 A1 | 8/2017 | Martinez Botella et al. | |
| 2018/0071315 A1 | 3/2018 | Cashman et al. | |
| 2019/0160078 A1 | 5/2019 | Masuoka et al. | |
| 2019/0177358 A1 | 6/2019 | Martinez Botella et al. | |
| 2019/0337975 A1 | 11/2019 | Bryson et al. | |

FOREIGN PATENT DOCUMENTS

| | | | | |
|---|---|---|---|---|
| CN | 101412742 A | 4/2009 | | |
| CN | 101624414 A | 1/2010 | | |
| CN | 104136452 A | 11/2014 | | |
| CN | 108727453 A | 11/2018 | | |
| DE | 2330342 A1 | 1/1974 | | |
| DE | 2526373 A1 | 12/1976 | | |
| DE | 2700267 A1 | 7/1977 | | |
| DE | 2632677 A1 | 1/1978 | | |
| EP | 0104489 A1 | 4/1984 | | |
| EP | 0554436 A1 | 8/1993 | | |
| EP | 0656365 A1 | 6/1995 | | |
| EP | 0701444 A1 | 3/1996 | | |
| EP | 1038880 A2 | 9/2000 | | |
| FR | 1994 M | 9/1963 | | |
| GB | 1380246 A | 1/1975 | | |
| GB | 1430942 A | 4/1976 | | |
| GB | 1494097 A | 12/1977 | | |
| GB | 1538869 A | 1/1979 | | |
| GB | 1570394 A | 7/1980 | | |
| GB | 1581234 A | 12/1980 | | |
| GB | 1581235 A | 12/1980 | | |
| RU | 2194712 C2 | 12/2002 | | |
| RU | 2243232 C2 | 12/2004 | | |
| RU | 2010100334 A | 7/2011 | | |
| RU | 2675855 C2 | 12/2018 | | |
| WO | 1991016897 A1 | 11/1991 | | |
| WO | 9309732 A1 | 3/1993 | | |
| WO | 9305786 A1 | 4/1993 | | |
| WO | 9318053 A1 | 9/1993 | | |
| WO | 9427608 A1 | 12/1994 | | |
| WO | WO 1995/021617 | * 8/1995 | ............ | A61K 31/58 |
| WO | 1996003421 A1 | 2/1996 | | |
| WO | 1996016076 A1 | 5/1996 | | |
| WO | 9640043 A2 | 12/1996 | | |
| WO | 9805337 A1 | 2/1998 | | |
| WO | 0066614 A1 | 11/2000 | | |
| WO | 2005051972 A1 | 6/2005 | | |
| WO | 2005105822 A2 | 11/2005 | | |
| WO | 2006037016 A2 | 4/2006 | | |
| WO | 2006131392 A1 | 12/2006 | | |
| WO | 2008151745 A1 | 12/2008 | | |
| WO | 2008157460 A1 | 12/2008 | | |
| WO | 2010003391 A2 | 1/2010 | | |
| WO | 2010054158 A2 | 5/2010 | | |
| WO | 2010107815 A1 | 9/2010 | | |
| WO | 2012013816 A1 | 2/2012 | | |
| WO | 2012083090 A2 | 6/2012 | | |
| WO | 2012109752 A1 | 8/2012 | | |
| WO | 2012110010 A1 | 8/2012 | | |
| WO | 2012116290 A2 | 8/2012 | | |
| WO | 2013019711 A2 | 2/2013 | | |
| WO | 2013036835 A1 | 3/2013 | | |
| WO | 2013056181 A1 | 4/2013 | | |
| WO | 2013188792 A2 | 12/2013 | | |
| WO | 2013192097 A1 | 12/2013 | | |
| WO | 2014058736 A1 | 4/2014 | | |
| WO | 2014071449 A1 | 5/2014 | | |
| WO | 2014100228 A1 | 6/2014 | | |
| WO | 2014108808 A2 | 7/2014 | | |
| WO | 2014122480 A1 | 8/2014 | | |
| WO | 2014169831 A1 | 10/2014 | | |
| WO | 2014169832 A1 | 10/2014 | | |
| WO | 2014169833 A1 | 10/2014 | | |
| WO | 2014169836 A1 | 10/2014 | | |
| WO | 2015010054 A2 | 1/2015 | | |
| WO | 2015027227 A1 | 2/2015 | | |
| WO | 2015180679 A1 | 12/2015 | | |
| WO | 2015195962 A1 | 12/2015 | | |
| WO | 2016036724 A1 | 3/2016 | | |
| WO | 2016061527 A1 | 4/2016 | | |
| WO | 2016061537 A1 | 4/2016 | | |

(56) References Cited

FOREIGN PATENT DOCUMENTS

| WO | 2016082789 A1 | 6/2016 |
|---|---|---|
| WO | 2016123056 A1 | 8/2016 |
| WO | 2016131414 A1 | 8/2016 |
| WO | 2016134301 A2 | 8/2016 |
| WO | 2016209847 A1 | 12/2016 |
| WO | 2017044659 A1 | 3/2017 |
| WO | 2017066626 A1 | 4/2017 |
| WO | 2017087864 A1 | 5/2017 |
| WO | 2017156103 A1 | 9/2017 |
| WO | 2017156418 A1 | 9/2017 |
| WO | 2018013613 A1 | 1/2018 |
| WO | 2018013615 A1 | 1/2018 |
| WO | 2018039378 A1 | 3/2018 |
| WO | 2019018119 A1 | 1/2019 |
| WO | 2019045121 A1 | 3/2019 |
| WO | 2019051264 A1 | 3/2019 |
| WO | 2019094724 A1 | 5/2019 |

OTHER PUBLICATIONS

Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Dorwald, "Side Reactions in Organic Synthesis", 2005, Wiley-VCH, Preface, p. IX.
Edgar et al. "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Extended European Search Report for application PCT/CN2014075593 dated Aug. 26, 2016.
Extended European Search Report for application PCT/CN2014075594 dated Aug. 26, 2016.
Gasior et al. "Neuroactive steroids: potential therapeutic use in neurological and psychiatric disorders" Trends in Pharmacological Science (1999) vol. 20, No. 3, pp. 107-112.
Harrison et al. "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hawkinson et al. "3a-Hydroxy-3B-trifluoromethyl-5a-pregnan-20-one (Co 2-1970): A Partial Agonist at the Neuroactive Steroid Site of the y-Aminobutyric acidA Receptor" Molecular Pharmacology (1996) vol. 49, pp. 897-906.
Hawkinson et al. "Correlation of Neuroactive Steroid Modulation of [35S]t-Butylbicyclophosphorothionate and [3H] Flunitrazepam Binding and y-Aminobutyric AcidA Receptor Function" Molecular Pharmacology (1994) vol. 46, pp. 977-985.
Hawkinson et al. "Substituted 3B-Phenylethynyl Derivatives of 3a-Hydroxy-5a-pregnan-20-one: Remarkably Potent Neuroactive Steroid Modulators of y-Aminobutyric AcidA Receptors" The Journal of Pharmacology and Experimental Therapeutics(1998) vol. 287, No. 1, pp. 198-207.
Hogenkamp et al. "Synthesis and in Vitro Activity of 3B-Substituted-3a-hydroxypregnan-20-ones: Allosteric Modulators of the GABAA Receptor" Journal of Medicinal Chemistry (1997) vol. 40, pp. 61-72.
Hu et al., "Journal of Medicinal Chemistry, Neurosteroid Analogues: Structure-Activity Studies of Benz(e] indene Modulators of GABM Receptor Function. 1. The Effect of 6-Melhyl Substitution on the Electrophysiological Activity of 7-Substituted Benz[e]indene-3- carbonitriles", 1993, 36 pp. 3956-3967.
International Search Report and Written Opinion for Corresponding International Application No. PCT/US2016/018748 dated Aug. 29, 2016.

International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report for International Application No. PCT/US2012/060136 dated Mar. 27, 2013.
Notification of Transmittal of the International Search Report and the Written Opinion of the International Searching authority, or the Declaration, International Application No. PCT/US13/45933, dated Dec. 3, 2013, 5 Pages.
Paul et al. "Neuroactive Steroids" The Journal of the Federation of American Societies of Experimental Biology, 1992, 5, pp. 2311-2322.
Phillipps et al., "A New Series of Steroidal Antidysrhythmic Agents," J. Steroid Biochem. 19(1):759-765 (1983).
Phillipps et al., "Water-soluble Steroidal Anaesthetics," Journal of Steroid Biochemistry 11:79-86 (1979).
Phillips "Structure-Activity Relationships in Steroidal Anaesthetics" Journal of Steroid Biochemistry (1975) vol. 6, pp. 607-613.
Rogawski et al., C. (2013), Neuroactive steroids for the treatment of status epilepticus. Epilepsia, 54: 93-98. doi: 10.1111/epi.12289.
Runyon et al., "European Journal of Pharmacology, 17b-Nitro-5a-androstan-3a-ol and its 3b-methyl derivative: Neurosteroid analogs with potent anticonvulsant and anxiolytic activities", 2009, 617 pp. 68-73.
Shu et al., "Characteristics of concatemeric GABM receptors containing alpha4/d subunits expressed in Xenopus oocytes" British Journal of Pharmacology (2012) 165, 2228-2243.
Supplemental European Search Report, European Patent Application No. 14826212.4, dated Feb. 16, 2017.
Upsani et. al. "3-Hydroxy-3β-(phenylethynyl)-5β-pregnan-20-ones:? Synthesis and Pharmacological Activity of Neuroactive Steroids with High Affinity for GABAA Receptors" J. Med. Chem. (1997) vol. 40, No. 1, pp. 73-84.
Vanover et al. "Behavioral characterization of Co 13444 (3a-hydroxy-21-(1"-imidazolyl}-3B-methoxymethyl-5a-pregnan-20-one), a novel sedative-hypnotic neuroactive steroid" Psychopharmacology (2001) vol. 155, pp. 285-291.
Vanover et al. "Characterization of the Anxiolytic Properties of a Novel Neuroactive Steroid, Co 2-6749 (GMA-839; WAY-141839; 3a, 21-Dihydroxy-3B-trifluoromethyl-19-nor-5B-pregnan-20-one), a Selective Modulator of y-Aminobutyric AcidA Receptors" The Journal of Pharmacology and Experimental Therapeutics (2000) vol. 295, No. 1, pp. 337-345.
Vanover et al. "Response-Rate Suppression in Operant Paradigm as Predictor of Soporific Potency in Rats and Identification of Three Novel Sedative-Hypnotic Neuroactive Steroids" The Journal of Pharmacology and Experimental Therapeutics (1999) vol. 291, No. 3, pp. 1317-1323.
Zeng et al. "Neurosteroid Analogues. 10. The Effect of Methyl Group Substitution at the C-6 and C-7 Positions on the GABA Modulatory and Anesthetic Actions of (3a,5a)- and (3a, 5B)-3-Hydroxypregnan-20-one" Journal of Medicinal Chemistry (2005) vol. 48, pp. 3051-3059.
U.S. Appl. No. 14/408,045, filed Dec. 15, 2014, Francesco G. Salituro et al., Pending.
U.S. Appl. No. 15/681,983, filed Aug. 21, 2017, Ravindra B. Upasani et al., Pending.

(56) References Cited

OTHER PUBLICATIONS

U.S. Appl. No. 15/698,151, filed Sep. 7, 2017, Gabriel Martinez Botella et al., Pending.
U.S. Appl. No. 15/143,312, filed Apr. 29, 2016, Gabriel Martinez Botella et al., Pending.
U.S. Appl. No. 14/785,192, filed Oct. 16, 2015, Gabriel Martinez Botella et al., Issued.
U.S. Appl. No. 15/273,125, filed Sep. 22, 2016, Gabriel Martinez Botella et al., Issued.
U.S. Appl. No. 16/007,556, filed Jun. 13, 2018, Gabriel Martinez Botella et al., Pending.
U.S. Appl. No. 14/785,171, filed Jun. 16, 2015, Gabriel Martinez Botella et al., Issued.
U.S. Appl. No. 16/020,641, filed Jun. 27, 2018, Gabriel Martinez Botella et al., Pending.
U.S. Appl. No. 15/297,845, filed Oct. 16, 2016, Gabriel Martinez Botella et al., Pending.
U.S. Appl. No. 14/785,175, filed Oct. 16, 2015, Gabriel Martinez Botella et al., Issued.
U.S. Appl. No. 15/639,702, filed Jun. 30, 2017, Gabriel Martinez Botella et al., Pending.
U.S. Appl. No. 14/913,920, filed Feb. 23, 2016, Gabriel Martinez Botella et al., Pending.
U.S. Appl. No. 14/132,386, filed Dec. 18, 2013, Albert Jean Robichaud et al., Issued.
U.S. Appl. No. 14/652,717, filed Dec. 18, 2013, Albert Jean Robichaud et al., Issued.
U.S. Appl. No. 15/586,853, filed May 4, 2017, Albert Jean Robichaud et al., Pending.
U.S. Appl. No. 15/459,492, filed Mar. 15, 2017, Albert Jean Robichaud et al., Pending.
U.S. Appl. No. 15/314,565, filed Nov. 29, 2016, Gabriel Martinez Botella et al., Pending.
U.S. Appl. No. 16/026,278, filed Jul. 3, 2018, Boyd L. Harrison et al., Pending.
U.S. Appl. No. 15/319,503, filed Dec. 16, 2016, Boyd L. Harrison et al., Pending.
U.S. Appl. No. 15/519,478, filed Apr. 14, 2017, Gabriel Martinez Botella et al., Pending.
Anderson et al., "Anesthetic Activity of Novel Water-Soluble 2b-Morpholinyl Steroids and Their Modulatory Effects at GABA-A Receptor", Journal of Medicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Berge et al., J. Pharmaceutical Sciences, 1977, vol. 66, pp. 1-19.
Bernstein, "Rett Syndrome Medication", Medscape, (2017).
Bjorkhem et al., "Steroid hormone metabolism in developing rates", Eur. J.Biochem., 1972, vol. 27, No. 2, pp. 318-326.
CAS registry No. 1040410-23-8.
CAS registry No. 162882-77-1.
CAS registry No. 162883-68-3.
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.

Chodounska et al., "Epalons: Synthesis of 3a, 7a-Dihydroxy-5a-Pregnan-20-One", Collection Symposium Series, vol. 53, No. 10, (1998), pp. 1543-1548.
Deluca et al., "Synthesis of 3b-Hydroxy[21-14C]-5b-pregn-8(14)-en-20-one from Chenodeoxycholic Acid", Helvetica Chemica Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
Evers et al., "A Synthetic 18-Norsleroid Distinguishes Between Two Neuroactive Steroid Binding Sites on GABAA receptors", Journal of Pharmacology and Experimental Therapeutics, 2010, vol. 333, No. 2, pp. 404-413.
Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.
Fesik et al., "Geometric Requirements for Membrance Perturbation and Anesthetic Activity", Molecular Pharmacology, 1985, vol. 27, pp. 624-629.
Green et al., "The nonfeminizing enantiomer of 17b-estradiol exerts protective effects in neuronal cultures and a rat model of cerebral ischemia", Endocrinology, 2001, vol. 142, pp. 400-406.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Heard et al., "Steroids VII. Preparation of of androstan-3(b)-o1-7-one from from dehydroisoandrosterone", Journal of Biological Chemistry, 1946, vol. 165, pp. 677-685.
Hewett et al., "Amino steroids. Part III. 2- and 3-Amino-5a-androstanes", Journal of the Chemical Society, 1968, vol. 9, pp. 1134-1140.
Hill et al., "Pholochemische Reaktionen. 32 Milleilung. UV-Bestrahlung von gesattigten und bela,gamma-ngesalligten, homoallylisch konjugierten steroidaldehyden", Helvetica Chimica Acta, 1946, vol. 49, No. 1, pp. 292-311.
Hogenkamp et al., "Pharmacological profile of a 17b-heteroaryl-substituted neuroactive steroid", Psychopharmacology, vol. 231, (2014), pp. 3517-3524.
Hu et al., "Neurosteroid analogues. Part 5. Enantiomers of neuroactive steroids and benz[e]indenes: total synthesis,18 electrophysiological effects on GABAA receptor function and anesthetic actions in tadpoles", J. Chem. Soc. Perkin Trans 1, 1997, pp. 3665-3671.
Im et al., "Studies on the Mechanism of Interactions between Anesthetic Steroids and y-Aminobutyric AcidA Receptors", Molecular Pharmacology (1990), 37(3), pp. 429-434.
International Search Report and Written Opinion for Corresponding International Application No. PCT/CN2014/078820 dated Feb. 27, 2015.
International Search Report and Written Opinion for Corresponding International Application No. PCT/CN2015/080216 dated Aug. 3, 2015.
International Search Report and Written Opinion for Corresponding International Application No. PCT/CN2015/095765 dated Mar. 4, 2016.
International Search Report and Written Opinion for Corresponding International Application No. PCT/US15/36500 dated Sep. 11, 2015.

(56) References Cited

OTHER PUBLICATIONS

International Search Report and Written Opinion for Corresponding International Application No. PCT/US15/56054 dated Feb. 9, 2016.
International Search Report and Written Opinion for Corresponding International Application No. PCT/US2013/076214 dated Aug. 29, 2016.
International Search Report and Written Opinion for Corresponding International Application No. PCT/US2014/052417 dated Nov. 19, 2014.
International Search Report and Written Opinion for Corresponding International Application No. PCT/US2014/092369 dated Aug. 25, 2015.
International Search Report and Written Opinion for Corresponding International Application No. PCT/US2015/056066 dated Feb. 8, 2016.
International Search Report and Written Opinion for Corresponding International Application No. PCT/US2016/014835 dated Jun. 9, 2016.
International Search Report and Written Opinion for Corresponding International Application No. PCT/US2016/062874 dated Jan. 30, 2017.
International Search Report and Written Opinion for Corresponding International Application No. PCT/US2017/041600 dated Dec. 1, 2017.
International Search Report and Written Opinion for Corresponding International Application No. PCT/US2017/041605 dated Dec. 12, 2017.
International Search Report and Written Opinion for Corresponding International Application No. PCT/US2017/048267 dated Aug. 29, 2016.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.
Jungmann et al., "7-Keto-5b-ätiansäure-Derivate. über Gallensäuren and verwandte Stoffe, 51. Mitteilung [Bile acids and related substances. LI. 7-0xo-5. beta.-etianic acid derivatives]", Helvetica Chimica Acta, vol. 41, No. 5, (1958), pp. 1206-1233.
Kaji et al., "Synthesis of 3-epi-6, 7-dideoxyxestobergsterol A", Chem. & Pharm. Bulletin, 2000, vol. 48, No. 10, pp. 1480-1483.
Katona et al., "Neurosteroid analogues. 12. Potent enhancement of GABA-mediated chloride currents at GABAA receptors by ent-androgens", European Journal of Medicinal Chemistry, 2008, vol. 43, pp. 107-113.
Knox et al., "Steroids. CCLXXVIII. Reductions of 19-substituted androst-4-en-3-ones and related compounds", Journal of Organic Chemistry, 1965, vol. 30, No. 7, pp. 2198-2205.
Krafft et al., "Synthesis of the C/D/E and A/B Rings of Xestobergsterol—(A)", Journal of Organic Chemistry, American Chemical Society, vol. 64, No. 7, (1999), pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lan et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Lehmann et al., "Schweinegallensauren Der Abbau von Hyocholsäure zu Pregnanderivaten", vol. 32, No. 3-4, (1966), pp. 217-224.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.

Matsui et al., "Comparative fate of testosterone and testosterone sulfate in female rats: C19O2 and C19O3 steroid metabolites in the bile", Journal of Steroid Biochemistry, 1977, 8(4), pp. 323-328.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al. "Metabolism of 19-hydroxycorticosterone. Isolation and characterization of three metabolites", Journal of Biological Chemistry, Jan. 1, 1961, vol. 236, No. 10, pp. PC68-PC69.
Phillipps, "Structure-Activity Relationships in Steroidal Anaesthetics", Nol. Mech. Gen. Anaesth. Glaxo Symposium, (1974), pp. 32-47.
PubChem-70249446 (2012), entire document.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of Medicinal Chemistry, 2014, vol. 57, No. 1, pp. 171-190.
Qian et al., "The efficient and enantiospecitic total synthesis of cyclopenta[b]phenanthrenes structurally related to neurosteroids", Adv. Syn. & Cata., 2010, vol. 352, Nos. 11-12, pp. 2057-2061.
Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.
Rychnovsky et al., "Synthesis of ent-cholesterol, the unnatural enantiomer", Journal of Organic Chemistry, 1992, vol. 57, No. 9, pp. 2732-2736.
Santaniello & Caspi, "Reduction of certain steroidal 19-sulfonic esters with metal hydrides", J. of Ster. Biochem, 1976, vol. 7, No. 3, pp. 223-227.
Sarett., "A new method for the preparation of 17(alpha)-hydroxy-20-ketopregnanes", J. Am. Chem. Soc., 1948, vol. 70, pp. 1454-1458.
Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.
Shen et al., "Microbial aromatization of 19-hydroxymethylepidehydroandrosterone acetate by Corynebacterium simplex", Huaxue Xuebao, 1983, vol. 41, No. 5, pp. 473-474.
Slavíkováet al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.
Spiegel et al., "Use of Nonaqueous Solvents in Parenteral Products", Journal of Pharmaceutical Sciences, 1963, vol. 52, No. 10, pp. 917-927.

(56) References Cited

OTHER PUBLICATIONS

Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.

Stastna et al., "Neurosteroid Analogues. 16. A New Explanation for the Lack of Anesthetic Effects in D16-Alphaxalone and Identification of a D17(20) Analogue with Potent Anesthetic Activity", Journal of Medicinal Chemistry, 2011, vol. 54, No. 11, pp. 3926-3934.

Stastna et al., "Stereoselectivity of sodium borohydride reduction of saturated steroidal ketones utilizing conditions of Luche reduction", Steroids, 2010, vol. 75, No. 10, pp. 721-725.

Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.

Stastna et al., "The use of symmetry in enantioselective synthesis: Four pairs of chrysene enantiomers prepared from 19-nortestosterone", Org. Biomol. Chem., 2011, vol. 9, pp. 4685-4694.

Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.

Wicha et al., "Transformations of steroidal neopentyl systems. II. Migration of acetate from the 3beta-to the 19-hydroxyl in delta 5 and A/B-trans steroids", Canadian Journal of Chemistry, 1967, vol. 45, No. 7, pp. 707-711.

Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.

Wicha et al., "Transformations of steroidal neopentyl systems. V. Synthesis and proof of the configuration of 19amethyl-195-alcohols", Journal of the Chemical Society [Section] C: Organic, 1969, vol. 6, pp. 947-951.

Wicha et al., "Transformations of steroidal neopentyl systems. VI. Intramolecular Claisen condensation of 19R-acetoxy-19A-methyl-3-ones of the 5alpha series", Tetrahedron, 1969, vol. 25, No. 17, pp. 3961-3968.

Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19—oxo-5alpha-analogs", Journal of Organic Chemistry, 1973, vol. 38 No. 7, pp. 1280-1283.

Wu "A New Classification of Prodrugs: Regulatory Perspectives", Pharmaceuticals, 2009, vol. 2, pp. 77-81.

Zonana et al., "The Neurobiology of Postpartum Depression", CNS Spectrums, (2005), pp. 792-799, 805.

Zorumski et al., "Enantioselective Modulation of GABAergic Synaptic Transmission by Steroids and Benz[dindenes in Hippocampal Microcultures", Synapse, (1998), vol. 29, pp. 162-171.

Eimon et al., "Brain activity patterns in high-throughput electrophysiology screen predict both drug efficacies and side effects", Nature Communications, (2018) 9:219, pp. 1-14.

Gottesmann, "GABA Mechanisms and Sleep", Neuroscience, (2002), vol. 111, No. 2, pp. 231-239.

Hawkins et al., "The synthetic neuroactive steroid SGE-516 reduces seizure burden and improves survival in a Dravet syndrome mouse model", Science Reports, (2017), pp. 1-8.

Möhler, "The GABA system in anxiety and depression and its therapeutic potential", Neuropharmacology, (2012) 62; pp. 42-53.

Adams et al., "The estrogenic activity and enzymic oxidation of 17b-estradiol-17a-d1", Steroids, Elsevier Science Publishers, (1965), pp. 75-84.

Anonymous: "Archive History for NCT03000530", Aug. 4, 2017, Retrieved from the Internet: <URL:https://www.clinicaltrials.gov/ct2/his>tory/NCT03000530?V-_6=View#StudyPageTop; [retrieved on Nov. 20, 2018].

Chen et al., "The mechanism investigation in substitution of 21-bromo-3a-hydroxy-3b-methoxymethyl-5a-pregnan-20-one with nucleophiles", Steroids, vol. 71, (2006), pp. 942-948.

Database Medline, US National Library of Medicine, Bethesda, MD, 1984, Welling: "Intentions affecting drug absorption", Database accession No. NLM6388952, abstract.

Durán et al., "Synthesis of 6-thia analogs of the natural neurosteroid allopregnanolone", Tetrahedron, Elsevier Science Publishers, 2006, vol. 62, No. 20, pp. 4762-4768.

Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.

International Search Report and Written Opinion for Corresponding International Application No. PCT/US2018/050012 dated Dec. 7, 2018.

International Search Report and Written Opinion for Corresponding International Application No. PCT/US2018/051048 dated Jan. 11, 2019.

International Search Report and Written Opinion for Corresponding International Application No. PCT/US2018/064546 dated Apr. 9, 2019.

International Search Report and Written Opinion for International Application No. PCT/US2018/067277 dated May 24, 2019.

International Search Report and Written Opinion for International Application No. PCT/US2018/067306 dated May 28, 2019.

International Search Report and Written Opinion for International Application No. PCT/US2019/013315 dated Jun. 14, 2019.

Itoh et al., "On the acid-catalyzed d-homoannulation of pregnanetriol 20-sulfate and its c-20 isomeric sulfate", Chemical and Pharmaceutical Bulletin. 1994, vol. 42, No. 9, pp. 1736-1744.

Kanes et al., "A multiple-ascending dose study of the neuroactive steroid Sage-217", Biological Psychiatry, vol. 81, No. 10, 2017, pp. S347.

Kanes et al., "A single-ascending dose study of the neuroactive steroid Sage-217", Biological Psychiatry, vol. 81, No. 10, 2017, pp. S31.

Kasal et al., "Neurosteroid analogues: synthesis of 6-aza-allopregnanolone", Tetrahedron, Elsevier Science Publishers, 2005, vol. 61, No. 9, pp. 2269-2278.

Mariangela et al., "The influence of neuroactive steroid lipophilicity on gabaa receptor modulation: Evidence for a low-affinity interaction", Journal of Neurophysiology, 2009, vol. 102, No. 2, pp. 1254-1264.

Nicoletti et al., "Synthesis and GABAA receptor activity of 6-oxa-analogs of neurosteroids", Steroids, Elsevier Science Publishers 2000, vol. 65, No. 6, pp. 349-356.

Rongone et al., "In vivo metabolism of d-homotestosterone", Steroids, vol. 1, No. 6, 1963, pp. 664-669.

Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil> es/80fflf35-fc4c-4eb2-9456-3228ec891a59; [retrieved on Dec. 21, 2018].

Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.

Shu et al., "Photodynamic effects of steroid-conjugated fluorophores on gabaa receptors", Molecular Pharmacology, 2009, vol. 76, No. 4, pp. 754-765.

Sunöl et al., "Activity of b-nor analogues of neurosteroids on the gabaa receptor in primary neuronal cultures", Journal of Medicinal Chemistry, 2006, vol. 49, No. 11, pp. 3225-3234.

Veleiro et al., "Structure-activity relationships of neuroactive steroids acting on the gabaa receptor", Current Medicinal Chemistry, 2009, vol. 16, No. 4, pp. 455-472.

Welling, "Interactions affecting drug absorption", Clinical Pharmacokinetics, vol. 9, No. 5, Sep. 1984 (Sep. 1984), pp. 404-434.

D'hulst et al., "Expression of the GABAergic system in animal models for fragile X syndrome and fragile X associated tremor/ataxia syndrome (FXTAS)", Brain Research, 2008, vol. 1253, pp. 176-183.

(56) References Cited

OTHER PUBLICATIONS

Galofre et al., "GABAA receptor and cell membrane potential as functional endpoints in cultured neurons to evaluate chemicals for human acute toxicity", Neurotoxicology and Teratology, (2009), vol. 32, pp. 52-61.
Guardia et al., "GABAergic and Glutamatergic Modulation in Binge Eating: Therapeutic Approach", Current pharmaceutical design, 2011, vol. 17, No. 14, pp. 1396-1409.
Gunduz-Bruce et al.,"Sage-217 in Major Depressive Disorder: A Multicenter, Randomized, Double-Blind, Phase 2 Placebo-Controlled Trial", European Nueuropsychopharmacology, vol. 29, 2019, pp. S59-S-60, Abstract.
International Search Report and Written Opinion for Corresponding International Application No. PCT/US2019/036848 dated Aug. 22, 2019.
Suthoff et al., "Assessment of Health-Related Quality of Life by the SF36V2 in a Phase 2, Randomized Placebo-Controlled Trial of the GABA A Receptor Positive Allosteric Modulator Sage-217 in Major Depressive Disorder", Value in Health, vol. 21, No. Suppl. 3, 2018, Abstract.
Veleiro et al., "Synthesis and GABAA Receptor Acitivity of a6, 19-Oxido Analogue of Pregnanolone", Bioorganic & Medicinal Chemistry Letters, (2003) , vol. 13, pp. 343-345.

\* cited by examiner

COMPOSITIONS AND METHODS FOR TREATING CNS DISORDERS

RELATED APPLICATIONS

This application is a U.S. National Stage Application filed under 35 U.S.C. § 371 of International Patent Application No. PCT/US2015/056054, filed Oct. 16, 2015, which claims the benefit of and priority to U.S. Provisional Application No. 62/064,961, filed Oct. 16, 2014, the contents of each of which are hereby incorporated by reference in their entirety.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization, e.g., a change of potential from −70 mV to −50 mV. This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the gamma-aminobutyric acid, GABA, receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids. See, e.g., Lan, N. C. et al., *Neurochem. Res.* (1991) 16:347-356.

Neuroactive steroids do occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

The ovarian hormone progesterone and its metabolites have been demonstrated to have profound effects on brain excitability (Backstrom, T. et al., *Acta Obstet. Gynecol. Scand. Suppl.* 130:19-24 (1985); Pfaff, D. W and McEwen, B. S., *Science* 219:808-814 (1983); Gyermek et al., *J Med Chem.* 11: 117 (1968); Lambert, J. et al., *Trends Pharmacol. Sci.* 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., *Premenstrual Syndrome and Progesterone Therapy*, $2^{nd}$ edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., *Lancet,* 1235-1237 (1956)). A more direct correlation has been observed with a reduction in progesterone metabolites (Rosciszewska et al., *J. Neurol. Neurosurg. Psych.* 49:47-51 (1986)).

In addition, for subjects with primary generalized petit mal epilepsy, the temporal incidence of seizures has been correlated with the incidence of the symptoms of premenstrual syndrome (Backstrom, T. et al., *J. Psychosom. Obstet. Gynaecol.* 2:8-20 (1983)). The steroid deoxycorticosterone has been found to be effective in treating subjects with epileptic spells correlated with their menstrual cycles (Aird, R. B. and Gordan, G., *J. Amer. Med. Soc.* 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome and Progesterone Therapy*, $2^{nd}$ edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al., *J Psychosom. Obstet. Gynaecol.* 2:8-20 (1983)); Dalton, K., Premenstrual Syndrome and Progesterone Therapy, $2^{nd}$ edition, Chicago Yearbook, Chicago (1984)) has prompted the use of progesterone in their treatment (Mattson et al., "Medroxyprogesterone therapy of catamenial epilepsy," in *Advances in Epileptology: XVth Epilepsy International Symposium*, Raven Press, New York (1984), pp. 279-282, and Dalton, K., *Premenstrual Syndrome and Progesterone Therapy*, $2^{nd}$ edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

Provided herein are C21-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder such as depression, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

In one aspect, provided is a compound of Formula (I):

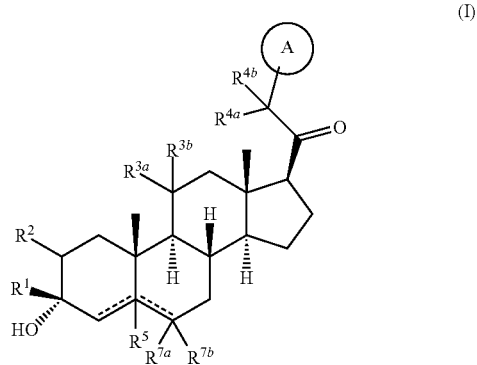

or a pharmaceutically acceptable salt thereof; wherein: ring A is substituted or unsubstituted carbocyclyl, heterocyclyl, aryl, or heteroaryl; $R^1$ is hydrogen, substituted or unsubstituted $C_{1-6}$ alkyl, substituted or unsubstituted $C_{2-6}$ alkenyl, or substituted or unsubstituted $C_{3-6}$ carbocylyl; $R^2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, or —$OR^{A2}$ wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl; $R^{3a}$ is hydrogen or —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{3b}$ is hydrogen; or $R^{3a}$ and $R^{3b}$ are joined to form an oxo (=O) group; $R^{4a}$ is hydrogen, substituted or unsubstituted $C_{1-6}$ alkyl, or —$OR^{A4}$, wherein $R^{A4}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{4b}$ is hydrogen or substituted or unsubstituted $C_{1-6}$ alkyl; $R^{4a}$ and $R^{4b}$ are joined to form an oxo (=O) group; or $R^{4a}$ and $R^{4b}$ together with the carbon atom to which they are attached form a ring (e.g., a 3-6-membered ring (e.g., carbocycyl or heterocyclyl ring). $R^{7a}$ is hydrogen or halogen; $R^{7b}$ is hydrogen; $R^5$ is absent or hydrogen; and ===== represents a single or double bond, wherein when one of ===== is a double bond, the other ===== is a single bond; and when one of the ===== is a double bond, $R^5$ is absent.

In an embodiment, A is Ring A is substituted or unsubstituted nitrogen containing heterocyclyl, or nitrogen containing heteroaryl. In an embodiment, A is attached through a nitrogen atom. In an embodiment, A is monocyclic heteroaryl or heterocylcyl, for example, a substituted monocyclic heteroaryl. In an embodiment, A is bicyclic heteroaryl, for example, a substituted bicyclic heteroaryl. Exemplary substituents are described herein.

In an embodiment, ring A is substituted carbocyclyl, heterocyclyl, aryl, or heteroaryl, for example, a substituted heterocyclyl or heteroaryl. In some embodiments, the heterocyclyl or heteroaryl is attached through a nitrogen atom. In an embodiment, A is a substituted heterocyclyl linked through a nitrogen atom. In an embodiment, A is an unsubstituted heterocyclyl linked through a nitrogen atom. In an embodiment, A is a substituted heteroaryl linked through a nitrogen atom. In an embodiment, A is an unsubstituted heteroaryl linked through a nitrogen atom.

In an embodiment, A is substituted or unsubstituted imidiaole or benzimidazole (e.g., a substituted imidazole or benzimidazole). In some embodiments the imidazole or benzimidazole is attached through a nitrogen atom.

In an embodiment, A is substituted or unsubstituted and is selected from:

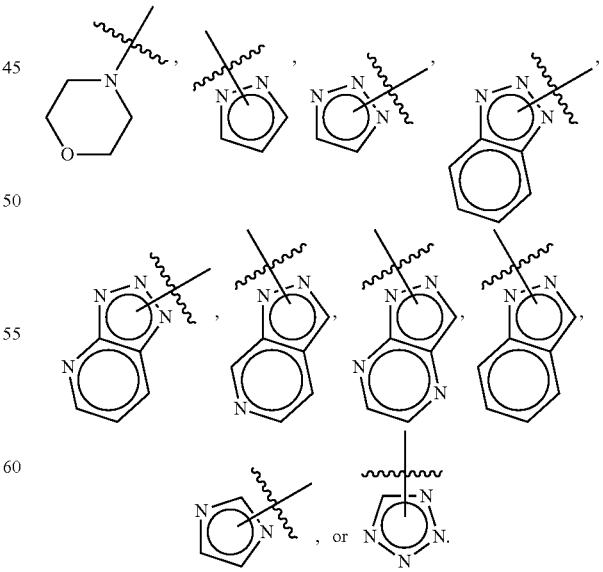

In an embodiment, A is substituted or unsubstituted and is selected from:

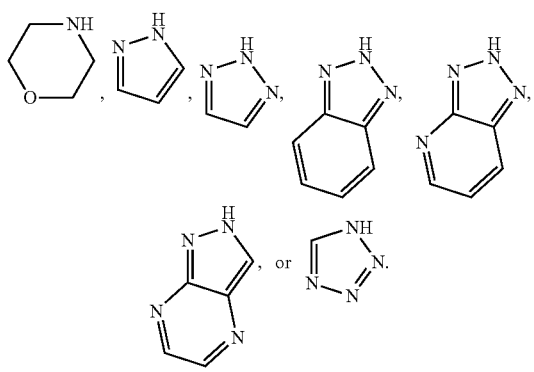

In an embodiment A is substituted or unsubstituted and is selected from:

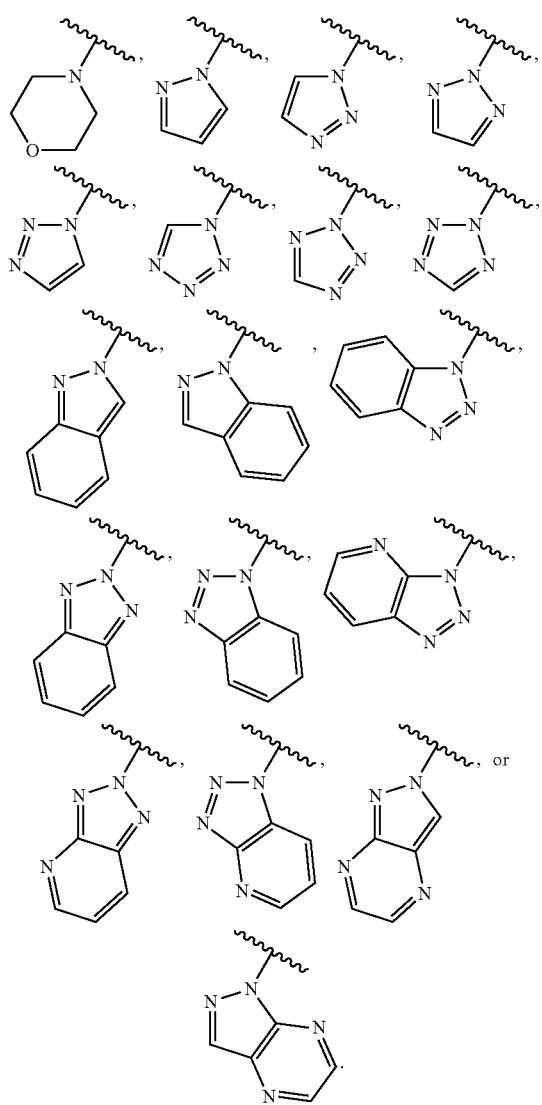

In an embodiment, $R^1$ is hydrogen, methyl, ethyl, or propyl (e.g., methyl). In an embodiment, $R^1$ is unsubstituted $C_{1-3}$ alkyl. In an embodiment, $R^1$ is substituted $C_{1-6}$ alkyl (e.g., haloalkyl or alkoxyalkyl such as methoxymethyl).

In an embodiment, at least one of $R^2$, $R^{3a}$, $R^{4a}$ or $R^{4b}$ is not hydrogen. For example, in an embodiment, at least 2 of $R^2$, $R^{3a}$, $R^{4a}$ or $R^{4b}$ is not hydrogen.

In an embodiment, $R^2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, or —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl. In an embodiment, $R^2$ is —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, for example, hydroxyl or alkoxy.

In an embodiment, $R^{3a}$ is —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{3b}$ is hydrogen; or $R^{3a}$ and $R^{3b}$ are joined to form an oxo (=O) group. In an embodiment, $R^{3a}$ is —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, for example, hydroxyl or alkoxy In an embodiment, $R^{4a}$ is substituted or unsubstituted $C_{1-6}$ alkyl, or —$OR^{A4}$, wherein $R^{A4}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{4b}$ is hydrogen or substituted or unsubstituted $C_{1-6}$ alkyl; or $R^{4a}$ and $R^{4b}$ are joined to form an oxo (=O) group.

In an embodiment, the compound is of the Formula (I-a):

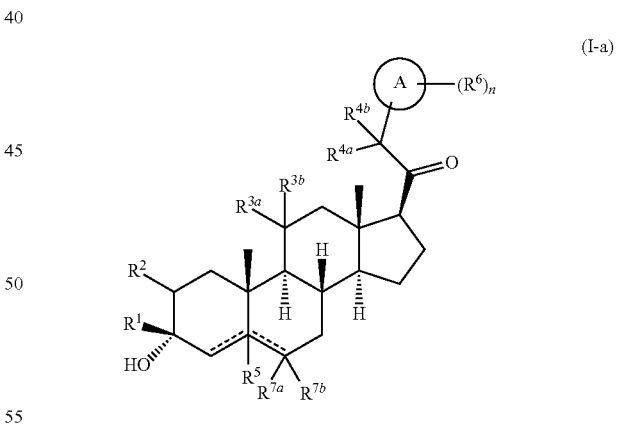

(I-a)

wherein: $R^6$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, $C_{1-6}$ haloalkyl, halogen, cyano, —$OR^{A6}$, —C(=O)$OR^{A6}$, —$SR^{B6}$, —S(=O)$R^{B6}$, or S(=O)$_2R^{B6}$, wherein $R^{A6}$ is hydrogen or substituted or unsubstituted $C_{1-6}$ alkyl, substituted or unsubstituted $C_{2-6}$ alkenyl, substituted or unsubstituted $C_{2-6}$ alkynyl, or unsubstituted $C_{3-6}$ carbocylyl, or $C_{1-6}$ haloalkyl, and $R^{B6}$ is substituted or unsubstituted $C_{1-6}$ alkyl or substituted or unsubstituted $C_{3-6}$ carbocylyl; and n is 0, 1, 2, or 3.

In an embodiment, the compound is of the Formula (I-b):

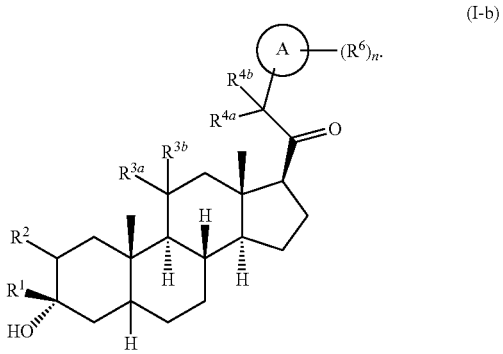

(I-b)

In an embodiment, the compound is of the Formula (I-c1) or (I-c2):

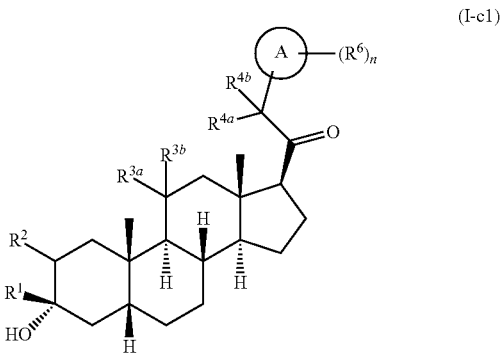

(I-c1)

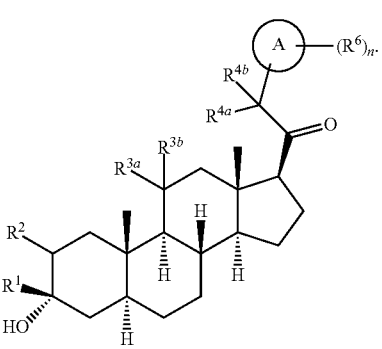

(I-c2)

In an embodiment, the compound is of the Formula (I-c1):

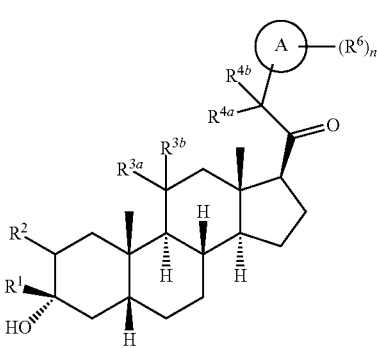

(I-c1)

or a pharmaceutically acceptable salt thereof; wherein: Ring A is substituted or unsubstituted carbocyclyl, heterocyclyl, aryl, or heteroaryl; $R^1$ is hydrogen, substituted or unsubstituted $C_{1-6}$ alkyl, substituted or unsubstituted $C_{2-6}$ alkenyl, or substituted or unsubstituted $C_{3-6}$ carbocylyl; $R^2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, or —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl; $R^{3a}$ is hydrogen or —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{3b}$ is hydrogen; or $R^{3a}$ and $R^{3b}$ are joined to form an oxo (=O) group; $R^{4a}$ is hydrogen, substituted or unsubstituted $C_{1-6}$ alkyl, or —$OR^{A4}$, wherein $R^{A4}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{4b}$ is hydrogen or substituted or unsubstituted $C_{1-6}$ alkyl; $R^{4a}$ and $R^{4b}$ are joined to form an oxo (=O) group; or $R^{4a}$ and $R^{4b}$ together with the carbon atom to which they are attached form a ring (e.g., a 3-6-membered ring (e.g., carbocycyl or heterocyclyl ring); $R^6$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, $C_{1-6}$ haloalkyl, halogen, cyano, —$OR^{A6}$, —$C(=O)OR^{A6}$, —$SR^{B6}$, —$S(=O)R^{B6}$, or $S(=O)_2R^{B6}$, wherein $R^{A6}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, or $C_{1-6}$ haloalkyl, and $R^{B6}$ is substituted or unsubstituted $C_{1-6}$ alkyl or substituted or unsubstituted $C_{3-6}$ carbocylyl; and n is 0, 1, 2, or 3.

In an embodiment, A is a carbon bound (e.g., A linked through a carbon atom) substituted or unsubstituted 5 or 6-membered heteroaryl, or 6-membered aryl.

In an embodiment, A is Ring A is substituted or unsubstituted nitrogen containing heterocyclyl, or nitrogen containing heteroaryl. In an embodiment, A is attached through a nitrogen. In an embodiment, A is monocyclic heteroaryl or heterocylcyl, for example, a substituted monocyclic heteroaryl. In an embodiment, A is bicyclic heteroaryl, for example, a substituted bicyclic heteroaryl. Exemplary substituents are described herein.

In an embodiment, $R^1$ is hydrogen. In an embodiment, $R^1$ is substituted or unsubstituted $C_{1-6}$ alkyl, for example, methyl.

In an embodiment, at least one of $R^2$, $R^{3a}$, $R^{4a}$ or $R^{4b}$ is not hydrogen. For example, in an embodiment, at least 2 of $R^2$, $R^{3a}$, $R^{4a}$ or $R^{4b}$ is not hydrogen.

In an embodiment, $R^2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, or —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl. In an embodiment, R is —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, for example, hydroxyl or alkoxy.

In an embodiment, $R^{3a}$ is —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{3b}$ is hydrogen; or $R^{3a}$ and $R^{3b}$ are joined to form an oxo (=O) group. In an embodiment, $R^{3a}$ is —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, for example, hydroxyl or alkoxy In an embodiment, $R^{4a}$ is substituted or unsubstituted $C_{1-6}$ alkyl, or —$OR^{A4}$, wherein $R^{A4}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{4b}$ is hydrogen or substituted or unsubstituted $C_{1-6}$ alkyl; or $R^{4a}$ and $R^{4b}$ are joined to form an oxo (=O) group.

In an embodiment, the compound is of the Formula (II):

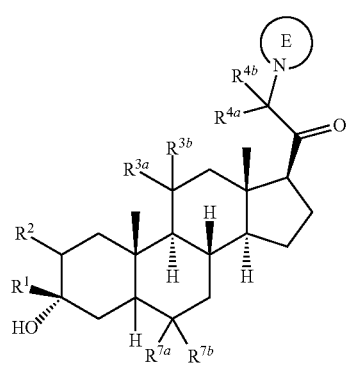

(II)

wherein: Ring E is substituted or unsubstituted heterocyclyl or heteroaryl.

In an embodiment, the compound is of the Formula (II-a1) or (II-a2):

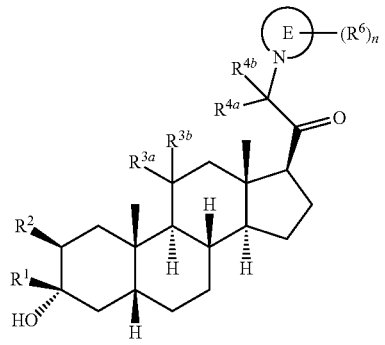

(II-a1)

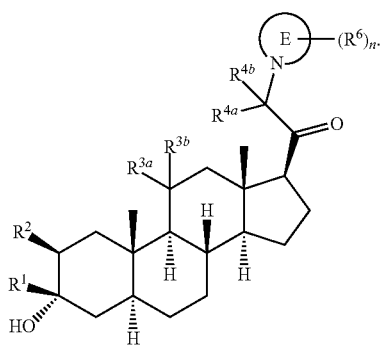

(II-a2)

In an embodiment, E is a ring comprising at least one nitrogen atom.

In an embodiment, A is a ring comprising at least one nitrogen atom.

In an embodiment, E is selected from:

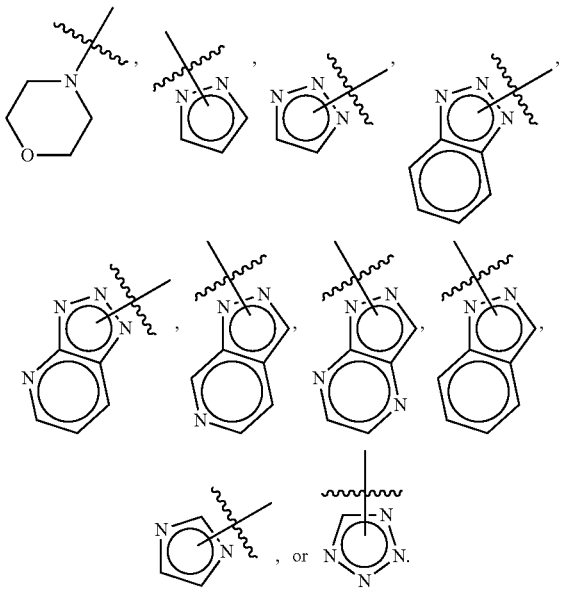

In an embodiment, E is selected from:

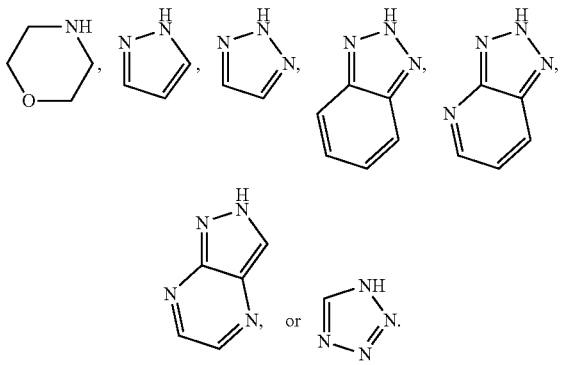

In an embodiment, A is:

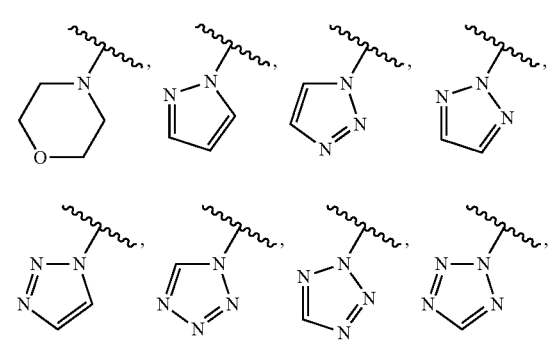

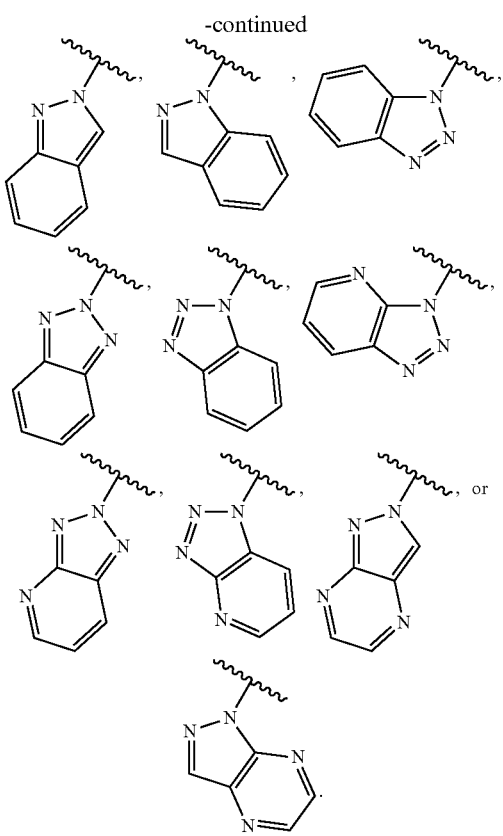

In an embodiment, E is a ring comprising at least two nitrogen atoms. In an embodiment, E is a ring comprising at least two nitrogen atoms and $R^1$ is substituted or unsubstituted $C_{2-6}$ alkyl. In an embodiment, E is a ring comprising at least two nitrogen atoms and at least one of $R^2$, $R^{3a}$, $R^{4a}$ or $R^{4b}$ is not hydrogen.

In an embodiment, E is a ring comprising at least three nitrogen atoms. In an embodiment, E is a ring comprising four nitrogen atoms.

In an embodiment, $R^1$ is substituted or unsubstituted $C_{2-6}$alkyl.

In an embodiment, at least one of $R^2$, $R^{3a}$, $R^{4a}$ or $R^{4b}$ is not hydrogen.

In an embodiment, E is a ring comprising 2, 3 or 4 nitrogen atoms.

In an embodiment, E is a ring selected from pyrazole, triazole, tetrazole, indazole, benzotriazole, triazolopyridine, triazolopyrazine, pyrazolopyrazine.

In an embodiment, A is a 6-membered heterocyclyl ring (e.g., a 6-membered heterocyclyl ring comprising at least two heteroatoms).

In an embodiment, A is a 5-6-membered heterocyclyl ring, and n is 1 or 2.

In an embodiment, E is morpholine and n is 1 or 2.

In an embodiment, $R^1$ is hydrogen or unsubstituted $C_{1-6}$ alkyl. In an embodiment, $R^1$ is or methyl. In an embodiment, $R^1$ is substituted or unsubstituted $C_{2-6}$ alkyl.

In an embodiment, $R^2$ is hydrogen, —$OR^{A2}$, wherein $R^{A2}$ is hydrogen, or substituted or unsubstituted $C_{1-6}$ alkyl (e.g., methyl, ethyl).

In an embodiment, $R^{3a}$ is —$OR^{A3}$, wherein $R^{A3}$ is hydrogen, or substituted or unsubstituted $C_{1-6}$ alkyl (e.g., methyl).

In an embodiment, $R^{3a}$ and $R^{3b}$ are joined to form an oxo (=O) group.

In an embodiment, $R^{4a}$ is hydrogen, or substituted or unsubstituted $C_{1-6}$ alkyl (e.g., methyl).

In an embodiment, $R^{4b}$ is hydrogen, or substituted or unsubstituted $C_{1-6}$ alkyl (e.g., methyl).

In an embodiment, $R^{4a}$ is hydrogen, and $R^{4b}$ is substituted or unsubstituted $C_{1-6}$ alkyl (e.g., methyl).

In an embodiment, $R^5$ is hydrogen.

In an embodiment, n is 0.

In an embodiment, n is 1 and $R^6$ is substituted or unsubstituted $C_{1-6}$ alkyl, $C_{1-6}$ haloalkyl, halogen (e.g., —F, —Br, —Cl), cyano, —$OR^{A6}$, —C(=O)$OR^{A6}$, —$SR^{B6}$, —S(=O)$R^{B6}$, or S(=O)$_2R^{B6}$, wherein $R^{A6}$ is hydrogen or substituted or unsubstituted $C_{1-6}$ alkyl (e.g., methyl, ethyl), $C_{1-6}$ haloalkyl (e.g., —$CF_3$), and $R^{B6}$ is substituted or unsubstituted $C_{1-6}$ alkyl.

In an embodiment, n is 1 and $R^6$ is halogen (e.g., —F, —Br, —Cl) or cyano. In an embodiment, n is 1 and $R^6$ is substituted or unsubstituted $C_{1-6}$ alkyl (e.g., methyl). In an embodiment, n is 1 and $R^6$ is $C_{1-6}$ haloalkyl, —$OR^{A6}$, or —C(=O)$OR^{A6}$, wherein $R^{A6}$ is hydrogen or substituted or unsubstituted $C_{1-6}$ alkyl (e.g., methyl, ethyl), $C_{1-6}$ haloalkyl (e.g., —$CF_3$). In an embodiment, n is 1 and $R^6$ is $SR^{B6}$, —S(=O)$R^{B6}$, or S(=O)$_2R^{B6}$, wherein $R^{B6}$ is substituted or unsubstituted $C_{1-6}$ alkyl (e.g., methyl).

In an embodiment, n is 2 and $R^6$ is independently selected from substituted or unsubstituted $C_{1-6}$ alkyl, $C_{1-6}$ haloalkyl, halogen (e.g., —F, —Br, —Cl), cyano, —$OR^{A6}$, —C(=O)$OR^{A6}$, —$SR^{B6}$, —S(=O)$R^{B6}$, or S(=O)$_2R^{B6}$, wherein $R^{A6}$ is hydrogen or substituted or unsubstituted $C_{1-6}$ alkyl (e.g., methyl, ethyl), $C_{1-6}$ haloalkyl (e.g., —$CF_3$), and $R^{B6}$ is substituted or unsubstituted $C_{1-6}$ alkyl.

In an embodiment, n is 2 and $R^6$ is independently selected from halogen (e.g., —F, —Br, —Cl). In an embodiment, n is 2 and one of $R^6$ is fluorine.

In an embodiment, n is 0 and $R^1$ is substituted or unsubstituted $C_{2-6}$ alkyl.

In an embodiment, $R^1$ is substituted or unsubstituted $C_{1-6}$ alkyl and at least one of $R^2$, $R^{3a}R^{4a}$ or $R^{4b}$ is not hydrogen.

In an embodiment, the compound is of the Formula (II-a1) and E is a heteroaryl ring comprising at least 3 nitrogen atoms.

In an embodiment, the compound is:

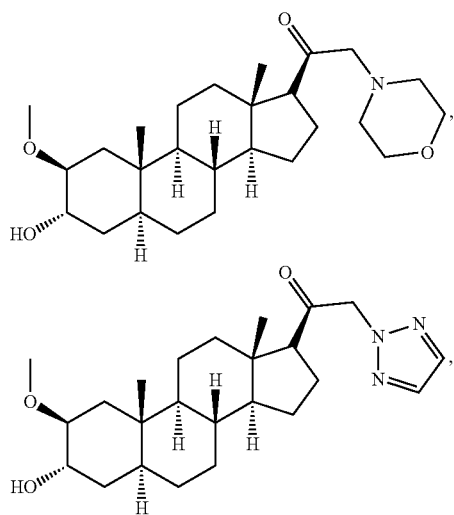

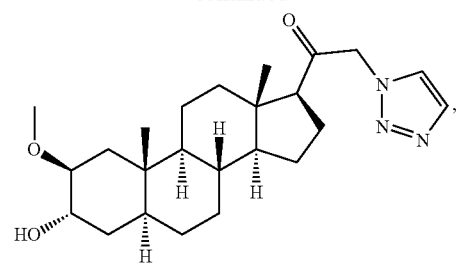
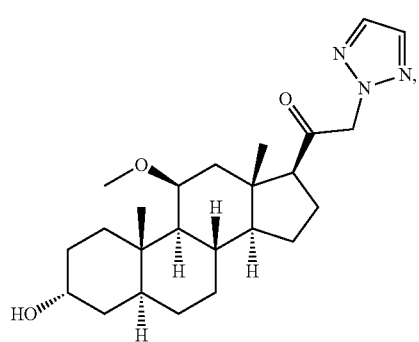
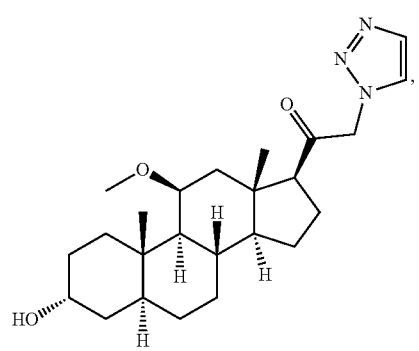
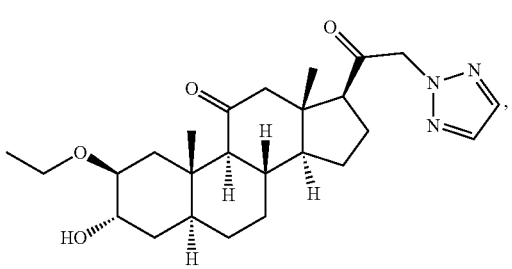
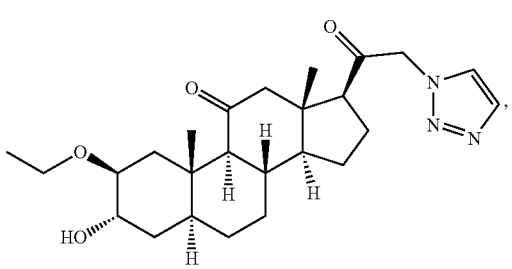
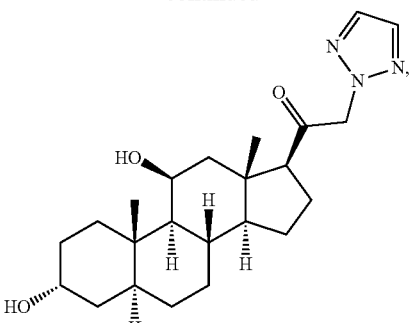
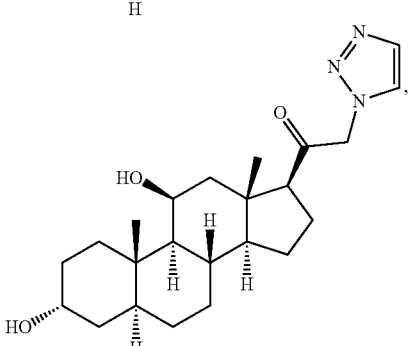
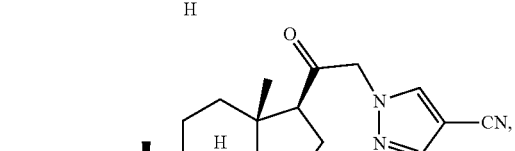
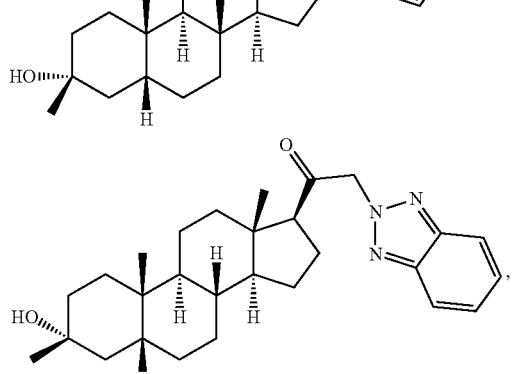
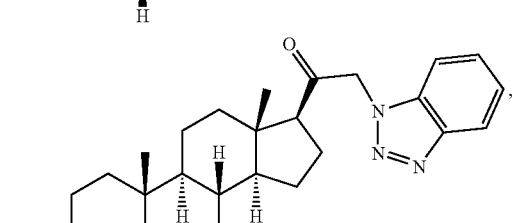
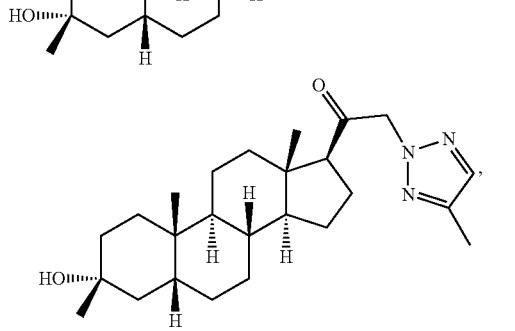

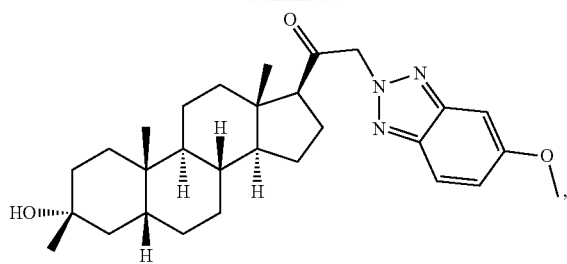
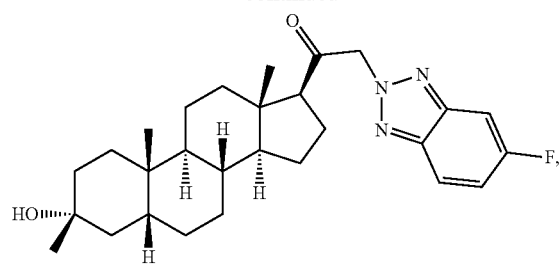
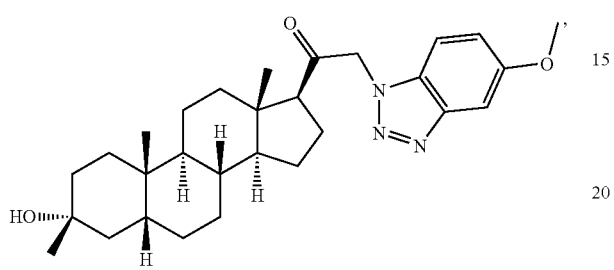
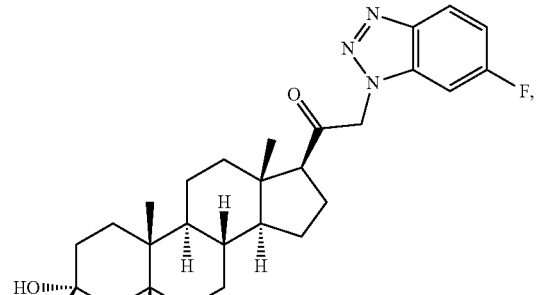
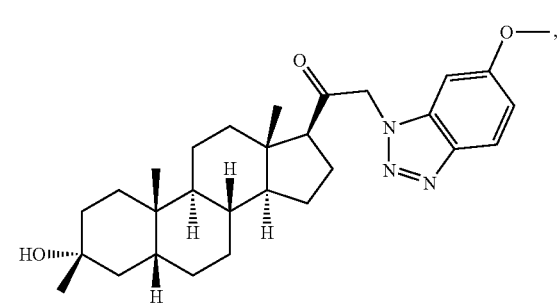
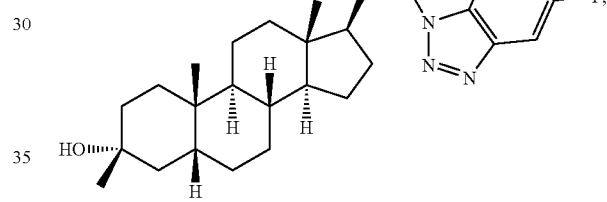
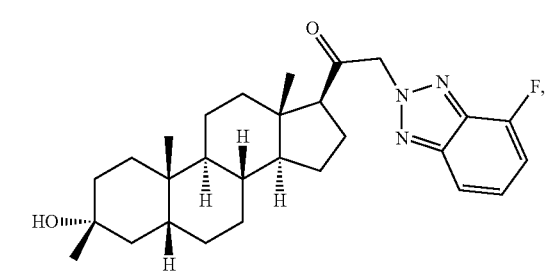
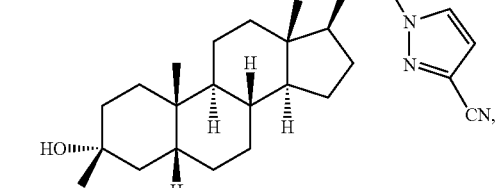
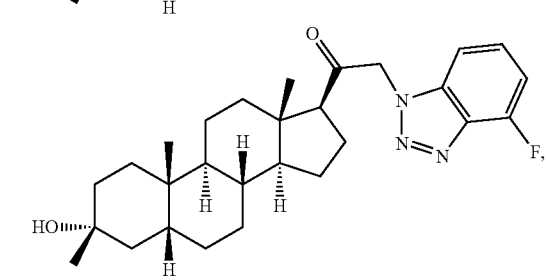
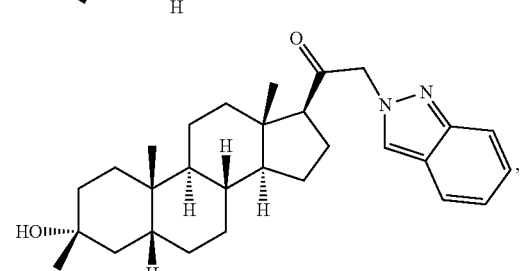
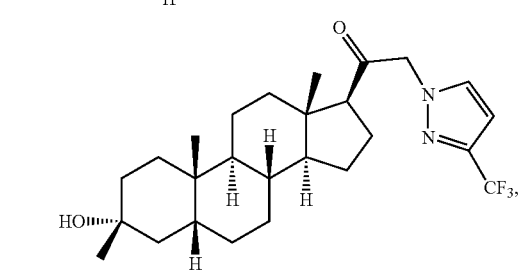
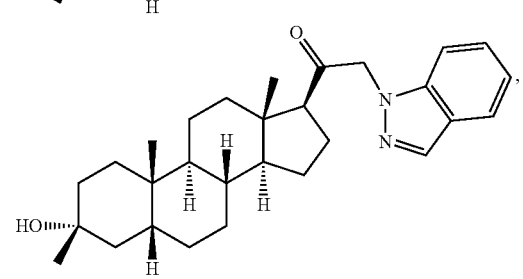

-continued
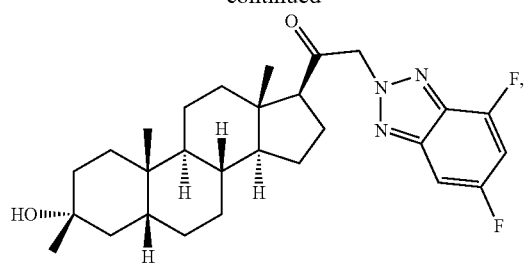
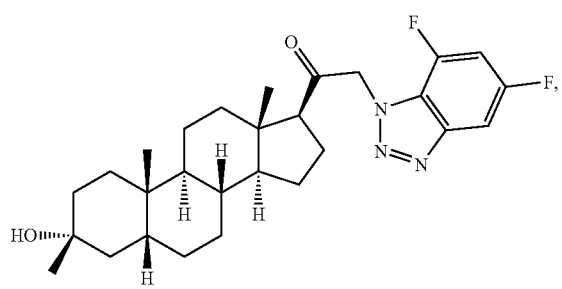
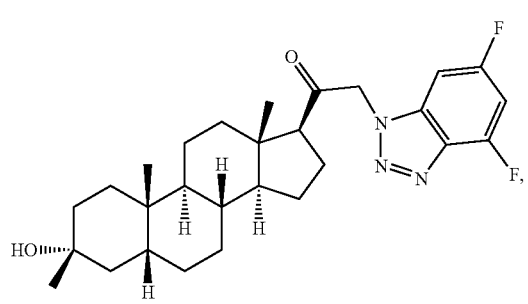
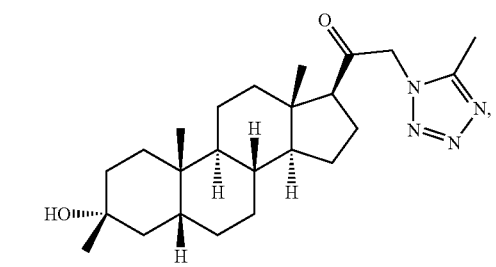
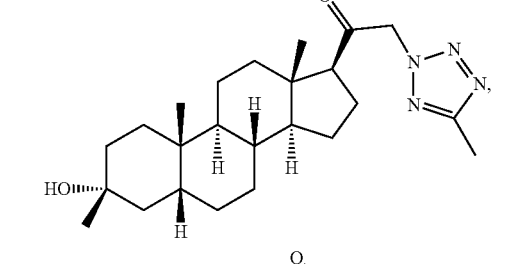
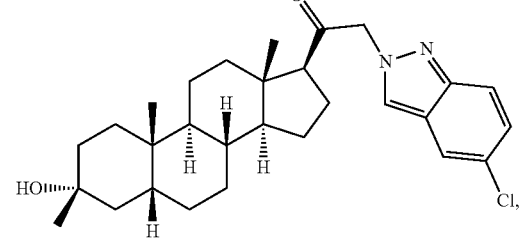
-continued
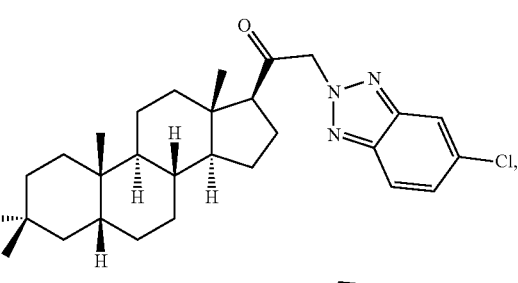
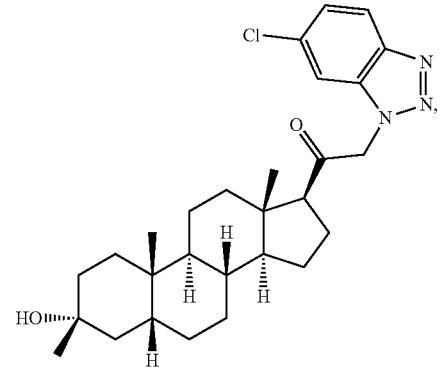
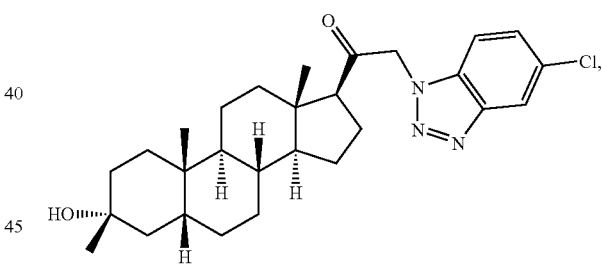
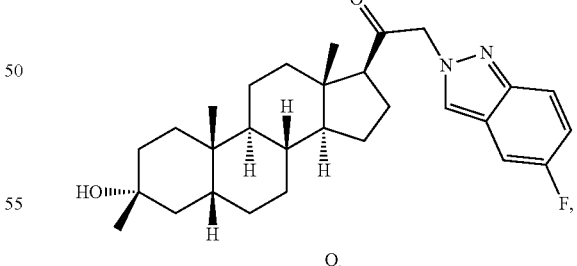
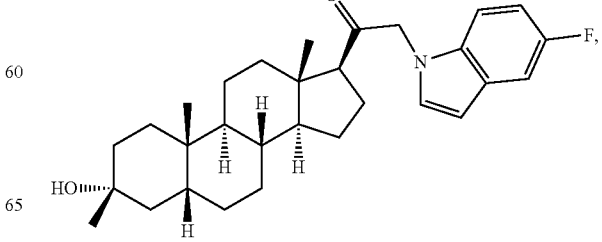

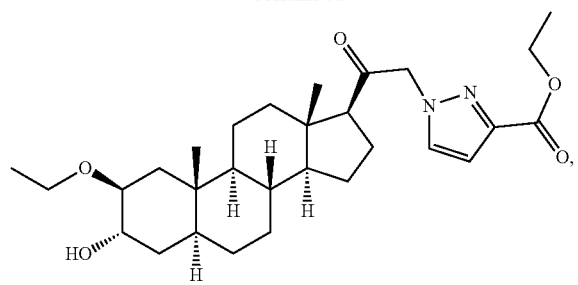
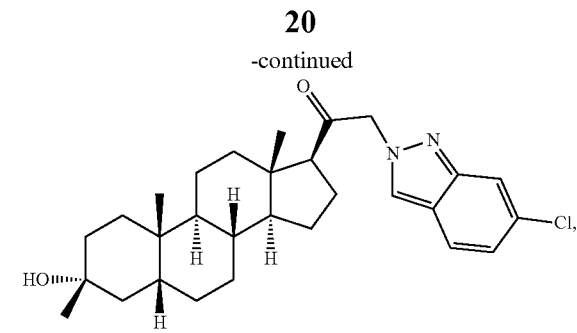
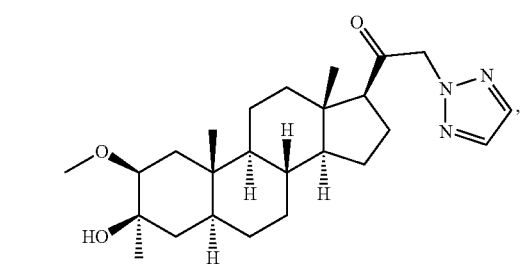
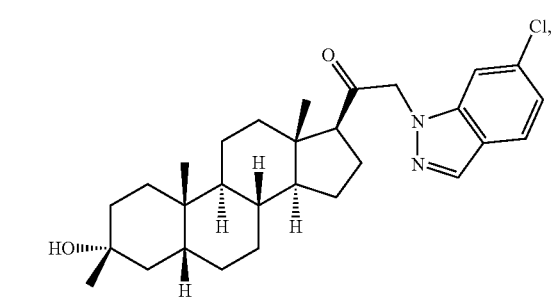
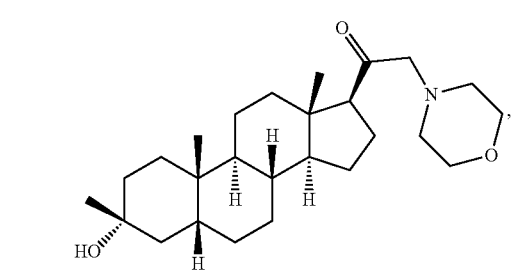
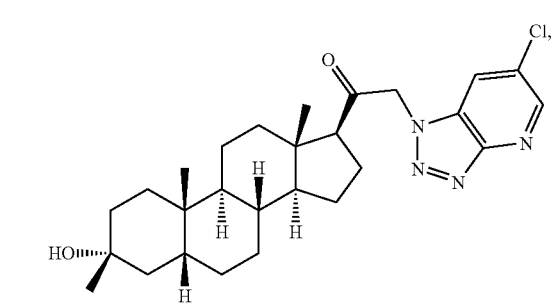
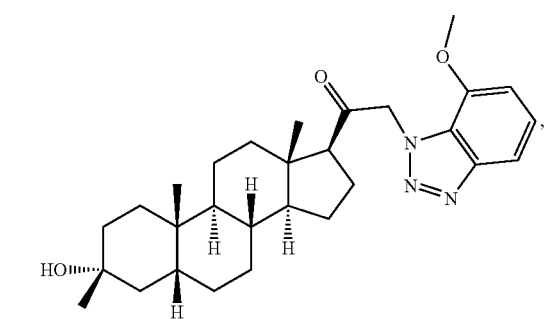
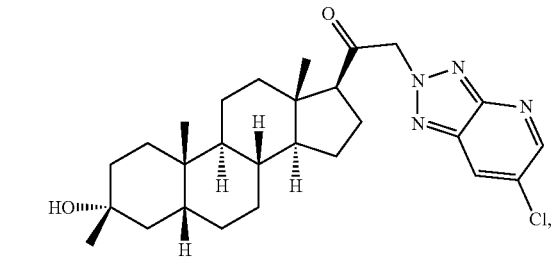
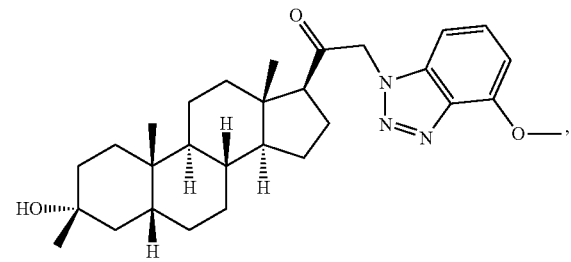
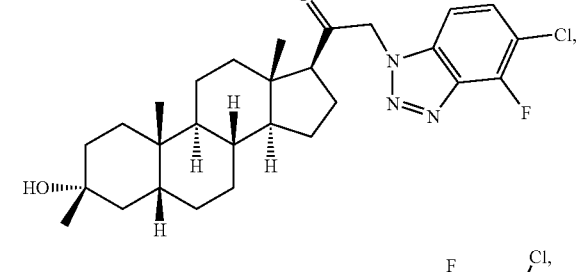
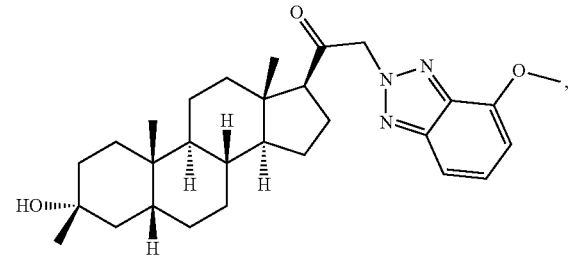
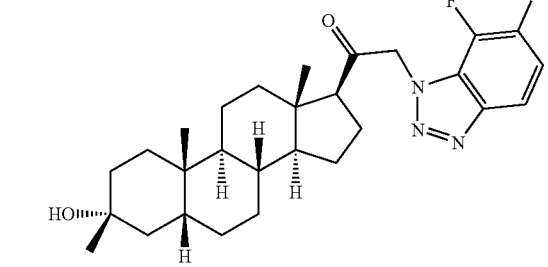

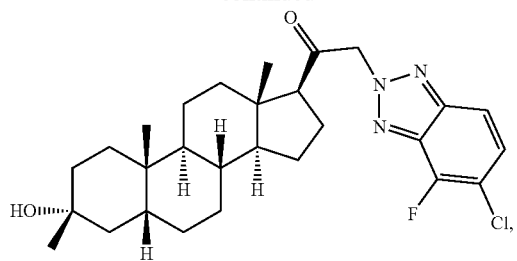
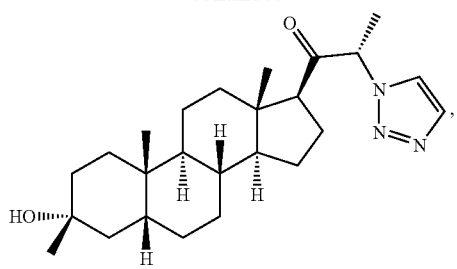
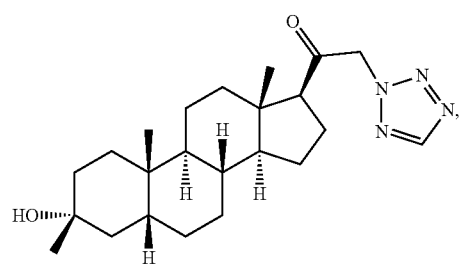
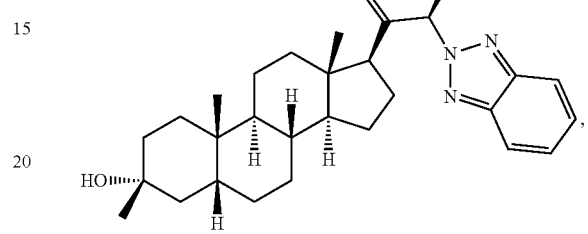
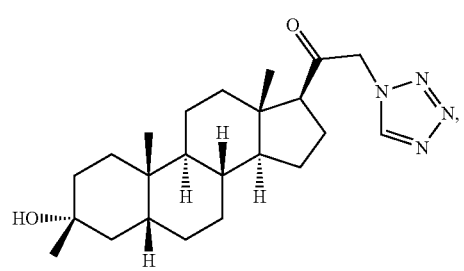
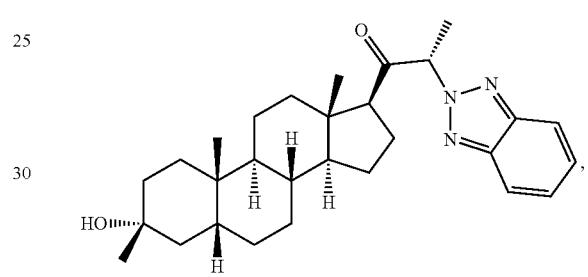
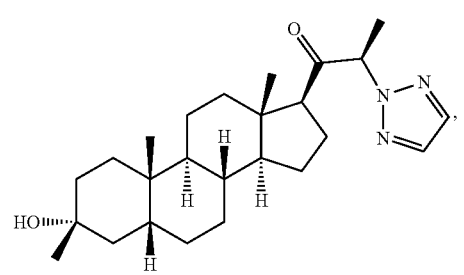
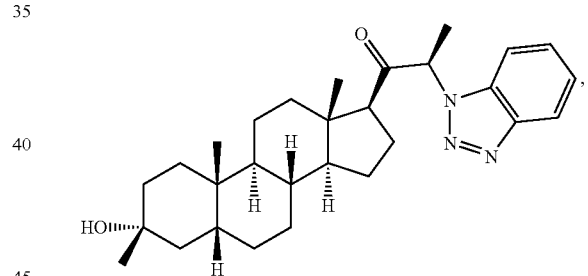
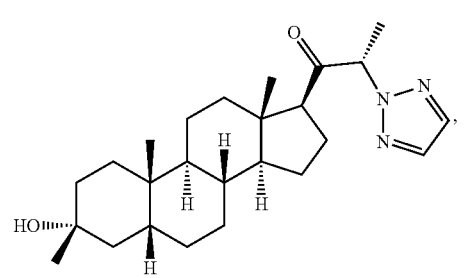
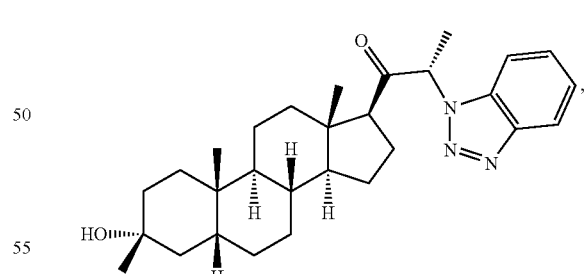
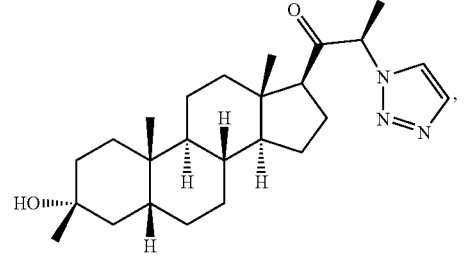
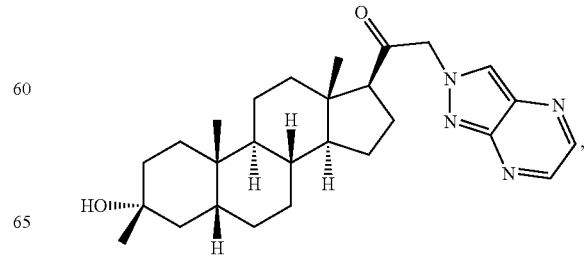

23
-continued
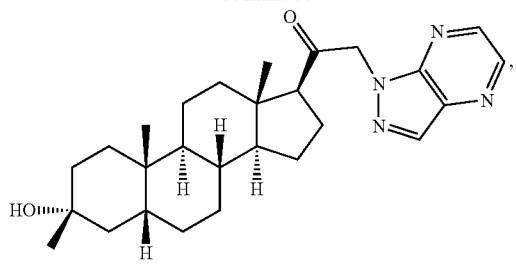
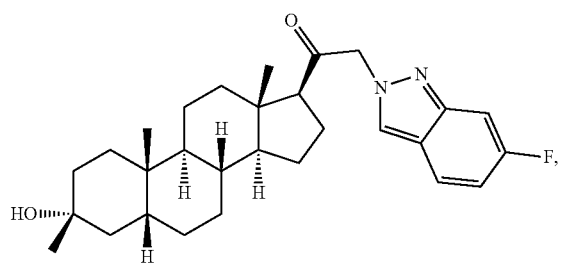
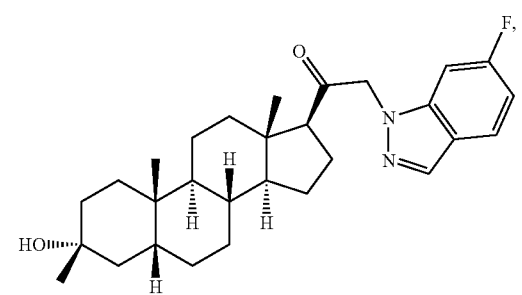
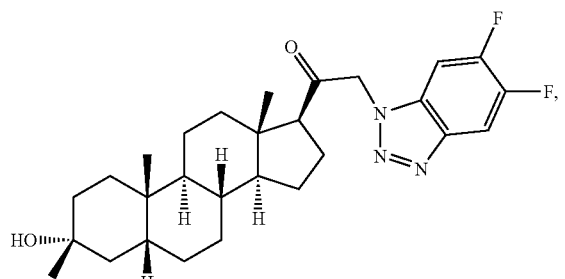
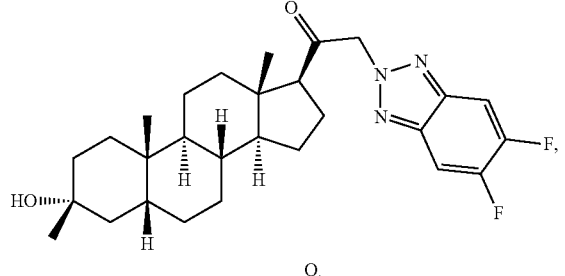
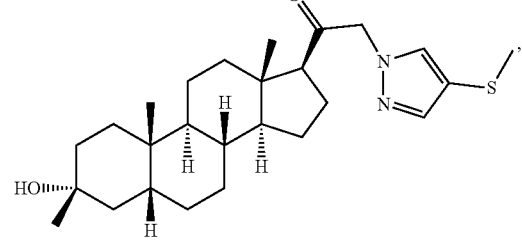
24
-continued
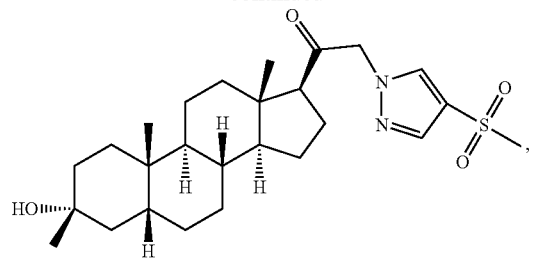
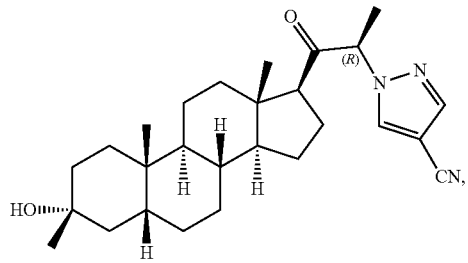
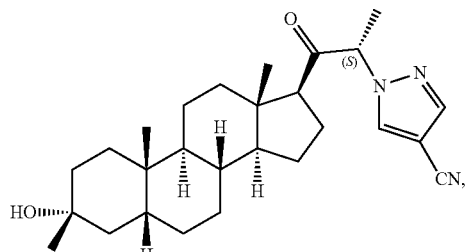
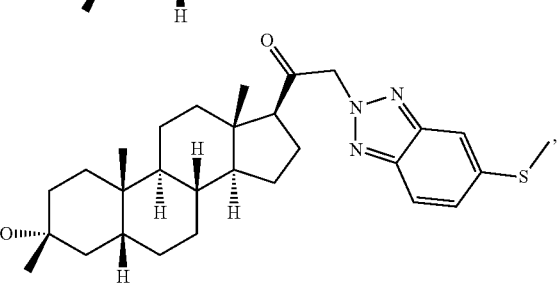
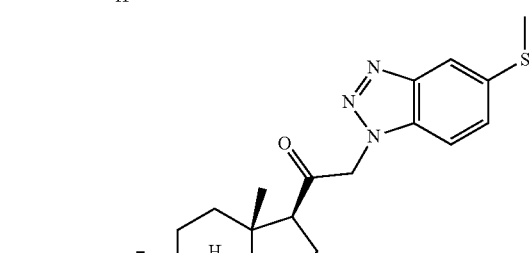
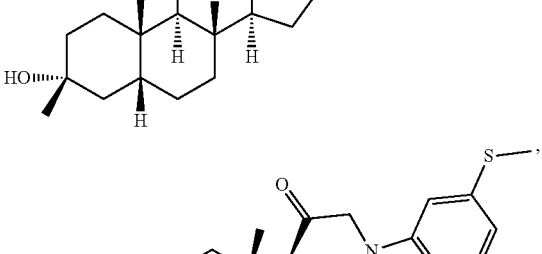
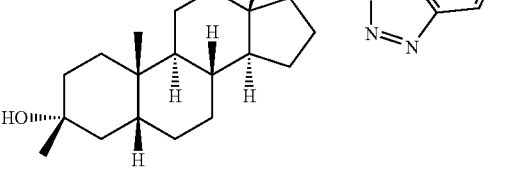

25
-continued
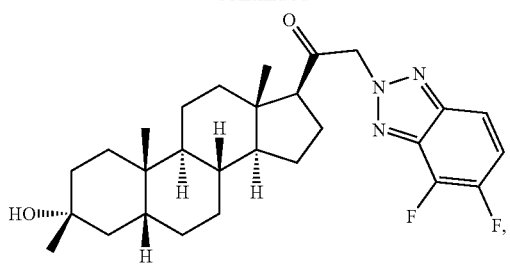
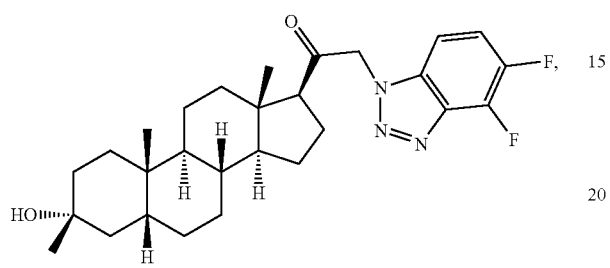
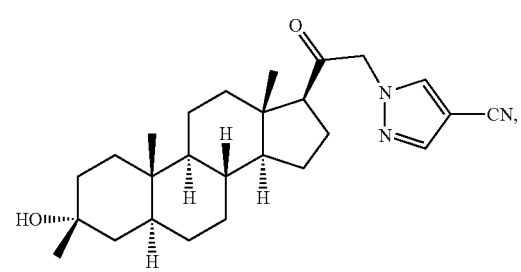
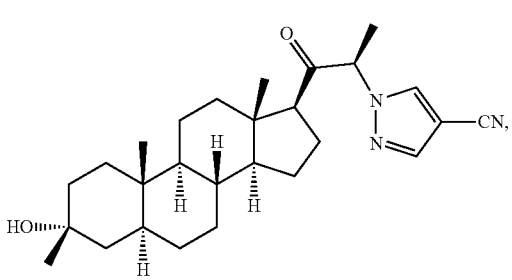
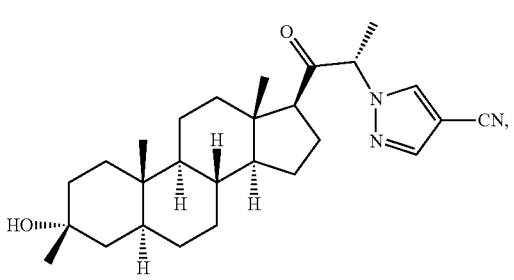
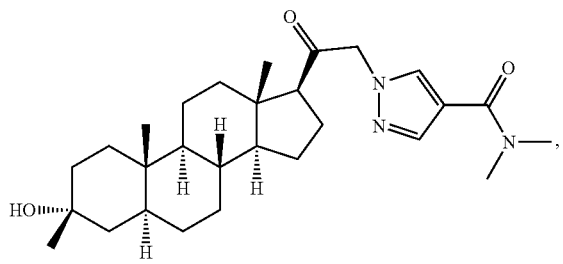
26
-continued
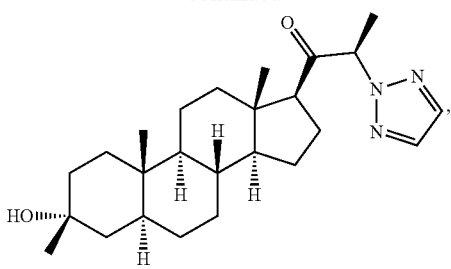
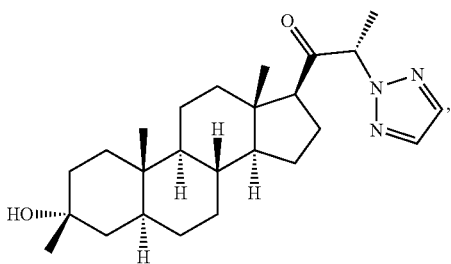
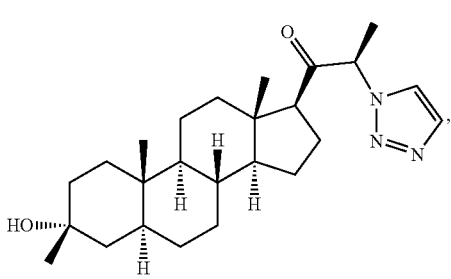
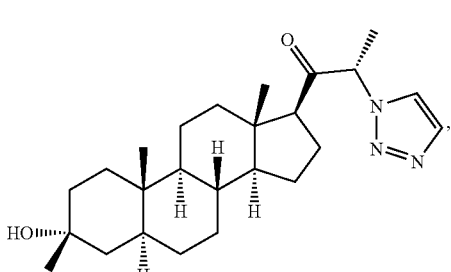
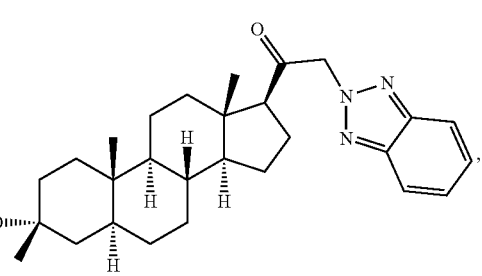
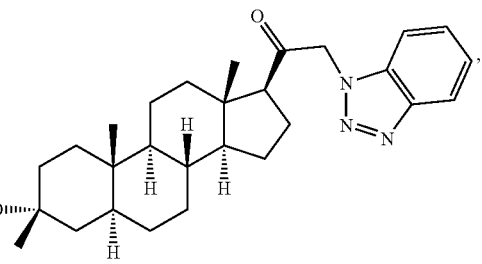

-continued
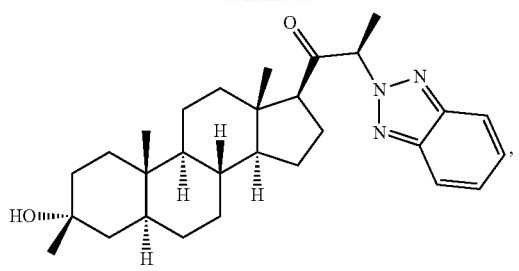
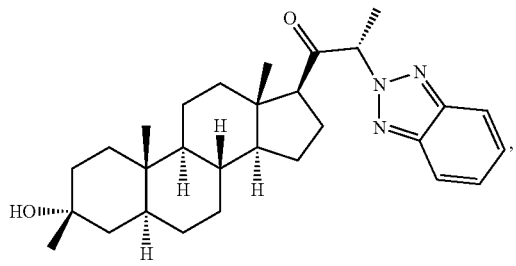
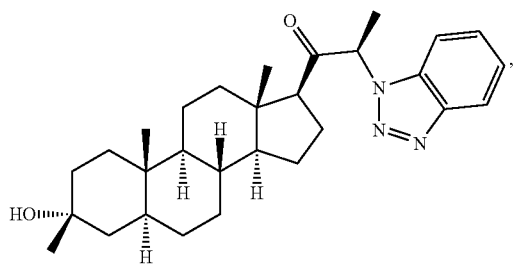
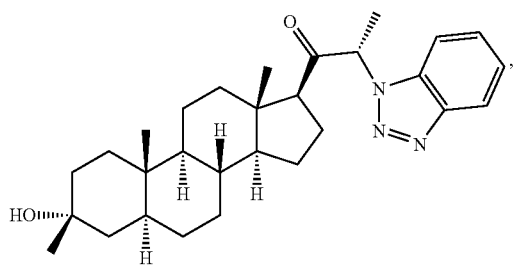
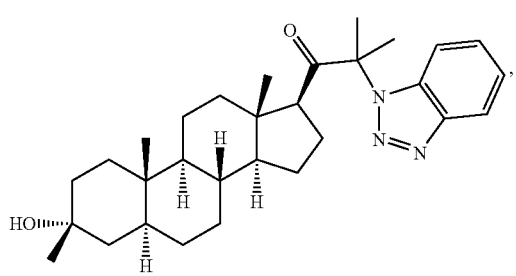
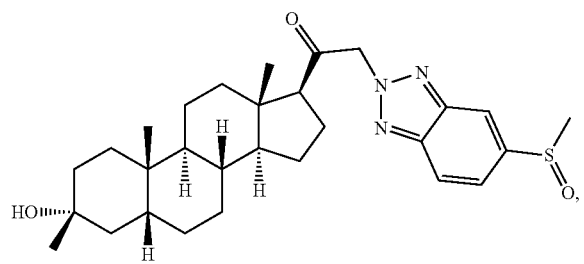
-continued
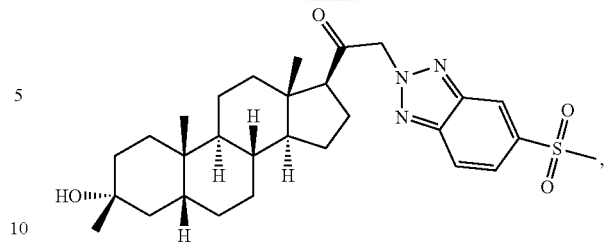
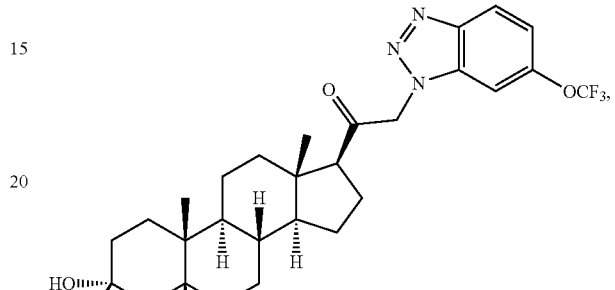
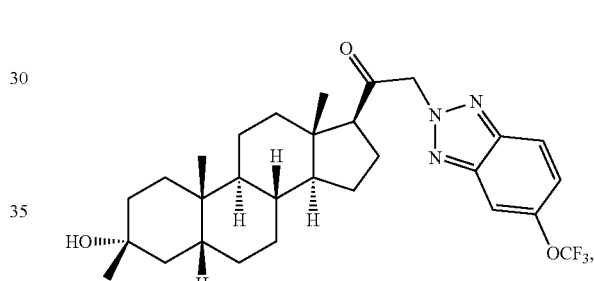
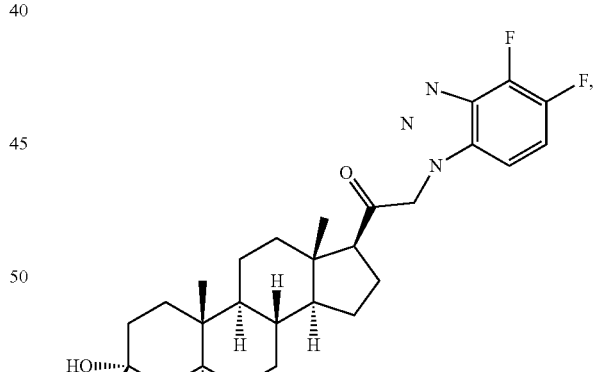
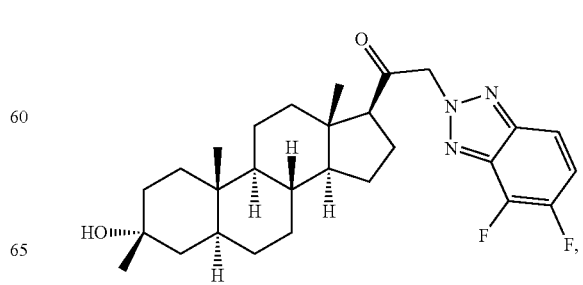

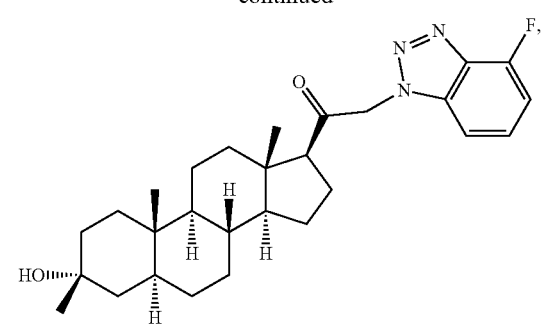
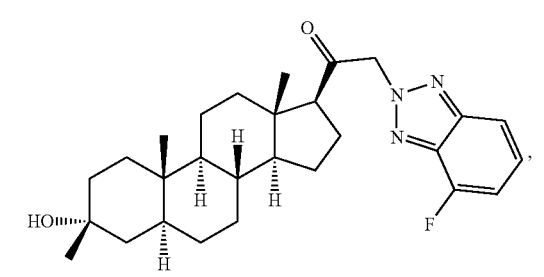
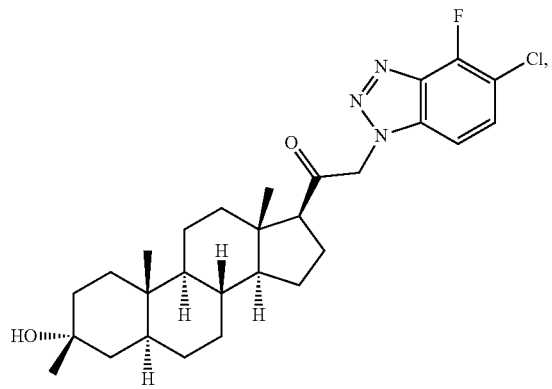
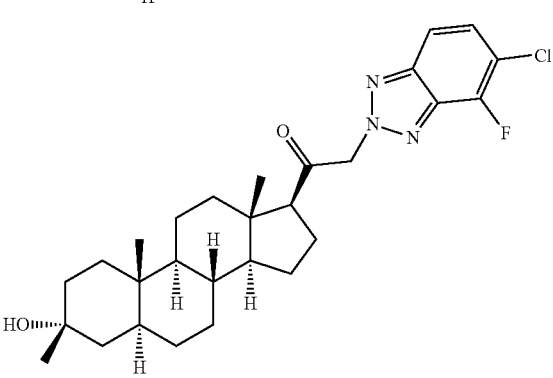
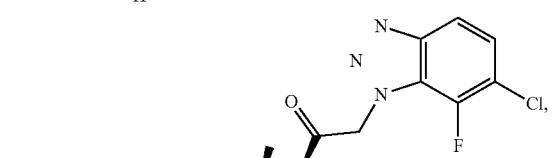
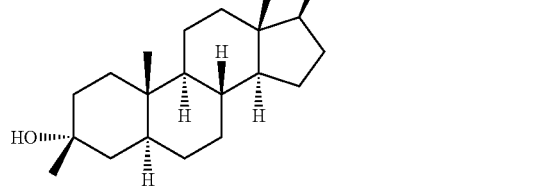
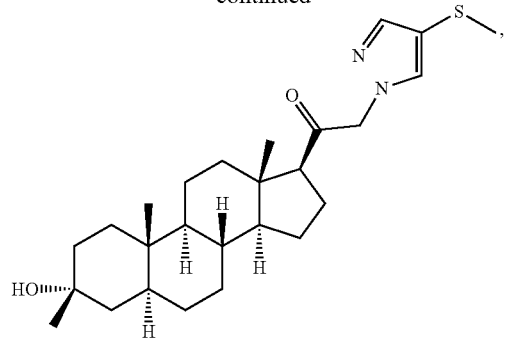
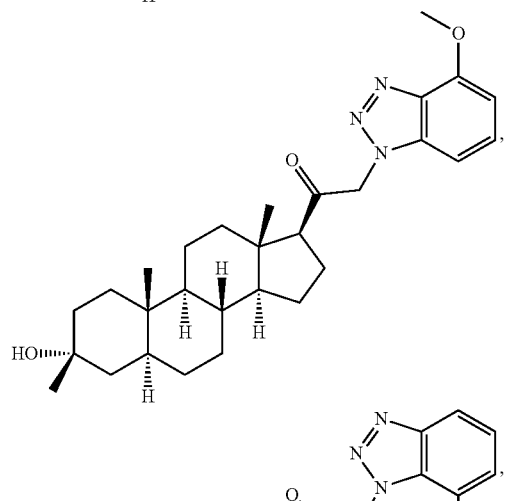
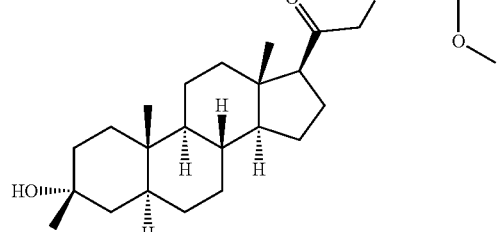
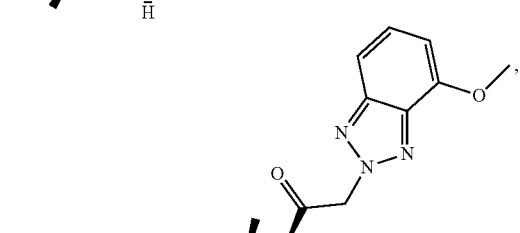
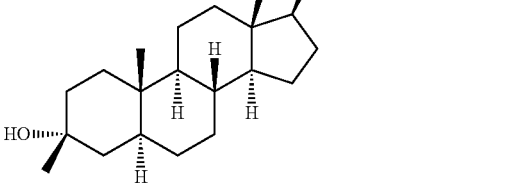
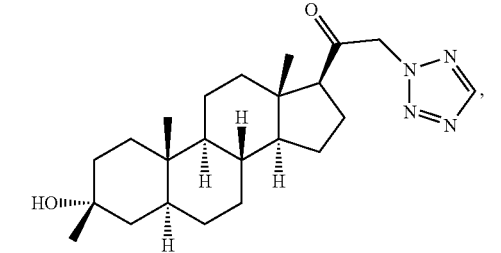

31
-continued
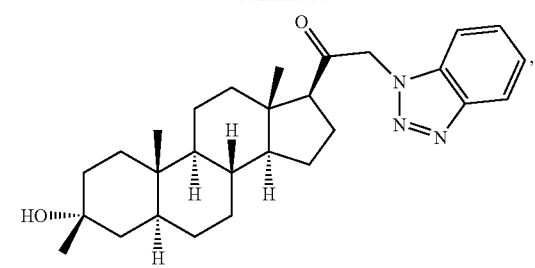
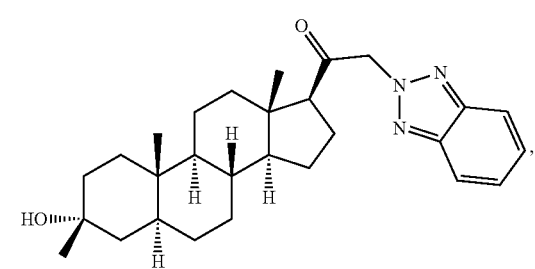
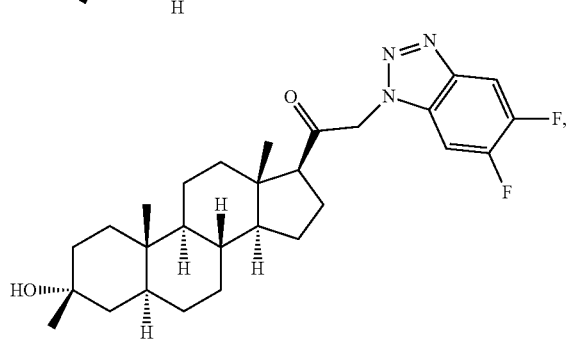
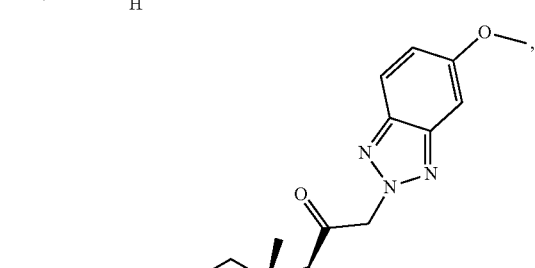
32
-continued
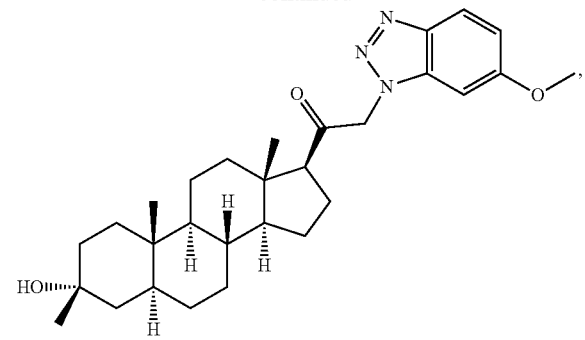
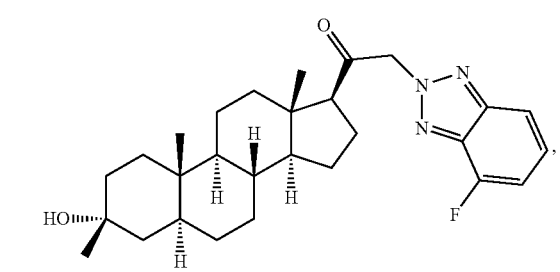
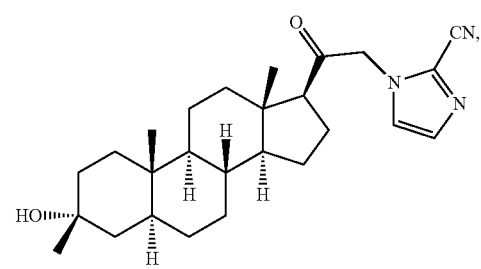
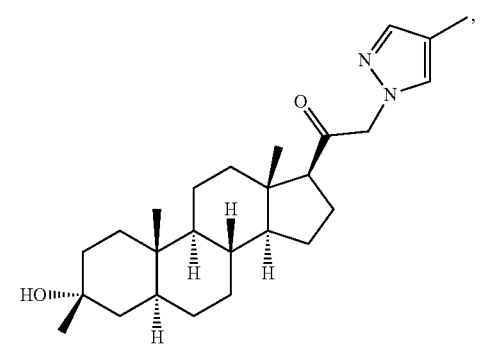

-continued
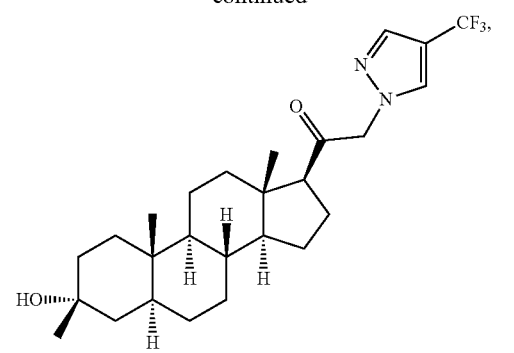
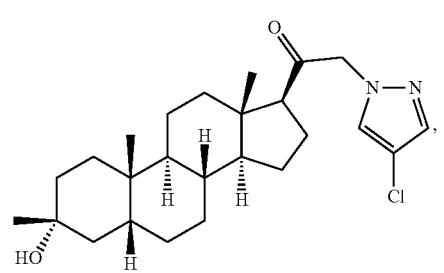
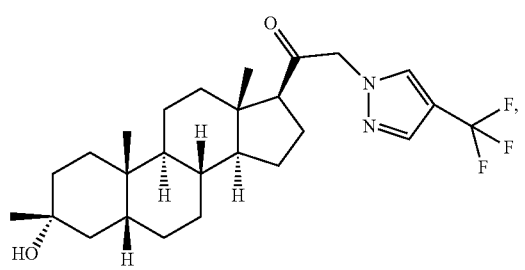
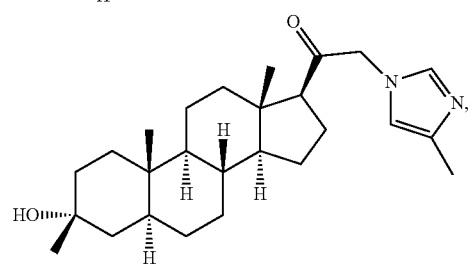
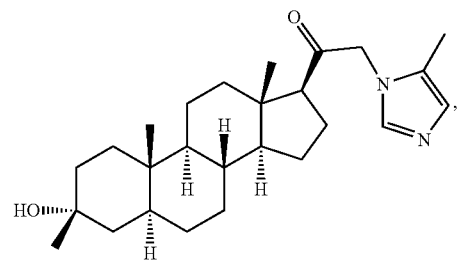
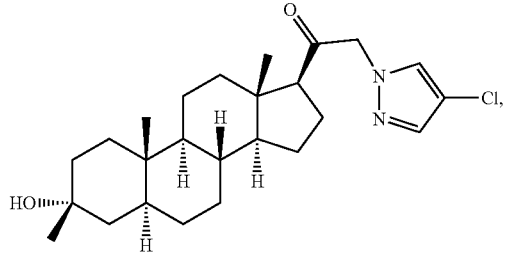
-continued
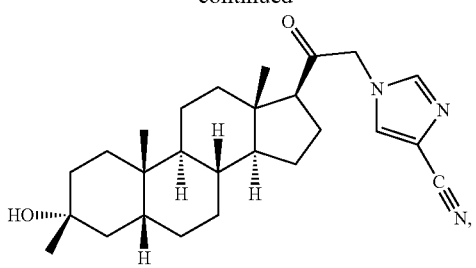
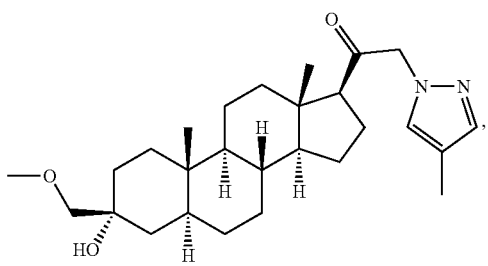
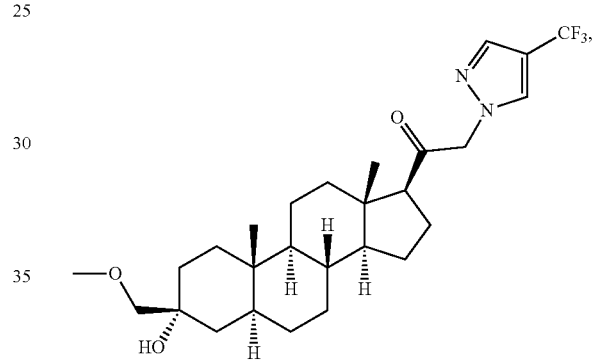
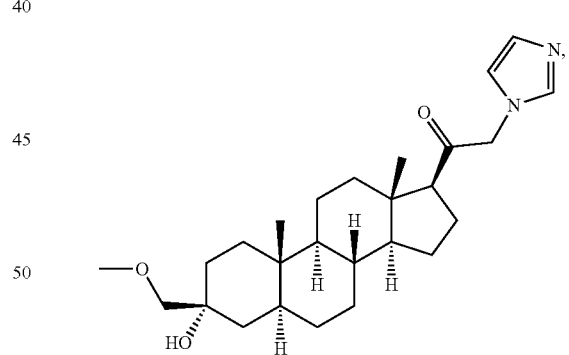
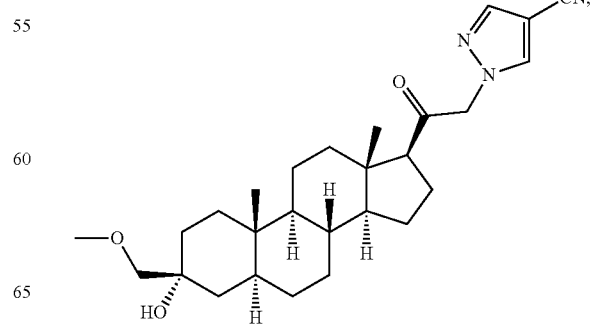

35
-continued
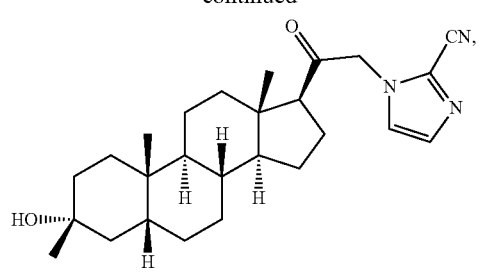
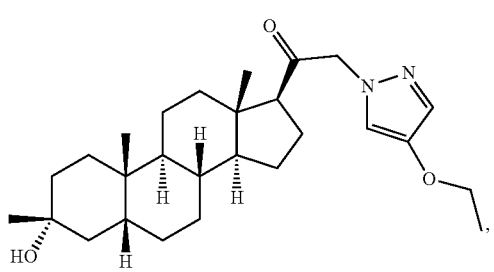
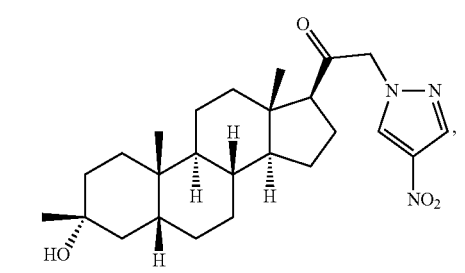
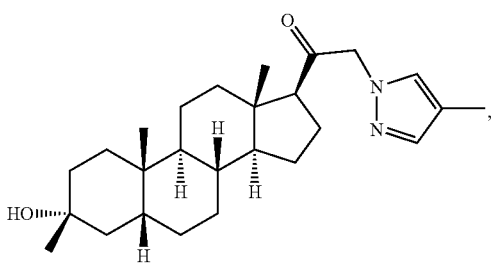
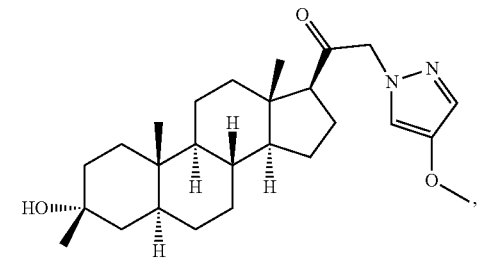
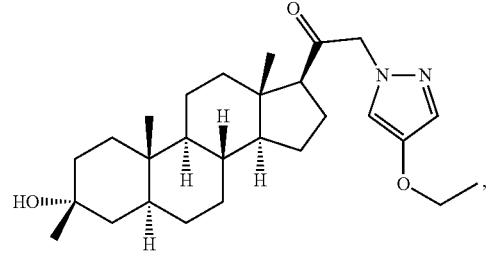
36
-continued
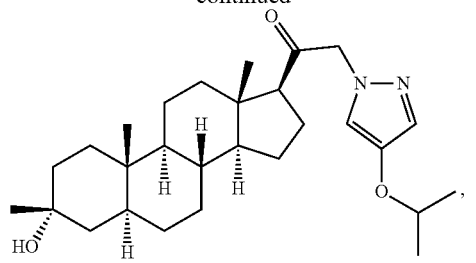
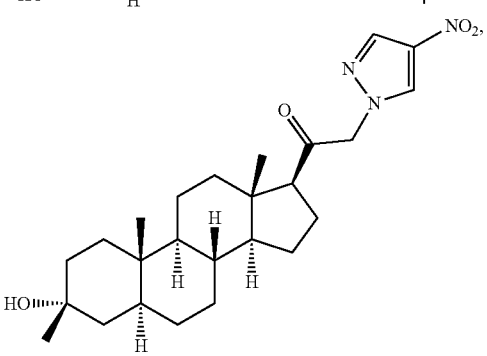
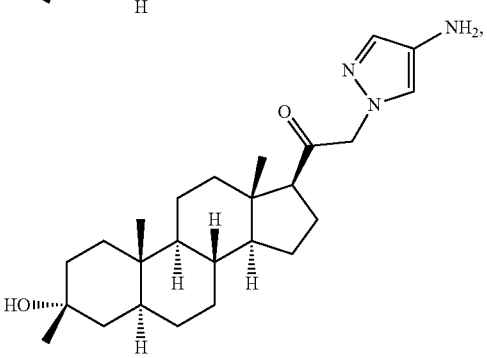
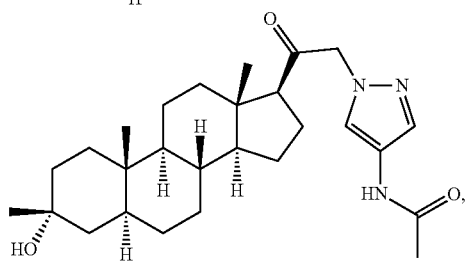
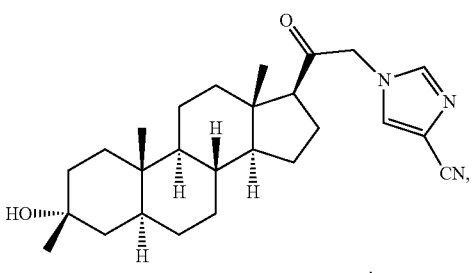
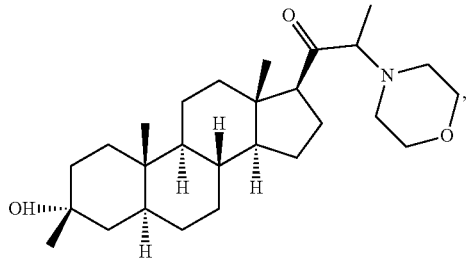

37
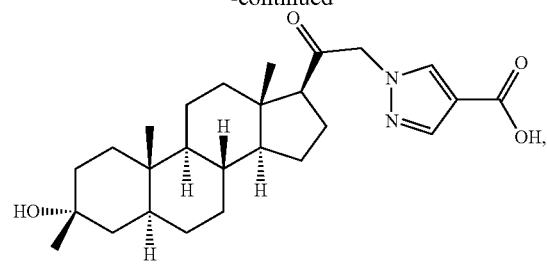
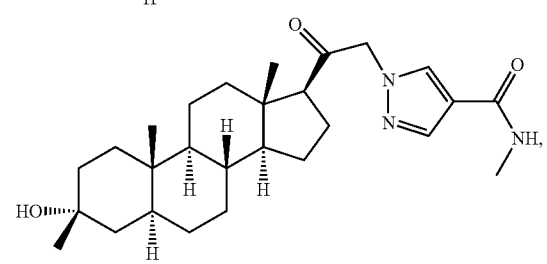
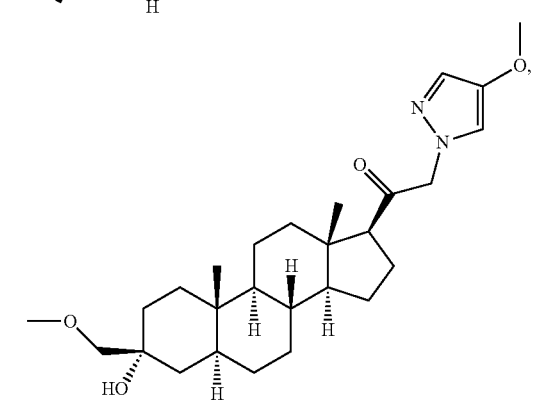
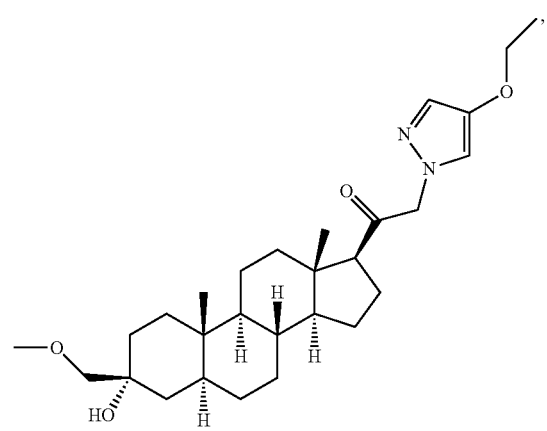
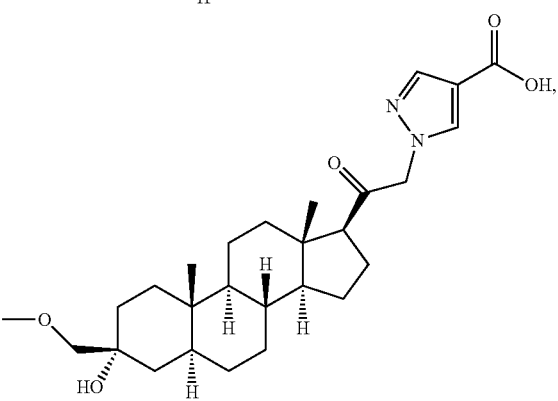
38
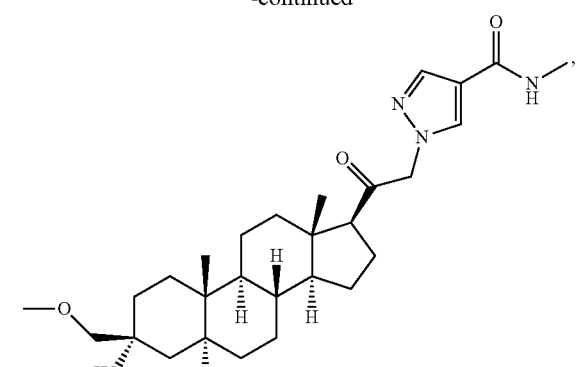
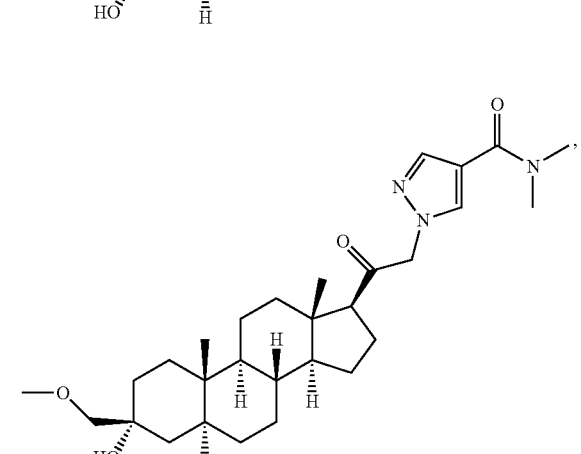
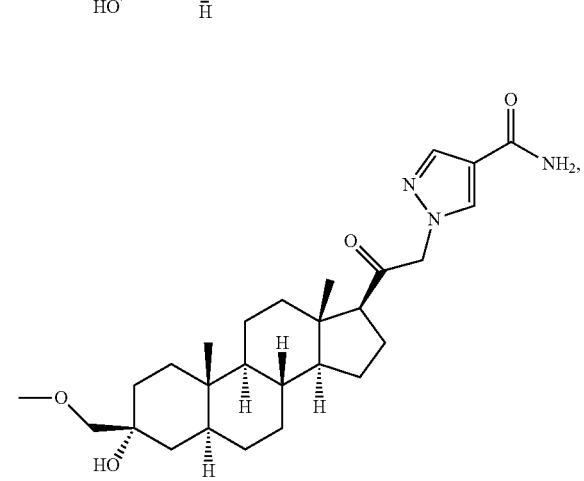
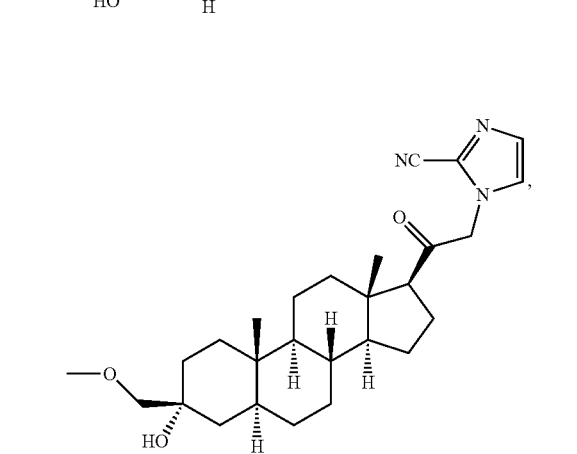

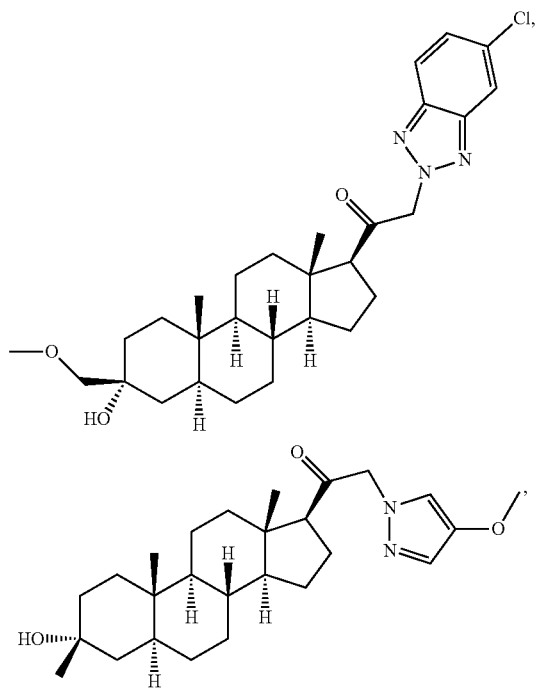
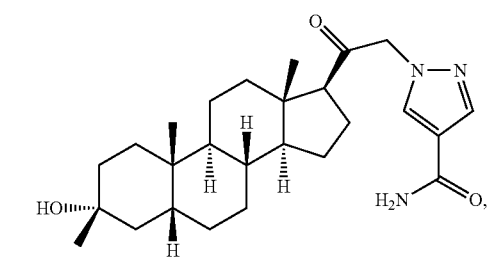
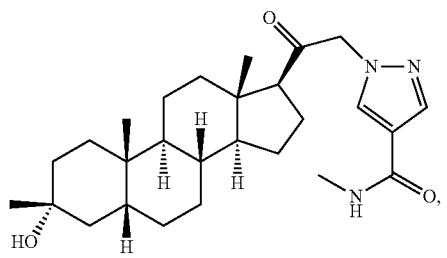
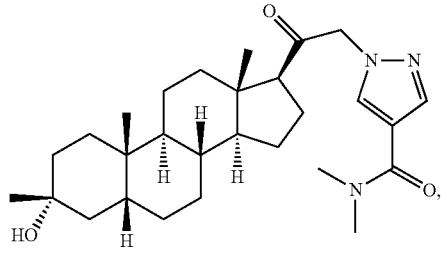
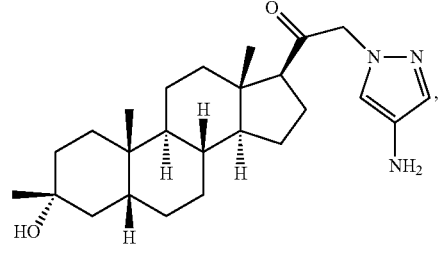
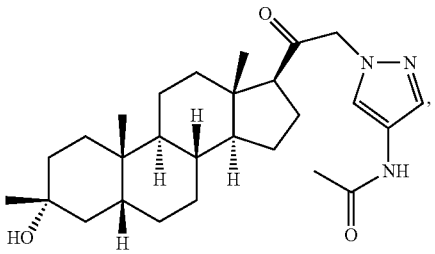
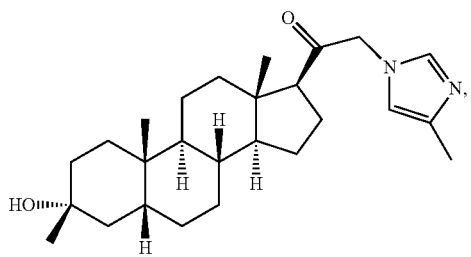
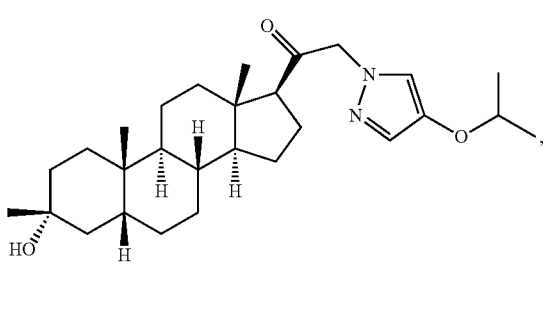
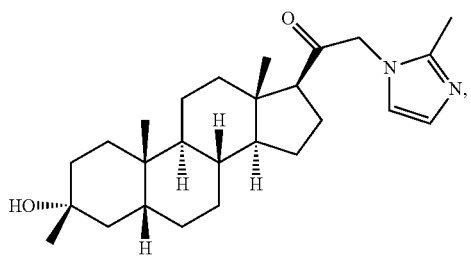
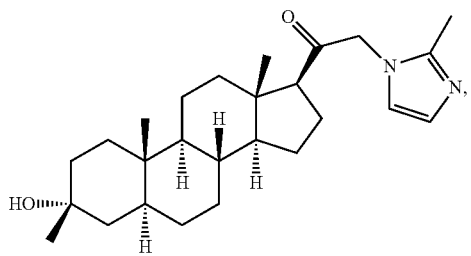
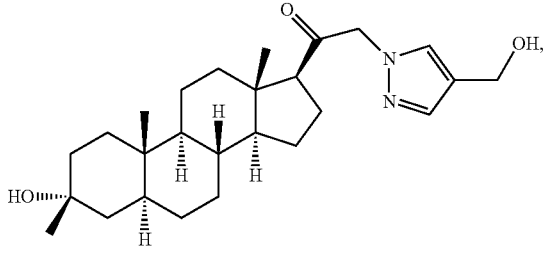

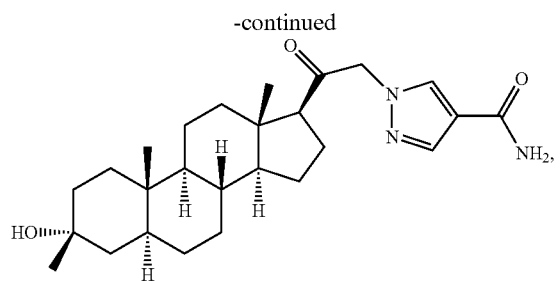
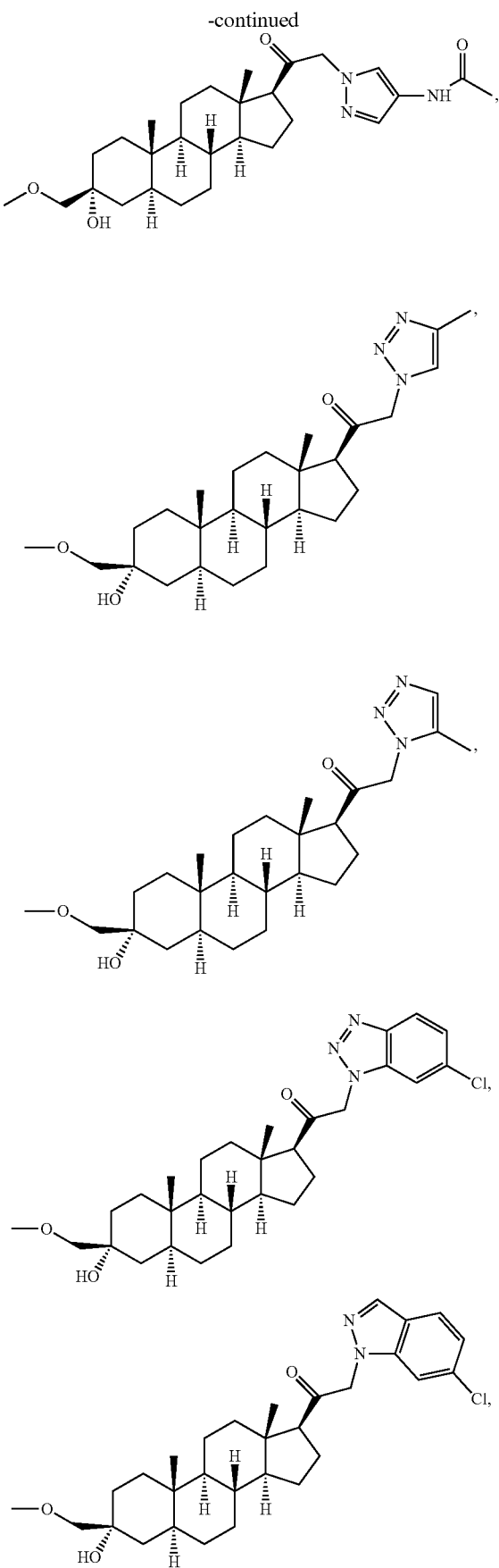

43
-continued
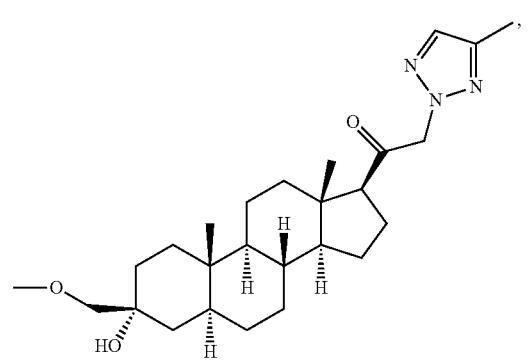
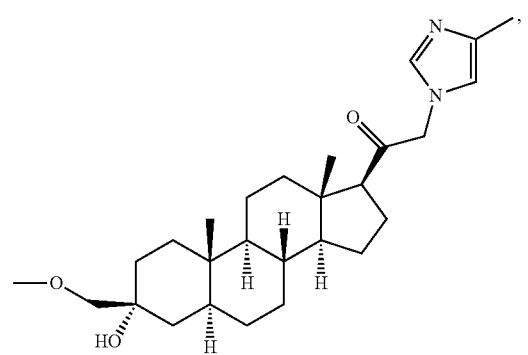
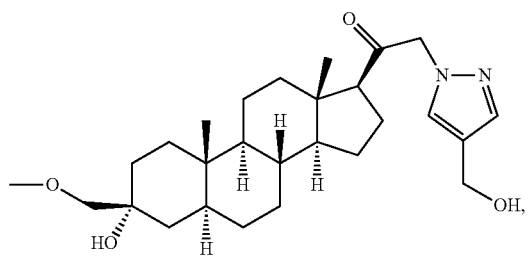
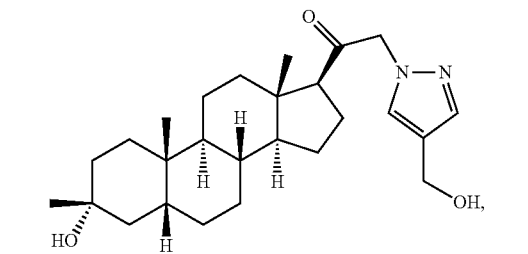
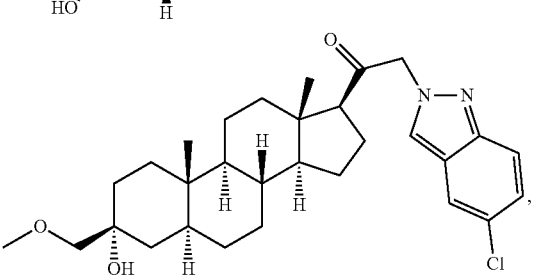
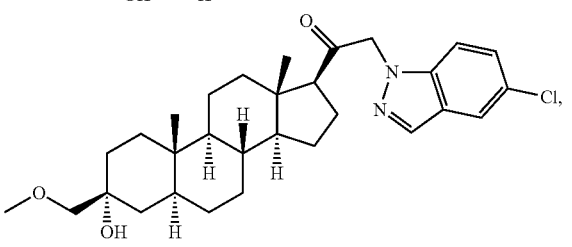
44
-continued
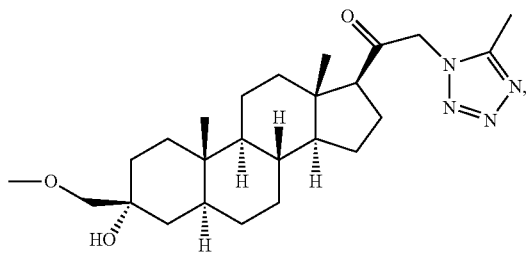
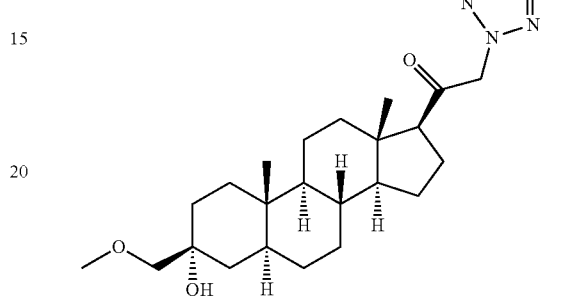
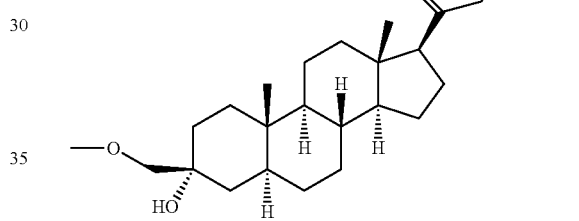
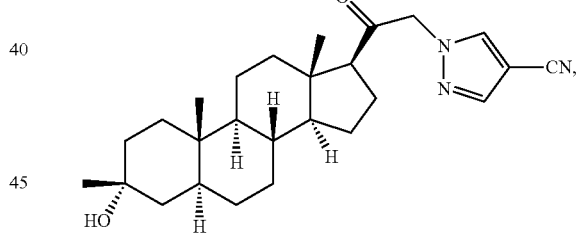
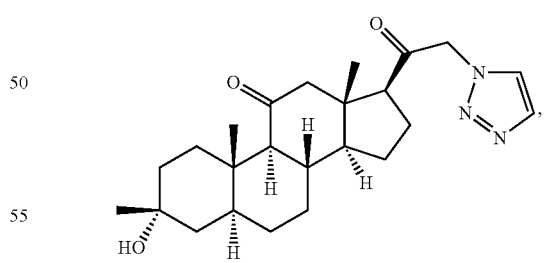
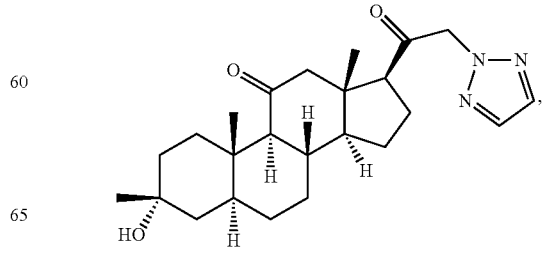

45
-continued
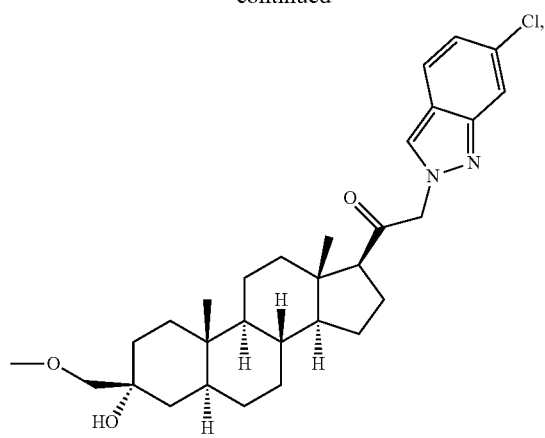
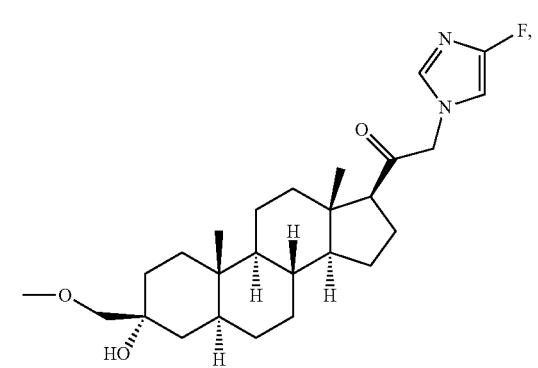
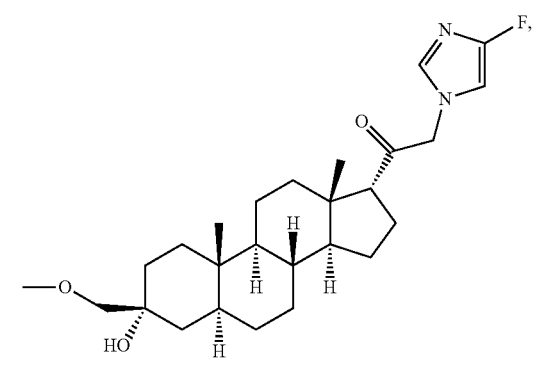
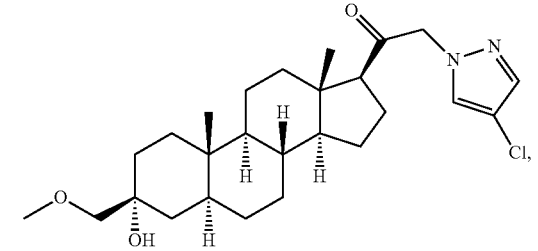
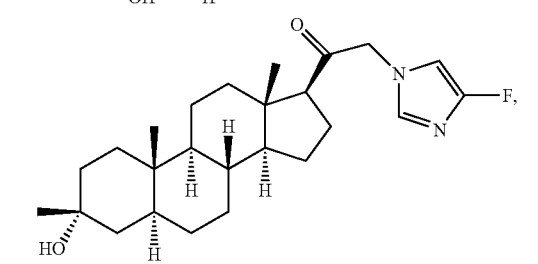
46
-continued
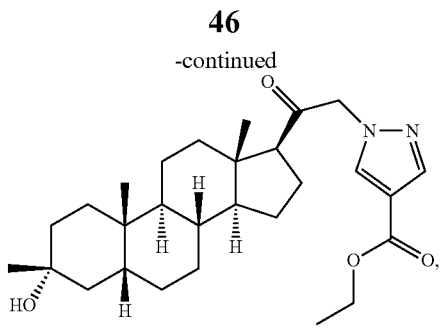
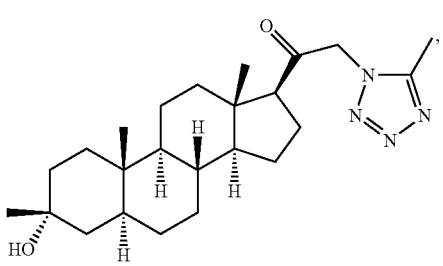
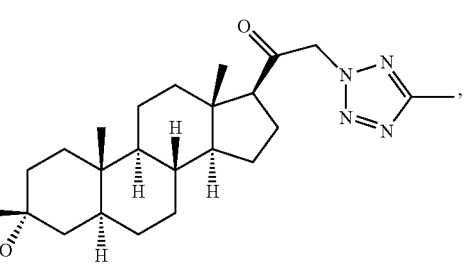
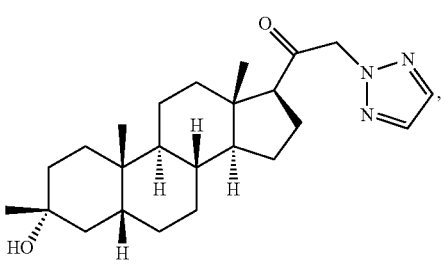
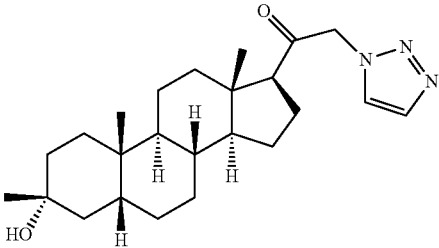
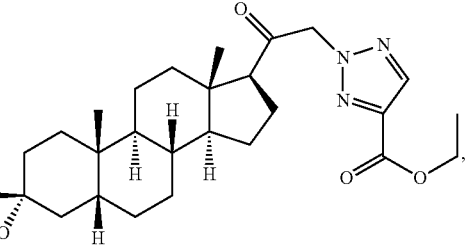

47
-continued
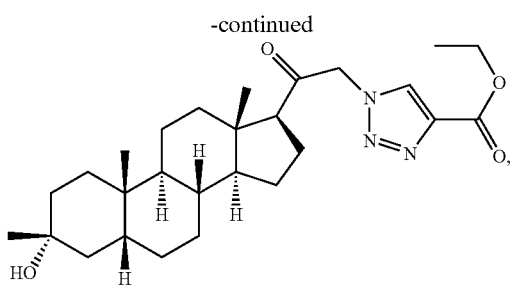
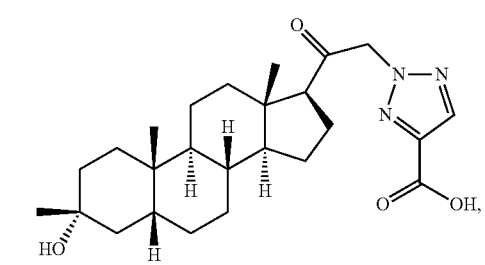
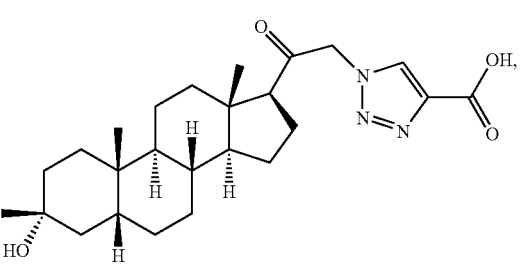
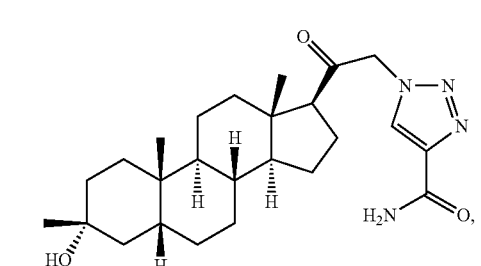
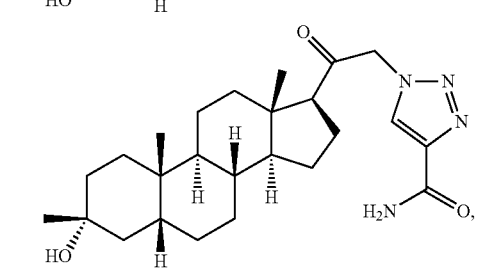
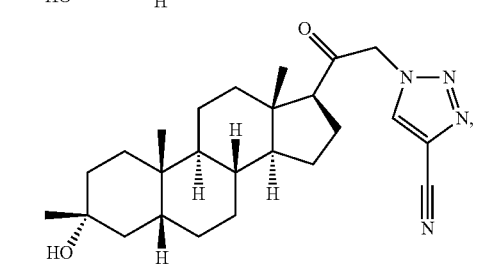
48
-continued
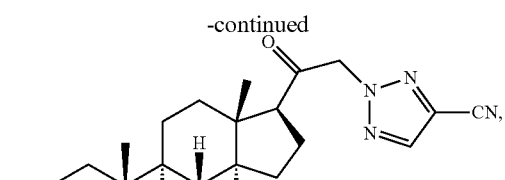
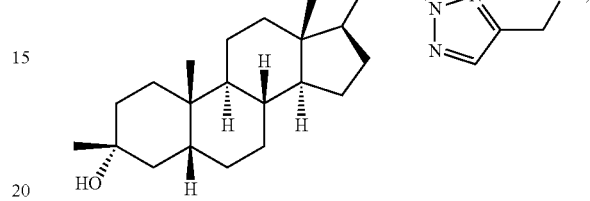
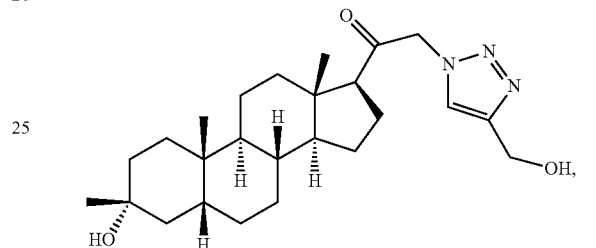
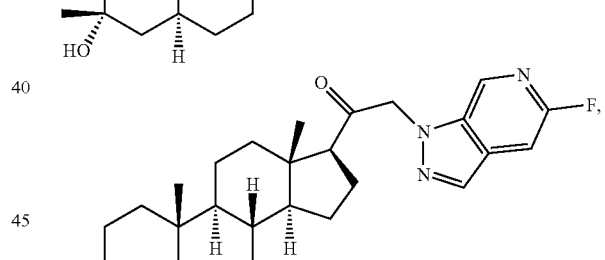
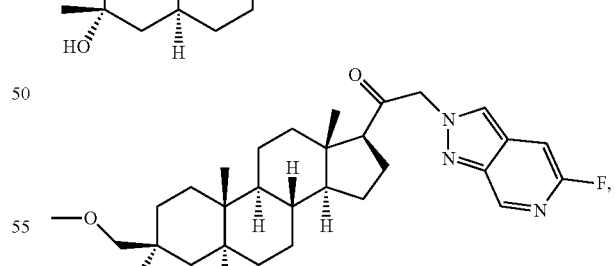
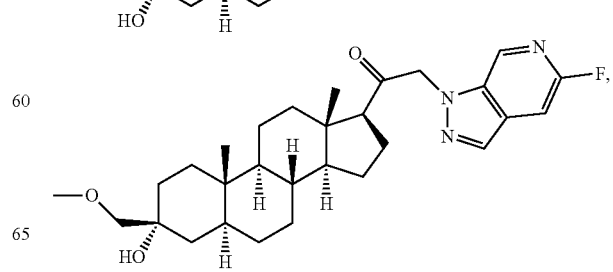

49
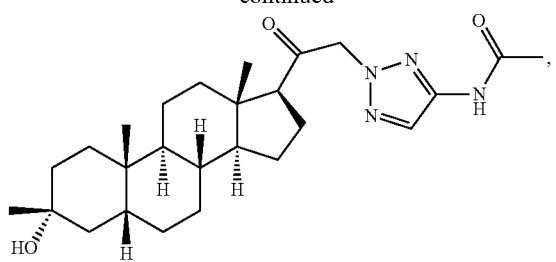
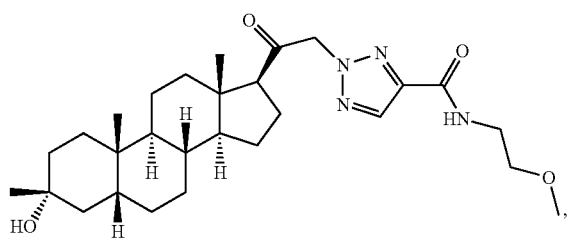
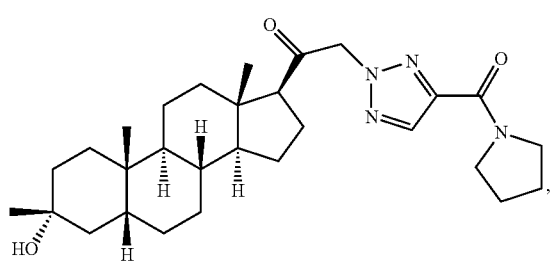
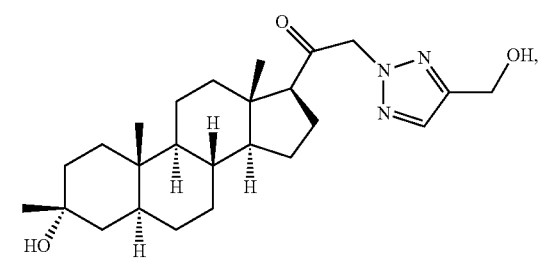
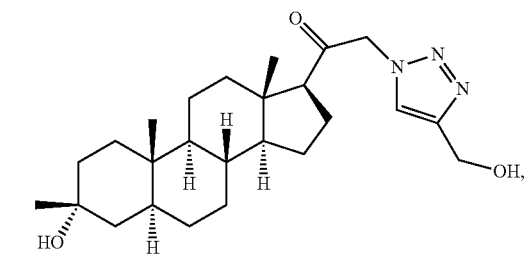
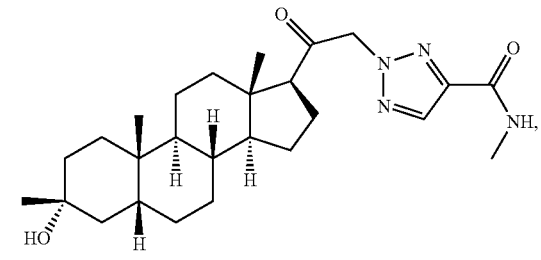
50
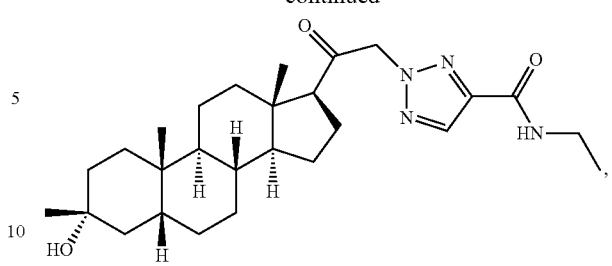
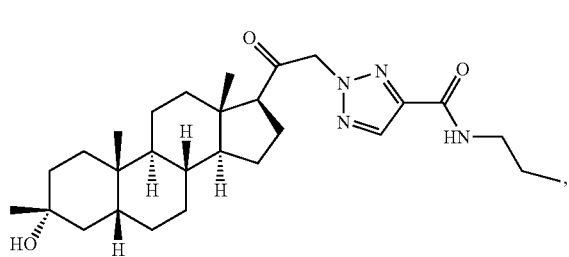
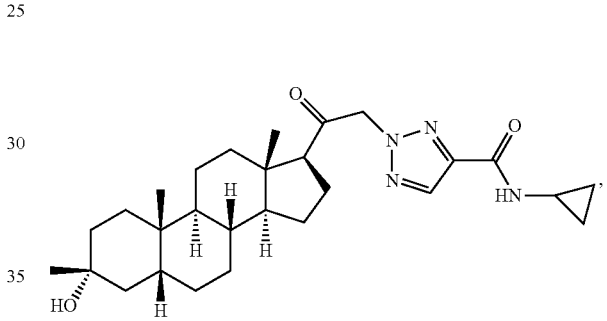
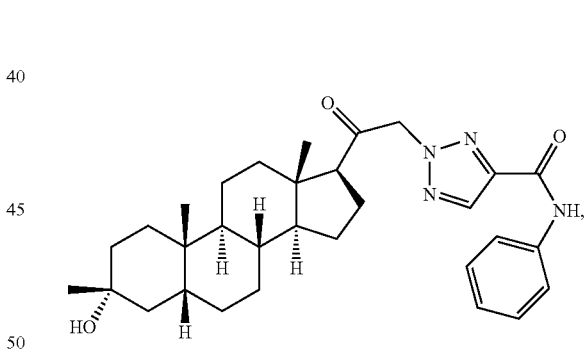
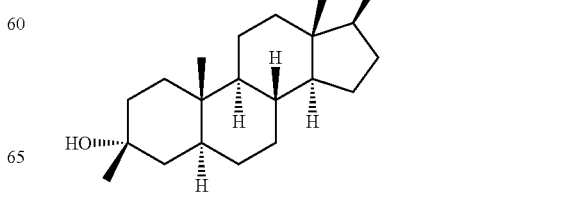

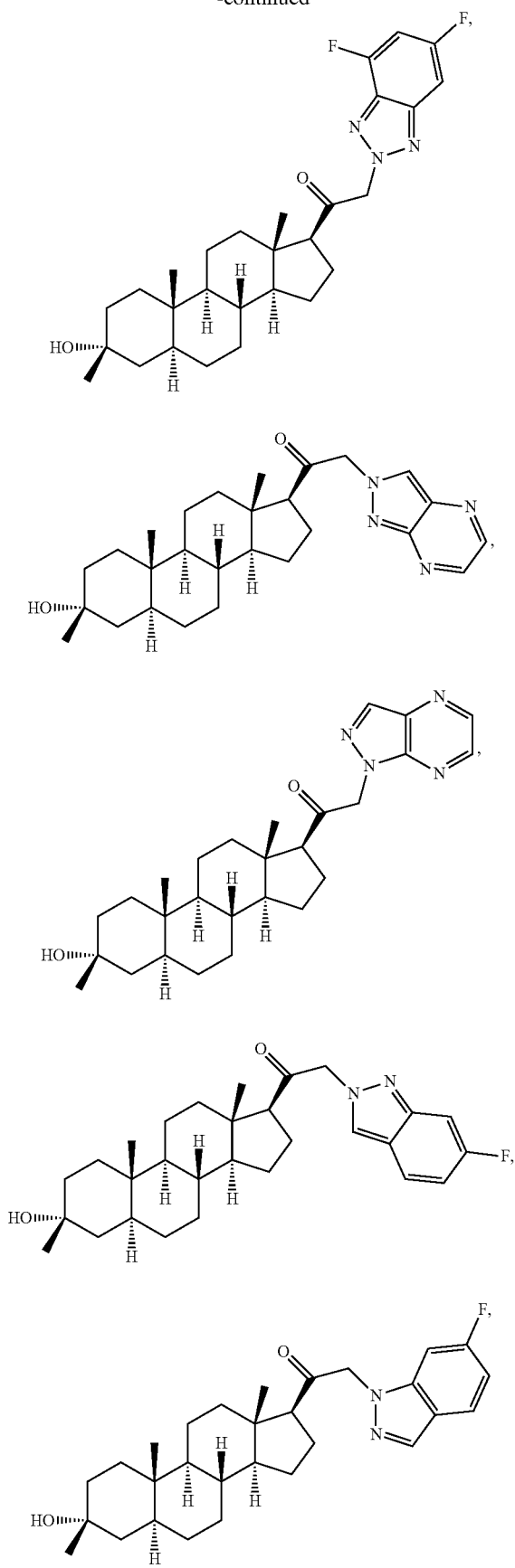
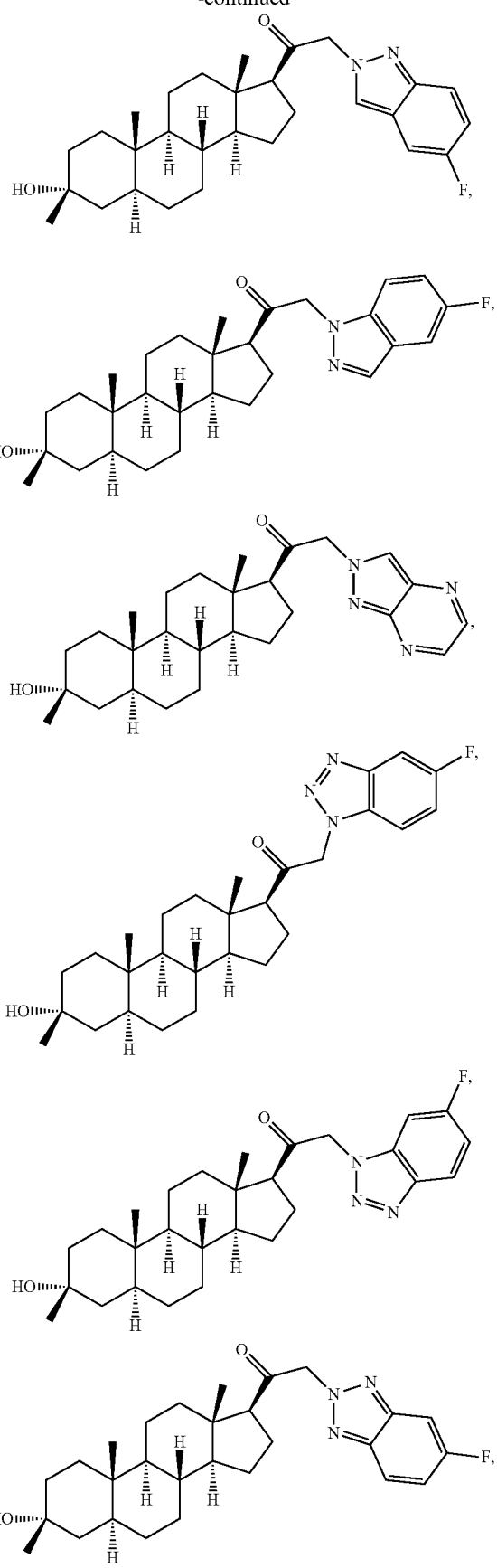

53
-continued
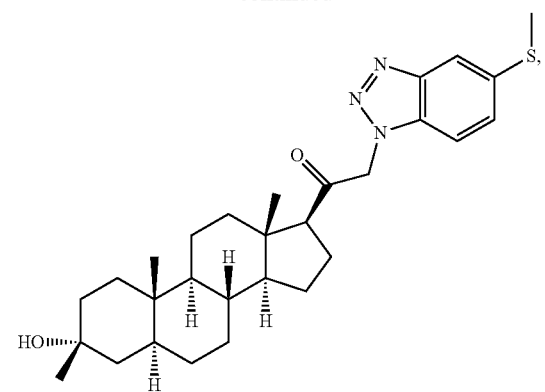
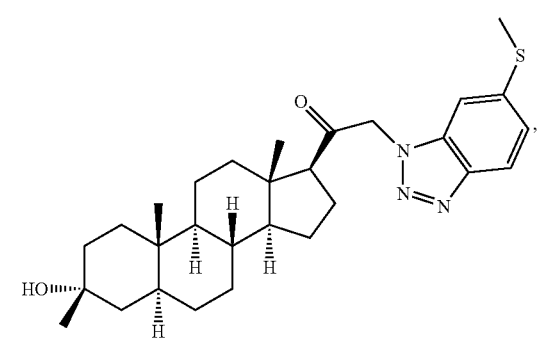
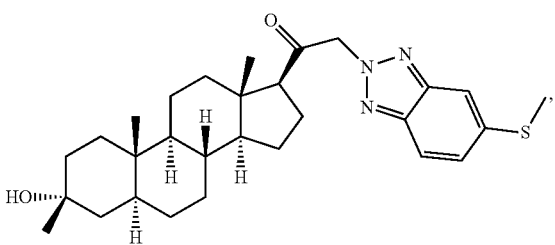

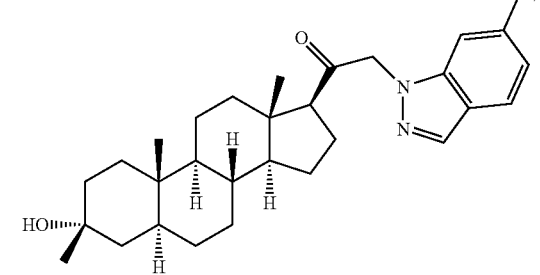
54
-continued
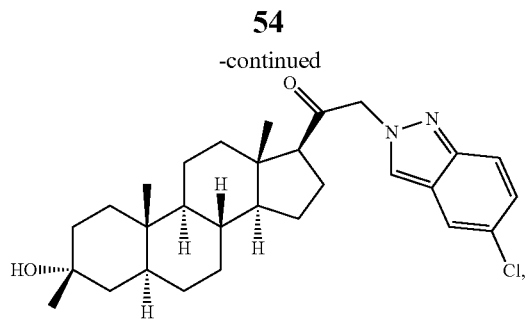
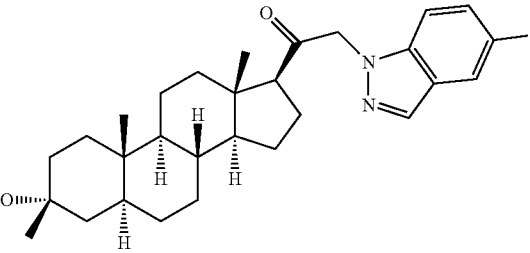
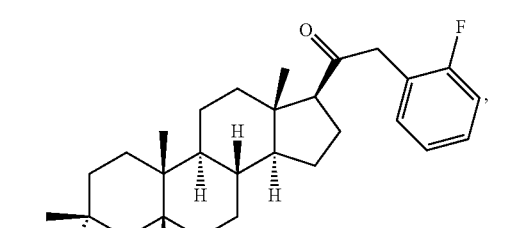
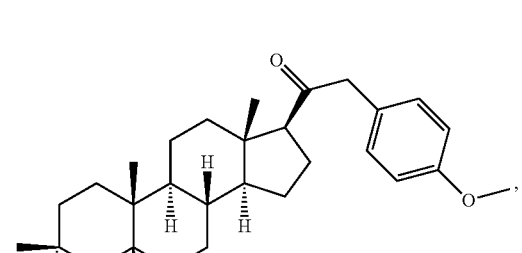
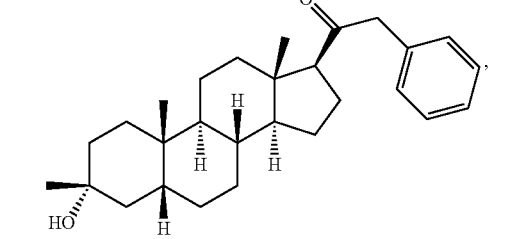
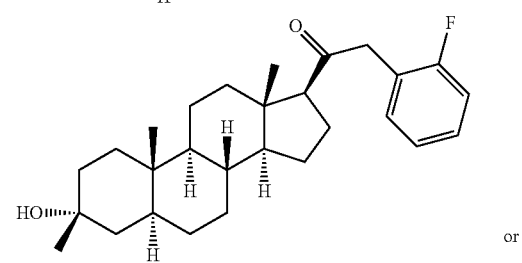
or

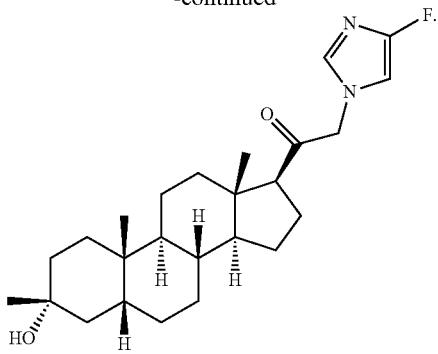

In one aspect, provided is a pharmaceutical composition comprising a compound of the Formula (I) and a pharmaceutically acceptable excipient.

In one aspect, provided is a method of inducing sedation and/or anesthesia in a subject, comprising administering to the subject an effective amount of a compound of the Formula (I), or a pharmaceutically acceptable salt thereof.

In one aspect, provided is a method of administering an effective amount of a compound, a pharmaceutically acceptable salt thereof, or pharmaceutical composition of a compound of Formula (I), to a subject in need thereof, wherein the subject experiences sedation and/or anesthesia within two hours of administration.

In an embodiment, the subject experiences sedation and/or anesthesia within one hour of administration.

In an embodiment, the subject experiences sedation and/or anesthesia instantaneously.

In an embodiment, the compound is administered by intravenous administration.

In an embodiment, the compound is administered chronically.

In an embodiment, the subject is a mammal. In an embodiment, the subject is a human.

In an embodiment, the compound is administered in combination with another therapeutic agent.

In one aspect, provided is a method for treating seizure in a subject, comprising administering to the subject an effective amount of a compound of the Formula (I) or a pharmaceutically acceptable salt thereof.

In one aspect, provided is a method for treating epilepsy or status or status epilepticus in a subject, the method comprising administering to the subject an effective amount of a compound of the Formula (I) or a pharmaceutically acceptable salt thereof. In an embodiment, the status epilepticus is convulsive status epilepticus (e.g., early status epilepticus, established status epilepticus, refractory status epilepticus, super-refractory status epilepticus) or non-convulsive status epilepticus, (e.g., generalized status epilepticus, complex partial status epilepticus).

In one aspect, provided is a method for treating disorders related to GABA function in a subject in need thereof, the method comprising administering to the subject a therapeutically effective amount of a compound, a pharmaceutically acceptable salt thereof, or pharmaceutical composition of one of a compound of the Formula (I).

In one aspect, provided is a method for treating a CNS-related disorder in a subject in need thereof, comprising administering to the subject an effective amount of a compound of the Formula (I) or a pharmaceutically acceptable salt thereof.

In an embodiment, the CNS-related disorder is a sleep disorder, a mood disorder such as depression, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus.

In an embodiment, the subject is a subject with Rett syndrome, Fragile X syndrome, or Angelman syndrome. In an embodiment, the CNS-related disorder is a sleep disorder, an eating disorder, a mood disorder such as depression, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus. In an embodiment, the CNS-related disorder is depression (e.g., post-partum depression). In an embodiment, the CNS-related disorder is tremor (e.g., essential tremor). In an embodiment, the CNS-related disorder is an eating disorder (e.g., anorexia nervosa, bulimia nervosa, binge-eating disorder, cachexia).

In an embodiment, the compound is administered orally. In an embodiment, the compound is administered intramuscularly.

In one aspect, provided is a kit comprising a solid composition comprising a compound of Formula (I) and a sterile diluent.

The present invention also provides pharmaceutical compositions comprising a compound of the present invention and methods of use and treatment, e.g., such as for inducing sedation and/or anesthesia, for treating a CNS-related disorder.

Steroids of Formula (I), sub-genera thereof, and pharmaceutically acceptable salts thereof are collectively referred to herein as "compounds of the present invention."

In another aspect, provided is a pharmaceutical composition comprising a compound of the present invention and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, the CNS-related disorder is selected from the group consisting of a sleep disorder, a mood disorder such as depression, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically. In certain embodiments, the compound is administered continuously, e.g., by continuous intravenous infusion.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC)), supercritical fluid chromatography (SFC), and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; and the like.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 8 carbon atoms ("$C_{1-8}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—CH$_3$), Et (—CH$_2$CH$_3$), iPr (—CH(CH$_3$)$_2$), nPr (—CH$_2$CH$_2$CH$_3$), n-Bu (—CH$_2$CH$_2$CH$_2$CH$_3$), or i-Bu (—CH$_2$CH(CH$_3$)$_2$).

"Alkenyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 8 carbon atoms ("C$_{2-8}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted C$_{2-10}$ alkenyl. In certain embodiments, the alkenyl group is substituted C$_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 8 carbon atoms ("C$_{2-8}$ alkynyl"). In some embodiments, an alkynyl group has 2 to 6 carbon atoms ("C$_{2-6}$ alkynyl").

In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted C$_{2-10}$ alkynyl. In certain embodiments, the alkynyl group is substituted C$_{2-10}$ alkynyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Aryl groups include, but are not limited to, phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

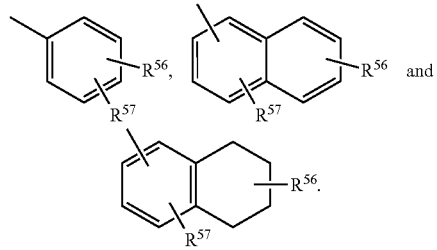

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$ NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, Soalkyl, SO$_2$alkyl, Saryl, Soaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$ haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

Other representative aryl groups having a fused heterocyclyl group include the following:

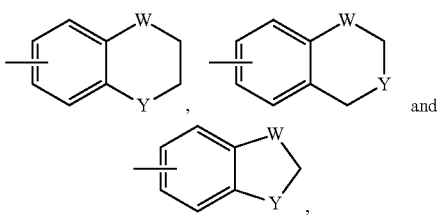

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

"Haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

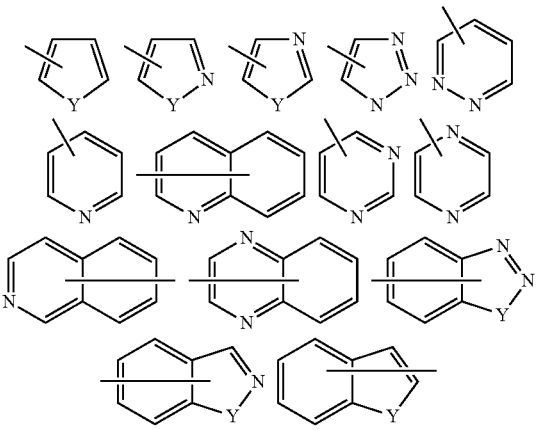

wherein each Y is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

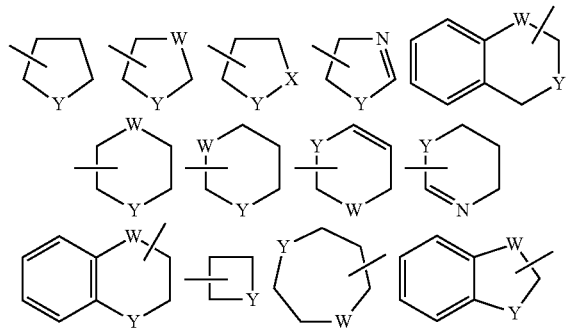

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Acyl" refers to a radical —C(O)$R^{20}$, where $R^{20}$ is hydrogen, substituted or unsubstitued alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstitued heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Acylamino" refers to a radical —$NR^{22}C(O)R^{23}$, where each instance of $R^{22}$ and $R^{23}$ is independently hydrogen, substituted or unsubstitued alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstitued heteroaryl, as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —$NR^{24}C(O)$—$C_1$-$C_8$ alkyl, —$NR^{24}C(O)$—(CH$_2$)$_t$($C_6$-$C_{10}$ aryl), —$NR^{24}C(O)$—(CH$_2$)$_t$(5-10 membered heteroaryl), —$NR^{24}C(O)$—(CH$_2$)$_t$($C_3$-$C_{10}$ cycloalkyl), and —$NR^{24}C(O)$—(CH$_2$)$_t$(4-10 membered heterocyclyl), wherein t is an integer from 0 to 4, and each $R^{24}$ independently represents hydrogen or $C_1$-$C_8$ alkyl. In certain embodiments, $R^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is H, $C_1$-$C_8$ alkyl, substituted with halo or hydroxy; $C_3$-$C_{10}$ cycloalkyl, 4-10-membered heterocyclyl, $C_6$-$C_{10}$ aryl, arylalkyl, 5-10-membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided at least one of $R^{25}$ and $R^{26}$ is other than H.

"Acyloxy" refers to a radical —OC(O)$R^{27}$, where $R^{27}$ is hydrogen, substituted or unsubstitued alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstitued heteroaryl, as defined herein. Representative examples include, but are not limited to, formyl, acetyl, cyclohexylcarbonyl, cyclohexylmethylcarbonyl, benzoyl, and benzylcarbonyl. In certain embodiments, $R^{28}$ is $C_1$-$C_8$ alkyl, substituted with halo or hydroxy; $C_3$-$C_{10}$ cycloalkyl, 4-10-membered heterocyclyl, $C_6$-$C_{10}$ aryl, arylalkyl, 5-10-membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —OR$^{29}$ where R$^{29}$ is substituted or unsubstituted alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstitued heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxy, nitro, thioalkoxy, thioaryloxy, thiol, alkyl-S(O)—, aryl-S(O)—, alkyl-S(O)$_2$— and aryl-S(O)$_2$—. Exemplary "substituted alkoxy" groups include, but are not limited to, —O—(CH$_2$)$_t$($C_6$-$C_{10}$ aryl), —O—(CH$_2$)$_t$(5-10 membered heteroaryl), —O—(CH$_2$)$_t$ ($C_3$-$C_{10}$ cycloalkyl), and —O—$(CH_2)_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —$OCF_3$, —$OCH_2CF_3$, —$OCH_2Ph$, —$OCH_2$-cyclopropyl, —$OCH_2CH_2OH$, and —$OCH_2CH_2Nme_2$.

"Amino" refers to the radical —$NH_2$.

"Substituted amino" refers to an amino group of the formula —$N(R^{38})_2$ wherein $R^{38}$ is hydrogen, substituted or unsubstituted alkyl, substituted or unsubstitued alkenyl, substituted or unsubstitued alkynyl, substituted or unsubstitued carbocyclyl, substituted or unsubstituted heterocyclyl, substituted or unsubstituted aryl, substituted or unsubstitued heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)_t(C_6$-$C_{10}$ aryl), —$(CH_2)_t$(5-10 membered heteroaryl), —$(CH_2)_t$($C_3$-$C_{10}$ cycloalkyl), or —$(CH_2)_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t(C_6$-$C_{10}$ aryl), —$NR^{39}$—$(CH_2)_t$(5-10 membered heteroaryl), —$NR^{39}$—$(CH_2)_t$($C_3$-$C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents hydrogen or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —C(O)$NH_2$.

"Substituted carbamoyl" or "substituted amido" refers to the radical —$C(O)N(R^{62})_2$ wherein each $R^{62}$ is independently hydrogen, substituted or unsubstituted alkyl, substituted or unsubstitued alkenyl, substituted or unsubstitued alkynyl, substituted or unsubstitued carbocyclyl, substituted or unsubstituted heterocyclyl, substituted or unsubstituted aryl, substituted or unsubstitued heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, and 5-10 membered heteroaryl; or $C_1$-$C_8$ alkyl substituted with halo or hydroxy; or $C_3$-$C_{10}$ cycloalkyl, 4-10 membered heterocyclyl, $C_6$-$C_{10}$ aryl, or 5-10 membered heteroaryl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

"Carboxy" refers to the radical —C(O)OH.

"Cyano" refers to the radical —CN.

"Hydroxy" refers to the radical —OH.

"Nitro" refers to the radical —$NO_2$.

"Ethenyl" refers to substituted or unsubstituted —(C=C)—. "Ethylene" refers to substituted or unsubstituted —(C—C)—. "Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3$$^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$Osi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —Osi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —Osi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14-membered heteroaryl, or two R$^{cc}$ groups attached to a nitrogen atom are joined to form a 3-14-membered heterocyclyl or 5-14-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is an amino protecting group (also referred to herein as a nitrogen protecting group). Amino protecting groups include, but are not limited to, —OH, —OR$^{aa}$, —N(R$^{cc}$)$_2$, —C(=O)R$^{aa}$, —C(=O)OR$^{aa}$, —C(=O)N(R$^{cc}$)$_2$, —S(=O)$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{2-10}$ alkenyl, C$_{2-10}$ alkynyl, C$_{3-10}$ carbocyclyl, 3-14-membered heterocyclyl, C$_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary amino protecting groups include, but are not limited to amide groups (e.g., —C(=O)R$^{aa}$), which include, but are not limited to, formamide and acetamide; carbamate groups (e.g., —C(=O)OR$^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2$R$^{aa}$), which include, but are not limited to, p-toluenesulfonamide (Ts), methanesulfonamide (Ms), and N-[2-(trimethylsilyl)ethoxy]methylamine (SEM).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

Other Definitions

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O, and $^{13}$N, and would be useful in Positron Emission Topography (PET) studies for examining substrate receptor occupancy. All isotopic variants of the compounds provided herein, radioactive or not, are intended to be encompassed within the scope of the invention.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides C21-substituted neuroactive steroids designed, for example, to act as GABA modulators. In certain embodiments, such compounds are envisioned to be useful as therapeutic agents for the inducement of anesthesia and/or sedation in a subject. In certain embodiments, such compounds are envisioned to be useful as therapeutic agents for treating a CNS-related disorder.

Compounds

In one aspect, provided is a compound of Formula (I):

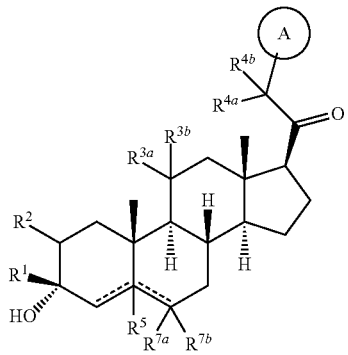
(I)

or a pharmaceutically acceptable salt thereof; wherein: ring A is substituted or unsubstituted carbocyclyl, heterocyclyl, aryl, or heteroaryl; $R^1$ is hydrogen, substituted or unsubstituted $C_{1-6}$ alkyl, substituted or unsubstituted $C_{2-6}$ alkenyl, or substituted or unsubstituted $C_{3-6}$ carbocyclyl; $R^2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, or —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl; $R^{3a}$ is hydrogen or —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, and $R^{3b}$ is hydrogen; or $R^{3a}$ and $R^{3b}$ are joined to form an oxo (=O) group; $R^{4a}$ is hydrogen, substituted or unsubstituted $C_{1-6}$ alkyl, or —$OR^{A4}$ wherein $R^{A4}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, and $R^{4b}$ is hydrogen or substituted or unsubstituted $C_{1-6}$ alkyl; $R^{4a}$ and $R^{4b}$ are joined to form an oxo (=O) group; or $R^{4a}$ and $R^{4b}$ together with the carbon atom to which they are attached form a ring (e.g., a 3-6-membered ring (e.g., carbocycyl or heterocyclyl ring). $R^{7a}$ is hydrogen or halogen; $R^{7b}$ is hydrogen; $R^5$ is absent or hydrogen; and ═══ represents a single or double bond, wherein when one of ═══ is a double bond, the other ═══ is a single bond; and when one of the ═══ is a double bond, $R^5$ is absent.

In one aspect, provided is a pharmaceutical composition comprising a compound of the Formula (I), (Ia), (Ib), (Ic-1), (Ic-2), (II), (II-a1), or (II-a2), and a pharmaceutically acceptable excipient.

In one aspect, provided is a method of inducing sedation and/or anesthesia in a subject, comprising administering to the subject an effective amount of a compound of the Formula (I), (Ia), (Ib), (Ic-1), (Ic-2), (II), (II-a1), or (II-a2), or a pharmaceutically acceptable salt thereof.

In one aspect, provided is a method of administering an effective amount of a compound, a pharmaceutically acceptable salt thereof, or pharmaceutical composition of a compound as described herein, e.g., a compound of the Formula (I), (Ia), (Ib), (Ic-1), (Ic-2), (II), (II-a1), or (II-a2), to a subject in need thereof, wherein the subject experiences sedation and/or anesthesia within two hours of administration.

In some embodiments, the subject experiences sedation and/or anesthesia within one hour of administration.

In some embodiments, the subject experiences sedation and/or anesthesia instantaneously.

In some embodiments, the compound is administered by intravenous administration.

In some embodiments, the compound is administered chronically.

In some embodiments, the subject is a mammal. In some embodiments, the subject is a human.

In some embodiments, the compound is administered in combination with another therapeutic agent.

In one aspect, provided is a method for treating seizure in a subject, comprising administering to the subject an effective amount of a compound of the Formula (I), (Ia), (Ib), (Ic-1), (Ic-2), (II), (II-a1), or (II-a2), or a pharmaceutically acceptable salt thereof.

In one aspect, provided is a method for treating epilepsy or status or status epilepticus in a subject, the method comprising administering to the subject an effective amount of a compound as described herein, e.g., a compound of the Formula (I), (Ia), (Ib), (Ic-1), (Ic-2), (II), (II-a1), or (II-a2), or a pharmaceutically acceptable salt thereof.

In one aspect, provided is a method for treating disorders related to GABA function in a subject in need thereof, the method comprising administering to the subject a therapeutically effective amount of a compound, a pharmaceutically acceptable salt thereof, or pharmaceutical composition of one of a compound as described herein, e.g., a compound of the Formula (I), (Ia), (Ib), (Ic-1), (Ic-2), (II), (II-a1), or (II-a2).

In one aspect, provided is a method for treating a CNS-related disorder in a subject in need thereof, comprising administering to the subject an effective amount of a compound as described herein, e.g., a compound of the Formula (I), (Ia), (Ib), (Ic-1), (Ic-2), (II), (II-a1), or (II-a2), or a pharmaceutically acceptable salt thereof. In some embodiments, the CNS-related disorder is a sleep disorder, a mood disorder such as depression, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus. In some embodiments, the subject is a subject with Rett syndrome, Fragile X syndrome, or Angelman syndrome.

In one aspect, provided is a kit comprising a solid composition comprising a compound as described herein, e.g., a compound of the Formula (I), (Ia), (Ib), (Ic-1), (Ic-2), (II), (II-a1), or (II-a2); and a sterile diluent.

Pharmaceutical Compositions

In one aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration (e.g., a nasal spray).

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17$^{th}$ edition, 1985, Mack Publishing Company, Easton, Pa., which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in Remington: The Science and Practice of Pharmacy 21$^{st}$ ed., Lippincott Williams & Wilkins, 2005.

Methods of Use and Treatment

As generally described herein, the present invention is directed to C21-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder such as depression, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

Thus, in one aspect, the present invention provides a method of inducing sedation and/or anesthesia in a subject, comprising administering to the subject an effective amount of a compound of the present invention or a composition thereof. In certain embodiments, the compound is administered by intravenous administration.

Earlier studies (see, e.g., Gee et al., European Journal of Pharmacology, 136:419-423 (1987)) demonstrated that certain 3α-hydroxylated steroids are orders of magnitude more potent as modulators of the GABA receptor complex (GRC) than others had reported (see, e.g., Majewska et al., Science 232:1004-1007 (1986); Harrison et al., J Pharmacol. Exp. Ther. 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of inducing anesthesia in a subject, comprising administering to the subject an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Neurodegenerative Diseases and Disorders

The compounds described herein can be used in a method described herein, for example in the treatment of a disorder described herein such as a neurodegenerative disease.

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Mood Disorders

The compounds described herein can be used in a method described herein, for example in the treatment of a disorder described herein such as a mood disorder.

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physchological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Premenstrual dysphoric disorder (PMDD) refers to a severe, at times disabling extension of premenstrual syndrome (PMS). PMDD causes extreme modd shifts with symptoms that typically begin seven to ten days before a female's period starts and continues for the first few days of a female's period. Symptoms include sadness or hopelessness, anxiety or tension, extreme moodiness, and marked irritability or anger.

Symptoms of depression include persistent anxious or sad feelings, feelings of helplessness, hopelessness, pessimism, worthlessness, low energy, restlessness, irritability, fatigue, loss of interest in pleasurable activities or hobbies, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

Anxiety Disorders

The compounds described herein can be used in a method described herein, for example in the treatment of a disorder described herein such as an anxiety disorder.

Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Eating Disorders

The compounds described herein can be used in a method described herein, for example in the treatment of a disorder described herein such as an eating disorder. Eating disorders feature disturbances in eating behavior and weight regulation, and are associated with a wide range of adverse psychological, physical, and social consequences. An individual with an eating disorder may start out just eating smaller or larger amounts of food, but at some point, their urge to eat less or more spirals out of control. Eating disorders may be characterized by severe distress or concern about body weight or shape, or extreme efforts to manage weight or food intake. Eating disorders include anorexia nervosa, bulimia nervosa, binge-eating disorder, cachexia, and their variants.

Individuals with anorexia nervosa typically see themselves as overweight, even when they are underweight. Individuals with anorexia nervosa can become obsessed with eating, food, and weight control. Individuals with anorexia nervosa typically weigh themselves repeatedly, portion food carefully, and eat very small quantities of only certain foods. Individuals with anorexia nervosa may engage in binge eating, followed by extreme dieting, excessive exercise, self-induced vomiting, or misuse of laxatives, diuretics, or enemas. Symptoms include extremely low body weight, severe food restriction, relentless pursuit of thinness and unwillingness to maintain a normal or healthy weight, intense fear of gaining weight, distorted body image and self-esteem that is heavily influenced by perceptions of body weight and shape, or a denial of the seriousness of low body weight, lack of menstruation among girls and women. Other symptoms include the thinning of the bones, brittle hair and nails, dry and yellowish skin, growth of fine hair all over the body, mild anemia, muscle wasting, and weakness, severe constipation, low blood pressure or slowed breathing and pulse, damage to the structure and function of the heart, brain damage, multi-organ failure, drop in internal body temperature, lethargy, sluggishness, and infertility.

Individuals with bulimia nervosa have recurrent and frequent episodes of eating unusually large amounts of food and feel a lack of control over these episodes. This binge eating is followed by behavior that compensates for the overeating such as forced vomiting, excessive use of laxatives or diuretics, fasting, excessive exercise, or a combination of these behaviors.

Unlike anorexia nervosa, people with bulimia nervosa usually maintain what is considered a healthy or normal weight, while some are slightly overweight. But like people with anorexia nervosa, they typically fear gaining weight, want desperately to lose weight, and are unhappy with their body size and shape. Usually, bulimic behavior is done secretly because it is often accompanied by feelings of disgust or shame. The binge eating and purging cycle can happen anywhere from several times a week to many times a day. Other symptoms include chronically inflamed and sore throat, swollen salivary glands in the neck and jaw area, worn tooth enamel, and increasingly sensitive and decaying teeth as a result of exposure to stomach acid, acid reflux disorder and other gastrointestinal problems, intestinal distress and irritation from laxative abuse, severe dehydration from purging of fluids, electrolyte imbalance (that can lead to a heart attack or stroke).

Individuals with binge-eating disorder lose control over their eating. Unlike bulimia nervosa, periods of binge eating are not followed by compensatory behaviors like purging, excessive exercise, or fasting. Individuals with binge-eating disorder often are overweight or obese. Obese individuals with binge-eating disorder are at higher risk for developing cardiovascular disease and high blood pressure. They also experience guilt, shame, and distress about their binge eating, which can lead to more binge eating.

Cachexia is also known as "wasting disorder," and is an eating-related issue experienced by many cancer patients. Individuals with cachexia may continue to eat normally, but their body may refuse to utilize the vitamins and nutrients that it is ingesting, or they will lose their appetite and stop eating. When an individual experiences loss of appetite and stops eating, they can be considered to have developed anorexia nervosa.

Epilepsy

The compounds described herein can be used in a method described herein, for example in the treatment of a disorder described herein such as epilepsy, status epilepticus, or seizure, for example as described in WO2013/112605 and WO/2014/031792, the contents of which are incorporated herein in their entirety.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grandmal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure.

In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

Tremor

The compounds described herein can be used in a method described herein, for example in the treatment of a disorder described herein such as tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawl, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Anesthesia/Sedation

The compounds described herein can be used in a method described herein, for example to induce anesthesia or sedation. Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway.

Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent eflon yla function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent eflon yla function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative heteroaryls and heterocyclyls that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

The stereochemistry assigned herein (e.g., the assignment of "R" or "S" to the C21 position of the steroid) may be tentatively (e.g., randomly) assigned. For example, a C21 position may be drawn in the "R" configuration when the C21 position is in the "S" configuration.

$^1$H-NMR reported herein (e.g., for intermediates) may be a partial representation of the full NMR spectrum of a compound, e.g., a compound described herein. For example, the reported $^1$H NMR may exclude the region between δ (ppm) of about 1 to about 2.5 ppm.

Exemplary general method for preparative HPLC: Column: Waters Rbridge prep 10 μm C18, 19*250 mm. Mobile phase: acetonitrile, water (NH$_4$HCO$_3$) (30 L water, 24 g NH$_4$HCO$_3$, 30 mL NH$_3$.H$_2$O). Flow rate: 25 mL/min Exemplary general method for analytical HPLC: Mobile phase: A: water (10 mM NH$_4$HCO$_3$), B: acetonitrile Gradient: 5%-95% B in 1.6 or 2 min Flow rate: 1.8 or 2 mL/min; Column: Xbridge C18, 4.6*50 mm, 3.5 m at 45 C.

Synthetic Methods

Example 1

Synthesis of 1

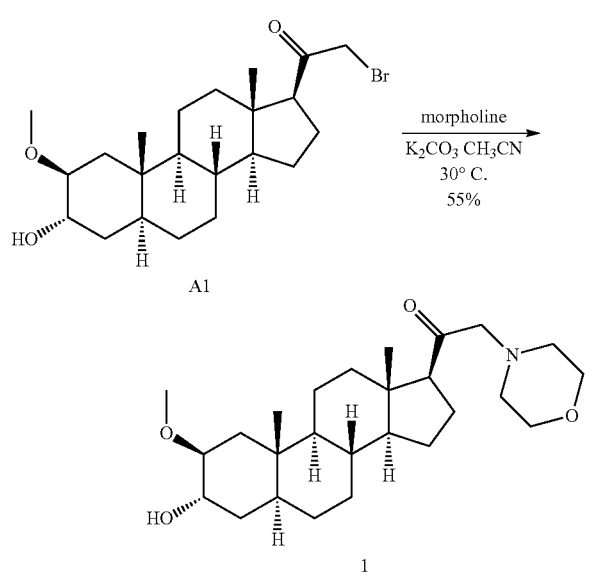

To a suspension of A1 (170 mg, 0.4 mmol) in acetonitrile (3.5 mL) was added potassium carbonate (340 mg, 2.4 mmol) and morpholine (340 mg, 3.9 mmol) at 10° C. The mixture was stirred at 30° C. for 5 hours and then concentrated under vacuum, washed with water, purified by column chromatography on silica gel (eluent:petrol ether:ethyl acetate=2:1 to 1:2) to give 1 (94.1 mg, 55%) as white solid.

$^1$H NMR: (400 MHz, CDCl3) δ 4.02-3.90 (m, 1H), 3.75 (t, J=4.4 Hz, 4H), 3.48-3.30 (m, 4H), 3.20-3.18 (m, 2H), 2.61-2.40 (m, 5H), 2.22-2.08 (m, 1H), 1.92-1.78 (m, 3H), 1.73-1.48 (m, 6H), 1.40-1.15 (m, 9H), 0.99-0.88 (m, 4H), 0.80-0.68 (m, 1H), 0.61 (s, 3H).

Example 2

Synthesis of 2 and 3

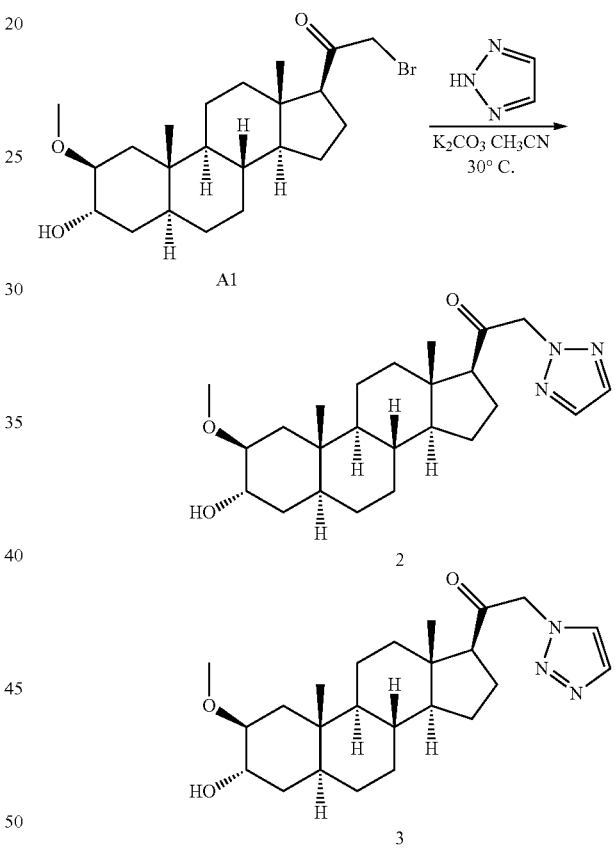

To a suspension of A1 (260 mg, 0.61 mmol) in acetonitrile (5 mL) was added potassium carbonate (500 mg, 3.6 mmol) and 1,2,3-triazole (500 mg, 7.2 mmol) at 10° C. The mixture was stirred at 30° C. for 5 hours and then concentrated under vacuum. To the residue was added washed, extracted with ethyl acetate. The organic layer was dried over anhydrous sodium sulfate, purified by prep-HPLC to give 2 (38.1 mg, 15%) and 3 (71.5 mg, 28%) as white solid.

$^1$H NMR (2): (400 MHz, CDCl3) δ 7.68 (s, 2H), 5.32-5.15 (m, 2H), 4.01-3.91 (m, 1H), 3.41-3.29 (m, 4H), 2.62-2.50 (m, 1H), 2.28-2.14 (m, 1H), 2.13-2.04 (m, 1H), 1.95-1.88 (m, 1H), 1.88-1.62 (m, 5H), 1.56-1.19 (m, 11H), 1.02-0.95 (m, 1H), 0.93 (s, 3H), 0.81-0.72 (m, 1H), 0.69 (s, 3H).

$^1$H NMR (3): (400 MHz, CDCl3) δ 7.75 (s, 1H), 7.64 (s, 1H), 5.32-5.09 (m, 2H), 4.01-3.91 (m, 1H), 3.41-3.29 (m,

4H), 2.70-2.58 (m, 1H), 2.28-2.14 (m, 1H), 2.12-2.04 (m, 1H), 1.95-1.88 (m, 1H), 1.88-1.62 (m, 5H), 1.56-1.20 (m, 11H), 1.03-0.95 (m, 1H), 0.93 (s, 3H), 0.81-0.72 (m, 1H), 0.66 (s, 3H).
Example 3
Synthesis of 4 and 5
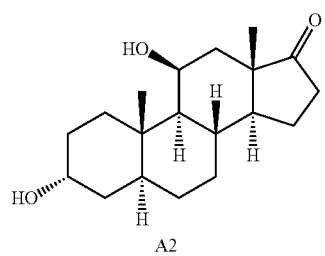
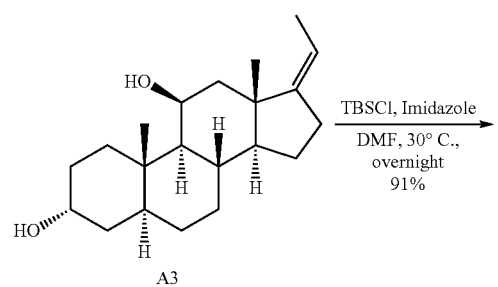
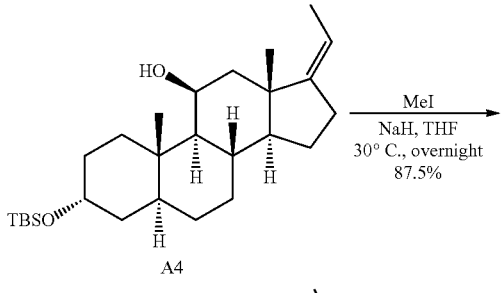
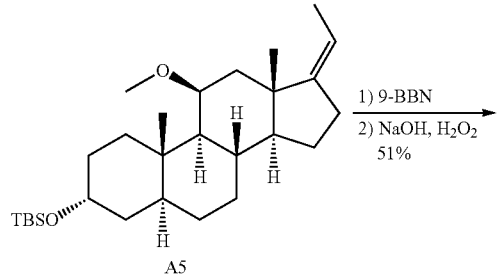
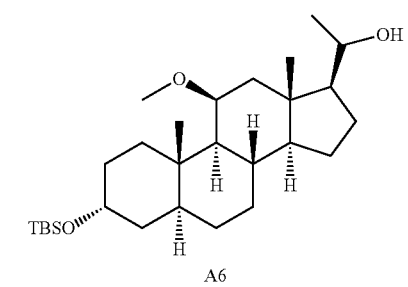
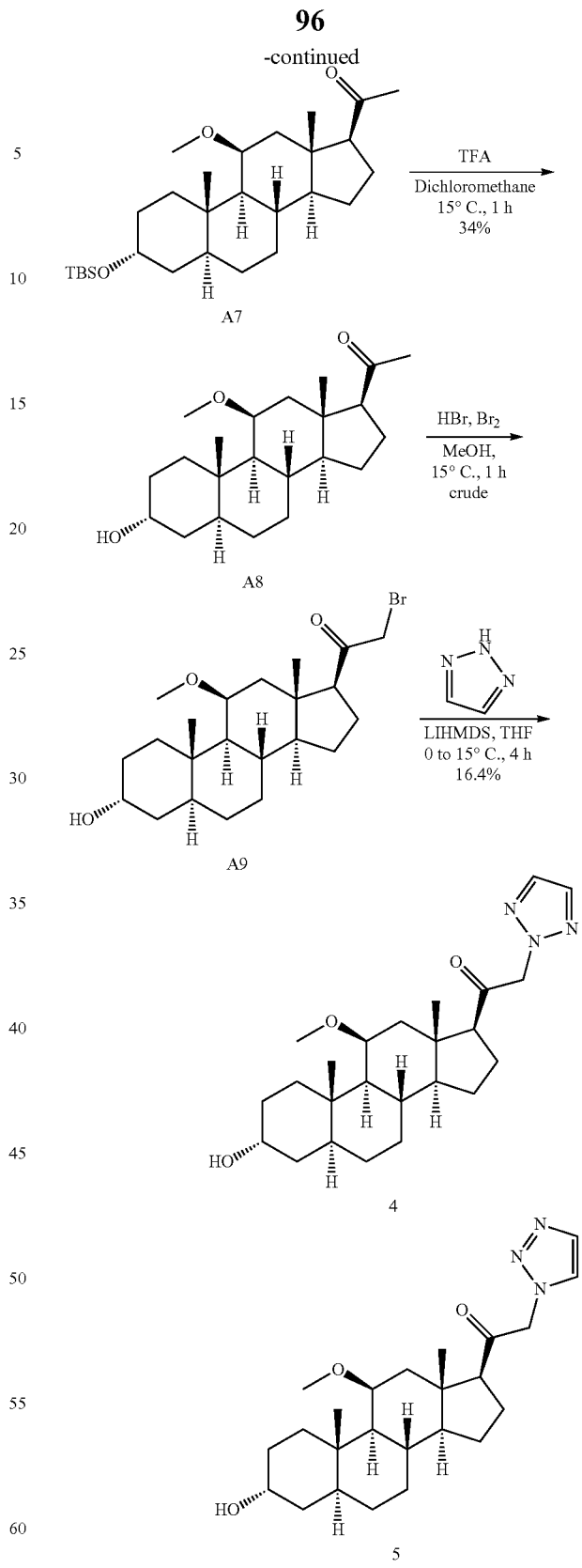
Step 1. Synthesis of A3. To a solution of Ph$_3$PCH$_2$CH$_2$Br (60.41 g, 163.16 mmol) in THF (40 mL) was added a solution of t-BuOK (18.31 g, 163.16 mmol) in THF (20 mL) under N$_2$ atmosphere. The mixture was stirred at 15° C. for 1 h. Then the solution of A2 (10 g, 32.63 mmol) in THF (40 mL) was added and the mixture was stirred under reflux for 3 h. TLC (ethyl acetate/petroleum ether=1/1) showed that the starting material was consumed completely. The mixture was cooled and quenched with saturate NH$_4$Cl aqueous (40 mL). The mixture was extracted with EtOAc (60 mL*3). The combined organic layers was washed with brine (50 mL), dried over anhydrous Na$_2$SO$_4$ and evaporated in vacuo to give crude, which was purified by column chromatography on silica gel (ethyl acetate/petroleum ether=1/10) to afford A3 (6.8 g, 65%) as a white solid.

$^1$H NMR (A3): (400 MHz, CDCl3) δ 5.11-5.02 (m, 1H), 4.39-4.35 (m, 1H), 4.07-4.02 (m, 1H), 2.41-2.32 (m, 2H), 2.21-2.09 (m, 2H), 1.91-1.71 (m, 4H), 1.70-1.57 (m, 8H), 1.57-1.42 (m, 4H), 1.41-1.29 (m, 3H), 1.11-1.06 (m, 4H), 1.06-1.04 (m, 3H), 1.01-0.93 (m, 2H), 0.89-0.81 (m, 1H).

Step 2. Synthesis of A4. To a solution of A3 (4.2 g, 13.19 mmol) and 1H-imidazole (1.80 g, 26.37 mmol) in DMF (35 mL) was added TBSCl (3.98 g, 26.37 mmol). The mixture was stirred at 30° C. overnight. TLC showed the starting material was consumed completely. The resulting mixture was added brine (35 mL) and the resulting solution was extracted with EtOAc (20 mL*3). The combined organic layers was washed with brine (25 mL*3), dried over anhydrous Na$_2$SO$_4$ and concentrated under vacuum to give crude, which was purified by column chromatography on silica gel (ethyl acetate/petroleum ether=1/100) to afford A4 (5.2 g, 91%) as a white solid.

$^1$H NMR (A4): (400 MHz, CDCl3) δ 5.10-5.03 (m, 1H), 4.40-4.37 (m, 1H), 4.88-4.84 (m, 1H), 4.44-4.31 (m, 2H), 2.20-2.09 (m, 1H), 1.89-1.72 (m, 4H), 1.69-1.63 (m, 4H), 1.61-1.48 (m, 7H), 1.43-1.11 (m, 6H), 1.11-1.04 (m, 4H), 1.04-0.94 (m, 5H), 0.90-0.81 (m, 12H), 0.2 (s, 6H).

Step 3. Synthesis of A5. To a suspension of NaH (4.81 g, 120.16 mmol) in THF (50 mL) was added a solution of compound A4 (5.2 g, 12.02 mmol) in THF (20 mL) dropwise at 0° C. under N$_2$. The mixture was stirred at 0° C. for 30 min. Then MeI (17.06 g, 120.16 mmol) was added dropwise. The mixture was stirred at 30° C. overnight. TLC (ethyl acetate/petroleum ether=1/200) showed that the reaction was completed. The reaction was quenched with aqueous NH$_4$Cl (30 mL). The resulting solution was extracted with ethyl acetate (35 mL*3) and the combined organic layers was dried and concentrated under vacuum to give the crude, which was purified by column chromatography on silica gel (ethyl acetate/petroleum ether=1/2) to afford A5 (4.7 g, 87.5%) as a white solid.

$^1$H NMR (A5): (400 MHz, CDCl3) δ 5.11-5.02 (m, 1H), 3.99-3.96 (m, 1H), 3.23-3.17 (m, 1H), 3.28 (s, 3H), 2.73-2.67 (m, 1H), 2.46-2.32 (m, 1H), 2.23-2.11 (m, 1H), 1.88-1.74 (m, 2H), 1.71-1.64 (m, 4H), 1.63-1.61 (m, 4H), 1.51-1.33 (m, 5H), 1.22-1.08 (m, 5H), 1.04 (s, 3H), 0.96 (s, 3H), 0.94-0.88 (m, 11H), 0.87-0.78 (m, 2H), 0.2 (s, 6H).

Step 4. Synthesis of A6. To a solution of 9-BBN (210 mL, 0.5 M) in THF was added a solution of A5 (4.7 g, 10.52 mmol) in THF (30 mL) dropwise with stirring at ice-bath under N$_2$ atmosphere. The mixture was stirred at 60° C. overnight. The reaction was cooled at ice-bath, and 10% NaOH aqueous (24 mL) was added dropwise, then 30% H$_2$O$_2$ aqueous (12 mL) was added dropwise, the resulting solution was stirred at 15° C. for 3 h. The mixture was quenched with saturated Na$_2$S$_2$O$_3$ aqueous (50 mL). The resulting mixture was extracted with EtOAc (100*3 mL) and the combined organic layers was dried over anhydrous Na$_2$SO$_4$ and concentrated under vacuum to give crude, which was purified by column chromatography on silica gel (ethyl acetate/petroleum ether=1/50) to afford A6 (2.5 g, 51%) as a white solid.

$^1$H NMR (A6): (400 MHz, CDCl3) δ 3.97-3.93 (m, 1H), 3.89-3.81 (m, 1H), 3.75-3.64 (m, 1H), 3.64-3.61 (m, 1H), 3.21 (s, 3H), 2.34-2.27 (m, 1H), 0.96-0.92 (m, 4H), 0.87 (s, 9H), 0.81 (s, 3H), 0.78-0.72 (m, 1H), 0.2 (m, 6H).

Step 5. Synthesis of A7. To a solution of A6 (2.5 g, 5.38 mmol) in Dichloromethane (20 mL) was added Dess-Matin (1.28 g, 3.01 mmol) under N$_2$ atmosphere. The mixture was stirred at 40° C. overnight. TLC showed the starting material was consumed completely. The mixture was quenched with saturated Na$_2$S$_2$O$_3$ aqueous (25 mL). The resulting mixture was extracted with EtOAc (20 mL*3). The combined organic layers was washed with saturated Na$_2$S$_2$O$_3$ aqueous (25 mL*4), saturated NaHCO$_3$ aqueous (20 mL), brine (15 mL) and dried over anhydrous Na$_2$SO$_4$ and concentrated under vacuum to give crude of A7 (2.7 g), which was used next step without further purification.

$^1$H NMR (A7): (400 MHz, CDCl3) δ 3.98-3.93 (m, 1H), 3.71-3.68 (m, 1H), 3.21 (s, 3H), 2.54-2.36 (m, 4H), 2.21-2.06 (m, 5H), 1.96-1.31 (m, 20H), 1.30-1.06 (m, 8H), 1.02-0.91 (m, 4H), 0.92-0.84 (m, 10H), 0.83-0.72 (m, 5H), 0.2 (m, 6H).

Step 6. Synthesis of A8. To a solution of A7 (2.7 g, 5.83 mmol) in dichloromathane (30 mL) was added TFA (5 mL, 67.09 mmol) dropwise. The mixture was stirred at 15° C. for 1 h. TLC showed that the reaction was completed. The mixture was quenched with saturated Na$_2$HCO$_3$ aqueous (25 mL). The resulting solution was extracted with Dichloromathane (20 mL*3). The combined organic layers was washed with brine (45 mL*3) and dried over anhydrous Na$_2$SO$_4$ and concentrated under vacuum to give crude, which was purified by column chromatography on silica gel (ethyl acetate/petroleum ether=1/3) to afford A8 (0.8 g, 34%) as a white solid.

$^1$H NMR (A8): (400 MHz, CDCl3) δ 4.07-4.02 (m, 1H), 3.71-3.68 (m, 1H), 3.21 (s, 3H), 2.49-2.41 (m, 2H), 2.19-2.08 (m, 4H), 1.74-1.57 (m, 8H), 1.56-1.49 (m, 3H), 1.48-1.40 (m, 3H), 1.38-1.32 (m, 1H), 1.31-1.16 (m, 5H), 1.16-1.03 (m, 1H), 0.97 (s, 3H), 0.84-0.78 (m, 1H), 0.77 (s, 3H).

Step 7. Synthesis of A9. To a solution of A8 (0.7 g, 2.01 mmol) in MeOH (20 mL) was added HBr aqueous (5 drops, 40% in water). Then Br$_2$ (353.07 mg, 2.21 mmol) was added with stirring. The mixture was stirred at 15° C. for 3 h. TLC showed that the reaction was completed. The mixture was quenched with saturated NH$_4$Cl aqueous (15 mL). The resulting solution was extracted with dichloromathane (20 mL*3). The combined organic layers was washed with brine (15 mL) and dried over anhydrous Na$_2$SO$_4$ and concentrated under vacuum to give crude of A9 (1.0 g), which was used next step without further purification.

$^1$H NMR (A9): (400 MHz, CDCl3) δ 4.08-4.04 (m, 1H), 3.91 (s, 2H), 3.71-3.68 (m, 1H), 3.28-3.19 (m, 3H), 2.77-2.71 (m, 1H), 2.51-2.35 (m, 2H), 2.34-2.24 (m, 1H), 2.22-2.11 (m, 1H), 1.83-1.68 (m, 7H), 1.67-1.48 (m, 10H), 1.47-1.38 (m, 2H), 1.21-1.10 (m, 4H), 0.98 (s, 3H), 0.77-0.86 (m, 4H).

Step 8. Synthesis of 4 and 5. To a solution of 1,2,3-triazole (824.10 mg, 11.93 mmol) in THF (15 mL) was added LiHMDS (11.93 mL, 11.93 mmol, 1 M in THF) at ice-bath under N$_2$ atmosphere. The mixture was stirred at 0° C. for 30 min. Then the solution of A9 (850 mg, 1.99 mmol) THF (5 mL) was added and the reaction was stirred at 15° C. for 4 h. TLC showed that the reaction was completed. The mixture was quenched with saturated NH$_4$Cl aqueous (15 mL). The resulting solution was extracted with EtOAc (20 mL*3).

The combined organic layers was washed with brine (15 mL*4) and dried over anhydrous Na₂SO₄ and concentrated under vacuum to give crude, which was purified by column chromatography on silica gel (ethyl acetate/petroleum ether=1/3) to afford 4 (77.5 mg, 9.4%) and 5 (57.4 mg, 7%) as yellow solid.

¹H NMR (4): (400 MHz, CDCl3) δ 7.78-7.70 (m, 2H), 5.28-5.26 (m, 2H), 4.10-4.03 (m, 1H), 3.73-3.68 (m, 4H), 3.26 (s, 3H), 2.48-2.57 (m, 1H), 2.23-2.12 (m, 1H), 1.78-1.69 (m, 4H), 1.47-1.42 (m, 2H), 1.41-1.07 (m, 8H), 1.04-0.93 (m, 4H), 0.93-0.82 (m, 5H).

¹H NMR (5): (400 MHz, CDCl3) δ 7.79 (s, 3H), 7.69 (s, 3H), 5.38-5.27 (d, J=17.6 Hz, 1H), 5.19-5.11 (d, J=18 Hz, 1H), 4.12-4.06 (m, 1H), 3.81-3.68 (m, 1H), 3.24 (s, 3H), 2.67-2.52 (m, 2H), 2.31-2.26 (m, 1H), 1.89-1.68 (m, 5H), 1.52-1.38 (m, 2H), 1.46-1.14 (m, 9H), 0.98 (s, 3H), 0.93-0.78 (m, 7H).

Example 4

Synthesis of 6 and 7

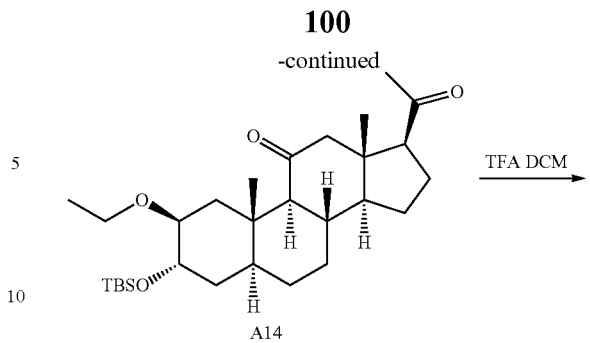

Step 1. Synthesis of A11. Potassium tert-butoxide (3.24 g, 28.7 mmol) in THF (90 mL) was added into a suspension of ethyltriphenylphosphonium bromide (10.66 g, 28.7 mmol) in THF (20 mL) dropwise at 0° C. The resulting reaction mixture was warmed to room temperature (15° C.) and stirred for an additional 1 h. Then a solution of compound A10 (2.5 g, 7.18 mmol) in THF (20 mL) was introduced slowly to the above suspension at 0° C. The solution was stirred for an additional 10-20 min and the mixture was allowed to warm to ambient temperature slowly. Stirring was continued for about 2 h. TLC (PE:EA=3:1) showed that the reaction was complete. The mixture was quenched by the addition of saturated NH$_4$Cl solution (10 mL). The solution was extracted with EtOAc (100 mL*3) and the combined organic layer was washed with brine and dried over anhydrous Na$_2$SO$_4$. The solvent was removed. The residue was purified by flash chromatography eluting with petroleum ether: ethyl acetate=6:1 to give A11 (2.06 g, 80%) as a white solid.

$^1$HNMR (A11): (400 MHz, CDCl$_3$) δ 5.32-5.18 (m, 1H), 3.98-3.88 (m, 1H), 3.79-3.70 (m, 1H), 3.42-3.33 (m, 2H), 2.88-2.82 (m, 1H), 2.78-2.72 (m, 1H), 2.60-2.51 (m, 1H), 2.48-2.28 (m, 2H), 1.94-1.68 (m, 6H), 1.64-1.60 (m, 3H), 1.58-1.38 (m, 2H), 1.38-1.24 (m, 4H), 1.24-1.16 (m, 7H), 1.16-1.12 (m, 1H), 0.84 (s, 3H).

Step 2. Synthesis of A12. To a solution of compound A11 (2 g, 5.5 mmol) in DMF (20 mL) was added imidazole (1.12 g, 16.5 mmol) and TBSCl (1.65 g, 11 mmol). Then the solution was heated to 30° C. and maintained the temperature for 16 h. TLC and LCMS showed that the reaction was complete. Brine and EtOAc were added into the solution and separated. The combined organic layer was washed with brine (100 mL*3). The organic layer was dried over anhydrous Na$_2$SO$_4$ and concentrated. The residue was purified by flash chromatography eluting with petroleum ether to give A12 (2.88 g, 99%) as a white solid.

$^1$HNMR (A12): (400 MHz, CDCl$_3$) δ 5.18-5.16 (m, 1H), 3.84-3.78 (m, 1H), 3.75-3.68 (m, 1H), 3.38-3.28 (m, 1H), 3.28-3.22 (m, 1H), 2.85-2.78 (m, 1H), 2.74-2.66 (m, 1H), 2.60-2.55 (m, 1H), 2.48-2.24 (m, 2H), 1.85-1.65 (m, 5H), 1.61-1.54 (m, 5H), 1.36-1.22 (m, 3H), 1.31-1.10 (m, 8H), 0.89-0.86 (m, 10H), 0.81 (s, 3H), 0.03 (s, 6H).

Step 3. Synthesis of A13. A solution of BH$_3$ in THF (20 mmol, 20 mL, 1M in THF) was added into a solution of A12 (1 g, 2.1 mmol) in THF (20 mL). The resulting solution was stirred at 45° C. for 20 h. The mixture was cooled in an ice bath and then saturated NaHCO$_3$ solution was added slowly, followed by the addition of H$_2$O$_2$ (30%, 40 mL). The resulting suspension was stirred at 30° C. for 3 h. It was extracted with EtOAc (30 mL*2). The combined organic layer was dried over anhydrous Na$_2$SO$_4$ and concentrated the solvent. The residue was purified by flash chromatography eluting with petroleum ether: ethyl acetate=8:1 to give A13 (800 mg, 77%) as a colorless solid.

$^1$HNMR (A13): (400 MHz, CDCl$_3$) δ 4.34-4.26 (m, 1H), 3.86-3.80 (m, 1H), 3.73-3.64 (m, 1H), 3.60-3.51 (m, 1H), 3.46-3.35 (m, 1H), 3.34-3.30 (m, 1H), 1.96-1.83 (m, 2H), 1.83-1.65 (m, 4H), 1.41-1.30 (m, 3H), 1.30-1.21 (m, 7H), 1.19-1.10 (m, 9H), 1.10-0.94 (m, 3H), 0.86 (s, 12H), 0.78-0.73 (m, 1H), 0.03 (s, 6H).

Step 4. Synthesis of A14. To a solution of A13 (600 mg, 1.2 mmol) in CH$_2$Cl$_2$ (25 mL) was added Dess-Martin reagent (1.55 g, 3.6 mmol). The mixture was stirred at 25° C. for 1 h. TLC showed that the reaction was complete. The reaction was quenched by the addition of saturated Na$_2$SO$_3$ solution and separated. The organic layer was washed with saturated NaHCO$_3$ solution and brine. The combined organic layer was dried over anhydrous Na$_2$SO$_4$ and concentrated the solvent to give the crude A14 (690 mg) as a pale yellow oil.

$^1$H NMR (A14) (400 MHz, CDCl$_3$) δ 3.87-3.80 (m, 1H), 3.75-3.68 (m, 1H), 3.40-3.26 (m, 2H), 2.78-2.70 (m, 2H), 2.58-2.46 (m, 2H), 2.31-2.15 (m, 2H), 2.20 (s, 3H), 1.86-1.66 (m, 6H), 1.40-1.05 (m, 13H), 0.95-0.84 (m, 9H), 0.59 (s, 3H), 0.05 (s, 3H).

Step 5. Synthesis of A15. To a solution of A14 (600 mg, 1.20 mmol) in DCM (10 mL) was added TFA (2 mL). The resulting solution was stirred at 25° C. for 3.5 h. TLC showed that the reaction was complete. Then brine was added into the solution. The organic layer was washed with saturated NaHCO$_3$ solution and brine. The organic layer was dried over anhydrous Na$_2$SO$_4$ and concentrated. The residue was dissolved with THF. Then aqueous LiOH solution was added. The resulting solution was stirred at 25° C. for 16 h. TLC and LCMS showed that the reaction was complete. The solvent was evaporated. The residue was washed with EtOAc and H$_2$O. The organic layer was washed with brine. The organic layer was dried over anhydrous Na$_2$SO$_4$ and concentrated to give the crude A15 (480 mg) as a pale yellow oil.

$^1$H NMR (A15) (400 MHz, CDCl$_3$) δ 3.96-3.88 (m, 1H), 3.78-3.70 (m, 1H), 3.42-3.34 (m, 2H), 2.76-2.68 (m, 2H), 2.60-2.45 (m, 2H), 2.30-2.18 (m, 1H), 2.12 (s, 3H), 1.92-1.73 (m, 8H), 1.61-1.50 (m, 2H), 1.38-1.25 (m, 9H), 1.25-1.14 (m, 10H), 0.93 (s, 3H), 0.59 (s, 3H).

Step 6. Synthesis of A16. To a solution of A15 (430 mg, 1.14 mmol) in MeOH (10 mL) was added HBr (0.08 mL) and Br$_2$ (0.16 mL) in MeOH (1 mL). The resulting solution was stirred at 25° C. for 1.5 h. TLC showed that the reaction was complete. The solvent was evaporated and the residue was extracted with DCM (50 mL*2). The organic layer was washed with brine. The organic layer was dried over anhydrous Na$_2$SO$_4$ and concentrated to give the crude A16 (510 mg) as a pale yellow oil.

$^1$H NMR (A16) (400 MHz, CDCl$_3$) δ 3.96-3.88 (m, 1H), 3.78-3.74 (m, 2H), 3.76-3.68 (m, 1H), 3.39-3.33 (m, 2H), 3.12-3.06 (m, 1H), 2.66-2.60 (m, 1H), 2.51-2.44 (m, 2H), 2.25-2.18 (m, 1H), 1.98-1.76 (m, 7H), 1.41-1.24 (m, 6H), 1.23-1.12 (m, 8H), 0.63 (s, 3H).

Step 7. Synthesis of 6 and 7. Into a over-dried flask was added 1,2,3-triazole (450 mg, 6.74 mmol), K$_2$CO$_3$ (468 mg, 3.36 mmol) and DMF (5 mL). The resulting suspension was stirred at 33° C. for 30 min under N$_2$. Then the solution of A16 (510 mg, 1.12 mmol) in DMF (5 mL) was added into the above suspension and it was stirred at 33° C. for additional 4 h. LCMS showed that the reaction was complete. The solution was quenched by the addition of saturated NH$_4$Cl solution. It was extracted with EtOAc. The organic layer was washed with brine. The organic layer was dried over anhydrous Na$_2$SO$_4$ and concentrated. The residue was purified by pre-HPLC to give 6 (55 mg, 9.9%) as a colorless solid and 7 (67 mg, 12.1%) as a pale yellow solid.

$^1$H NMR (6) (400 MHz, CDCl$_3$) δ 7.71 (s, 2H), 5.21-5.20 (m, 2H), 3.95-3.90 (m, 1H), 3.80-3.70 (m, 1H), 3.42-3.33 (m, 2H), 2.78-2.70 (m, 2H), 2.63-2.58 (m, 1H), 2.40-2.35 (m, 1H), 1.90-1.70 (m, 7H), 1.43-1.25 (m, 7H), 1.24-1.13 (m, 8H), 0.69 (s, 3H).

$^1$H NMR (7) (400 MHz, CDCl$_3$) δ 7.79 (s, 1H), 7.65 (s, 1H), 5.26-5.10 (m, 2H), 3.98-3.90 (m, 1H), 3.80-3.70 (m, 1H), 3.40-3.35 (m, 2H), 2.85-2.80 (m, 1H), 2.75-2.65 (m, 1H), 2.60-2.45 (m, 2H), 2.31-2.20 (m, 1H), 1.98-1.78 (m, 7H), 1.46-1.25 (m, 7H), 1.24-1.13 (m, 7H), 0.68 (s, 3H).

Example 5

Synthesis of 8 and 9

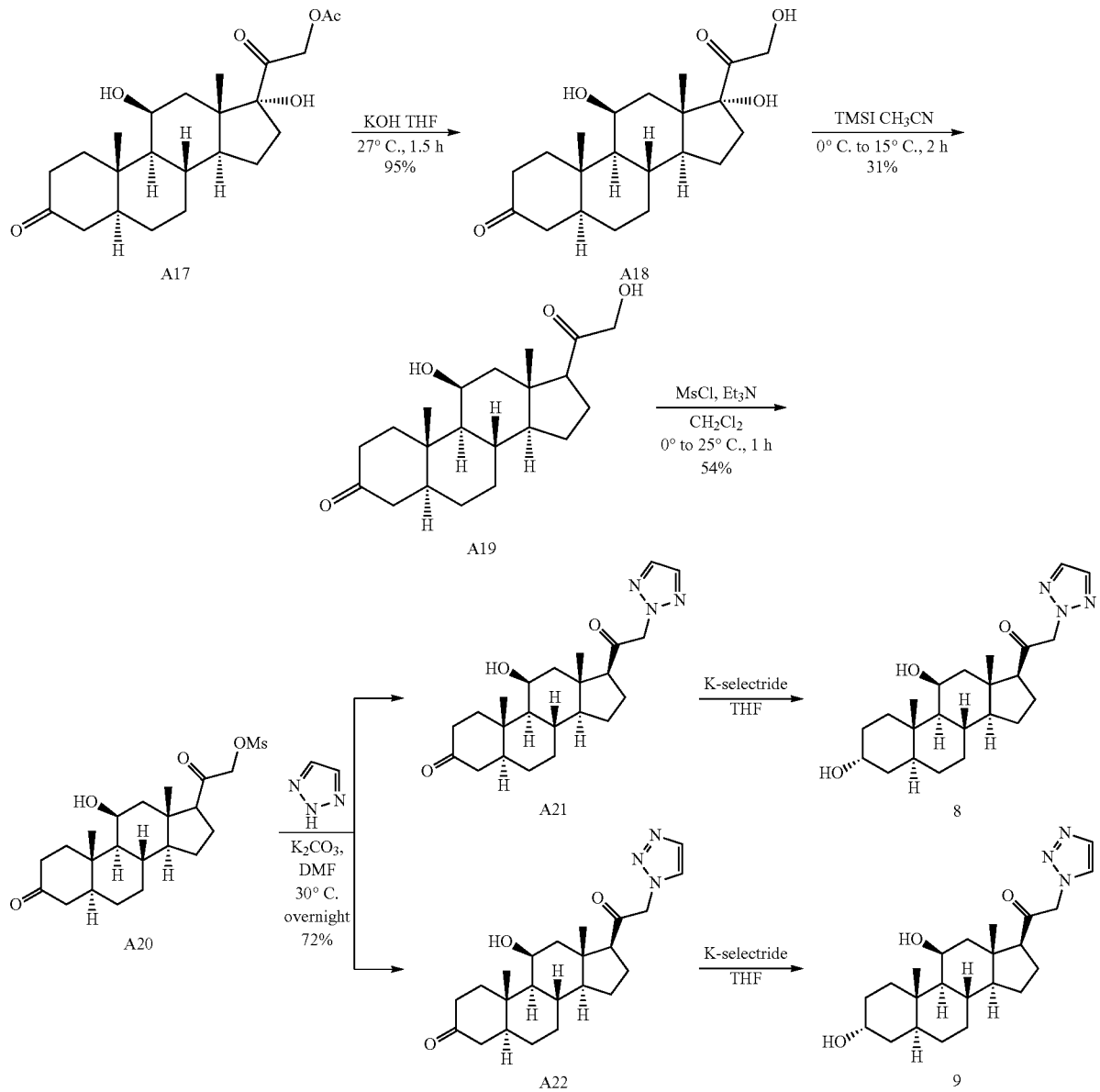

Step 1. Synthesis of A18. To a solution of A17 (20.0 g, 49.2 mmol) in THF (100 mL) was added KOH (8.28 g, 147.6 mmol). The mixture was stirred at 27° C. for 1.5 h. TLC (petroleum ether/ethyl acetate=1/1) indicated that the starting material was consumed completely. The reaction was added H$_2$O (50 mL) and the resulting solution was extracted with EtOAc (80 mL*3). The combined organic layers was washed with brine (150 mL), dried over anhydrous Na$_2$SO$_4$ and concentrated to give crude of A18 (17 g, 95%) as a white solid.

Step 2. Synthesis of A19. To a solution of A18 (17 g, 46.64 mmol) in CH$_3$CN (1.5 L) was added TMSI (18.67 g, 93.28 mmol) at ice-bath under N$_2$ atmosphere. The mixture was stirred at 15° C. for 2 h. TLC (petroleum ether/ethyl acetate=1/1) showed the starting material was consumed completely. The reaction was quenched with Na$_2$S$_2$O$_3$ (100 mL). The resulting mixture was extracted with EtOAc (45 mL*3) and the combined organic layers was dried over anhydrous Na$_2$SO$_4$ and concentrated under vacuum to give crude, which was purified by column chromatography on silica gel (ethyl acetate/petroleum ether=1/3) to afford A19 (5.5 g, 31%) as a yellow solid.

$^1$H NMR (A19): (400 MHz, CDCl3) δ 4.74-4.61 (m, 1H), 4.39-4.36 (m, 1H), 4.35-3.31 (m, 1H), 4.22-4.15 (m, 2H), 3.29-3.22 (m, 1H), 3.16-3.05 (m, 1H), 2.77-2.58 (m, 1H), 2.54-2.36 (m, 3H), 2.38-2.13 (m, 8H), 1.15 (s, 3H), 0.88 (s, 3H).

Step 3. Synthesis of A20. To a solution of A19 (2.4 g, 6.89 mmol) and Et$_3$N (2.09 mg, 20.66 mmol) in CH$_2$Cl$_2$ (70 mL) was added MsCl (11.05 g, 96.42 mmol) dropwise at 0° C. under N$_2$ atmosphere. The reaction was stirred at 25° C. for 1 h. TLC (petroleum ether/ethyl acetate=3/1) showed that the reaction was completed. The reaction was added ice-water (35 mL) at 0° C. with stirring. The resulting solution was extracted with CH₂Cl₂ (35 mL*3). The combined organic layers was dried and concentrated to give crude of A20 (1.6 g, 54%) as a white solid.

Step 4. Synthesis of A21 and A22. To a solution of A20 (1.4 g, 3.28 mmol) and 2H-1,2,3-triazole (1.13 g, 16.41 mmol) in DMF (25 mL) was added K₂CO₃ (2.27 g, 16.41 mmol). The reaction was stirred at 30° C. overnight. TLC (petroleum ether/ethyl acetate=1/2) showed that the reaction was completed. The reaction was added brine (20 mL). The resulting solution was extracted with EtOAc (25 mL*3). The combined organic layers was dried and concentrated to give crude, which was purified by column chromatagraphy on silica gel (ethyl acetate/petroleum ether=2/1 to 1/2) to afford A21 (460 mg) and A22 (480 mg) as white solid.

Step 5-1. Synthesis of 8. To a solution of A21 (360 mg, 901.07 μmol) in THF (15 mL) was added K-selectride (1.08 mL, 1M) at −78° C. under N₂ atmosphere. The reaction was stirred at −78° C. for 2 h. TLC (DCM/MeOH=20/1) showed that the reaction was completed. The reaction was quenched with H₂O₂ (0.1 mL, 30%). The resulting solution was extracted with EtOAc (15 mL*3) and the combined organic layers was washed with saturated Na₂S₂O₄ aqueous (15 mL*2) and brine (15 mL*1). The mixture was dried and concentrated to give crude, which was purified by column chromatagraphy on silica gel (petroleum ether/ethyl acetate=2/1) and further purified by SFC to afford 8 (60.6 mg, 16.7%) as a white solid.

¹H NMR (8): (400 MHz, CDCl3) δ 7.74-7.62 (m, 2H), 5.32-5.18 (m, 2H), 4.47-4.38 (m, 1H), 4.12-4.03 (m, 2H), 2.57-2.45 (m, 1H), 2.33-2.15 (m, 2H), 1.91-1.63 (m, 6H), 1.55-1.45 (m, 2H), 1.42-1.09 (m, 7H), 1.11-1.05 (m, 1H), 1.03 (s, 3H), 0.96 (s, 3H), 0.94-0.82 (m, 1H).

Step 5-2. Synthesis of 9. To a solution of A22 (380 mg, 951.13 μmol) in THF (15 mL) was added K-selectride (1.14 mL, 1M) at −78° C. under N₂ atmosphere. The reaction was stirred at −78° C. for 2 h. TLC (DCM/MeOH=20/1) showed that the reaction was completed. The reaction was quenched with H₂O₂ (0.1 mL, 30%). The resulting solution was extracted with EtOAc (15 mL*3) and the combined organic layers was washed with saturated Na₂S₂O₄ aqueous (15 mL*2) and brine (15 mL*1). The mixture was dried and concentrated to give crude, which was purified by column chromatagraphy on silica gel (petroleum ether/ethyl acetate=1/1) and further purified by chiral SFC-HPLC to afford 9 (79.8 mg, 21%) as a white solid.

¹H NMR (9): (400 MHz, CDCl3) δ 7.78 (s, 1H), 7.68 (s, 1H), 5.31-5.25 (d, J=17.6 Hz, 1H), 5.20-5.14 (d, J=17.6 Hz, 1H), 4.48-4.45 (m, 1H), 4.12-4.03 (m, 1H), 2.65-2.53 (m, 2H), 2.32-2.15 (m, 1H), 1.92-1.71 (m, 5H), 1.68-1.59 (m, 4H), 1.54-1.42 (m, 1H), 1.41-1.15 (m, 4H), 1.13-1.05 (m, 1H), 1.04 (s, 3H), 0.94-0.85 (m, 4H).

Example 6

Synthesis of 10

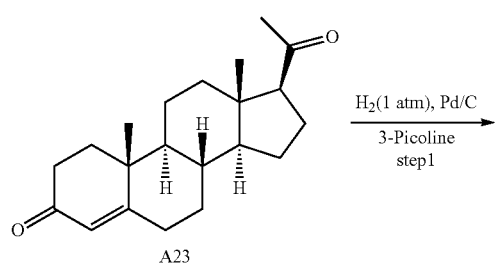

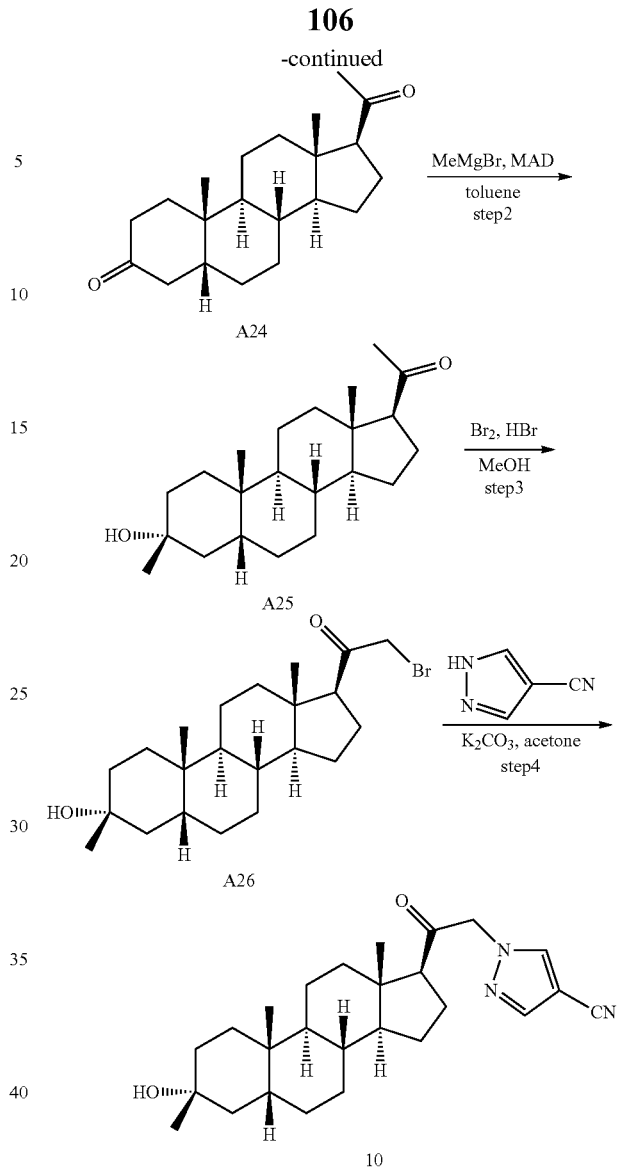

Step 1. Synthesis of A24. To a solution of compound (8S,9S,10R,13S,14S,17S)-17-acetyl-10,13-dimethyl-6,7,8,9,10,11,12,13,14,15,16,17-dodecahydro-1H-cyclopenta[a]phenanthren-3(2H)-one (A23, 30 g, 95.5 mmol) in 3-Picoline (150 mL) was added Pd/C (10%, 3.0 g) under argon. The suspension was degassed under vacuum and purged with H₂ several times. The mixture was stirred under H₂ (1 atm) at 25° C. for 12 h. TLC (petroleum ether/ethyl acetate=3/1) showed that the starting material was consumed completely. The suspension was filtered through a pad of celite and the pad was washed with EtOAc (200 mL×3). The combined filtrates were washed with HCl (200 mL×3, 1M), then concentrated to dryness to give (5R,8R,9S,10S,13S,14S,17S)-17-acetyl-10,13-dimethyltetradecahydro-1H-cyclopenta[a]phenanthren-3(2H)-one (A24, 29 g, 96%) as white solid which was used directly in the next step without purification.

Step 2. Synthesis of A25. To a solution of compound 2,6-di-tert-butyl-4-methylphenol (A24, 120 g, 549 mmol) in toluene (400 mL) was added a solution of AlMe₃ (137 mL 274 mmol, 2 M) at room temperature, at which time the methane gas was evolved immediately. The resulting mixture was stirred at room temperature for 1 h. A solution of (5R,8R,9S,10S,13S,14S,17S)-17-acetyl-10,13-dimethyltetradecahydro-1H-cyclopenta[a]phenanthren-3(2H)-one A24 (29.0 g, 91.7 mmol) in toluene (300 mL) was added at −78° C. under nitrogen. Then the reaction mixture was stirred for 30 min, then MeMgBr (91.3 mL, 274 mmol, 3.0 M) was added dropwise at −78° C. The reaction mixture was stirred at this temperature for 3 h. The reaction mixture was quenched with saturated aqueous $NH_4C$ solution (300 mL) at −0.78° C. The suspension was filtered and the filter cake was washed with EtOAc (300 mL×3), The combined organic phases were dried over $Na_2SO_4$, evaporated to afford crude product. The crude product was purified by column chromatography on silica gel (PE: EtOAc-=10:1 to 6:1) to afford 1-((3R,5R,8S,9S,10S,13S,14S,17S)-3-hydroxy-3,10,13-trimethylhexadecahydro-1H-cyclopenta[a]phenanthren-17-yl)ethanone A25 (6.0 g, 16.3%) as light yellow solid.

1H NMR (A25) (400 MHz, $CDCl_3$) δ 2.54-2.52 (m, 1H), 2.13-2.10 (m, 4H), 1.98-1.63 (m, 4H), 1.49-1.30 (m, 8H), 1.25-1.00 (m, 12H), 0.91 (s, 3H), 0.90-0.85 (m, 1H), 0.58 (s, 3H).

Step 3. Synthesis of A26. To a stirred solution of (3S, 14S,17S)-3-hydroxy-3,3,10,13-trimethylhexadecahydro-1H-cyclopenta[a]phenanthren-17-yl)ethanone A25 (6.0 g, 18.04 mmol) in MeOH (100 mL) was added HBr (0.29 g, 3.61 mmol), then $Br_2$ (1.35 mL, 27.06 mmol) was added dropwise. The mixture was stirred at room temperature for 2 hours. TLC showed the reaction was complete. The mixture was quenched by a saturated aqueous $NaHCO_3$ and adjusted to pH=7. Then water (200 mL) was added and the solid was precipitated. The solid was filtered and washed with petroleum (100 mL×2). The solid was collected and dried by reduced pressure. 2-bromo-1-((3R,5R,8R,9S,10S,13S,14S 17S)-3-hydroxy-3,10,13-trimethylhexadecahydro-1H-cyclopenta[a]phenanthren-17-yl)ethanone A26 (6.0 g) was obtained as white solid.

$^1$H NMR (A26) (400 MHz, $CDCl_3$) δ 3.94-3.87 (m, 2H), 2.83-2.79 (m, 1H), 2.18-2.16 (m, 1H), 1.94-1.71 (m, 6H), 1.57-1.47 (m, 8H), 1.26-1.10 (m, 11H), 0.93 (s, 3H), 0.61 (s, 3H).

Step 4. Synthesis of 10. To a mixture of 2-bromo-1-((3R, 5R,8R,9S,10S,13S,14S,17S)-3-hydroxy-3,10,13-trimethylhexadecahydro-1H-cyclopenta[a]phenanthren-17-yl)ethanone (A26, 100 mg, 0.24 mmol) and $K_2CO_3$ (70 mg, 0.48 mmol) in 3 mL Acetone was added 1H-pyrazole-4-carbonitrile (30 mg, 0.36 mmol) at 25° C. The reaction mixture was stirred at the 40° C. for 3 h. The reaction mixture was filtered and the filtrate was concentrated in vacuum. The residue was purified by silica gel column (PE/EtOAc=5/1 to 2/1) to give the 1-(2-((3R,5R,8R,9S,10S,13S,14S,17S)-3-hydroxy-3,10, 13-trimethylhexadecahydro-1H-cyclopenta[a]phenanthren-17-yl)-2-oxoethyl)-1H-pyrazole-4-carbonitrile (10, 25.5 mg, 25%) as white solid.

$^1$H NMR (10) (400 MHz, $CDCl_3$) δ 7.85 (s, 1H), 7.80 (s, 1H), 5.03-4.87 (m, 2H), 2.25-2.15 (m, 1H), 2.10-1.80 (m, 3H), 1.75-1.71 (m, 3H), 1.54-1.35 (m, 8H), 1.33-0.95 (m, 10H), 0.94 (s, 3H), 0.64 (s, 3H). LCMS $t_R$=1.268 min in 2 min chromatography, 10-80AB, MS ESI calcd. For $C_{26}H_{37}N_3O_2Na$ [M+Na]$^+$ 446, found 446.

Example 7

Synthesis of 11 and 12

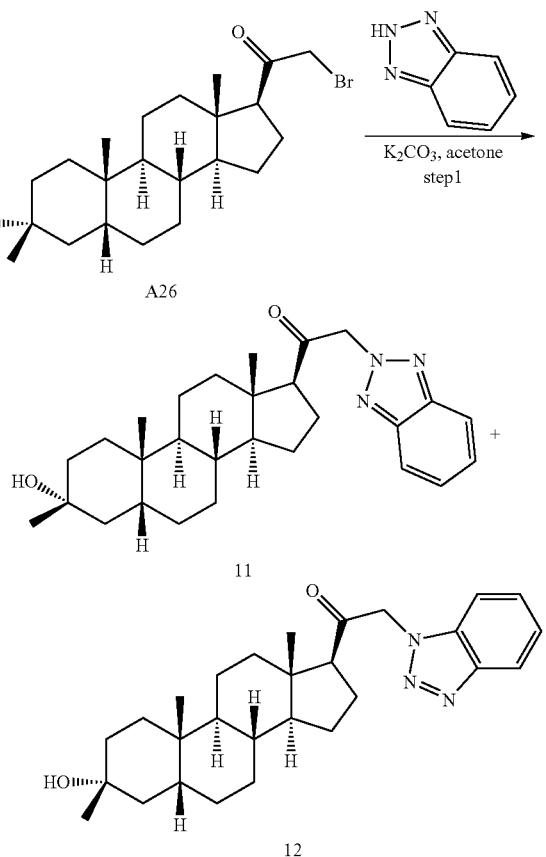

The title compounds were prepared according to Example 5, step 4.

$^1$H NMR (11): (400 MHz, $CDCl_3$) δ 7.89-7.86 (dd, J, =2.8 Hz, $J_2$=6.4 Hz, 2H), 5.52-5.47 (m, 2H), 2.66-2.62 (t, J=8.8 Hz, 1H), 2.21-2.16 (m, 2H), 1.95-1.73 (m, 7H), 1.55-1.27 (m, 14H), 1.22-1.08 (m, 2H), 0.94 (s, 3H), 0.73 (s, 3H). LCMS $t_R$=1.512 min in 2 min chromatography, 10-80AB, MS ESI calcd. For $C_{28}H_{40}N_3O_2$ [M+H]$^+$ 450, found 432 ([M+H−18].

$^1$H NMR (12): (400 MHz, $CDCl_3$) δ 8.09-8.07 (d, J=8.4 Hz, 1H), 7.51-7.40 (m, 1H), 7.38-7.32 (m, 2H), 5.41-5.40 (m, 2H), 2.72-2.70 (m, 1H), 2.20-2.17 (m, 2H), 1.96-1.74 (m, 7H), 1.45-1.23 (m, 14H), 1.22-1.08 (m, 2H), 0.96 (s, 3H), 0.71 (s, 3H). LCMS $R_r$=1.438 min in 2 min chromatography, 10-80AB, MS ESI calcd. For $C_{28}H_{40}N_3O_2$ [M+H]$^+$ 450, found 450.

Example 8

Synthesis of 13

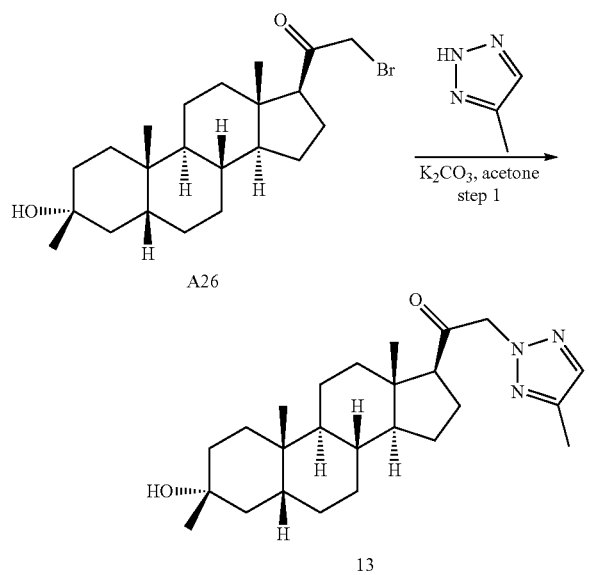

The title compounds were prepared according to Example 5, step 4.

$^1$H NMR (13): (400 MHz, CDCl$_3$) δ 7.41 (s, 1H), 5.13-5.12 (m, 2H), 2.57-2.52 (m, 1H), 2.32 (s, 3H), 2.25-2.15 (m, 1H), 2.10-2.00 (m, 1H), 1.94-1.59 (m, 5H), 1.52-1.40 (m, 9H), 1.26-1.06 (m, 10H), 0.94 (s, 3H), 0.67 (s, 3H). LCMS R$_t$=0.93 min in 1.5 min chromatography, 5-95AB, MS ESI calcd. For C$_{25}$H$_{40}$N$_3$O$_2$ [M+H]$^+$ 414, found 414.

Example 9

Synthesis of 14, 15, and 16

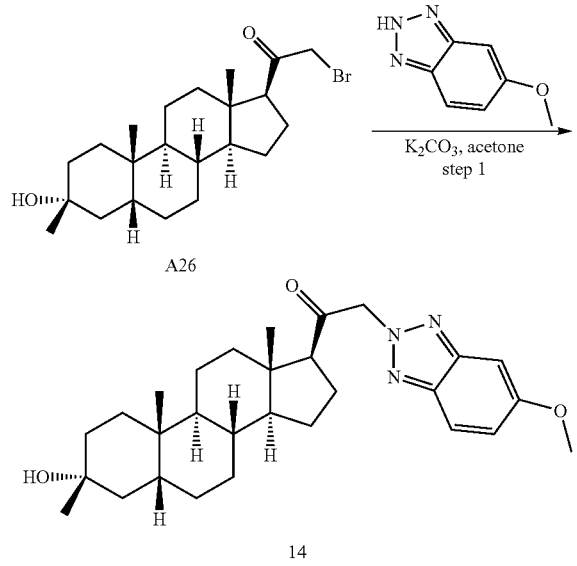

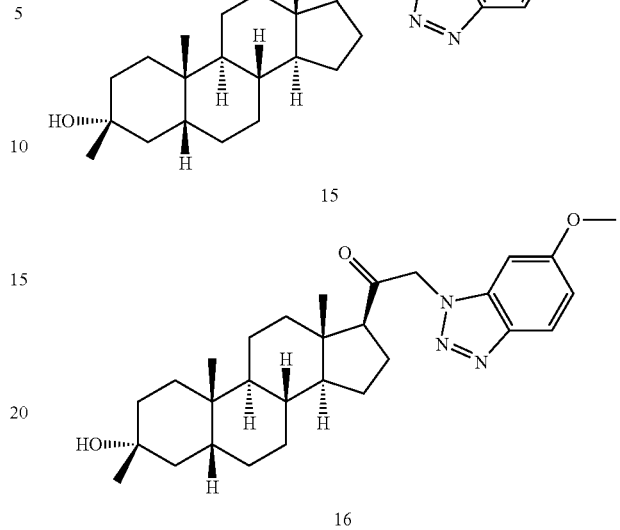

The title compounds were prepared according to Example 5, step 4.

$^1$H NMR (14): (400 MHz, CDCl$_3$) δ 7.73-7.71 (m, 1H), 7.07-7.05 (m, 2H), 5.43-5.42 (m, 2H), 3.87 (s, 3H), 2.64-2.62 (m, 1H), 2.25-2.12 (m, 2H), 1.95-1.63 (m, 5H), 1.53-1.48 (m, 8H), 1.44-1.26 (s, 8H), 1.24-1.06 (m, 2H), 0.95 (s, 3H), 0.71 (s, 3H). LCMS R$_t$=0.993 min in 1.5 min chromatography, 5-95AB, MS ESI calcd. For C$_{29}$H$_{42}$N$_3$O$_3$ [M+H]$^+$ 480, found 480.

$^1$H NMR (15): (400 MHz, CDCl$_3$) δ 7.38 (s, 1H), 7.21-7.19 (m, 1H), 7.15-7.13 (m, 1H), 5.36-5.35 (m, 2H), 3.88 (s, 3H), 2.67-2.65 (m, 1H), 2.25-2.10 (m, 2H), 1.95-1.63 (m, 5H), 1.52-1.44 (m, 8H), 1.43-1.26 (m, 8H), 1.22-1.08 (m, 2H), 0.95 (s, 3H), 0.69 (s, 3H). LCMS R$_t$=0.944 min in 1.5 min chromatography, 5-95 AB, MS ESI calcd. For C$_{29}$H$_{42}$N$_3$O$_3$ [M+H]$^+$ 480, found 480.

$^1$H NMR (16): (400 MHz, CDCl$_3$) δ 7.92-7.90 (d, J=9.6 Hz, 1H), 7.02-6.99 (dd, J=2.8 Hz, J$_2$=9.6 Hz, 1H), 5.38-5.27 (m, 2H), 3.88 (s, 3H), 2.70-2.68 (m, 1H), 2.25-2.10 (m, 2H), 1.95-1.62 (m, 5H), 1.54-1.45 (m, 9H), 1.43-1.26 (m, 8H), 1.22-1.08 (m, 2H), 0.95 (s, 3H), 0.71 (s, 3H). LCMS R$_t$=0.939 min in 1.5 min chromatography, 5-95 AB, MS ESI calcd. For C$_{29}$H$_{42}$N$_3$O$_3$ [M+H]$^+$ 480, found 480.

Example 10

Synthesis of 17 and 18

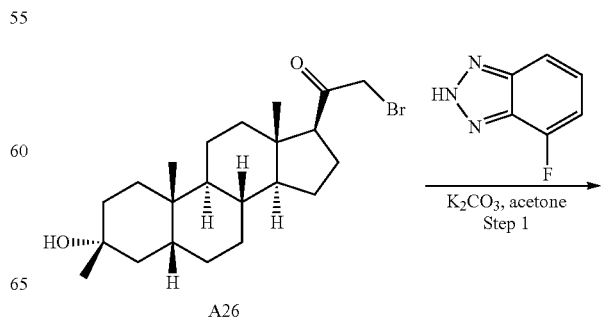

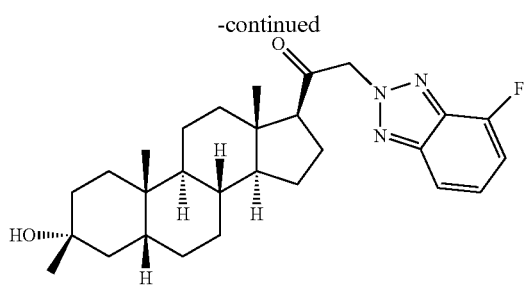

17

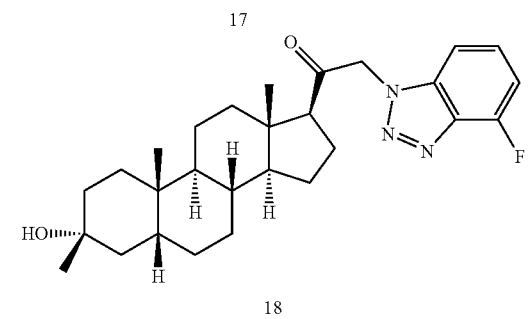

18

The title compounds were prepared according to Example 5, step 4.

¹HNMR (17): (400 MHz, CDCl₃) δ 7.67 (d, J=9.2 Hz, 1H), 7.35-7.27 (m, 1H), 7.06-7.02 (m, 1H), 5.59-5.50 (m, 2H), 2.67 (d, J=4 Hz, 1H), 2.22-1.74 (m, 8H), 1.59-1.44 (m, 8H), 1.27-1.12 (m, 10H), 0.97 (s, 3H), 0.74 (s, 3H). LCMS R$_t$=0.992 min in 1.5 min chromatography, 5-95AB, MS ESI calcd. For C$_{28}$H$_{39}$FN$_3$O$_2$[M+H]⁺ 468, found 450[M+H−18].

¹HNMR (18): (400 MHz, CDCl₃) δ 7.45-7.41 (m, 1H), 7.10 (d, J=8 Hz, 1H) 7.04 (t, J=8 Hz, 1H), 5.47-5.37 (m, 2H), 2.70 (t, J=12 Hz, 1H), 2.21-1.74 (m, 10H), 1.56-1.44 (m, 5H), 1.27-1.09 (m, 11H), 0.96 (s, 3H), 0.70 (s, 3H). LCMS R$_t$=1.402 min in 2 min chromatography, 10-80AB, MS ESI calcd. For C$_{28}$H$_{39}$FN$_3$O$_2$[M+H]⁺ 468, found 468.

Example 11

Synthesis of 19 and 20

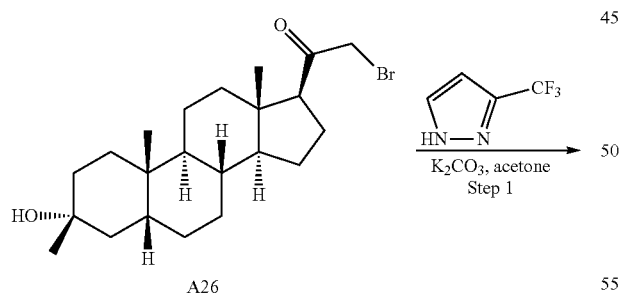

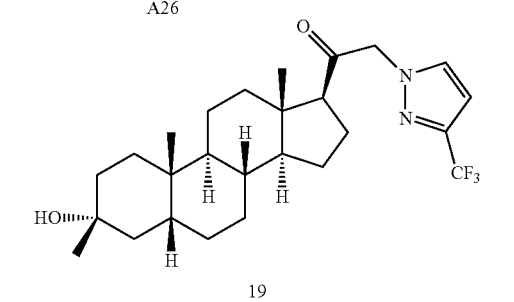

19

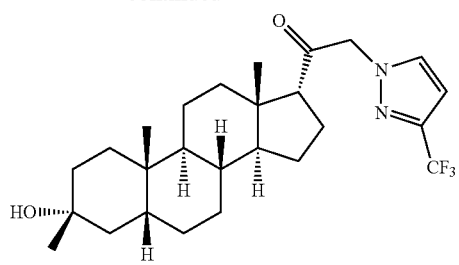

20

The title compounds were prepared according to Example 5, step 4.

¹H NMR (19): (400 MHz, CDCl₃) δ 7.46 (s, 1H), 6.58 (d, J=2 Hz, 1H), 5.02-4.91 (m, 2H), 2.59 (d, J=8 Hz, 1H), 2.06-1.72 (m, 7H), 1.59-1.42 (m, 8H), 1.27-1.07 (m, 10H), 0.95 (s, 3H), 0.66 (s, 3H). LCMS R$_t$=2.667 min in 3 min chromatography, 10-80AB, MS ESI calcd. For C$_{26}$H$_{38}$F$_3$N$_2$O$_2$[M+H]⁺ 467, found 449 [M+H−18].

¹H NMR (20): (400 MHz, CDCl₃) δ 7.49 (s, 1H), 6.60 (d, J=1.6 Hz, 1H), 5.05-4.91 (m, 2H), 2.75 (t, J=8 Hz, 1H), 1.88-1.80 (m, 8H), 1.57-1.41 (m, 8H), 1.38-0.95 (m, 10H), 0.92 (d, J=8 Hz, 6H). LCMS R$_t$=2.687 min in 3 min chromatography, 10-80AB, MS ESI calcd. For C$_{26}$H$_{38}$F$_3$N$_2$O$_2$[M+H]⁺ 467, found 449 [M+H−18].

Example 12

Synthesis of 21, 22, and 23

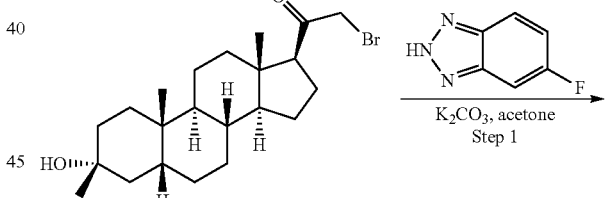

A26

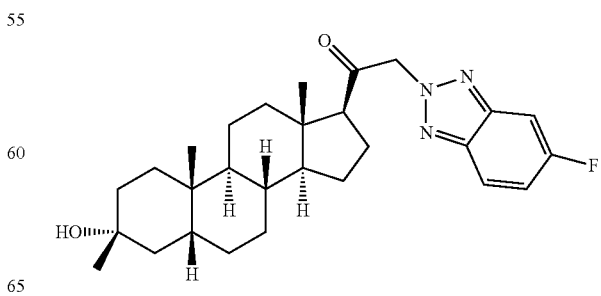

21

-continued

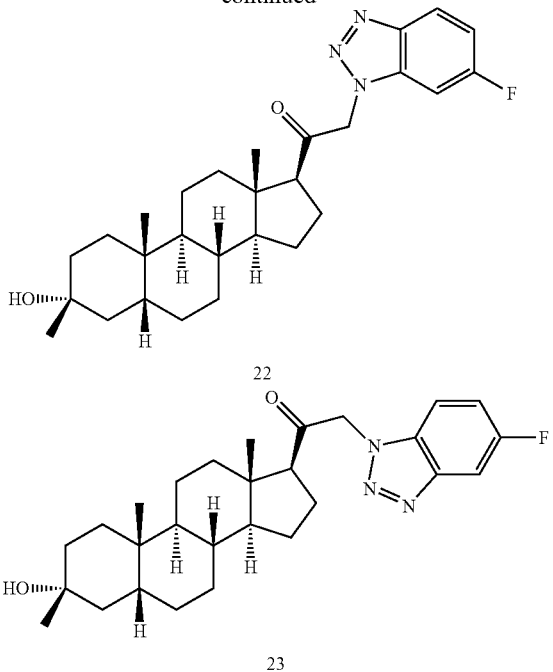

22

23

The title compounds were prepared according to Example 5, step 4.

$^1$H NMR (21): (400 MHz, CDCl$_3$) δ 7.86-7.84 (m, 1H), 7.46 (d, J=8 Hz, 1H), 7.20 (t, J=20 Hz, 1H) 5.49-5.44 (m, 2H), 2.64 (t, J=16 Hz, 1H), 2.21-1.74 (m, 8H), 1.56-1.43 (m, 7H), 1.33-0.96 (m, 10H), 0.83 (s, 3H), 0.73 (s, 3H). LCMS R$_t$=2.712 min in 3 min chromatography, 10-80AB, MS ESI calcd. For C$_{28}$H$_{39}$FN$_3$O$_2$[M+H]$^+$ 468, found 450 ([M+H]$^+$−18).

$^1$H NMR (22): δ 8.05-8.02 (m, 1H), 7.16 (t, J=9.2 Hz, 1H), 6.99-6.96 (m, 1H), 5.43-5.31 (m, 2H), 2.72 (d, J=8.4 Hz, 1H), 2.17-1.97 (m, 2H), 1.78-1.57 (m, 6H), 1.47-1.42 (m, 6H), 1.28-1.08 (m, 10H), 0.97 (s, 3H), 0.71 (s, 3H). LCMS R$_t$=2.589 min in 3 min chromatography, 10-80AB, MS ESI calcd. For C$_{28}$H$_{39}$FN$_3$O$_2$[M+H]$^+$ 468, found 468.

$^1$H NMR (23): (400 MHz, CDCl$_3$) δ 7.70 (d, J=8 Hz, 1H), 7.28 (t, J=12 Hz, 2H), 5.46-5.35 (m, 2H), 2.71 (d, J=8 Hz, 1H), 2.16-1.75 (m, 7H), 1.58-1.43 (m, 8H), 1.27-1.08 (m, 9H), 0.96 (s, 3H), 0.70 (s, 3H). LCMS R$_t$=2.569 min in 3 min chromatography, 10-80AB, MS ESI calcd. For C$_{28}$H$_{39}$FN$_3$O$_2$[M+H]$^+$ 468, found 468.

Example 13

Synthesis of 24 and 25

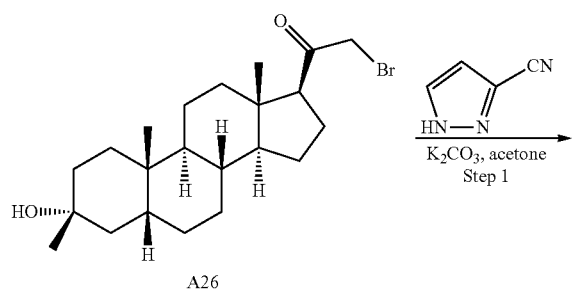

A26

-continued

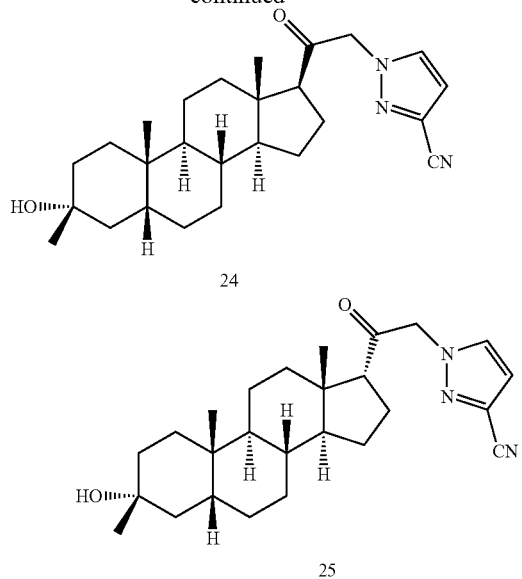

24

25

The title compounds were prepared according to Example 5, step 4.

$^1$H NMR (24): (400 MHz, CDCl$_3$) δ 7.48 (d, J=1.6 Hz, 1H), 6.72 (d, J=2.4 Hz, 1H), 5.04-4.89 (m, 2H), 2.60 (d, J=4 Hz, 1H), 2.58-1.72 (m, 8H), 1.58-1.42 (m, 8H), 1.31-1.07 (m, 10H), 0.95 (s, 3H), 0.65 (s, 3H). LCMS R$_t$=2.385 min in 3 min chromatography, 10-80AB, MS ESI calcd. For: C$_{26}$H$_{38}$N$_3$O$_2$ [M+H]$^+$ 424, found 406 [M+H−18]$^+$.

$^1$H NMR (25): (400 MHz, CDCl$_3$) δ 7.50 (s, 1H), 6.72 (d, J=2.4 Hz, 1H), 6.75 (s, 1H), 5.09-4.89 (m, 2H), 2.76 (d, J=4 Hz, 1H), 1.88-1.81 (m, 8H), 1.57-1.41 (m, 8H), 1.38-1.20 (m, 10H), 1.01 (d, J=48 Hz, 6H). LCMS R$_t$=2.415 min in 3 min chromatography, 10-80AB, MS ESI calcd. For: C$_{26}$H$_{37}$N$_3$O$_2$[M+H]$^+$ 424, found 446 [M+23]$^+$.

Example 14

Synthesis of 26 and 27

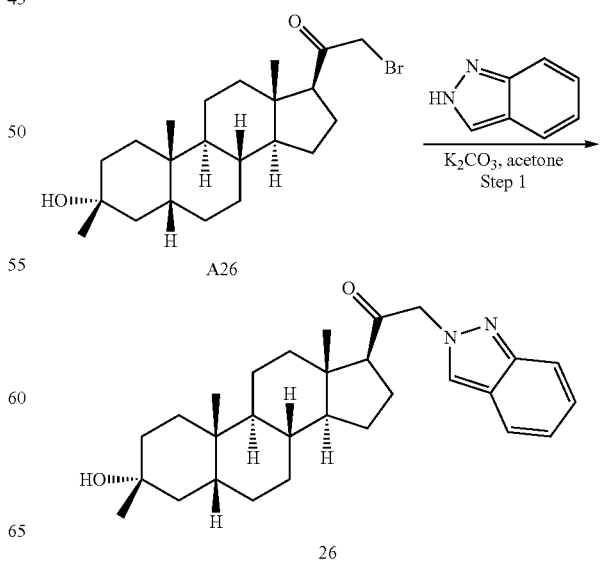

A26

26

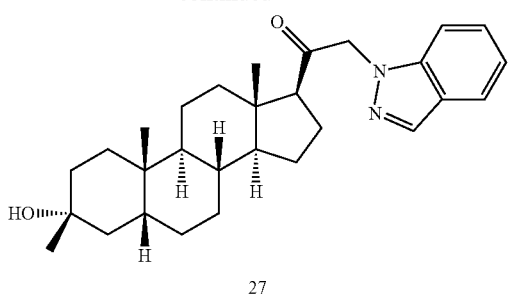

27

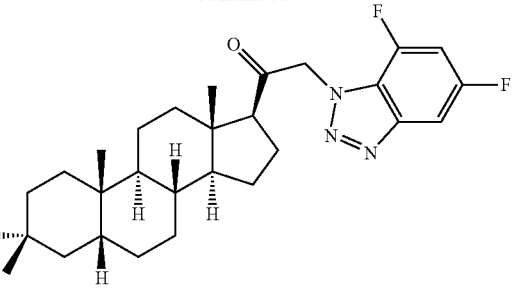

29

The title compounds were prepared according to Example 5, step 4.

¹H NMR (26): (400 MHz, CDCl₃) δ 7.93 (s, 1H), 7.68 (t, J=20 Hz, 2H), 7.29 (d, J=8 Hz, 1H), 7.08 (t, J=16 Hz, 2H), 5.25-5.14 (m, 2H), 2.63 (d, J=8 Hz, 1H), 2.20-1.72 (m, 9H), 1.57-1.42 (m, 6H), 1.26-1.07 (m, 10H), 0.95 (s, 3H), 0.69 (s, 3H). LCMS R$_t$=1.194 min in 2 min chromatography, 30-90AB, MS ESI calcd. For C$_{29}$H$_{41}$N$_2$O$_2$ [M+H]$^+$ 449, found 449.

¹HNMR (27): (400 MHz, CDCl₃) δ 8.05 (s, 1H), 7.75 (t, J=8 Hz, 1H), 7.37 (d, J=8 Hz, 1H), 7.22-7.14 (m, 2H), 5.14 (m, 2H), 2.61 (t, J=16 Hz, 1H), 2.22-1.69 (m, 9H), 1.55-1.42 (m, 7H), 1.26-1.06 (m, 10H), 0.95 (s, 3H), 0.70 (s, 3H). LCMS R$_t$=1.213 min in 2 min chromatography, 30-90AB, MS ESI calcd. For C$_{29}$H$_{41}$N$_2$O$_2$ [M+H]$^+$ 449, found 449.

Example 15

Synthesis of 28, 29, and 30

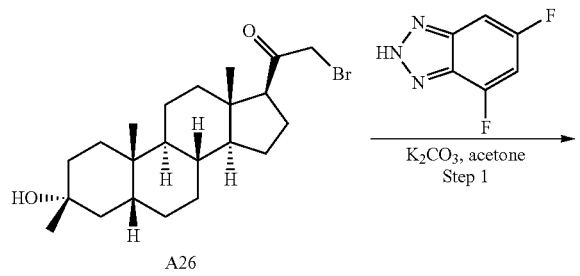

30

The title compounds were prepared according to Example 5, step 4.

¹HNMR (28): (400 MHz, CDCl₃) δ 7.30 (d, J=8 Hz, 1H), 6.91 (t, J=20 Hz, 1H), 5.55-5.46 (m, 2H), 2.65 (t, J=16 Hz, 1H), 2.20-1.74 (m, 8H), 1.60-1.43 (m, 8H), 1.27-1.08 (m, 10H), 0.96 (s, 3H), 0.72 (s, 3H). LCMS R$_t$=2.662 min in 3 min chromatography, 10-80AB, MS ESI calcd. For Chemical Formula: C$_{28}$H$_{37}$F$_2$N$_3$O$_2$[M+H]$^+$ 468, found 468.

¹H NMR (29): (400 MHz, CDCl₃) δ 7.54 (d, J=8 Hz, 2H), 7.00 (t, J=8 Hz, 1H), 5.52-5.37 (m, 2H), 2.73-2.63 (m, 1H), 2.12-1.75 (m, 9H), 1.59-1.45 (m, 6H), 1.36-1.10 (m, 10H), 0.98 (s, 3H), 0.71 (s, 3H). LCMS R$_t$=2.576 min in 3 min chromatography, 10-80AB, MS ESI calcd. For C$_{28}$H$_{37}$F$_2$N$_3$O$_2$[M+H]$^+$ 468, found 468.

¹HNMR (30): (400 MHz, CDCl₃) δ 6.89-6.79 (m, 2H), 5.43-5.31 (m, 2H), 2.70 (t, J=16 Hz, 1H), 2.22-1.74 (m, 8H), 1.57-1.44 (m, 8H), 1.35-1.08 (m, 10H), 0.97 (s, 3H), 0.70 (s, 3H). LCMS R$_t$=2.551 min in 3 min chromatography, 10-80AB, MS ESI calcd. For C$_{28}$H$_{37}$F$_2$N$_3$O$_2$[M+H]$^+$ 468, found 468.

Example 16

Synthesis of 31 and 32

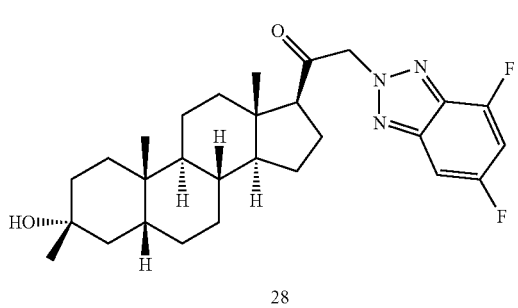

28

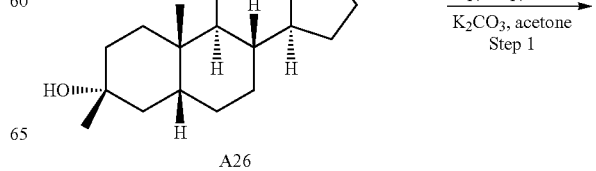

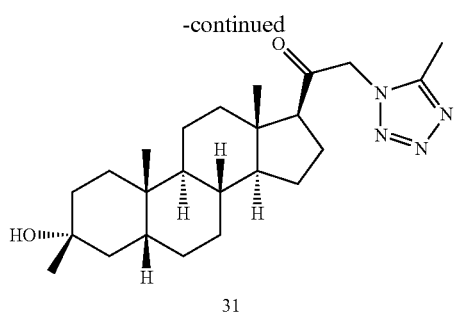

31

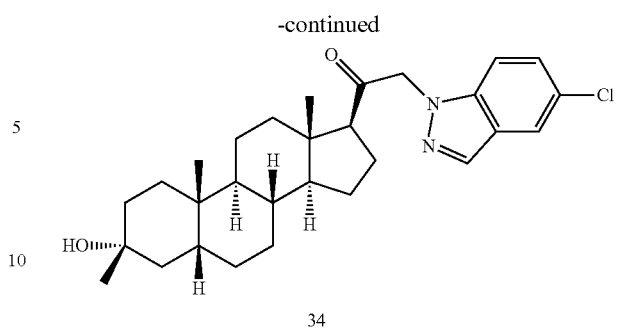

34

The title compounds were prepared according to Example 5, step 4.

¹H NMR (33): (400 MHz, DMSO-d6) δ 8.32 (s, 1H), 7.86 (s, 1H), 7.64 (d, J=8 Hz, 1H), 7.23 (d, J=8 Hz, 1H), 5.55-5.34 (m, 2H), 4.28 (s, 1H), 2.51 (s, 1H), 1.86-1.47 (m, 7H), 1.40-1.38 (m, 6H), 1.27-1.02 (m, 9H), 0.93 (s, 3H), 0.61 (s, 3H). LCMS Rt=1.444 min in 2 min chromatography, 10-80AB, MS ESI calcd. For $C_{29}H_{39}ClN_2O_2[M+H]^+$ 483, found 483.

32

The title compounds were prepared according to Example 5, step 4.

¹H NMR (31): (400 MHz, CDCl₃) δ 5.16-5.02 (m, 2H), 2.66-2.64 (m, 1H), 2.46 (s, 3H), 2.16-1.76 (m, 1H), 1.73-1.55 (m, 7H), 1.51-1.43 (m, 8H), 1.33-1.08 (m, 10H), 0.96 (s, 3H), 0.66 (s, 3H). LCMS $R_t$=1.070 min in 2 min chromatography, 30-90AB, MS ESI calcd. For $C_{24}H_{39}N_4O_2$ $[M+H]^+$ 415, found 415.

¹H NMR (34): (400 MHz, CDCl3) δ 7.98 (s, 1H), 7.86 (s, 1H), 7.71 (d, J=1.6 Hz, 1H), 7.13 (d, J=0.8 Hz, 1H), 5.16-5.07 (m, 2H), 2.62 (d, J=8.8 Hz, 1H), 221-1.95 (m, 2H), 1.77-1.52 (m, 6H), 1.49-1.27 (m, 8H), 1.25-1.08 (m, 8H), 0.97 (s, 3H), 0.69 (s, 3H). LCMS Rt=1.476 min in 2 min chromatography, 10-80AB, MS ESI calcd. For $C_{29}H_{39}ClN_2O_2[M+H]^+$ 483, found 483.

¹H NMR (32): (400 MHz, CDCl₃) δ 5.34 (s, 2H), 2.62-2.56 (m, 4H), 2.17-2.06 (m, 1H), 1.96-1.52 (m, 8H), 1.49-1.27 (m, 7H), 1.23-1.09 (m, 10H), 0.95 (s, 3H), 0.69 (s, 3H). LCMS $R_t$=2.447 min in 3 min chromatography, 10-80AB, MS ESI calcd. For $C_{24}H_{39}N_4O_2$ $[M+H]^+$ 415, found 415.

Example 18

Synthesis of 35, 36, and 37

Example 17

Synthesis of 33 and 34

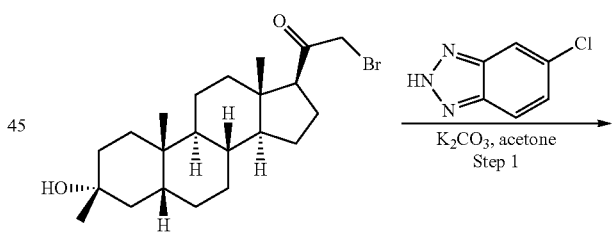

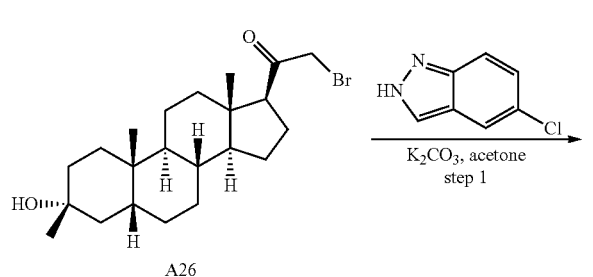

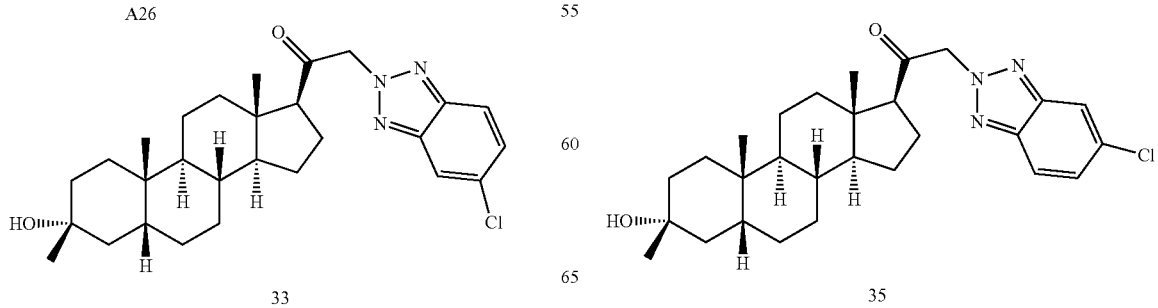

119

-continued

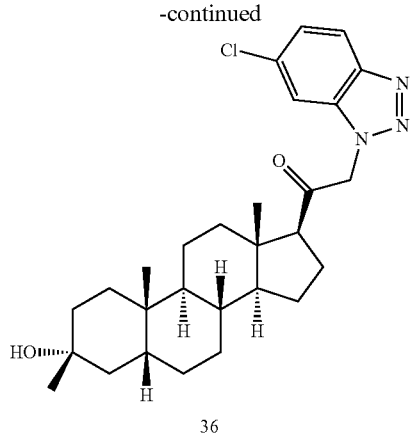

36

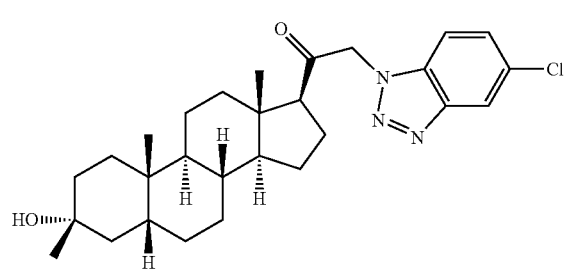

37

The title compounds were prepared according to Example 5, step 4.

¹H NMR (35): (400 MHz, CDCl₃) δ 7.87 (d, J=1.6 Hz, 1H), 7.82 (d, J=4.4 Hz, 1H), 7.36-7.33 (m, 1H), 5.54-5.45 (m, 2H), 2.65 (d, J=4 Hz, 1H), 2.23-2.00 (m, 2H), 1.96-1.58 (m, 5H), 1.51-1.42 (m, 9H), 1.27-1.08 (m, 10H), 0.96 (s, 3H), 0.72 (s, 3H). LCMS $R_t$=1.311 min in 2 min chromatography, 30-90AB, MS ESI calcd. For $C_{28}H_{38}ClN_3O_2$[M+H]⁺ 484, found [M+H−18]⁺ 466.

¹H NMR (36): (400 MHz, CDCl₃) δ 8.00 (d, J=4.6 Hz, 1H), 7.34 (d, J=6.4 Hz, 2H), 5.44-5.31 (m, 2H), 2.71 (t, J=8.8 Hz, 1H), 2.21-2.14 (m, 2H), 1.97-1.74 (m, 6H), 1.59-1.52 (m, 9H), 1.44-1.09 (m, 10H), 0.97 (s, 3H), 0.71 (s, 3H). LCMS $R_t$=1.230 min in 2 min chromatography, 30-90AB, MS ESI calcd. For $C_{28}H_{38}ClN_3O_2$[M+H]⁺ 484, found 484.

¹H NMR (37): (400 MHz, CDCl₃) δ 8.06 (s, 1H), 7.44 (d, J=8 Hz, 1H), 7.30 (d, J=20 Hz, 1H) 5.45-5.34 (m, 2H), 2.70 (d, J=4 Hz, 1H), 2.19-2.17 (m, 2H), 1.96-1.74 (m, 6H), 1.56-1.51 (m, 9H), 1.46-1.09 (m, 10H), 0.96 (s, 3H), 0.70 (s, 3H). LCMS $R_t$=1.261 min in 2 min chromatography, 30-90AB, MS ESI calcd. For $C_{28}H_{38}ClN_3O_2$[M+H]⁺ 484, found 484.

120

Example 19

Synthesis of 38 and 39

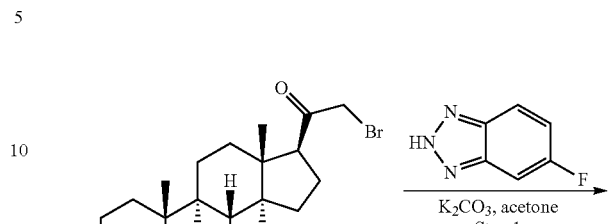

A26

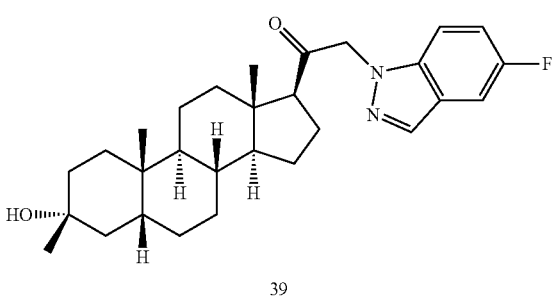

38

39

The title compounds were prepared according to Example 5, step 4.

¹HNMR (38): (400 MHz, CDCl₃) δ 7.89 (s, 1H), 7.68-7.65 (m, 1H), 7.25 (t, J=2.4 Hz, 1H), 7.09 (t, J=2.4 Hz, 1H), 5.24-5.12 (m, 2H), 2.64 (t, J=8.4, 1H), 2.20-1.54 (m, 8H), 1.48-1.43 (m, 8H), 1.27-1.08 (m, 10H), 0.95 (s, 3H), 0.69 (s, 3H). LCMS $R_t$=1.145 min in 2 min chromatography, 30-90AB, MS ESI calcd. For $C_{30}H_{41}FN_2O_2$[M+H]⁺ 467, found 467.

¹HNMR (39): (400 MHz, CDCl₃) δ 7.99 (s, 1H), 7.35 (d, J=9.2 Hz, 1H), 7.14 (d, J=6 Hz, 1H), 5.12 (m, 2H), 2.61 (t, J=8.8, 1H), 2.20-1.95 (m, 2H), 1.72-1.53 (m, 7H), 1.43-1.10 (m, 18H), 0.95 (s, 3H), 0.69 (s, 3H). LCMS $R_t$=1.117 min in 2 min chromatography, 30-90AB, MS ESI calcd. For $C_{29}H_{39}FN_2O_2$[M+H]⁺ 467, found 467.

Example 20

Synthesis of 40

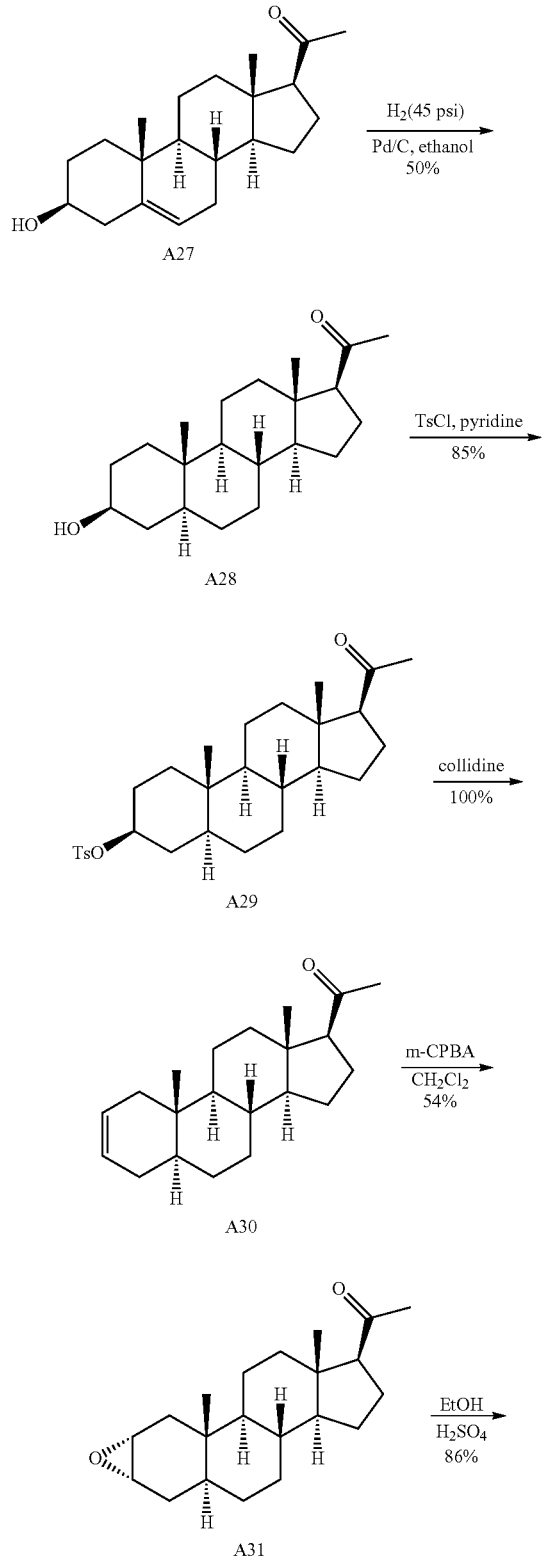

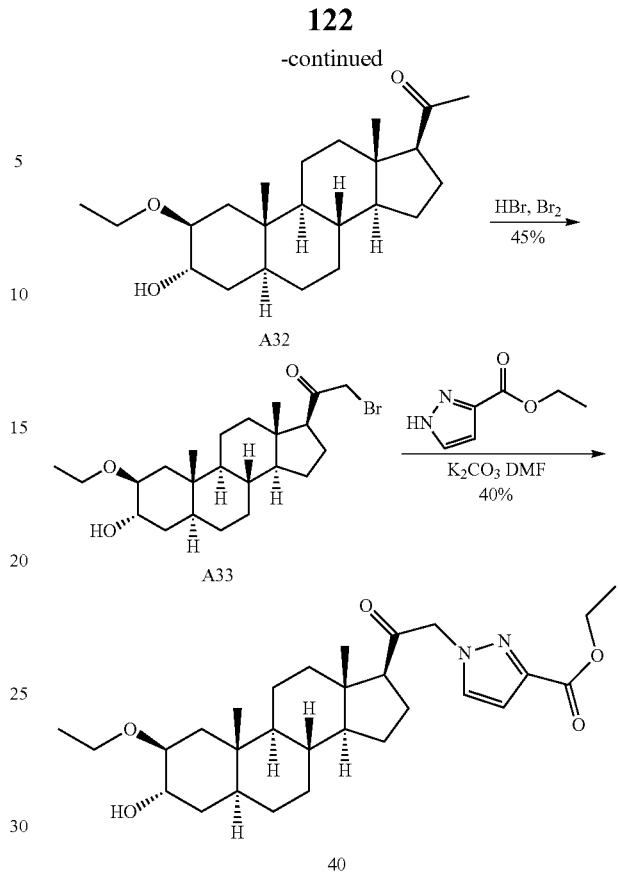

Step 1. Synthesis of A28. To a solution of A27 (15 g, 47 mmol) in EtOH (150 mL) was added Pd/C (1.5 g, 10%), The mixture was stirred at 40° C. for 12 hours under $H_2$ (45 psi). The mixture was filtered to give the organic layer and concentrated to give A28 (7.5 g) as a white solid.

$^1$H NMR (A28): (400 MHz, CDCl3) δ 3.62-3.52 (m, 1H), 2.57-2.51 (m, 1H), 2.20-2.12 (m, 4H), 2.05-1.98 (m, 1H), 1.87-1.78 (m, 1H), 1.75-1.58 (m, 6H), 1.45-1.09 (m, 11H), 1.03-0.89 (m, 2H), 0.81 (s, 3H), 0.71-0.63 (m, 1H), 0.60 (s, 3H).

Step 2. Synthesis of A29. To a solution of A28 (7.5 g, 23.6 mmol) in dry pyridine (70 mL) was added TsCl (6.79 g, 35.4 mmol) in portions. The mixture was stirred at 40° C. for 6 hours. Water was added slowly, then the white solid was precipitated. The white solid was filtered, and washed with HCl (1 M) (200 mL*3), then with water (200 mL*3). The filtrate was dried by reduced pressure to give A29 (9.5 g) as a yellow solid.

Step 3. Synthesis of A30. To a stirred solution of collidine (100 mL) was added A29 (9.5 g, 20 mmol). The mixture was stirred at 130° C. for 4 hours. After TLC showed the starting material was consumed, the mixture was treated with $H_2SO_4$ (500 mL, 10%) and the solid was precipitated. The solid was filtrated and the residue was washed with $H_2SO_4$ (200 mL*3), concentrated to give A30 (6 g) as a yellow solid.

Step 4. Synthesis of A31. To a solution of A30 (6 g, 20 mmol) in $CH_2Cl_2$ (100 mL) was added m-CPBA (6.8 g, 39.6 mmol) in portions at 0° C. The mixture was stirred at 0° C. for 1 hour, then at 15° C. for 12 hours. The solution was washed successively with a saturated aqueous solution of $Na_2S_2O_3$ (50 mL) and a saturated aqueous solution of $Na_2CO_3$ (200 mL), dried over $NaSO_4$, filtered and evaporated to dryness. Purification by flash by column chromatography on silica gel (eluent:petroleum ether:ethyl acetate=50:1) to give the A31 (0.92 g) and mixture (2.5 g) as white solid.

$^1$H NMR (A31): (400 MHz, CDCl3) δ 3.19-3.11 (m, 2H), 2.58-2.50 (m, 1H), 2.11 (s, 3H), 2.08-1.82 (m, 3H), 1.70-1.08 (m, 17H), 0.90-0.82 (m, 1H), 0.78 (s, 3H), 0.72-0.63 (m, 1H), 0.59 (s, 3H).

Step 5. Synthesis of A32. A solution of the A31 (1 g, 3.16 mmol) in EtOH (20 mL) was added 12 drops of fuming sulfuric acid. The mixture was stirred at 19° C. for 3 h, the reaction mixture was quenched by aqueous NaHCO$_3$ and evaporated to low volume. The mixture was treated with water and extracted with EtOAc (50 mL*3). The organic layer was washed with brine, dried over Na$_2$SO$_4$, filtered and evaporated to give the A32 (0.95 g) as white solid.

Step 6. Synthesis of A33. To a solution of A32 (0.95 g, 2.6 mmol) in MeOH (50 mL) was added aq. HBr (0.2 mL, 48% in water) and Br$_2$ (0.5 g, 3.14 mmol). The mixture was stirred at 19° C. for 2 h. Then the mixture was quenched with saturated aqueous NH$_4$Cl (20 mL). The mixture was concentrated, added water (50 mL) and extracted with EtOAc (50 mL*3). The organic phase was dried over Na$_2$SO$_4$ and concentrated to give crude product. The residue was purified by column chromatography (petroleum ether: ethyl acetate=13:1) to give the A33 (500 mg) as a white solid.

$^1$H NMR: (400 MHz, CDCl3) δ 3.95-3.88 (m, 3H), 3.60-3.52 (m, 1H), 3.45-3.37 (m, 2H), 2.83-2.78 (m, 1H), 2.23-2.13 (m, 1H), 1.94-1.78 (m, 3H), 1.80-1.61 (m, 4H), 1.44-1.12 (m, 14H), 0.96-0.89 (m, 4H), 0.80-0.70 (m, 1H), 0.62 (s, 3H).

Step 7. Synthesis of 40. To a solution of K$_2$CO$_3$ (94 mg, 0.66 mmol) in DMF (8 mL) was added ethyl 1H-pyrazole-3-carboxylate (158 mg, 1.12 mmol). The mixture was stirred at 20° C. for 0.5 h under N$_2$. Then to mixture was added a solution of A33 (100 mg, 0.22 mmol) in DMF (4 mL), and stirred at 20° C. for 3 h. The mixture was diluted with EtOAc (50 mL), washed with brine (50 mL*3) and the organic layer was dried over anhydrous Na$_2$SO$_4$, and then concentrated to give crude product. It was purification by column chromatography (petroleum ether: ethyl acetate=4:1) to give the 40 (45 mg) as a yellow solid.

$^1$H NMR (40): (400 MHz, CDCl3) δ 7.44 (d, J=2 Hz, 1H), 6.87 (d, J=2.4 Hz, 1H), 5.30 (s, 3H), 4.40 (dd, J=7.6 Hz, J=14.8 Hz, 2H), 3.96-3.91 (m, 1H), 3.60-3.53 (m, 1H), 3.47-3.38 (m, 2H), 2.60-2.52 (m, 1H), 2.21-2.11 (m, 1H), 2.07-2.00 (m, 1H), 1.90-1.61 (m, 6H), 1.52-1.15 (m, 17H), 1.03-0.92 (m, 4H), 0.82-0.72 (m, 1H), 0.66 (s, 3H).

Example 21

Synthesis of 42

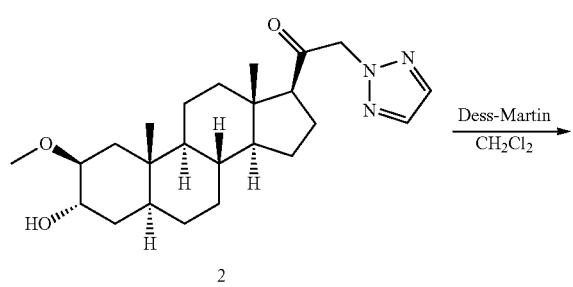

2

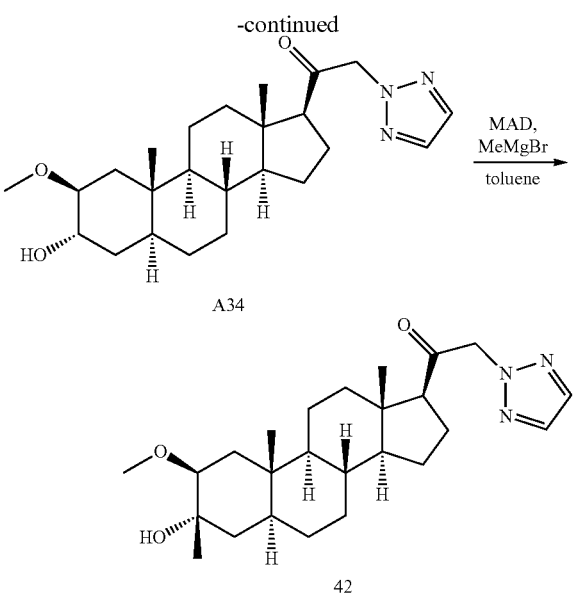

A34

42

Step 1. Synthesis of A34. To a solution of 2 (60 mg, 0.14 mmol) in CH$_2$Cl$_2$ (4 mL) was added Dess-Martin reagent (0.12 g, 0.28 mmol) at 0° C. The reaction mixture was stirred at 30° C. for 1.5 h. After TLC showed that the starting material was consumed completely, the mixture was quenched with a mixture of aqueous NaHCO$_3$ and aqueous Na$_2$S$_2$O$_3$ (5 mL). The mixture was extracted with CH$_2$Cl$_2$ (15 mL). The organic layer was washed with brine (8 mL×2), dried over Na$_2$SO$_4$ and concentrated in vacuum. The residue was purified by column chromatograph on silica gel (petroleum ether/ethyl acetate=20/1 to 10/1) to give A34 (27.2 mg) as a white solid.

$^1$H NMR (A34): (400 MHz, CDCl3) δ 7.68 (s, 2H), 5.30-5.18 (m, 2H), 3.66-3.60 (m, 1H), 3.30 (s, 3H), 2.64-2.52 (m, 2H), 2.23-2.03 (m, 4H), 1.76-1.68 (m, 4H), 1.48-1.15 (m, 9H), 1.04 (s, 3H), 0.97-0.88 (m, 1H), 0.82-0.75 (m, 1H), 0.71 (s, 3H).

Step 2. Synthesis of 42. To a stirred solution of MAD (182.2 mg, 0.56 mmol) in 5 mL of toluene was added dropwise a solution of A34 (0.1 g, 0.24 mmol) in toluene (15 mL) at −78° C. during a period of 1 h under nitrogen. After stirring at the same temperature for 0.5 h, a solution of MeMgBr (0.52 mL, 1.4 mmol) was added dropwise at −78° C. The reaction was warmed to −40° C. and stirred for 3 h. After TLC showed the reaction was complete, the reaction was poured into aqueous NH$_4$Cl and extracted with EtOAc (30 mL). The organic layer was dried over Na$_2$SO$_4$, filtered and concentrated in vacuum. The product was purified by column chromatograph on silica gel (PE/EA=15/1 to 10/1) to give 42 (40 mg) as a white solid.

$^1$H NMR (42): (400 MHz, CDCl$_3$) δ 7.68 (s, 2H), 5.31-5.16 (m, 2H), 3.31 (s, 3H), 3.06-2.98 (m, 1H), 2.59-2.55 (m, 1H), 2.22-1.95 (m, 3H), 1.45-1.11 (m, 16H), 1.04-0.94 (m, 1H), 0.92 (s, 3H), 0.83-0.874 (m, 1H), 0.70 (s, 3H).

Example 22

Synthesis of 43

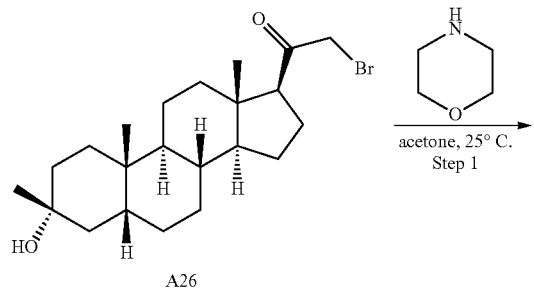

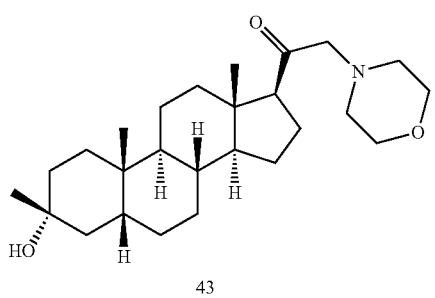

To a solution of A26 (500 mg, 1.21 mmol) in acetone (5 mL) was added morpholine (500 mg, 5.73 mmol). After stirring at 25° C. for 2 h, TLC showed the reaction was completed. To the reaction mixture was added water (2 mL), extracted with EtOAc (20 mL*2). The combined organic layer was washed with water (10 mL), dried over $Na_2SO_4$, concentrated under vacuum to give 1-((3R,5R,8R,9S,10S,13S,14S,17S)-3-hydroxy-3,10,13-trimethylhexadecahydro-1H-cyclopenta[a]phenanthren-17-yl)-2-morpholinoethanone (0.47 g) as light yellow solid.

$^1$H NMR (43): (400 MHz, $CDCl_3$) δ 3.74 (t, J=4.8 Hz, 1H), 3.21-3.11 (m, 2H), 2.62-2.45 (m, 5H), 2.22-2.10 (m, 1H), 2.00-1.05 (m, 25H), 0.93 (s, 3H), 0.60 (s, 3H). LCMS $R_t$=0.973 min in 2 min chromatography, 10-80AB, MS ESI calcd. For $C_{26}H_{44}NO_3$ $[M+H]^+$ 418, found 418.

Example 23

Synthesis of 44, 45, and 46

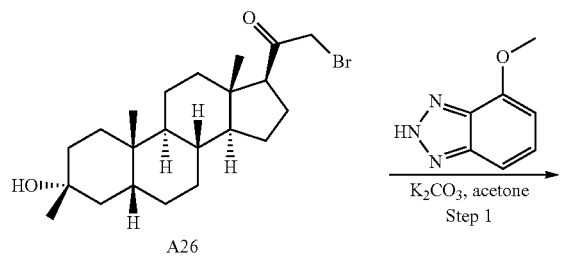

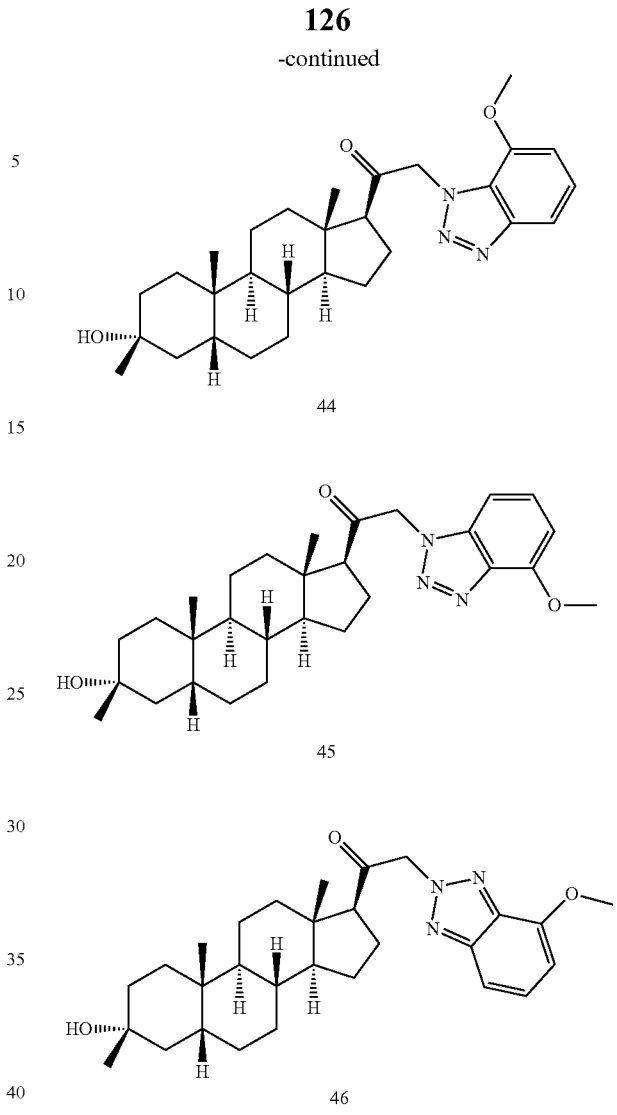

The title compounds were prepared according to Example 5, step 4.

$^1$HNMR (44): (400 MHz, $CDCl_3$) δ 7.63 (d, J=8 Hz, 1H), 7.23 (d, J=8.4 Hz, 1H), 6.76 (d, J=8 Hz, 1H), 5.58 (d, J=1.6 Hz, 2H), 3.89 (s, 3H), 2.66 (t, J=8.4 Hz, 1H), 2.19-1.97 (m, 2H), 1.78-1.57 (m, 5H), 1.46-1.41 (m, 7H), 1.27-1.09 (m, 7H), 0.97 (s, 3H), 071 (s, 3H). LCMS $R_t$=0.943 min in 1.5 min chromatography, 5-95AB, MS ESI calcd. For $C_{29}H_{41}N_3O_3$ $[M+H]^+$ 480, found 480

$^1$HNMR (45): (400 MHz, $CDCl_3$) δ 7.38 (t, J=8 Hz, 1H), 6.86 (d, J=8 Hz, 1H), 6.69 (d, J=8.4 Hz, 1H), 5.37 (s, 2H), 4.12 (s, 3H), 2.67 (t, J=8.4 Hz, 1H), 2.19-1.95 (m, 2H), 1.77-1.55 (m, 5H), 1.50-1.42 (m, 8H), 1.27-1.08 (m, 11H), 0.96 (s, 3H), 070 (s, 3H). LCMS $R_t$=1.113 min in 2 min chromatography, 30-90AB, MS ESI calcd. For $C_{29}H_{41}N_3O_3$ $[M+H]^+$ 480, found 480

$^1$HNMR (46): (400 MHz, $CDCl_3$) δ 7.43 (d, J=9.2 Hz, 1H), 9.30 (t, J=8 Hz, 1H), 6.64 (d, J=6.8 Hz, 1H), 5.49 (s, 2H), 4.03 (s, 3H), 2.65-2.60 (m, 1H), 2.04-1.95 (m, 2H), 1.77-1.54 (m, 7H), 1.54-1.42 (m, 6H), 1.27-1.08 (m, 11H), 0.96 (s, 3H), 072 (s, 3H). LCMS $R_t$=1.168 min in 2 min chromatography, 30-90AB, MS ESI calcd. For $C_{29}H_{41}N_3O_3$ $[M+H]^+$ 480, found $[M+H-18]^+$ 462.

Example 24

Synthesis of 47 and 48

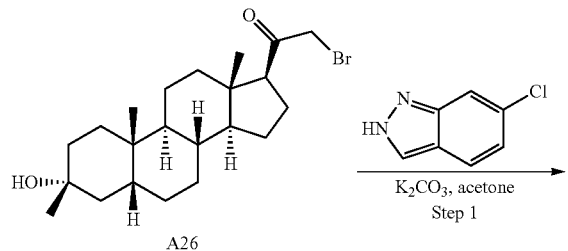

Example 25

Synthesis of 49 and 50

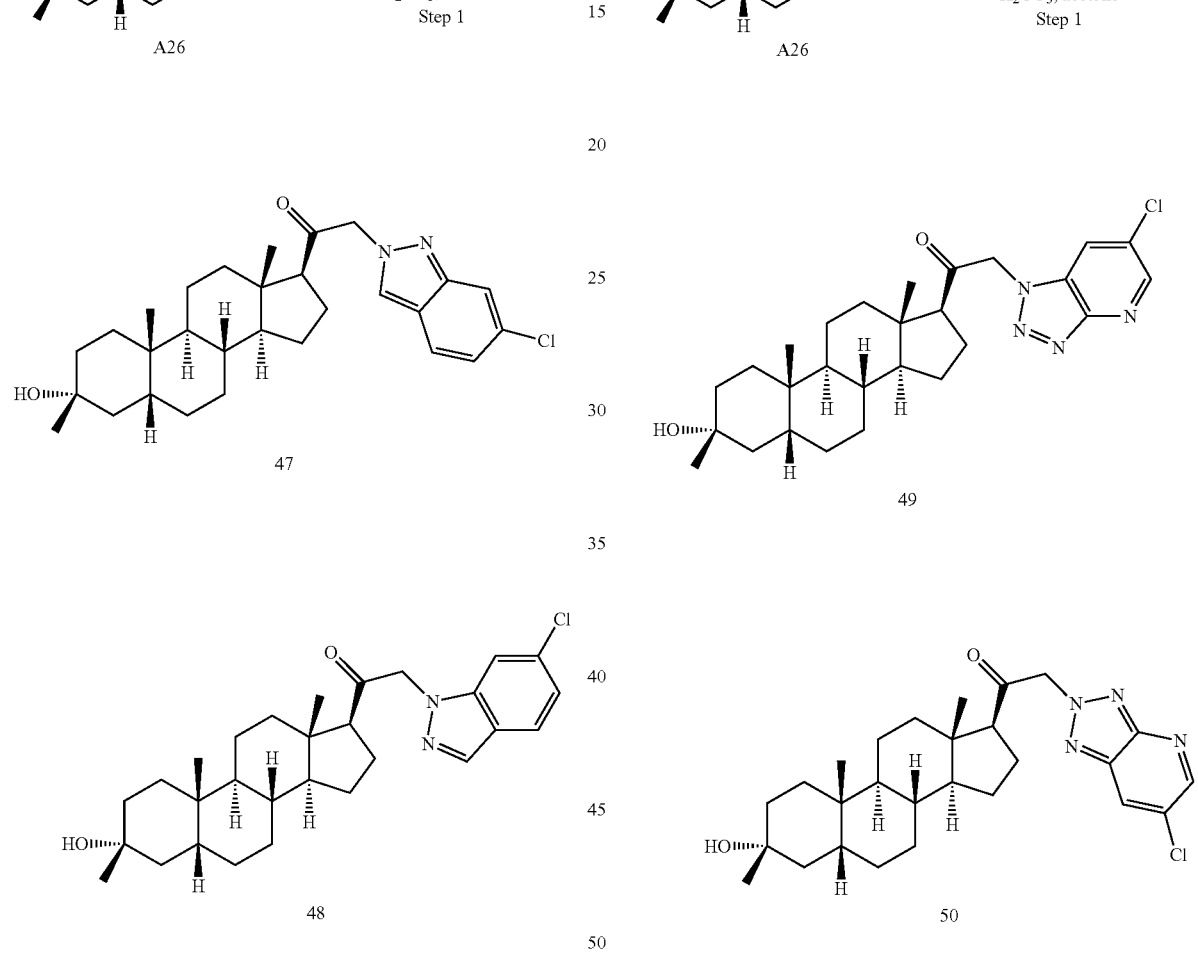

The title compounds were prepared according to Example 5, step 4.

¹HNMR (47) (400 MHz, CDCl$_3$) δ 7.92 (s, 1H), 7.68 (s, 1H), 7.20 (d, J=8.4 Hz, 1H), 7.03 (t, J=8.4 Hz, 1H), 5.23-5.11 (m, 2H), 2.63 (t, J=8.4, 1H), 2.22-1.95 (m, 2H), 1.77-1.54 (m, 5H), 1.45-1.07 (m, 19H), 0.95 (s, 3H), 0.66 (s, 3H). LCMS R$_t$=1.214 min in 2 min chromatography, 30-90AB, MS ESI calcd. For C$_{29}$H$_{39}$ClN$_2$O$_2$[M+H]$^+$ 483, found 483.

¹HNMR (48): (400 MHz, CDCl$_3$) δ 8.00 (s, 1H), 7.65 (d, J=8.4 Hz, 1H), 7.20 (s, 1H), 7.14-7.11 (m, 1H), 5.14-5.04 (m, 2H), 2.64 (t, J=8.4, 1H), 2.17-1.96 (m, 2H), 1.73-1.52 (m, 6H), 1.48-1.11 (m, 18H), 0.96 (s, 3H), 0.70 (s, 3H). LCMS R$_t$=1.239 min in 2 min chromatography, 30-90AB; MS ESI calcd. For C$_{29}$H$_{39}$ClN$_2$O$_2$[M+H]$^+$ 483, found 483.

The title compounds were prepared according to Example 5, step 4.

¹HNMR (49): (400 MHz, CDCl$_3$) δ 8.68 (d, J=2, 1H), 7.76 (d, J=2, 1H), 5.51-5.34 (m, 2H), 2.73 (t, J=8.8, 1H), 2.21-1.97 (m, 2H), 1.78-1.54 (m, 5H), 1.47-1.30 (m, 9H), 1.28-1.09 (m, 10H), 0.97 (s, 3H), 0.72 (s, 3H). LCMS R$_t$=1.137 min in 2 min chromatography, 30-90AB, MS ESI calcd. For C$_{27}$H$_{37}$ClN$_4$O$_2$[M+H]$^+$ 485, found 467[M+H–18]$^+$ ¹HNMR (50): (400 MHz, CDCl$_3$) δ 8.73 (d, J=2, 1H), 8.22 (d, J=2, 1H), 5.59-5.49 (m, 2H), 2.66 (t, J=8.4, 1H), 2.17-1.96 (m, 2H), 1.73-1.53 (m, 6H), 1.45-1.43 (m, 8H), 1.27-1.08 (m, 10H), 0.96 (s, 3H), 0.72 (s, 3H). LCMS R$_t$=0.977 min in 1.5 min chromatography, MS ESI calcd. For C$_{27}$H$_{37}$ClN$_4$O$_2$ [M+H]$^+$ 485, found 467[M+H–18]$^+$ Example 26

Synthesis of 51, 52 and 53

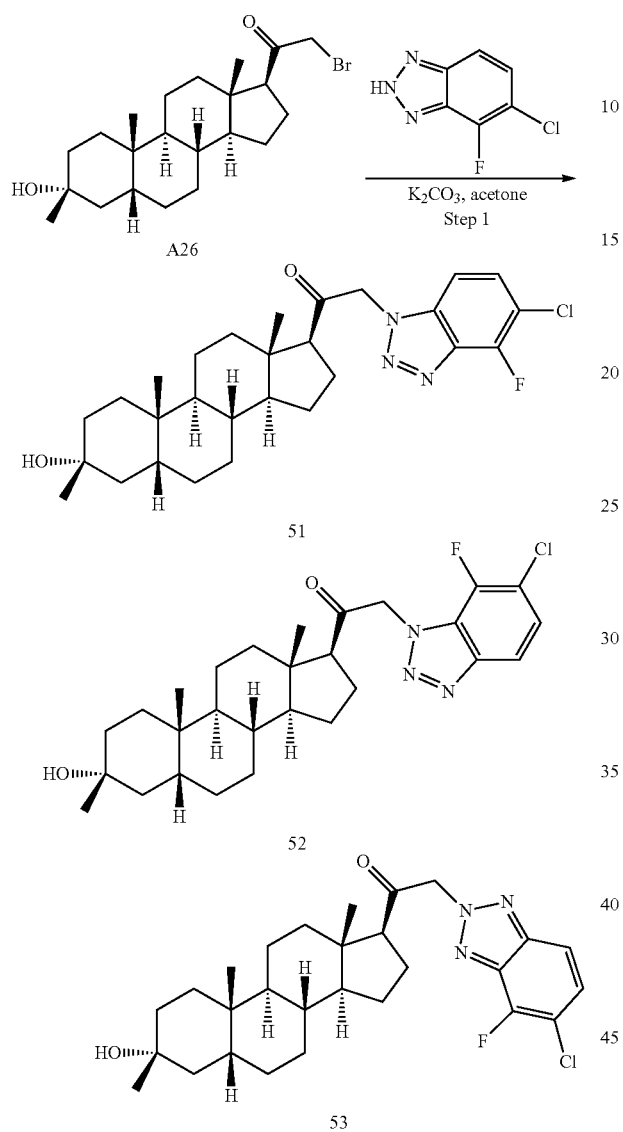

The title compounds were prepared according to Example 5, step 4.

¹HNMR (51): (400 MHz, CDCl₃) δ 7.49-7.45 (m, 1H), 7.06 (d, J=8.2, 1H), 5.47-5.35 (m, 2H), 2.71 (d, J=8.8, 1H), 2.19-1.96 (m, 2H), 1.87-1.55 (m, 7H), 1.46-1.44 (m, 6H), 1.27-1.09 (m, 11H), 0.96 (s, 3H), 0.69 (s, 3H). LCMS $R_t$=1.234 min in 2 min chromatography, 30-90AB, MS ESI calcd. For $C_{28}H_{37}ClFN_3O_2[M+H]^+$ 502, found 502.

¹HNMR (52) (400 MHz, CDCl₃) δ 7.79 (d, J=8.8, 1H), 7.36-7.33 (m, 1H), 5.52 (s, 2H), 2.72 (d, J=8.4, 1H), 2.20-1.97 (m, 2H), 1.84-1.55 (m, 7H), 1.47-1.44 (m, 6H), 1.27-1.09 (m, 11H), 0.97 (s, 3H), 0.71 (s, 3H). LCMS $R_t$=1.013 min in 1.5 min chromatography, MS ESI calcd. For $C_{28}H_{37}ClFN_3O_2[M+H]^+$ 502, found 502.

¹HNMR (53): (400 MHz, CDCl₃) δ 7.63 (t, J=8.8, 1H), 7.38-7.34 (m, 1H), 5.57-5.48 (m, 2H), 2.65 (t, J=8.8, 1H), 2.20-2.04 (m, 2H), 1.77-1.57 (m, 6H), 1.45-1.43 (m, 7H), 1.27-1.08 (m, 11H), 0.96 (s, 3H), 0.72 (s, 3H). LCMS $R_t$=1.310 min in 2 min chromatography, MS ESI calcd. For $C_{28}H_{37}ClFN_3O_2[M+H]^+$ 502, found 484[M+H−18]⁺.

Example 27

Synthesis of 54 and 55

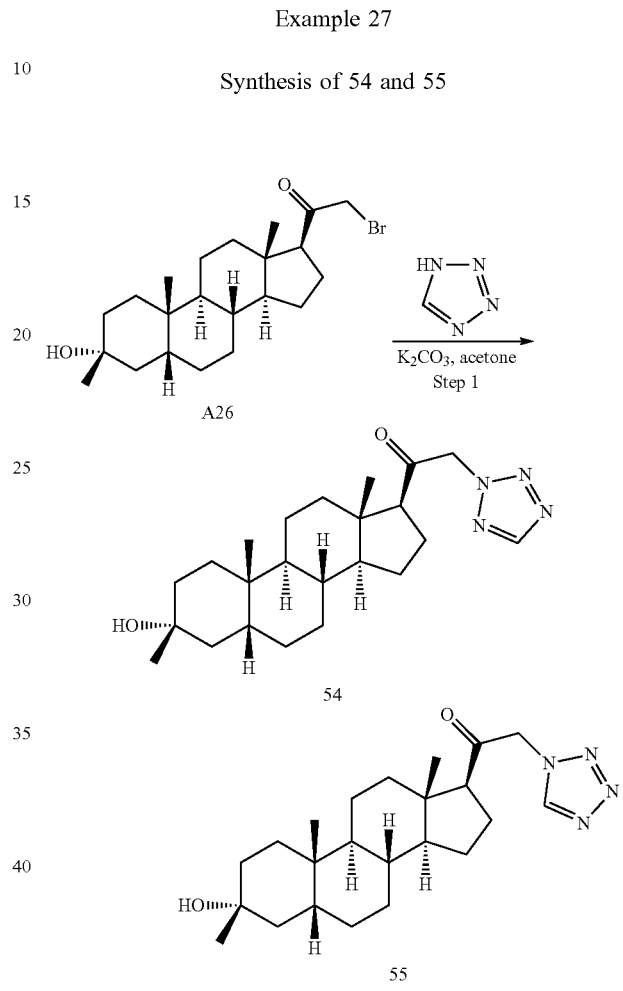

The title compounds were prepared according to Example 5, step 4.

¹HNMR (54): (400 MHz, CDCl₃) δ 8.57 (s, 1H), 5.45 (s, 2H), 2.63 (t, J=8.8 Hz, 1H), 2.19-1.54 (m, 8H), 1.50-1.43 (m, 7H), 1.27-1.08 (m, 11H), 0.96 (s, 3H), 0.70 (s, 3H). LCMS $R_t$=0.899 min in 1.5 min chromatography, MS ESI calcd. For $C_{23}H_{36}N_4O_2$ [M+H]⁺ 401, found [M+H−18]⁺ 383

¹HNMR (55): (400 MHz, CDCl₃) δ 8.74 (s, 1H), 5.33-5.16 (m, 2H), 2.67 (d, J=8.8 Hz, 1H), 2.20-1.54 (m, 8H), 1.51-1.43 (m, 8H), 1.31-1.09 (m, 10H), 0.95 (s, 3H), 0.65 (s, 3H). LCMS $R_t$=0.8827 min in 1.5 min chromatography, MS ESI calcd. For $C_{23}H_{36}N_4O_2$ [M+H]⁺ 401, found [M+H−18]⁺ 383

Example 28

Synthesis of 56, 57, 58, and 59

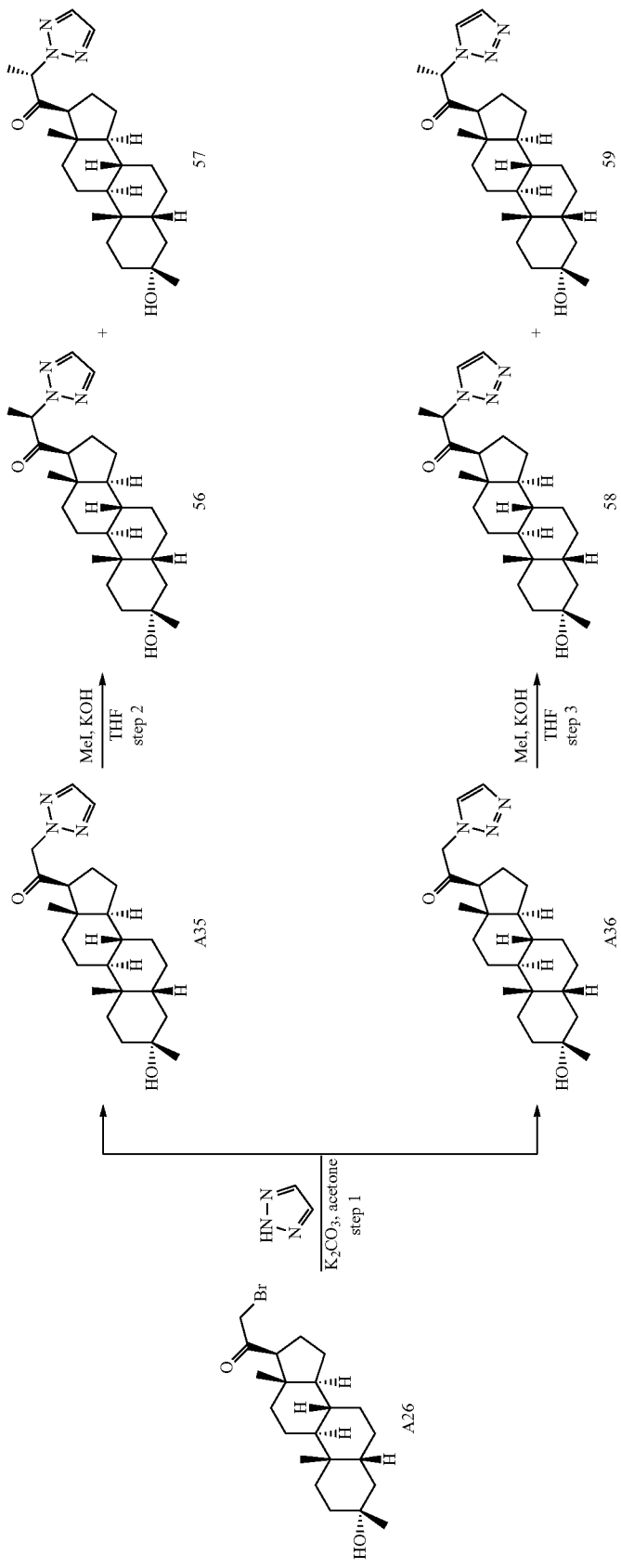

Step 1. Synthesis of A35 and A36. To a solution of A26 (300 mg, 729 umol, 1.00 eq) in acetone (5 mL) was added $K_2CO_3$ (200 mg, 1.45 mmol, 2.0 eq) and 2H-1,2,3-triazole (60.3 mg, 874 umol, 1.2 eq) at 25° C. The reaction mixture was stirred at 25° C. for 16 hrs. Then, TLC showed the material was disappeared. The mixture was diluted with water (20 mL) and extracted with EA (30 mL×2). The combined organic layers were washed with brine (30 mL), dried over $Na_2SO_4$ and concentrated in vacuum. The residue was purified by silica gel chromatography (100-200 mesh silica gel, Petroleum ether/Ethyl acetate=2/1 to EA) to afford 1-((3R,5R,8R,9S,10S,13S,14S,17S)-3-hydroxy-3,10,13-trimethylhexadecahydro-1H-cyclopenta[a]phenanthren-17-yl)-2-(2H-1,2,3-triazol-2-yl)ethanone (120 mg, 285 umol) and 1-((3R,5R,8R,9S,10S,13S,14S,17S)-3-hydroxy-3,10,13-trimethylhexadecahydro-1H-cyclopenta[a]phenanthren-17-yl)-2-(1H-1,2,3-triazol-1-yl)ethanone (130 mg, 309 umol) as an off-white solid.

$^1$H NMR (A35): (400 MHz, $CDCl_3$) δ 7.69 (s, 2H), 5.28-5.19 (m, 2H), 2.59-2.55 (m, 1H), 0.95 (s, 3H), 0.69 (s, 3H).

$^1$H NMR (A36): (400 MHz, $CDCl_3$) δ 7.76 (d, J=8 Hz, 1H), 7.64 (d, J=8 Hz, 1H), 5.29-5.11 (m, 2H), 2.66-2.62 (m, 1H), 0.95 (s, 3H), 0.66 (s, 3H).

Step 2. Synthesis of 56 and 57. To a solution of A35 (120 mg, 300 umol, 1.00 eq) and KOH (33.6 mg, 600 umol, 2 eq) in THF (4.00 mL) was added CH3I (51 mg, 360 umol, 1.2 eq). The mixture was stirred at 25° C. for 3 hrs. TLC showed the material was disappeared. The reaction was quenched with water and extracted with EA (2×20 mL). The combined organic phase was washed with brine and dried over $Na_2SO_4$, filtered and concentrated to give crude product. The residue was purified by prep-HPLC (0.5% HCl) to afford (R)-1-((3R,5R,8R,9S,10S,13S,14S,17S)-3-hydroxyl-3,10,13-trimethylhexadecahydro-1H-cyclopenta[a]phenanthren-17-yl)-2-(2H-1,2,3-triazol-2-yl)propan-1-one (21 mg, 49.7 umol) and (S)-1-((3R,5R,8R,9S,10S,13S,14S,17S)-3-hydroxy-3,10,13-trimethylhexadecahydro-1H-cyclopenta[a]phenanthren-17-yl)-2-(2H-1,2,3-triazol-2-yl)propan-1-one (30 mg, 72.5 umol) as a white solid.

$^1$H NMR (56): (400 MHz, $CDCl_3$) δ 7.68 (s, 2H), 5.25 (q, J=6.8 Hz, 1H), 2.23-2.14 (m, 1H), 2.10-2.00 (m, 1H), 1.90-1.75 (m, 3H), 1.58-1.50 (m, 5H), 1.49-1.25 (m, 8H), 1.24-1.07 (m, 9H), 1.04-1.00 (m, 3H), 0.95 (s, 3H), 0.64 (s, 3H). LCMS Rt=0.945 min in 1.5 min chromatography, MS ESI calcd. for C25H39N3O2 [M+H]$^+$ 414, found 396([M+H−18]

$^1$H NMR (57): (400 MHz, $CDCl_3$) δ 7.67 (s, 2H), 5.40 (q, J=7.6 Hz, 1H), 2.65-2.63 (m, 1H), 2.14-2.12 (m, 2H), 1.95-1.66 (m, 5H), 1.60-1.49 (m, 3H), 1.55-1.25 (m, 10H), 1.42-1.00 (m, 10H), 0.95 (s, 3H), 0.67 (s, 3H). LCMS Rt=0.927 min in 1.5 min chromatography, MS ESI calcd. for C25H39N3O2 [M+H]$^+$ 414, found 396([M+H−18]$^+$ Step 3. Synthesis of 58 and 59. To a solution of A36 (130 mg, 325 umol, 1.00 eq) and KOH (36.4 mg, 650 umol, 2 eq) in THF (5.00 mL) was added CH3I (55.3 mg, 390 umol, 1.2 eq). The mixture was stirred at 25° C. for 3 hrs. TLC showed the material was disappeared. The reaction was quenched with water and extracted with EA (2*30 mL); the combined organic phase was washed with brine and dried over $Na_2SO_4$, filtered and concentrated to give crude product. The residue was purified by Prep-HPLC (0.5% HCl) to afford (R)-1-((3R,5R,8R,9S,10S,13S,14S,17S)-3-hydroxy-3,10,13-trimethyl hexadecahydro-1H-cyclopenta[a]phenanthren-17-yl)-2-(1H-1,2,3-triazol-1-yl)propan-1-one (41.5 mg, 98.5 umol) and (S)-1-((3R,5R,8R,9S,10S,13S,14S,17S)-3-hydroxy-3,10,13-trimethylhexadecahydro-1H-cyclopenta[a]phenanthren-17-yl)-2-(1H-1,2,3-triazol-1-yl)propan-1-one (24.5 mg, 58.5 umol) as a white solid.

$^1$H NMR (58): (400 MHz, $CDCl_3$) δ 7.77 (s, 1H), 7.60 (s, 1H), 5.47 (q, J=7.6 Hz, 1H), 2.56-2.51 (m, 1H), 2.15-2.00 (m, 1H), 1.90-1.75 (m, 3H), 1.66-1.64 (m, 3H), 1.60-1.54 (m, 2H), 1.50-1.39 (m, 9H), 1.25-1.00 (m, 11H), 0.94 (s, 3H), 0.66 (s, 3H). LCMS Rt=1.054 min in 2 min chromatography, MS ESI calcd. for C25H39N3O2 [M+H]$^+$ 414, found 396([M+H−18]

$^1$H NMR (59): (400 MHz, $CDCl_3$) δ 7.79 (s, 1H), 7.74 (s, 1H), 5.64 (q, J=7.2 Hz, 1H), 2.80-2.78 (m, 1H), 2.22-2.20 (m, 2H), 1.96-1.75 (m, 2H), 1.69-1.54 (m, 6H), 1.58-1.43 (m, 9H), 1.40-1.00 (m, 10H), 0.93 (s, 3H), 0.51 (s, 3H). LCMS Rt=1.012 min in 2 min chromatography, MS ESI calcd. for C25H39N3O2 [M+H]$^+$ 414, found 396([M+H−18]

Example 29

Synthesis of 60, 61, 62, and 63

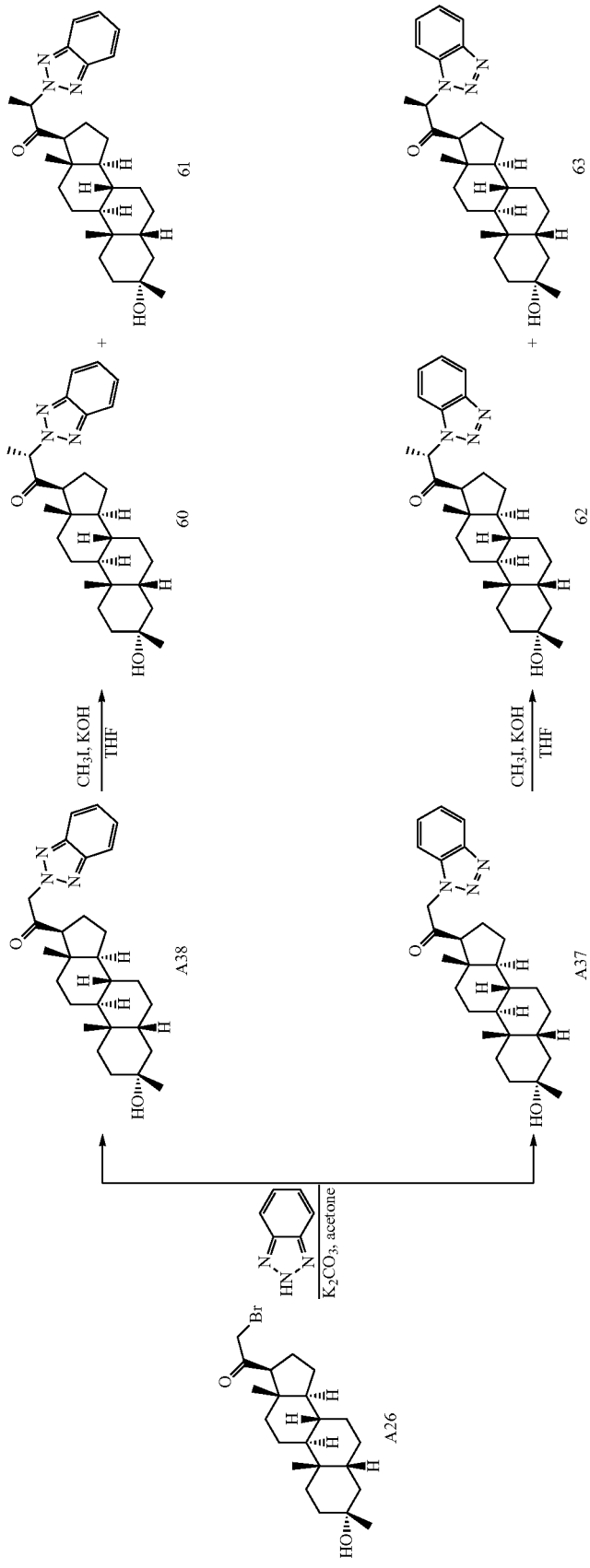

Step 7. Synthesis of A37 and A38. To a solution of A26 (400 mg, 972 umol) in acetone (5 mL) was added K$_2$CO$_3$ (268 mg, 1.94 mmol) and 2H-benzo[d][1,2,3]triazole (138 mg, 1.16 mmol) at 25° C. The reaction mixture was stirred at 25° C. for 16 hrs. Then, TLC showed the material was disappeared and the mixture was diluted with water (20 mL) and the mixture was extracted with EA (20 mL×2). The combined organic layers were washed with brine (30 mL), dried over Na$_2$SO$_4$ and concentrated in vacuum. The residue was purified by silica gel chromatography (100-200 mesh silica gel, petroleum ether/ethyl acetate=3/1) to afford 2-(2H-benzo[d][1,2,3]triazol-2-yl)-1-((3R,5R,8R,9S,10S,13S,14S,17S)-3-hydroxy-3,10,13-trimethylhexadecahydro-1H-cyclopenta[a]phenanthren-17-yl)ethanone (95.0 mg, 211 umol) and 2-(1H-benzo[d][1,2,3]triazol-1-yl)-1-((3R,5R,8R,9S,10S,13S,14S,17S)-3-hydroxy-3,10,13-trimethylhexadecahydro-1H-cyclopenta[a]phenanthren-17-yl)ethanone (290.0 mg, 612 umol) as an off-white solid.

$^1$H NMR (A37): 400 MHz δ 7.87 (dd, J$_1$=3.2 Hz, J$_2$=6.4 Hz, 2H), 7.39 (dd, J$_1$=3.2 Hz, J$_2$=6.8 Hz, 2H), 5.52-5.51 (m, 2H), 2.65-2.63 (m, 1H), 0.96 (s, 3H), 0.73 (s, 3H).

$^1$H NMR (A38): 400 MHz δ 8.09 (d, J=8.4 Hz, 1H), 7.49-7.47 (m, 1H), 7.40-7.26 (m, 2H), 5.42-5.41 (m, 2H), 2.72-2.68 (m, 1H), 0.96 (s, 3H), 0.71 (s, 3H).

Step 7. Synthesis of 60 and 61. To a solution of A38 (95 mg, 211 umol) and KOH (23.6 mg, 422 umol) in THF (3.00 mL) was added CH$_3$I (35.9 mg, 253 umol). The mixture was stirred at 25° C. for 16 hrs. TLC showed the material was disappeared. Then, the reaction was quenched with water and extracted with EA (2*20 mL); the combined organic phase was washed with brine and dried over Na$_2$SO$_4$, filtered and concentrated to give crude product. The residue was purified by prep-HPLC (0.5% HCl) to afford (R)-2-(2H-benzo[d][1,2,3]triazol-2-yl)-1-((3R,5R,8R,9S,10S,13S,14S,17S)-3-hydroxy-3,10,13-trimethylhexadecahydro-1H-cyclopenta[a]phenanthren-17-yl)propan-1-one (9.4 mg, 20.0 umol) and (S)-2-(2H-benzo[d][1,2,3]triazol-2-yl)-1-((3R,5R,8R,9S,10S,13S,14S,17S)-3-hydroxy-3,10,13-trimethylhexadecahydro-1H-cyclopenta[a]phenanthren-17-yl)propan-1-one (15.2 mg, 32.4 umol) as a white solid.

$^1$H NMR (60): 400 MHz δ 7.88 (dd, J$_1$=3.2 Hz, J$_2$=6.8 Hz, 2H), 7.40 (dd, J$_1$=3.2 Hz, J$_2$=6.8 Hz, 2H), 5.74-5.68 (m, 1H), 2.74-2.69 (m, 1H), 2.25-2.1 (m, 1H), 2.00-1.75 (m, 8H), 1.60-1.29 (m, 10H), 1.28-1.25 (m, 8H), 1.25-1.00 (m, 2H), 0.97 (s, 3H), 0.73 (s, 3H). LCMS R$_t$=0.997 min in 1.5 min chromatography, MS ESi calcd. for C29H41N3O2 [M+H]$^+$ 464, found 446([M+H−18]

$^1$H NMR (61): 400 MHz δ 7.88 (dd, J$_1$=2.8 Hz, J$_2$=6.4 Hz, 2H), 7.42 (dd, J$_1$=3.2 Hz, J$_2$=6.4 Hz, 2H), 5.54-5.49 (m, 1H), 2.26-2.05 (m, 2H), 1.95-1.50 (m, 8H), 1.48-1.30 (m, 8H), 1.28-1.15 (m, 9H), 1.13-1.04 (m, 3H), 0.93 (s, 3H), 0.67 (s, 3H)

LCMS R$_t$=1.006 min in 1.5 min chromatography, MS ESi calcd. for C29H41N3O2 [M+H]$^+$464, found 446([M+H−18]

Step 7. Synthesis of 62 and 63. To a solution of A37 (290 mg, 6444 umol, 1.00 eq) and KOH (71.8 mg, 1280 umol, 2 eq) in THF (6.00 mL) was added CH$_3$I (109 mg, 772 umol, 1.2 eq). The mixture was stirred at 25° C. for 3 hrs. TLC showed the material was disappeared. Then, the reaction was quenched with water and extracted with EA (2*30 mL), the combined organic phase was washed with brine and dried over Na$_2$SO$_4$, filtered and concentrated to give crude product. The residue was purified by Prep-HPLC (0.5% HCl) to afford (R)-2-(1H-benzo[d][1,2,3]triazol-1-yl)-1-((3R,5R,8R,9S,10S,13S,14S,17S)-3-hydroxy-3,10,13-trimethylhexadecahydro-1H-cyclopenta[a]phenanthren-17-yl)propan-1-one (41 mg, 84.7 umol) and (S)-2-(1H-benzo[d][1,2,3]triazol-1-yl)-1-((3R,5R,8R,9S,10S,13S,14S,17S)-3-hydroxy-3,10,13-trimethylhexadecahydro-1H-cyclopenta[a]phenanthren-17-yl)propan-1-one (47.5 mg, 100 umol) as a white solid.

$^1$H NMR (62): 400 MHz δ 8.09 (d, J=8.0 Hz, 1H), 7.57-7.55 (m, 1H), 7.49-7.47 (m, 1H), 7.39-7.37 (m, 1H), 5.81-5.79 (m, 1H), 2.72-2.68 (m, 1H), 2.01-1.75 (m, 8H), 1.65-1.55 (m, 2H), 1.50-1.25 (m, 8H), 1.24-1.00 (m, 11H), 0.93 (s, 3H), 0.61 (s, 3H). LCMS t$_R$=1.161 min in 2 min chromatography, 30-90AB, MS ESI calcd. for C29H41N3O2 [M+H]$^+$ 464, found 446([M+H−18]

$^1$H NMR (63): 400 MHz δ 8.10 (d, J=7.6 Hz, 1H), 7.51-7.47 (m, 1H), 7.42-7.39 (m, 2H), 5.64-5.58 (m, 1H), 2.36-2.33 (m, 1H), 2.20-2.00 (m, 1H), 1.77-1.57 (m, 7H), 1.50-1.25 (m, 10H), 1.25-1.10 (m, 8H), 1.24-1.03 (m, 3H), 0.92 (s, 3H), 0.66 (s, 3H). LCMS R$_t$=1.186 min in 2 min chromatography, MS ESI calcd. for C29H41N3O2 [M+H]$^+$ 464, found 446([M+H−18]

Example 30

Synthesis of 64 and 65

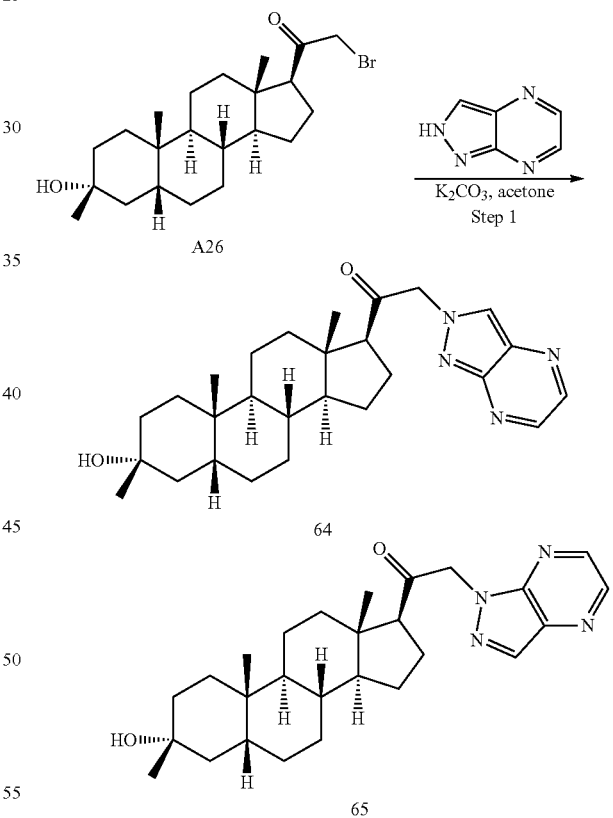

The title compounds were prepared according to Example 5, step 4.

$^1$HNMR (64): (400 MHz, CDCl$_3$) δ 8.64 (s, 1H), 8.56 (s, 1H), 8.27 (s, 1H), 5.37-5.21 (m, 2H), 2.70 (t, J=8.4, 1H), 2.22-1.96 (m, 2H), 1.77-1.58 (m, 6H), 1.51-1.43 (m, 8H), 1.27-1.08 (m, 10H), 0.96 (s, 3H), 0.69 (s, 3H). LCMS R$_t$=0.937 min in 2 min chromatography, MS ESI calcd. For C$_{27}$H$_{38}$N$_4$O$_2$ [M+H]$^+$ 451, found 473 [M+23]$^+$.

$^1$HNMR (65): (400 MHz, CDCl$_3$) δ 8.58 (d, J=1.6 Hz, 1H), 8.44 (d, J=2 Hz, 1H), 8.34 (s, 1H), 5.36-5.25 (m, 2H), 2.70 (t, J=8.4, 1H), 2.24-1.87 (m, 2H), 1.74-1.54 (m, 6H), 1.46-1.43 (m, 8H), 1.27-1.08 (m, 10H), 0.96 (s, 3H), 0.70 (s, 3H). LCMS $R_t$=0.916 min in 1.5 min chromatography, for $C_{27}H_{38}N_4O_2$ [M+H]$^+$ 451, found 451.

Example 31

Synthesis of 66 and 67

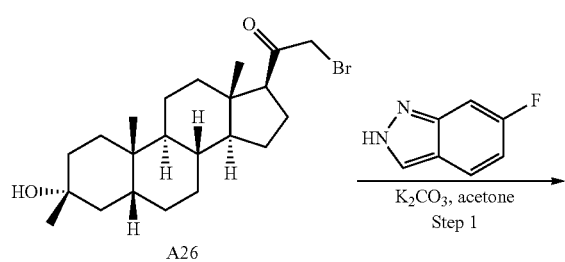

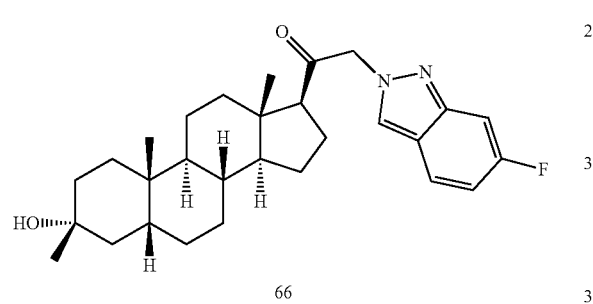

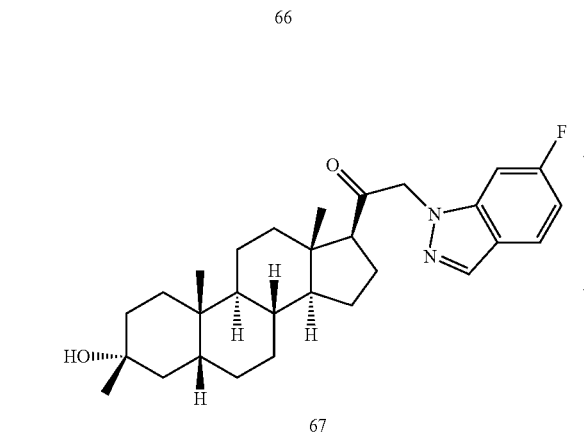

The title compounds were prepared according to Example 5, step 4.

$^1$HNMR (66): (400 MHz, CDCl$_3$) 7.94 (s, 1H), 7.66-7.62 (m, 1H), 7.29 (s, 1H), 6.90 (t, J=8 Hz, 1H), 5.18 (s, 2H), 2.64 (s, 1H), 2.13-2.00 (m, 2H), 1.95-1.54 (m, 6H), 1.49-1.43 (m, 8H), 1.27-1.08 (m, 10H), 0.95 (s, 3H), 0.69 (s, 3H). LCMS $R_t$=0.949 min in 1.5 min chromatography, MS ESI calcd. For $C_{30}H_{41}FN_2O_2$[M+H]$^+$ 467, found 467.

$^1$HNMR (67): (400 MHz, CDCl$_3$) δ 8.01 (s, 1H), 7.69-7.66 (m, 1H), 6.96-6.93 (m, 1H), 6.91-6.83 (m, 1H), 5.12-5.03 (m, 2H), 2.62 (t, J=9.2, 1H), 2.17-1.95 (m, 2H), 1.77-1.54 (m, 6H), 1.47-1.43 (m, 8H), 1.27-1.07 (m, 10H), 0.73 (s, 3H), 0.69 (s, 3H). LCMS $R_t$=1.151 min in 2 min chromatography, MS ESI calcd. For $C_{29}H_{39}FN_2O_2$[M+H]$^+$ 467, found 467.

Example 32

Synthesis of 68 and 69

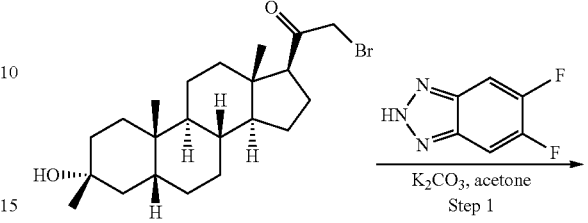

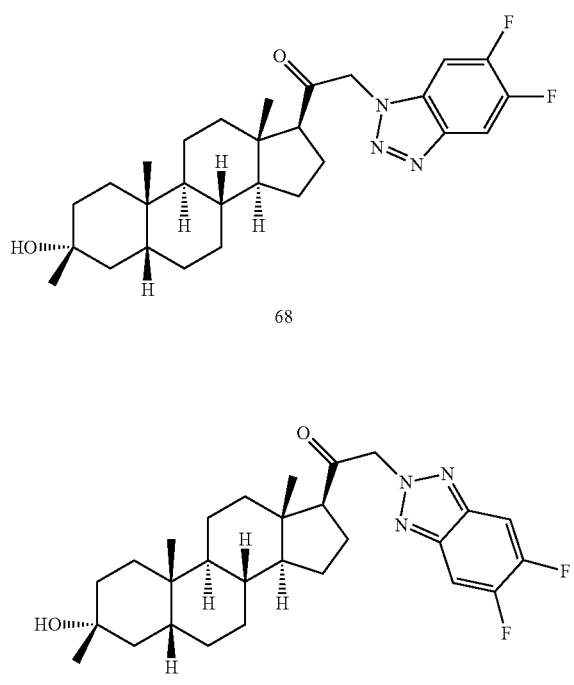

The title compounds were prepared according to Example 5, step 4.

$^1$HNMR (68): (400 MHz, CDCl$_3$) δ 7.82 (t, J=8.4, 1H), 7.12 (t, J=8, 1H), 5.44-5.31 (m, 2H), 2.72 (t, J=8.4, 1H), 2.19-1.96 (m, 2H), 1.87-1.70 (m, 7H), 1.43-1.27 (m, 5H), 1.12-1.08 (m, 11H), 0.96 (s, 3H), 0.69 (s, 3H). LCMS $R_t$=0.968 min in 1.5 min chromatography, MS ESI calcd. For $C_{28}H_{37}F_2N_3O_2$[M+H]$^+$ 486, found 486.

$^1$HNMR (69): (400 MHz, CDCl$_3$) δ 7.60 (t, J=8 Hz, 2H), 5.52-5.42 (m, 2H), 2.64 (t, J=9.2, 1H), 2.14-1.96 (m, 2H), 1.87-1.53 (m, 6H), 1.47-1.43 (m, 9H), 1.27-1.08 (m, 10H), 0.97 (s, 3H), 0.72 (s, 3H). LCMS $R_t$=1.004 min in 1.5 min chromatography, MS ESI calcd. For $C_{28}H_{37}F_2N_3O_2$[M+H]$^+$ 486, found [M+H−18]$^+$ 468.

Example 33

Synthesis of 70 and 71

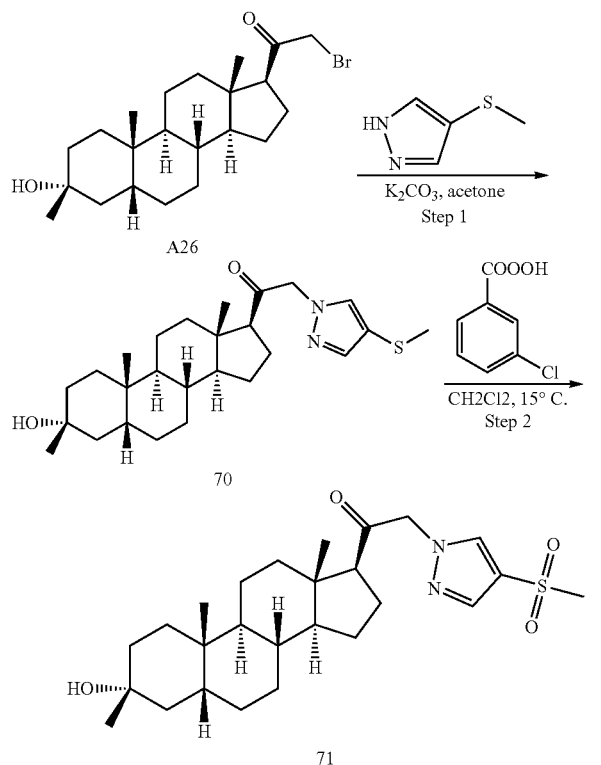

Step 1. Synthesis of 70. To a solution of A26 (300 mg, 0.729 mmol) in acetone (2 mL) was added 4-(methylthio)-1H-py (247 mg, 2.17 mmol), followed by K2CO3 (200 mg, 1.45 mmol). The resulting reaction mixture was stirred at 40° C. for 16 hours, at which point LCMS indicated the starting material was consumed completely. The mixture was diluted with water (10 mL) and then extracted with EtOAc (8 mL*3). The combined organic phases were concentrated to give a residue, which was purified by HPLC.

Step 2. Synthesis of 71. To a solution of 70 (25 mg, 56.2 μmol) in 2 mL of $CH_2Cl_2$ was added m-CPBA (24.1 mg, 140 μmol) at 25° C. The reaction mixture was stirred for 3 h at the same temperature. TLC (petroleum ether/ethyl acetate=2:1, PMA) showed the reaction was complete. The reaction mixture was poured into saturated aqueous $Na_2S_2O_3$ and extracted with $CH_2Cl_2$ (10 mL×2). The organic layers were washed with saturated aqueous $NaHCO_3$ (10 mL), brine (10 mL), dried over anhydrous $Na_2SO_4$ and concentrated in vacuum. The residue was purified by purified by column chromatography on silica gel (petroleum ether/ethyl acetate=5/1-1/2) to give 71 (17.3 mg) as a white solid.

$^1$HNMR (71): (400 MHz, CDCl3) δ 7.92 (s, 1H), 7.87 (s, 1H), 5.04-4.89 (m, 2H), 3.13 (s, 3H), 2.62 (d, J=9.2 Hz, 1H), 2.19-1.52 (m, 7H), 1.47-1.43 (m, 9H), 1.27-1.09 (m, 11H), 0.95 (s, 3H), 0.66 (s, 3H). LCMS $R_t$=1.265 min in 2 min chromatography, MS ESI calcd. for chemical Formula: $C_{26}H_{40}N_2O_4S$ [M+H]$^+$ 477, found [M+H−18]$^+$ 459.

Example 34

Synthesis of 72 and 73

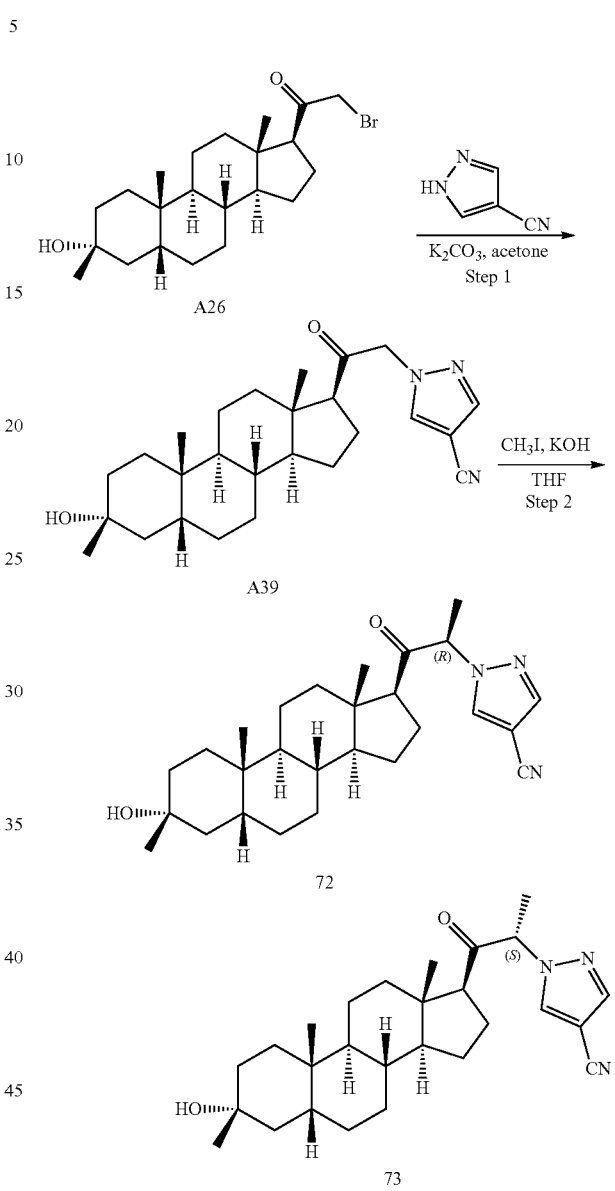

Step 1. Synthesis of A39. To a solution of A26 (300 mg, 729 umol, 1.00 Eq) in acetone (5 mL) was added $K_2CO_3$ (200 mg, 1.45 mmol, 2.0 Eq) and 1H-pyrazole-4-carbonitrile (81.3 mg, 874 umol, 1.2 Eq) at 25° C. The reaction mixture was stirred at 25° C. for 16 hrs. Then, TLC showed the material was disappeared. The mixture was diluted with water (20 mL) and extracted with EA (30 mL×2). The combined organic layers were washed with brine (30 mL), dried over $Na_2SO_4$ and concentrated in vacuum. The residue was purified by silica gel chromatography (100-200 mesh silica gel, petroleum ether/ethyl acetate=2/1) to afford A39 (245 mg, 549 umol) as a off-white solid.

$^1$H NMR (A39): 400 MHz δ 7.86 (s, 1H), 7.81 (s, 1H), 5.04-4.88 (m, 2H), 2.62-2.58 (m, 1H), 0.95 (s, 3H), 0.65 (s, 3H).

Step 2. Synthesis of 72 and 73. To a solution of A39 (150 mg, 354 umol, 1.00 eq) and KOH (39.7 mg, 708 umol, 2 eq)

in THF (4.00 mL) was added CH₃I (60.1 mg, 424 umol, 1.2 eq). The mixture was stirred at 25° C. for 3 hrs. TLC showed the material was disappeared. The reaction was quenched with water and extracted with EA (2*30 mL), the combined organic phase was washed with brine and dried over Na₂SO₄, filtered and concentrated to give crude product. The residue was purified by Prep-HPLC (0.5% HCl) to afford 65 mg (P1 and P2, mixture) product. The mixture product was purified by SFC (0.2% NH4OH) to afford 1-((R)-1-((3R,5R,8R,9S,10S,13S,14S,17S)-3-hydroxy-3,10, 13-trimethylhexadecahydro-1H-cyclopenta[a]phenanthren-17-yl)-1-oxopropan-2-yl)-1H-pyrazole-4-carbonitrile (20 mg, 45.5 umol) and 1-((S)-1-((3R,5R,8R,9S,10S,13S,14S,17S)-3-hydroxy-3,10,13-trimethylhexadecahydro-1H-cyclopenta[a]phenanthren-17-yl)-1-oxopropan-2-yl)-1H-pyrazole-4-carbonitrile (35 mg, 79.9 umol) as a white solid.

¹H NMR (72): 400 MHz δ 7.99 (s, 1H), 7.77 (s, 1H), 5.26 (q, J=7.6 Hz, 1H), 2.71-2.62 (m, 1H), 2.18-2.16 (m, 2H), 2.00-1.72 (m, 2H), 1.70-1.65 (m, 6H), 1.52-1.41 (m, 10H), 1.43-1.02 (m, 11H), 0.94 (s, 3H), 0.55 (s, 3H). LCMS Rt=1.122 min in 2 min chromatography, MS ESI calcd. for C27H39N3O2 [M+H−18]⁺ 420, found 460([M+23].

¹H NMR (73): 400 MHz δ 7.77 (s, 1H), 7.72 (s, 1H), 5.04 (q, J=7.6 Hz, 1H), 2.49-2.47 (m, 1H), 2.07-2.00 (m, 1H), 1.92-1.88 (m, 3H), 1.67-1.62 (m, 6H), 1.60-1.40 (m, 8H), 1.27-1.06 (m, 11H), 0.94 (s, 3H), 0.65 (s, 3H). LCMS Rt=1.132 min in2 min chromatography, MS ESI calcd. for C27H39N3O2 [M+H−18]⁺ 420, found 460([M+Na].

Example 35

Synthesis of 74, 75, and 76

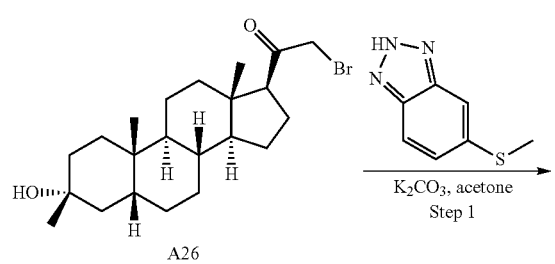

A26

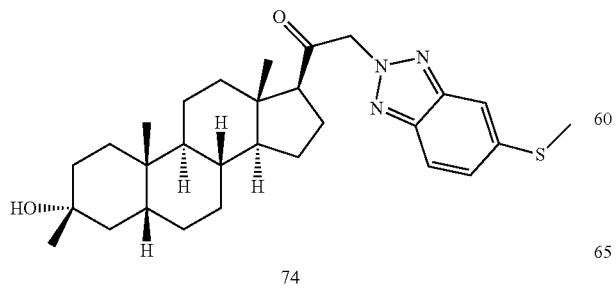

74

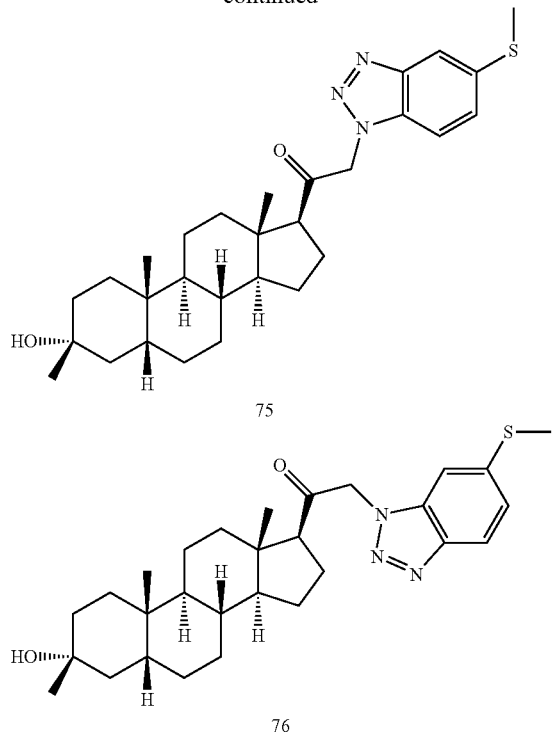

75

76

The title compounds were prepared according to Example 5, step 4.

¹HNMR (74) (400 MHz, CDCl₃) δ 7.75 (d, J=8.8 Hz, 1H), 7.57 (s, 1H), 7.28 (d, J=1.6 Hz, 1H) 5.51-5.41 (m, 2H), 2.63 (t, J=8.4, 1H), 2.55 (s, 3H), 2.20-1.95 (m, 2H), 1.77-1.59 (m, 5H), 1.54-1.42 (m, 9H), 1.27-1.08 (m, 11H), 0.96 (s, 3H), 0.72 (s, 3H). LCMS R_f=1.468 min in 2 min chromatography, MS ESI calcd. For C₂₉H₄₁N₃O₂S [M+H]⁺ 496, found 478 [M+H−18]⁺.

¹HNMR (75) (400 MHz, CDCl₃) δ 7.87 (s, 1H), 7.40 (d, J=9.2 Hz, 1H), 7.23 (d, J=8.8 Hz, 1H) 5.42-5.32 (m, 2H), 2.70-2.66 (m, 1H), 2.56 (s, 3H), 1.96-1.52 (m, 7H), 1.45-1.43 (m, 8H), 1.27-1.08 (m, 11H), 0.96 (s, 3H), 0.69 (s, 3H). LCMS R_f=0.963 min in 1.5 min chromatography, MS ESI calcd. For C₂₉H₄₁N₃O₂S [M+H]⁺ 496, found 496.

¹HNMR (76): (400 MHz, CDCl₃) δ 7.93 (d, J=8.8 Hz, 1H), 7.27-7.25 (m, 1H), 5.40-5.30 (m, 2H), 2.69 (t, J=8.8, 1H), 2.53 (s, 3H), 2.22-1.96 (m, 2H), 1.77-1.52 (m, 8H), 1.51-1.27 (m, 6H), 1.24-1.08 (m, 12H), 0.96 (s, 3H), 0.71 (s, 3H). LCMS R_f=1.160 min in 2 min chromatography, MS ESI calcd. For C₂₉H₄₁N₃O₂S [M+H]⁺ 496, found 496.

Example 36

Synthesis of 77 and 78

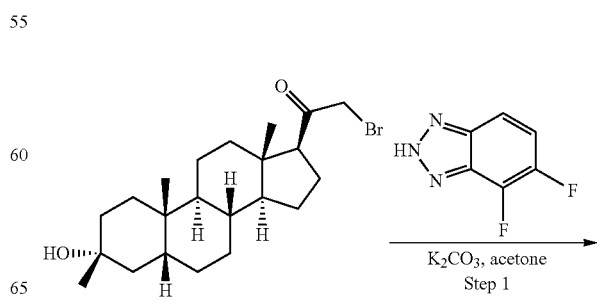

A26

-continued

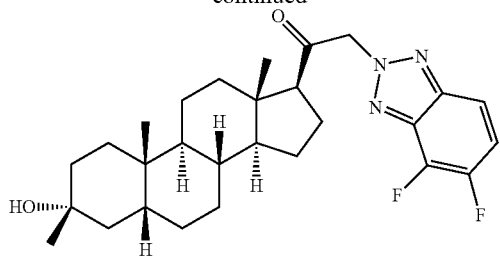

77

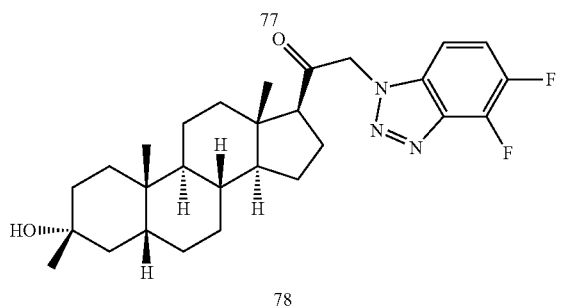

78

The title compounds were prepared according to Example 5, step 4.

¹HNMR (77): (400 MHz, CDCl₃) δ 7.40-7.35 (m, 1H), 7.06-7.04 (m, 1H), 5.46-5.35 (m, 2H), 2.71 (d, J=8.4 Hz, 1H), 2.18-1.96 (m, 2H), 1.76-1.54 (m, 5H), 1.45-1.30 (m, 7H), 1.27-1.08 (m, 10H), 0.96 (s, 3H), 0.67 (s, 3H). LCMS R$_t$=0.973 min in 1.5 min chromatography, MS ESI calcd. For C$_{28}$H$_{37}$F$_2$N$_3$O$_2$[M+H]⁺ 468, found 468.

¹HNMR (78): (400 MHz, CDCl₃) δ 7.38-7.33 (m, 1H), 7.06-7.04 (m, 1H), 5.46-5.35 (m, 2H), 2.71 (d, J=8.8 Hz, 1H), 2.15-1.96 (m, 2H), 1.77-1.54 (m, 6H), 1.46-1.43 (m, 6H), 1.27-1.09 (m, 10H), 0.96 (s, 3H), 0.69 (s, 3H). LCMS R$_t$=1.252 min in 2 min chromatography, MS ESI calcd. For C$_{28}$H$_{37}$F$_2$N$_3$O$_2$[M+H]⁺ 468, found 468.

Example 37

Synthesis of 79, 80, and 81

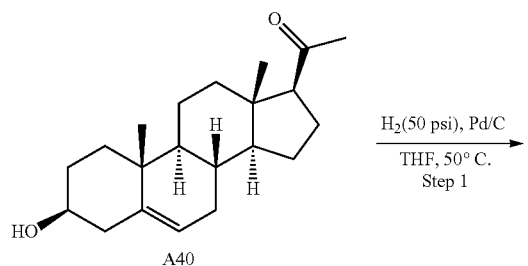

A40

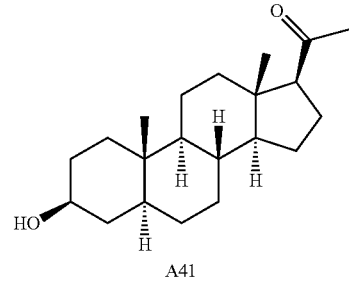

A41

-continued

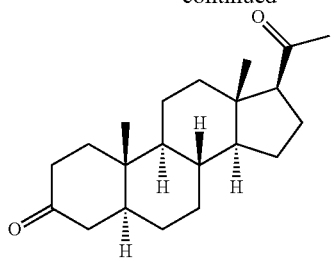

A42

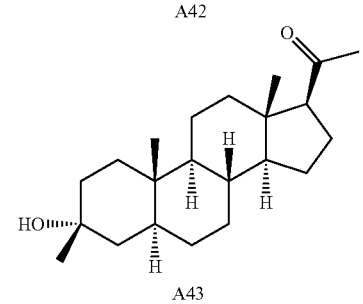

A43

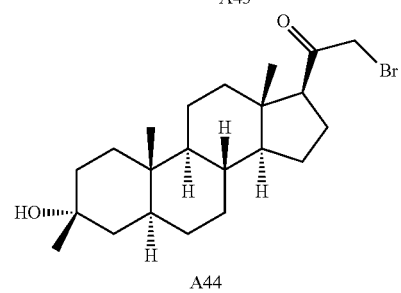

A44

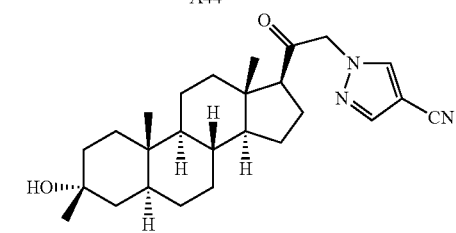

79

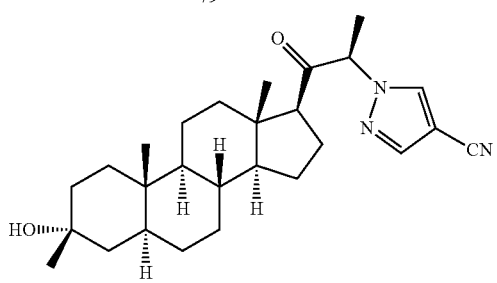

80

+

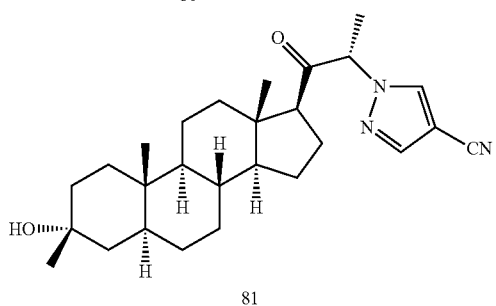

81

Step 1. Synthesis of A41. To a solution of A40 (21 g, 66.3 mmol) in THF (300 mL) was added Pd/C (dry, 10%, 2.1 g). After degassing for three times with $H_2$, the reaction mixture was stirred for 16 h at 50° C. in $H_2$ atmosphere (50 psi). When HNMR showed the starting material was consumed, and desired product was produced, the catalyst was removed by suction, and the filtrate was concentrated to give A41 (21 g) as white solid, which was used for next step directly without further purification.

$^1$H NMR (A41): 400 MHz δ 2.53-2.48 (m, 1H), 2.00 (S, 3H), 1.81-1.58 (m, 9H), 1.38-1.16 (m, 12H), 1.29-1.07 (m, 10H), 0.98 (s, 3H), 067 (s, 3H).

Step 2. Synthesis of A42. To a solution of A41 (21 g, 65.9 mmol) in DCM (300 mL) was added Dess-Martin reagent (41.9 g, 98.8 mmol) at 0° C. After the addition, the mixture was stirred for 3 h at 25° C. When H NMR showed the starting material was consumed, and desired product was produced. The reaction was quenched with $Na_2S_2O_3$ (3 g), saturated $NaHCO_3$ (50 mL) solution, dried over $Na_2SO_4$ (10 g) and concentrated to give A42 (20 g) as white solid, which was used for next step directly without further purification.

$^1$HNMR (A42): 400 MHz δ 2.55-2.53 (m, 1H), 2.27-2.03 (m, 4H), 2.00 (S, 3H), 1.69-1.62 (m, 3H), 1.43-1.19 (m, 14H), 0.92 (s, 3H), 062 (s, 3H).

Step 3. Synthesis of A43. To a solution of A42 (1.0 g, 3.15 mmol) in toluene (10 mL) was added methylmagnesium bromide (9.45 mmol, 3.15 mL, 3M in ether) at −70° C. The mixture was stirred at this temperature for 2 hours. TLC (PE:EA=3:1, PMA) indicated the reaction was finished and two main spots were found. Saturated $NH_4Cl$ (20 mL) was added to the mixture and then extracted with EtOAc (20 mL*3). The combined organic phase was dried over $Na_2SO_4$ and concentrated to give a residue, which was purified by combi-flash (PE:EA=100%-60%) to give A43 (0.3 g) as a white solid.

$^1$H NMR (A43): (400 MHz, $CDCl_3$) δ 2.52 (t, J=8.8 Hz, 1H), 2.17-2.12 (m, 1H), 2.11 (s, 3H), 1.70-1.18 (m, 23H), 1.05-0.85 (m, 1H), 0.80-0.79 (m, 1H), 0.74 (s, 3H), 0.59 (s, 3H).

Step 4. Synthesis of A44. To a solution of A43 (0.3 g, 0.902 mmol) in MeOH (10 mL) was added one drop of HBr. $Br_2$ (215 mg, 1.35 mmol) was added in one portion. The reaction solution was stirred at 25° C. for 1 hour. TLC (PE:EA=3:1, PMA) indicated the reaction was finished and a main spot was found. The mixture was quenched with saturated $NaHCO_3$ solution to pH=7, concentrated to give a residue, to which was added water (20 mL) and then extracted with EtOAc (15 mL*3). The organic layers were combined, dried over $Na_2SO_4$ and concentrated to give crude A44 (0.4 g) as a white solid.

$^1$H NMR (A44): (400 MHz, CDCl3) δ 3.94-3.87 (m, 2H), 2.81 (t, J=8.8 Hz, 1H), 2.18-2.11 (m, 1H), 1.95-1.85 (m, 1H), 1.80-1.10 (m, 22H), 1.00-0.75 (m, 2H), 0.74 (s, 3H), 0.62 (s, 3H).

Step 5. Synthesis of 79. To a solution of A44 (400 mg, 0.97 mmol) in acetone (2 mL) was added 4H-pyrazole-4-carbonitrile (134 mg, 1.45 mmol), followed by $K_2CO_3$ (267 mg, 1.94 mmol). The resulting reaction mixture was stirred at 25° C. for 2 hours. TLC (PE:EA=3:1, PMA) indicated the reaction was finished and a main spot was found. To the mixture was added water (4 mL) and then extracted with EtOAc (2 mL*3). The combined organic phases was concentrated to give a residue, which was purified by combi-flash (PE:EA=100%-50%) to give 79 (0.4 g) as white solid.

$^1$H NMR (79): (400 MHz, $CDCl_3$) δ 7.85 (s, 1H), 7.80 (s, 1H), 5.03-4.86 (m, 2H), 2.59 (t, J=8.4 Hz, 1H), 2.25-2.10 (m, 1H), 2.05-1.95 (m, 1H), 1.80-1.15 (m, H), 1.05-0.76 (m, 4H), 0.75 (s, 3H), 0.65 (s, 3H). LCMS $R_t$=1.312 min in 2 min chromatography, MS ESI calcd. for C26H38N3O2[M+H]$^+$ 423, found 406[M+H−$H_2O$]$^+$.

Step 6. Synthesis of 80 and 81. To a solution of 79 (0.2 g, 0.472 mmol) in THF (5 mL) was added KOH (52.8 mg, 0.944 mmol) and MeI (80.3 mg, 0.566 mmol). The final reaction mixture was stirred at 25° C. for 1 hours TLC (PE:EA=3:1) indicated the reaction was finished. To the reaction solution was added water (10 mL) and then extracted with EtOAc (5 mL*2). The combined organic phase was concentrated and then purified by prep-HPLC to give 1-((R)-1-((3R,5S,8R,9S,10S,13S,14S,17S)-3-hydroxy-3,10,13-trimethylhexadecahydro-1H-cyclopenta[a]phenanthren-17-yl)-1-oxopropan-2-yl)-1H-pyrazole-4-carbonitrile (12 mg) and 1-((S)-1-((3R,5S,8R,9S,10S,13S,14S,17S)-3-hydroxy-3,10,13-trimethylhexadecahydro-1H-cyclopenta[a]phenanthren-17-yl)-1-oxopropan-2-yl)-1H-pyrazole-4-carbonitrile (9 mg) as a white solid.

$^1$H NMR (80): (400 MHz, $CDCl_3$) δ 7.86 (s, 1H), 7.80 (s, 1H), 5.07-5.01 (m, 1H), 2.49 (t, J=8.8 Hz, 1H), 2.15-1.80 (m, 2H), 1.75-1.15 (m, 25H), 0.95-0.85 (m, 1H), 0.84-0.75 (m, 1H), 0.74 (s, 3H), 0.65 (s, 3H). LCMS $R_t$=1.370 min in 2 min chromatography, MS ESI calcd. for C27H40N3O2 [M+H]$^+$ 438, found 420 [M+H−$H_2O$]$^+$.

$^1$H NMR (81): (400 MHz, $CDCl_3$) δ 7.99 (s, 1H), 7.77 (s, 1H), 5.30-5.24 (m, 1H), 2.73 (t, J=8.8 Hz, 1H), 2.17-2.14 (m, 2H), 1.75-1.15 (m, 25H), 1.00-0.90 (m, 1H), 0.85-0.75 (m, 1H), 0.74 (s, 3H), 0.55 (s, 3H). LCMS $R_t$=1.374 min in 2 min chromatography, MS ESI calcd. for C27H40N3O2 [M+H]$^+$ 438, found 420 [M+H−$H_2O$]$^+$.

Example 40

Synthesis of 89

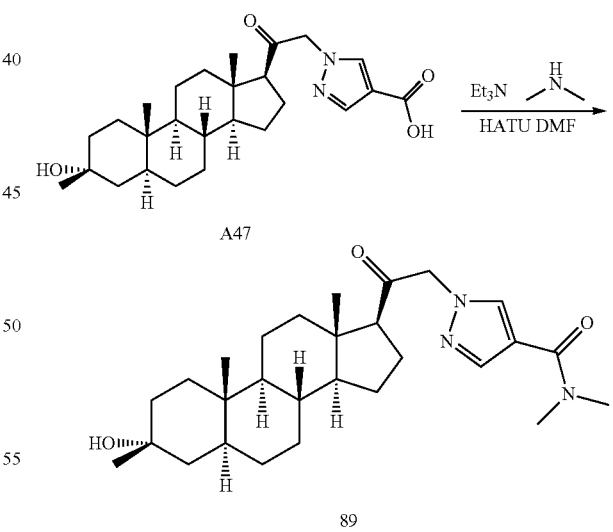

The synthesis of A47 was carried out according to Example 5, step 4. To a solution of 1-(2-((3R,5S,8R,9S,10S,13S,14S,17S)-3-hydroxy-3,10,13-trimethyl hexadecahydro-1H-cyclopenta[a]phenanthren-17-yl)-2-oxoethyl)-1H-pyrazole-4-carboxylic acid (A47, 100 mg, 0.225 mmol) in DMF (2 mL) was added TEA (45.5 mg) and HATU (170 mg, 0.450 mmol), followed by dimethylamine (15.1 mg, 0.337 mmol). The resulting reaction mixture was stirred at 25° C. for 16 hours, at which point TLC analysis (DCM:MeOH=10:1) indicated the starting material was consumed completely. Water (10 mL) was added, and the mixture was extracted with EtOAc (8 mL*3). The combined organic phases were concentrated and the resulting residue was purified by prep-HPLC to give 1-(2-((3R,5S,8R,9S,10S,13S,14S,17S)-3-hydroxy-3,10,13-trimethylhexadecahydro-1H-cyclopenta[a]phenanthren-17-yl)-2-oxoethyl)-N,N-dimethyl-1H-pyrazole-4-carboxamide (6 mg). $^1$HNMR (106): (400 MHz, Methanol-d4) δ 8.00 (s, 1H), 783 (s, 1H), 5.16-5.07 (m, 2H), 3.29 (s, 3H), 3.10 (s, 3H), 2.75 (t, J=8.8 Hz, 1H), 2.20-2.17 (m, 2H), 1.77-1.25 (m, 25H), 1.18-0.85 (m, 3H), 0.82 (s, 3H), 0.70 (s, 3H). LCMS: Rt=0.861 min in 1.5 min chromatography, MS ESI calcd. For $C_{28}H_{43}N_3O_3$ $[M+Na]^+$ 492, found 492.

Example 41

Synthesis of 90, 91, 92, and 93

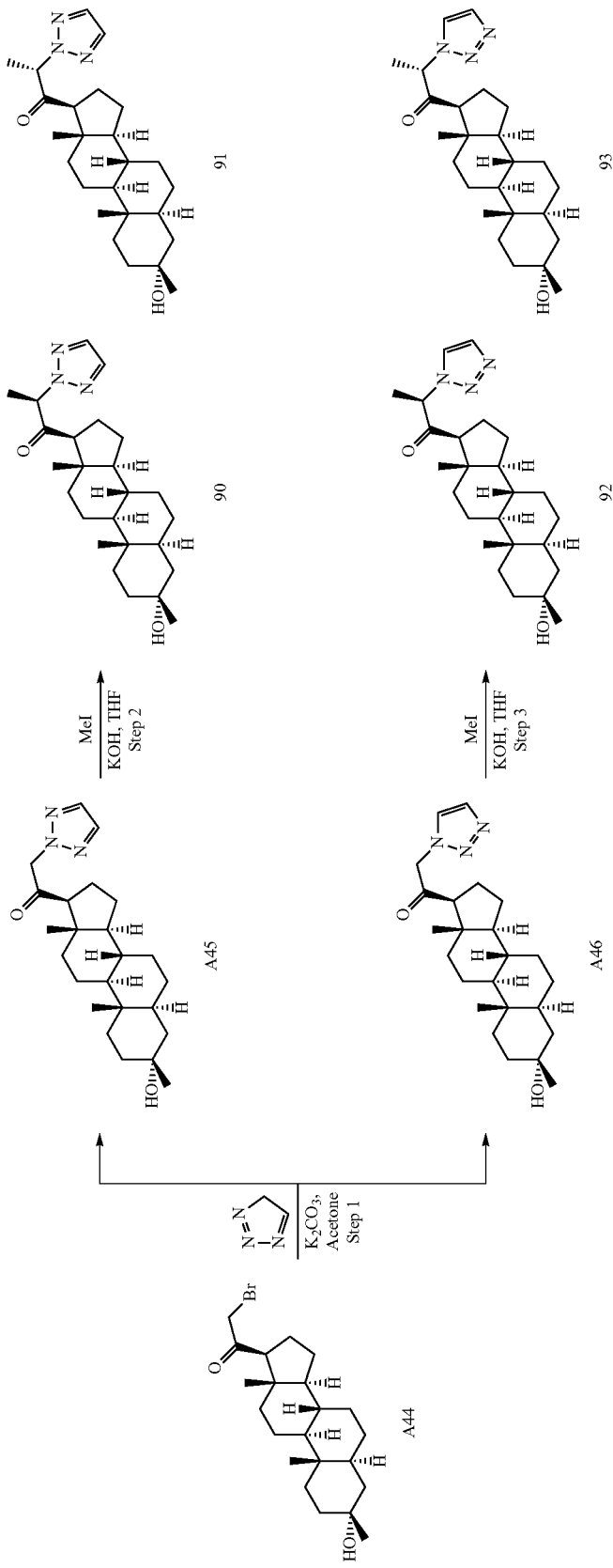

Step 1. Synthesis of A45 and A46. To a solution of A44 (400 mg, 0.97 mmol) in acetone (5 mL) was added 2H-1,2,3-triazole (100 mg, 1.45 mmol), followed by $K_2CO_3$ (267 mg, 1.94 mmol). The resulting reaction mixture was stirred at 25° C. for 2 hours. TLC (PE:EA=3:1, PMA) indicated the reaction was finished and a main spot was found. To the mixture was added water (4 mL) and then extracted with EtOAc (2 mL*3). The combined organic phases was concentrated to give a residue, which was purified by combi-flash (PE:EA=100%-50%) to give 1-((3R,5S,8R,9S,10S,13S,14S,17S)-3-hydroxy-3,10,13-trimethylhexadecahydro-1H-cyclopenta[a]phenanthren-17-yl)-2-(2H-1,2,3-triazol-2-yl)ethanone (0.1 g) and 1-((3R,5S,8R,9S,10S,13S,14S,17S)-3-hydroxy-3,10,13-trimethylhexadecahydro-1H-cyclopenta[a]phenanthren-17-yl)-2-(1H-1,2,3-triazol-1-yl)ethanone (0.2 g) as white solid.

$^1$H NMR (A45): (400 MHz, $CDCl_3$) δ 7.73 (s, 1H), 7.63 (s, 1H), 5.28-5.10 (m, 2H), 2.63 (t, J=8.8 Hz, 1H), 2.25-2.10 (m, 1H), 1.80-0.80 (m, 25H), 0.68 (s, 3H), 0.65 (s, 3H).

$^1$H NMR (A46): (400 MHz, $CDCl_3$) δ 7.73 (s, 2H), 5.29-5.18 (m, 2H), 2.57 (t, J=8.4 Hz, 1H), 2.25-2.10 (m, 1H), 1.80-0.80 (m, 25H), 0.75 (s, 3H), 0.69 (s, 3H).

Step 2. Synthesis of 90 and 91. To a solution of 90 (0.1 g, 0.25 mmol) in THF (5 mL) was added KOH (28 mg, 0.5 mmol) and MeI (42.5 mg, 0.3 mmol). The final reaction mixture was stirred at 25° C. for 1 hour. LCMS indicated the reaction was finished. To the reaction solution was added water (10 mL) and then extracted with EtOAc (5 mL*2). The combined organic phase was concentrated and then purified by prep-HPLC to give (R)-1-((3R,5S,8R,9S,10S,13S,14S,17S)-3-hydroxy-3,10,13-trimethylhexadecahydro-1H-cyclopenta[a]phenanthren-17-yl)-2-(2H-1,2,3-triazol-2-yl)propan-1-one (92, 10.6 mg) and (S)-1-((3R,5S,8R,9S,10S,13S,14S,17S)-3-hydroxy-3,10,13-trimethylhexadecahydro-1H-cyclopenta[a]phenanthren-17-yl)-2-(2H-1,2,3-triazol-2-yl)propan-1-one (93, 12.5 mg) as white solid.

$^1$H NMR (90): (400 MHz, $CDCl_3$) δ 7.66 (s, 2H), 5.28-5.22 (m, 1H), 2.24 (t, J=8.8 Hz, 1H), 2.14-1.95 (m, 3H), 1.85-1.70 (m, 3H), 1.65-0.75 (m, H), 0.71 (s, 3H), 0.64 (s, 3H). LCMS Rt=1.381 min in 2 min chromatography, MS ESI calcd. for C25H39N3O2 [M+H]+ 414, found 414.

$^1$H NMR (91): (400 MHz, $CDCl_3$) δ7.66 (s, 2H), 5.43-5.37 (m, 1H), 2.65 (t, J=8.8 Hz, 1H), 2.14-1.95 (m, 3H), 1.85-1.70 (m, 3H), 1.65-0.75 (m, 23H), 0.74 (s, 3H), 0.67 (s, 3H). LCMS Rt=1.349 min in 2 min chromatography, MS ESI calcd. for C25H39N3O2 [M+H]+ 414, found 414.

Step 3. Synthesis of 92 and 93. To a solution of 91 (0.2 g, 0.5 mmol) in THF (5 mL) was added KOH (56 mg, 1.0 mmol) and MeI (85.1 mg, 0.6 mmol). The final reaction mixture was stirred at 25° C. for 1 hour. LCMS indicated the reaction was finished. To the reaction solution was added water (10 mL) and then extracted with EtOAc (5 mL*2). The combined organic phase was concentrated and then purified by prep-HPLC to give (R)-1-((3R,5S,8R,9S,10S,13S,14S,17S)-3-hydroxy-3,10,13-trimethylhexadecahydro-1H-cyclopenta[a]phenanthren-17-yl)-2-(1H-1,2,3-triazol-1-yl)propan-1-one (92, 6.9 mg) and (S)-1-((3R,5S,8R,9S,10S,13S,14S,17S)-3-hydroxy-3,10,13-trimethylhexadecahydro-1H-cyclopenta[a]phenanthren-17-yl)-2-(1H-1,2,3-triazol-1-yl)propan-1-one (93, 1.5 mg) as white solid.

$^1$H NMR (92): (400 MHz, $CDCl_3$) δ 7.76 (s, 1H), 7.60 (s, 1H), 5.48-5.46 (m, 1H), 2.57 (t, J=8.8 Hz, 1H), 2.15-1.05 (m, 26H), 1.00-0.74 (m, 3H), 0.74 (s, 3H), 0.66 (s, 3H). LCMS Rt=1.295 min in 2 min chromatography, MS ESI calcd. for C25H39N3O2 [M+H]$^+$ 414, found 414.

$^1$H NMR (93): (400 MHz, $CDCl_3$) δ 7.79 (s, 1H), 7.75 (s, 1H), 5.68-5.64 (m, 1H), 2.78 (t, J=8.8 Hz, 1H), 2.20-2.14 (m, 2H), 1.75-1.15 (m, 25H), 1.00-0.90 (m, 1H), 0.85-0.75 (m, 1H), 0.73 (s, 3H), 0.51 (s, 3H). LCMS Rt=1.260 min in 2 min chromatography, MS ESI calcd. for C25H39N3O2 [M+H]$^+$ 414, found 414.

Example 42

Synthesis of 96, 97, 98, 99, 100, 101, and 102

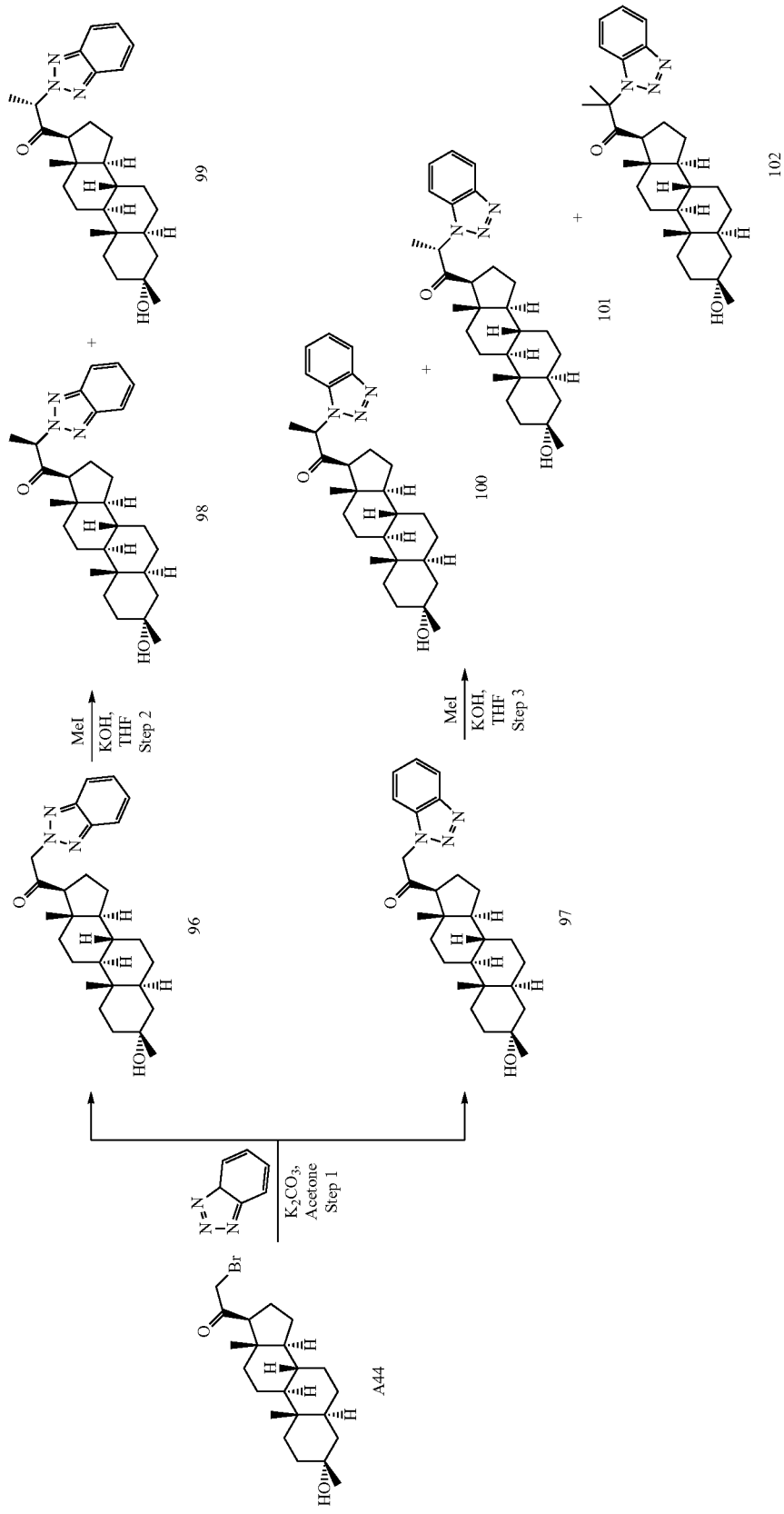

Step 1. Synthesis of 96 and 97. To a solution of A44 (0.4 g, 0.972 mmol) in acetone (5 mL) was added 2H-benzo[d][1,2,3]triazole (172 mg, 1.45 mmol), followed by $K_2CO_3$ (267 mg, 1.94 mmol). The resulting reaction mixture was stirred at 25° C. for 16 hours. TLC indicated the reaction was finished. To the mixture was added water (5 mL) and then extracted with EtOAc (5 mL*3). The combined organic phases was concentrated to give a residue, which was purified by combi-flash (PE:EA=100%-50%) to give 2-(2H-benzo[d][1,2,3]triazol-2-yl)-1-((3R,5S,8R,9S,10S,13S,14S,17S)-3-hydroxy-3,10,13-trimethylhexadecahydro-1H-cyclopenta[a]phenanthren-17-yl)ethanone (96, 0.1 g) and 2-(1H-benzo[d][1,2,3]triazol-1-yl)-1-((3R,5S,8R,9S,10S,13S,14S,17S)-3-hydroxy-3,10,13-trimethylhexadecahydro-1H-cyclopenta[a]phenanthren-17-yl)ethanone (97, 0.2 g) as a white solid.

$^1$H NMR (96): (400 MHz, $CDCl_3$) δ 7.88-7.86 (m, 2H), 7.40-7.37 (m, 2H), 5.56-5.51 (m, 2H), 2.65 (t, J=8.8 Hz, 1H), 2.25-2.10 (m, 2H), 1.80-0.80 (m, 24H), 0.75 (s, 3H), 0.73 (s, 3H).

$^1$H NMR (97): (400 MHz, $CDCl_3$) δ 8.09-8.07 (m, 1H), 7.50-7.40 (m, 1H), 7.39-7.32 (m, 2H), 5.46-5.36 (m, 2H), 2.70 (t, J=8.8 Hz, 1H), 2.25-2.10 (m, 2H), 1.80-0.80 (m, 24H), 0.77 (s, 3H), 0.72 (s, 3H).

Step 2. Synthesis of 98 and 99. To a solution of 96 (0.1 g, 0.22 mmol) in THF (5 mL) was added KOH (24.8 mg, 0.44 mmol) and MeI (37.7 mg, 0.266 mmol). The final reaction mixture was stirred at 25° C. for 1 hour. LCMS indicated the reaction was finished. To the reaction solution was added water (10 mL) and then extracted with EtOAc (5 mL*2). The combined organic phase was concentrated and then purified by prep-HPLC to give ((R)-2-(2H-benzo[d][1,2,3]triazol-2-yl)-1-((3R,5S,8R,9S,1S,13S,14S,17S)-3-hydroxy-3, 10,13-trimethylhexadecahydro-1H-cyclopenta[a]phenanthren-17-yl)propan-1-one (98, 8.6 mg) and (S)-2-(2H-benzo[d][1,2,3]triazol-2-yl)-1-((3R,5S,8R,9S,10S,13S,14S,17S)-3-hydroxy-3, 10,13-trimethylhexadecahydro-1H-cyclopenta[a]phenanthren-17-yl)propan-1-one (99, 9.7 mg) as white solid.

$^1$H NMR (98): (400 MHz, $CDCl_3$) δ7.89-7.86 (m, 2H), 7.42-7.38 (m, 2H), 5.54-5.49 (m, 1H), 2.26 (t, J=8.Hz, 1H), 2.20-2.05 (m, 2H), 1.85-1.75 (m, 3H), 1.75-0.78 (m, 24H), 0.69 (s, 3H), 0.67 (s, 3H). LCMS Rt=1.493 min in 2 min chromatography, MS ESI calcd. For $C_{29}H_{42}N_3O_2$ [M+H]+ 464, found 446[M+H–H2O]$^+$.

$^1$H NMR (99): (400 MHz, $CDCl_3$) δ7.89-7.86 (m, 2H), 7.39-7.36 (m, 2H), 5.72-5.66 (m, 1H), 2.71 (t, J=8.Hz, 1H), 2.19-2.05 (m, 2H), 2.00-1.90 (m, 3H), 1.75-0.78 (m, 24H), 0.75 (s, 3H), 0.70 (s, 3H). LCMS $R_f$=1.466 min in 2 min chromatography, MS ESI calcd. for $C_{29}H_{42}N_3O_2$ [M+H]+ 464, found 464.

Step 3. Synthesis of 100, 101, and 102. To a solution of 97 (0.2 g, 0.44 mmol) in THF (5 mL) was added KOH (49.7 mg, 0.88 mmol) and MeI (126 mg, 0.88 mmol). The reaction mixture was stirred at 25° C. for 1 hour. LCMS indicated the reaction was finished. $H_2O$ (10 mL) was added to the solution and extracted with EtOAc (5 mL*2). The combined organic phase was concentrated and then purified by prep-HPLC to give (R)-2-(1H-benzo[d][1,2,3]triazol-1-yl)-1-((3R,5S,8R,9S,10S,13S,14S,17S)-3-hydroxy-3,10,13-trimethylhexadecahydro-1H-cyclopenta[a]phenanthren-17-yl)propan-1-one (100, 3.8 mg), (S)-2-(1H-benzo[d][1,2,3]triazol-1-yl)-1-((3R,5S,8R,9S,10S,13S,14S,17S)-3-hydroxy-3, 10,13-trimethylhexadecahydro-1H-cyclopenta[a]phenanthren-17-yl)propan-1-one (101, 10.3 mg) and 2-(1H-benzo[d][1,2,3]triazol-1-yl)-1-((3R,5S,8R,9S,10S,13S,14S,17S)-3-hydroxy-3, 10,13-trimethylhexadecahydro-1H-cyclopenta[a]phenanthren-17-yl)-2-methylpropan-1-one (102, 24.7 mg) as white solid.

$^1$H NMR (100): (400 MHz, $CDCl_3$) δ 8.09-8.07 (m, 1H), 7.48-7.36 (m, 3H), 5.64-5.59 (m, 1H), 2.34 (t, J=8.8 Hz, 1H), 2.15-1.75 (m, 2H), 1.74-1.70 (m, 3H), 1.70-0.75 (m, 24H), 0.71 (s, 3H), 0.66 (s, 3H). LCMS $R_f$=1.411 min in 2 min chromatography, MS ESI calcd. for C29H42N3O2 [M+H]$^+$ 464, found 464.

$^1$H NMR (101): (400 MHz, $CDCl_3$) δ 8.08-8.06 (m, 1H), 7.56-7.54 (m, 1H), 7.49-7.47 (m, 1H), 7.37-7.35 (m, 1H), 5.81-5.75 (m, 1H), 2.70 (t, J=8.8 Hz, 1H), 2.15-1.95 (m, 2H), 1.95-1.85 (m, 3H), 1.70-0.75 (m, 24H), 0.73 (s, 3H), 0.61 (s, 3H). LCMS Rt=1.391 min in 2 min chromatography, MS ESI calcd. for C29H42N3O2 [M+H]$^+$ 464, found 464.

$^1$H NMR (102): (400 MHz, $CDCl_3$) δ 8.09-8.07 (m, 1H), 7.43-7.34 (m, 3H), 2.32 (t, J=8.8 Hz, 1H), 2.05 (s, 3H), 1.90 (s, 3H), 1.70-1.00 (m, 22H), 0.90-0.50 (m, 10H). LCMS Rt=1.467 min in 2 min chromatography, MS ESI calcd. for C30H44N3O2 [M+H]+ 478, found 478.

Example 43

Synthesis of 103

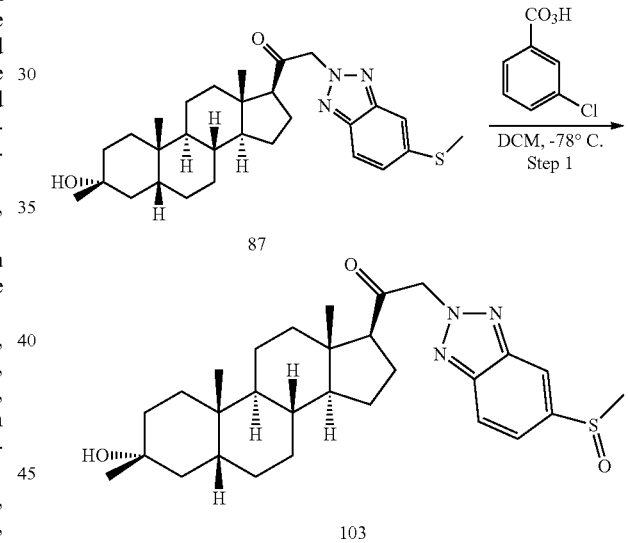

To a solution of 87 (50 mg, 0.1 mmol) in 10 mL of DCM was added m-CPBA (18.9 mg, 0.11 mmol) at –78° C. The reaction mixture was stirred at the same temperature for 3 h. TLC (petroleum ether/ethyl acetate=1:1, PMA) showed the reaction was complete. The reaction mixture was poured into saturated $Na_2S_2O_3$ and extracted with $CH_2Cl_2$ (50 mL×2). The organic layers were washed with saturated $NaHCO_3$ (50 mL), brine (50 mL), dried over anhydrous $Na_2SO_4$ and concentrated in vacuum. The residue was purified by prep-TLC (PE:EtOAc=1:1.5) to give 103 (14 mg) as white solid.

$^1$H NMR: (103): 400 MHz δ 8.29 (s, 1H), 8.03 (d, J=9.2 Hz, 1H), 7.55 (t, J=7.2 Hz, 1H), 5.61-5.51 (m, 2H), 2.78 (s, 3H), 2.68 (d, J=8.8 Hz, 1H), 2.17-2.15 (m, 2H), 1.96-1.53 (m, 5H), 1.49-1.43 (m, 8H), 1.27-1.08 (m, 12H), 0.96 (s, 3H), 0.73 (s, 3H). LCMS $R_f$=0.877 min in 1.5 min chromatography, MS ESI calcd. For $C_{29}H_{41}N_3O_3S$ [M+H]$^+$ 512, found 494[M+H–18]$^+$.

Example 44

Synthesis of 104

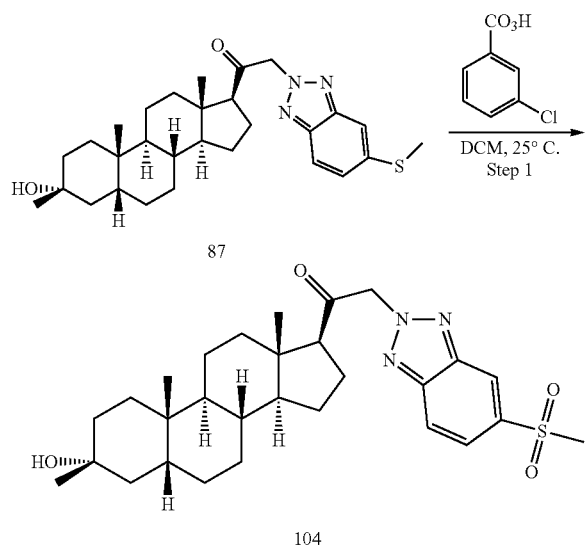

To a solution of 87 (50 mg, 100 mmol) in 10 mL of CH$_2$Cl$_2$ was added m-CPBA (43.1 mg, 250 mmol) at 25° C. The reaction mixture was stirred for 3 h at the same temperature. TLC (petroleum ether/ethyl acetate=1:1, PMA) showed the reaction was completed. The reaction mixture was poured into saturated Na$_2$S$_2$O$_3$ and extracted with CH$_2$Cl$_2$ (50 mL×2). The organic layers were washed with saturated NaHCO$_3$ (50 mL), brine (50 mL), dried over anhydrous Na$_2$SO$_4$ and concentrated in vacuum. The residue was purified by prep-TLC (PE:EtOAc=1:1.5) to give 1-((3R,5R,8R,9S,10S,13S,14S,17S)-3-hydroxy-3,10,13-trimethyl hexadecahydro-1H-cyclopenta[a]phenanthren-17-yl)-2-(5-(methylsulfonyl)-2H-benzo[d][1,2,3]triazol-2-yl)ethanone (104, 8 mg) as a white solid.

$^1$H NMR: (104): 400 MHz δ 8.62 (s, 1H), 8.07 (d, J=9.2 Hz, 1H), 7.88 (t, J=1.6 Hz, 1H), 5.64-5.55 (m, 2H), 3.12 (s, 3H), 2.68 (t, J=8.8 Hz, 1H), 2.21-2.17 (m, 2H), 1.96-1.54 (m, 6H), 1.51-1.44 (m, 9H), 1.27-1.09 (m, 11H), 0.97 (s, 3H), 0.73 (s, 3H). LCMS R$_f$=0.913 min in 1.5 min chromatography, MS ESI calcd. For C$_{29}$H$_{41}$N$_3$O$_4$S [M+H]$^+$ 528, found 510[M+H−18]$^+$.

Example 45

Synthesis of 105 and 106

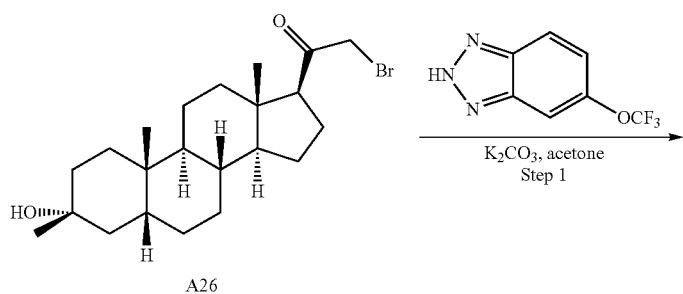

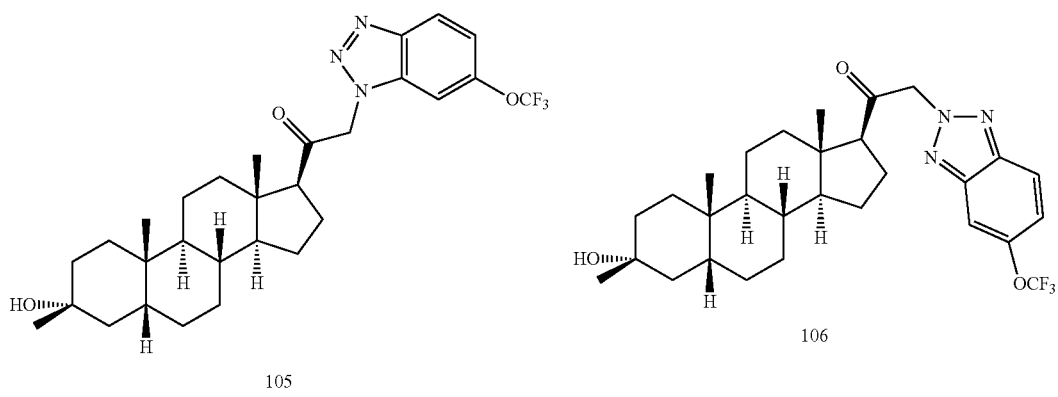

The title compounds were prepared according to Example 5, step 4.

¹HNMR (105): (400 MHz, CDCl₃) δ 8.09 (d, J=8.8 Hz, 1H), 7.27 (s, 1H), 7.18 (s, 1H), 5.47-5.35 (m, 2H), 2.72 (t, J=8.4, 1H), 2.21-1.97 (m, 2H), 1.86-1.55 (m, 5H), 1.47-1.44 (m, 10H), 1.29-1.09 (m, 8H), 0.97 (s, 3H), 0.71 (s, 3H). LCMS R$_t$=0.994 min in 1.5 min chromatography, MS ESI calcd. For C$_{29}$H$_{38}$F$_3$N$_3$O$_3$[M+H]$^+$ 534, found 534.

Example 47

Synthesis of 107 and 108

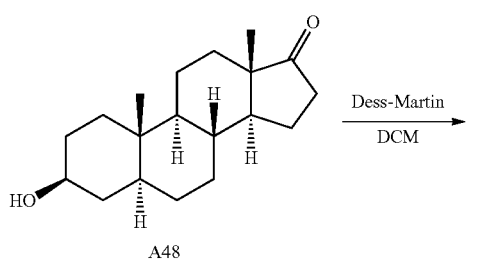
A48

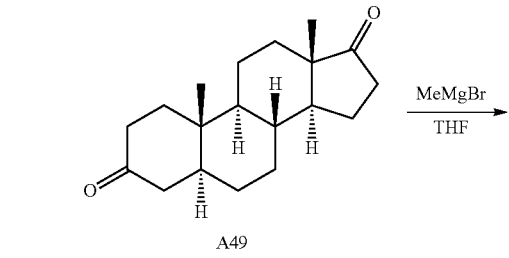
A49

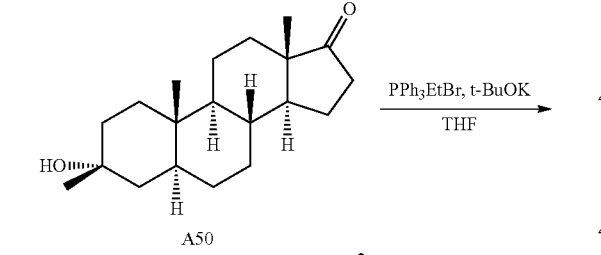
A50

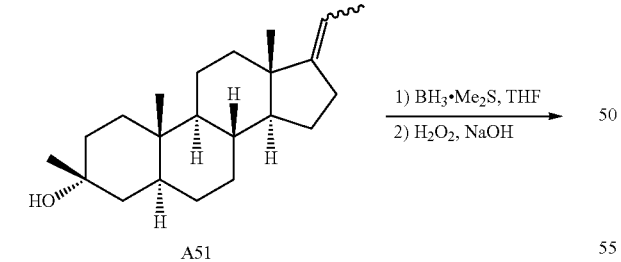
A51

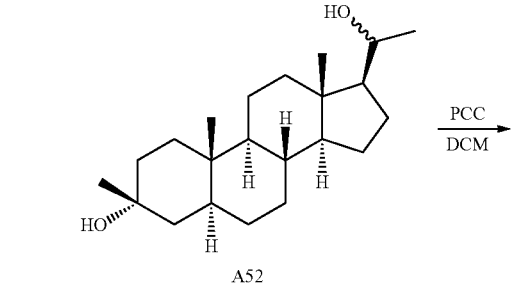
A52

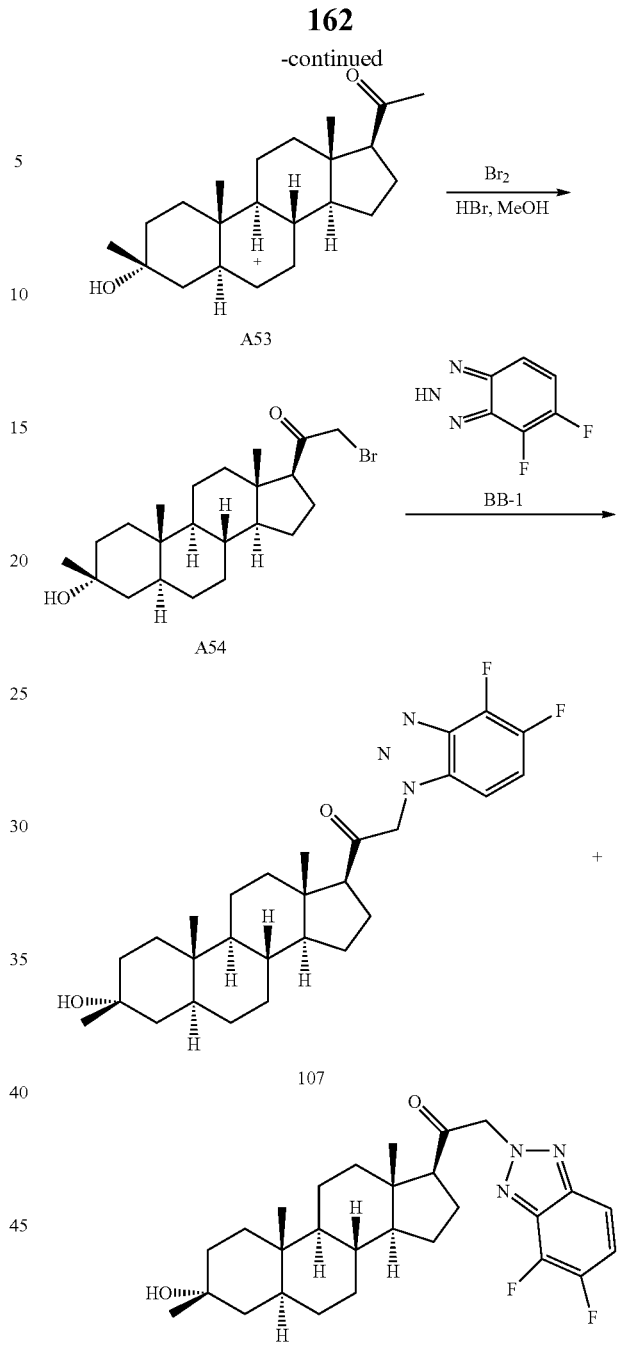

Synthesis of A49: To a solution of (3S,5S,8R,9S,10S,13S,14S)-3-hydroxy-10,13-dimethyltetradecahydro-1H-cyclopenta[a]phenanthren-17(2H)-one (A48, 30 g, 103 mmol) in DCM (300 mL) was added DMP (65.3 g, 154 mmol) in portions at 0° C. After addition, the mixture was stirred at 25° C. for 2 hours, at which point TLC analysis (PE:EA=3:1, PMA) indicated the reaction was finished. The mixture was quenched with saturated Na₂S₂O₃ and NaHCO₃ solution (v:v=1:1) until the solution turned clear. The mixture was then diluted with water (200 mL) and then extracted with DCM (200 mL*3), and the combined organic layers were dried over Na₂SO₄ and concentrated to give crude (5S,8R,9S,10S,13S,14S)-10,13-dimethyldodecahydro-1H-cyclopenta[a]phenanthrene-3,17(2H,4H)-dione (35 g) as a white solid.

¹H NMR (400 MHz, CDCl₃) δ 2.44-2.22 (m, 4H), 2.15-1.75 (m, 6H), 1.70-1.20 (m, 10H), 1.10-0.65 (m, 8H).

Synthesis of A50: To a solution of (5S,8R,9S,10S,13S,14S)-10,13-dimethyldodecahydro-1H-cyclopenta[a]phenanthrene-3,17(2H,4H)-dione (A49, 15.0 g, 52.0 mmol) in THF (200 mL) was added methylmagnesium bromide (156 mmol, 52 mL, 3M in ether) at −70° C. The mixture was stirred at −70° C. for 3 hours, at which TLC analysis (PE:EA=3:1, PMA) indicated the reaction was finished. The reaction mixture was quenched with saturated NH₄Cl solution (300 mL) and concentrated, and the residue was extracted with DCM (500 mL*3). The organic phase was dried, concentrated and purified by combi-flash (PE:EA=100%-60%) to give (3R,5S,8R,9S,1 S,13S,14S)-3-hydroxy-3,10,13-trimethyltetradecahydro-1H-cyclopenta[a]phenanthren-17(2H)-one (A50, 6.5 g) as a white solid.

Synthesis of A51: To a solution of Ph₃PEtBr (39.2 g, 106 mmol) in THF (50 mL) was added a slurry of t-BuOK (11.8 g, 106 mmol) in THF (50 mL) under N₂. The mixture turned red and was stirred at 60° C. for 1 hour, and a solution of (3R,5S,8R,9S,10S,13S,14S)-3-hydroxy-3,10,13-trimethyltetradecahydro-1H-cyclopenta[a]phenanthren-17(2H)-one (A50, 6.5 g, 21.3 mmol) was then added in one portion. The reaction mixture was stirred at 60° C. for 16 hours, at which point TLC analysis (PE:EA=3:1, PMA) indicated the reaction was complete. The reaction mixture was cooled, diluted with water (200 mL), and extracted with EtOAc (100 mL*3). The combined organic phase was dried, concentrated, and purified by combi-flash (PE:EA=100%-85%) to give (3R,5S,8R,9S,10S,13S,14S)-17-ethylidene-3,10,13-trimethylhexadecahydro-1H-cyclopenta[a]phenanthren-3-ol (A51, 5.5 g) as white solid. ¹H (400 MHz, CDCl₃) δ 5.12-5.09 (m, 1H), 2.40-2.10 (m, 4H), 1.75-1.10 (m, 23H), 1.05-0.75 (m, 8H).

Synthesis of A52: To a solution of (3R,5S,8R,9S,10S,13S,14S)-17-ethylidene-3,10,13-trimethylhexadecahydro-1H-cyclopenta[a]phenanthren-3-ol (A51, 5.5 g, 17.3 mmol) in THF (100 mL) was added dropwise a solution of BH₃-Me₂S (17.2 mL, 172 mmol) at 0° C. The solution was stirred at 25° C. for 3 h. TLC (PE/EtOAc=3/1) showed the reaction was completed. After cooling to 0° C., a solution of NaOH (100 mL, 3M) was added very slowly. After the addition was complete, H₂O₂(100 mL, 30%) was added slowly and the inner temperature was maintained below 10° C. The resulting solution was stirred at 25° C. for 2 h. The resulting solution was extracted with EtOAc (100×3). The combined organic solution was washed with saturated aqueous Na₂S₂O₃ (100 mL×3), brine (200 mL), dried over Na₂SO₄ and concentrated in vacuum to give the crude product (6 g) as a white solid. The crude product was used for the next step without further purification.

Synthesis of A53: To a solution of (3R,5S,8R,9S,10S,13S,14S,17S)-17-(1-hydroxyethyl)-3,10,13-trimethylhexadecahydro-1H-cyclopenta[a]phenanthren-3-ol (A52, 6 g, 17.9 mmol) in DCM (50 mL) was added PCC (5.77 g, 26.8 mmol) and SiliaBond Thiol (6 g). The reaction mixture was stirred at 25° C. for 2 hours, at which point TLC analysis (PE:EA=3:1) indicated the reaction was complete. The mixture was concentrated and purified by combi-flash (PE:EA=100%-70%) to give 1-((3R,5S,8R,9S,10S,13S,14S,17S)-3-hydroxy-3,10,13-trimethylhexadecahydro-1H-cyclopenta[a]phenanthren-17-yl)ethanone (A53, 4 g) as white solid.

Synthesis of A54: To a solution of 1-((3R,5S,8R,9S,10S,13S,14S,17S)-3-hydroxy-3,10,13-trimethylhexadecahydro-1H-cyclopenta[a]phenanthren-17-yl)ethanone (A53, 4 g, 12 mmol) in MeOH (50 mL) was added one drop of HBr. Br₂ (2.28 g, 14.3 mmol) was then added in one portion, and the reaction was stirred at 2 5° C. for 1 hour until TLC analysis (PE:EA=3:1, PMA) indicated the reaction was complete. The mixture was quenched with saturated NaHCO₃ solution until the pH reached 7, and the reaction was concentrated and filtered to give 2-bromo-1-((3R,5S,8R,9S,10S,13S,14S,17S)-3-hydroxy-3,10,13-trimethylhexadecahydro-1H-cyclopenta[a]phenanthren-17-yl)ethanone (A54, 4.5 g) as white solid. ¹H NMR (400 MHz, CDCl₃) δ 3.91-3.90 (m, 2H), 2.85-2.75 (m, 1H), 2.25-1.80 (m, 2H), 1.75-1.10 (m, 20H), 1.05-0.63 (m, 10H).

Synthesis of 107 and 108. To a solution of (2-bromo-1-((3R,5S,8R,9S,10S,13S,14S,17S)-3-hydroxy-3,10,13-trimethylhexadecahydro-1H-cyclopenta[a]phenanthren-17-yl)ethanone (A54, 0.2 g, 0.486 mmol) in acetone (2 mL) was added 4,5-difluoro-2H-benzo[d][1,2,3]triazole (75.3 mg, 0.486 mmol), followed by K₂CO₃ (134 mg, 0.972 mmol). The resulting reaction mixture was stirred at 25° C. for 16 hours, at which point TLC indicated the reaction was finished. The reaction was diluted with water (5 mL) and then extracted with EtOAc (5 mL*3), and the combined organic phase was concentrated to give a residue that was purified prep-HPLC to give 2-(4,5-difluoro-1H-benzo[d][1,2,3]triazol-1-yl)-1-((3R,5S,8R,9S,10S,13S,14S,17S)-3-hydroxy-3,10,13-trimethylhexadecahydro-1H-cyclopenta[a]phenanthren-17-yl)ethanone (Compound 107, 51.9 mg) and 2-(4,5-difluoro-2H-benzo[d][1,2,3]triazol-2-yl)-1-((3R,5S,8R,9S,10S,13S,14S,17S)-3-hydroxy-3,10,13-trimethylhexadecahydro-1H-cyclopenta[a]phenanthren-17-yl)ethanone (Compound 108, 36.3 mg) as a white solid.

Compound 107: ¹H NMR (400 MHz, CDCl₃) δ 7.38-7.33 (m, 1H), 7.06-7.03 (m, 1H), 5.46-5.34 (m, 2H), 2.71 (t, J=8.8 Hz, 1H), 2.21-2.14 (m, 2H), 1.80-1.15 (m, 22H), 1.05-0.80 (m, 2H), 0.77 (s, 3H), 0.70 (s, 3H). LCMS: Rt=1.421 min in 2 min Chromatography, MS ESI calcd. for $C_{28}H_{38}F_2N_3O_2$ [M+H]⁺ 486, found 486. Compound 108: ¹H NMR (400 MHz, CDCl₃) δ 7.65-7.62 (m, 1H), 7.31-7.25 (m, 1H), 5.57-5.47 (m, 2H), 2.66 (t, J=8.8 Hz, 1H), 2.30-2.14 (m, 2H), 1.80-1.15 (m, 22H), 1.05-0.73 (m, 8H). LCMS Rt=1.475 min in 2 min Chromatography, MS ESI calcd. for $C_{28}H_{38}F_2N_3O_2$[M+H]⁺ 486, found 468[M+H−18]⁺.

Example 48

Synthesis of 109 and 110

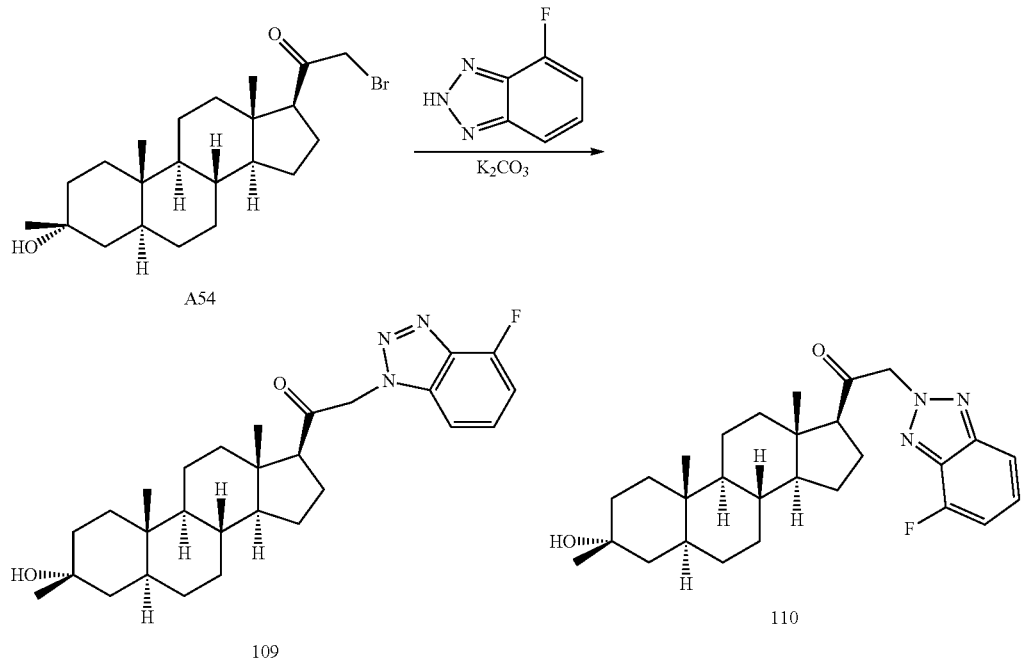

The title compounds were prepared according to Example 47, step 7.

Compound 109: $^1$H NMR (400 MHz, CDCl$_3$) δ 7.44-7.40 (m, 1H), 7.12-7.09 (m, 1H), 7.09-7.03 (m, 1H), 5.47-5.36 (m, 2H), 2.70 (t, J=8.8 Hz, 1H), 2.21-2.16 (m, 2H), 1.80-1.10 (m, 21H), 1.05-0.55 (m, 9H). LCMS: R$_t$=1.387 min in 2 min chromatography, MS ESI calcd. for C$_{28}$H$_{39}$FN$_3$O$_2$ [M+H]$^+$ 468, found 468.

Compound 110: $^1$H NMR (400 MHz, CDCl$_3$) δ 7.89-7.82 (m, 1H), 7.33-7.27 (m, 1H), 7.18-7.07 (m, 1H), 5.54 (s, 2H), 2.76-2.67 (m, 1H), 2.27-2.10 (m, 3H), 1.81-1.10 (m, 19H), 1.09-0.80 (m, 4H), 0.77 (s, 3H), 0.72 (s, 3H). LCMS: R$_t$=1.408 min in 2 min chromatography, MS ESI calcd. for C$_{28}$H$_{39}$FN$_3$O$_2$[M+H]$^+$ 468, found 468.

Example 49

Synthesis of 111, 112, and 113

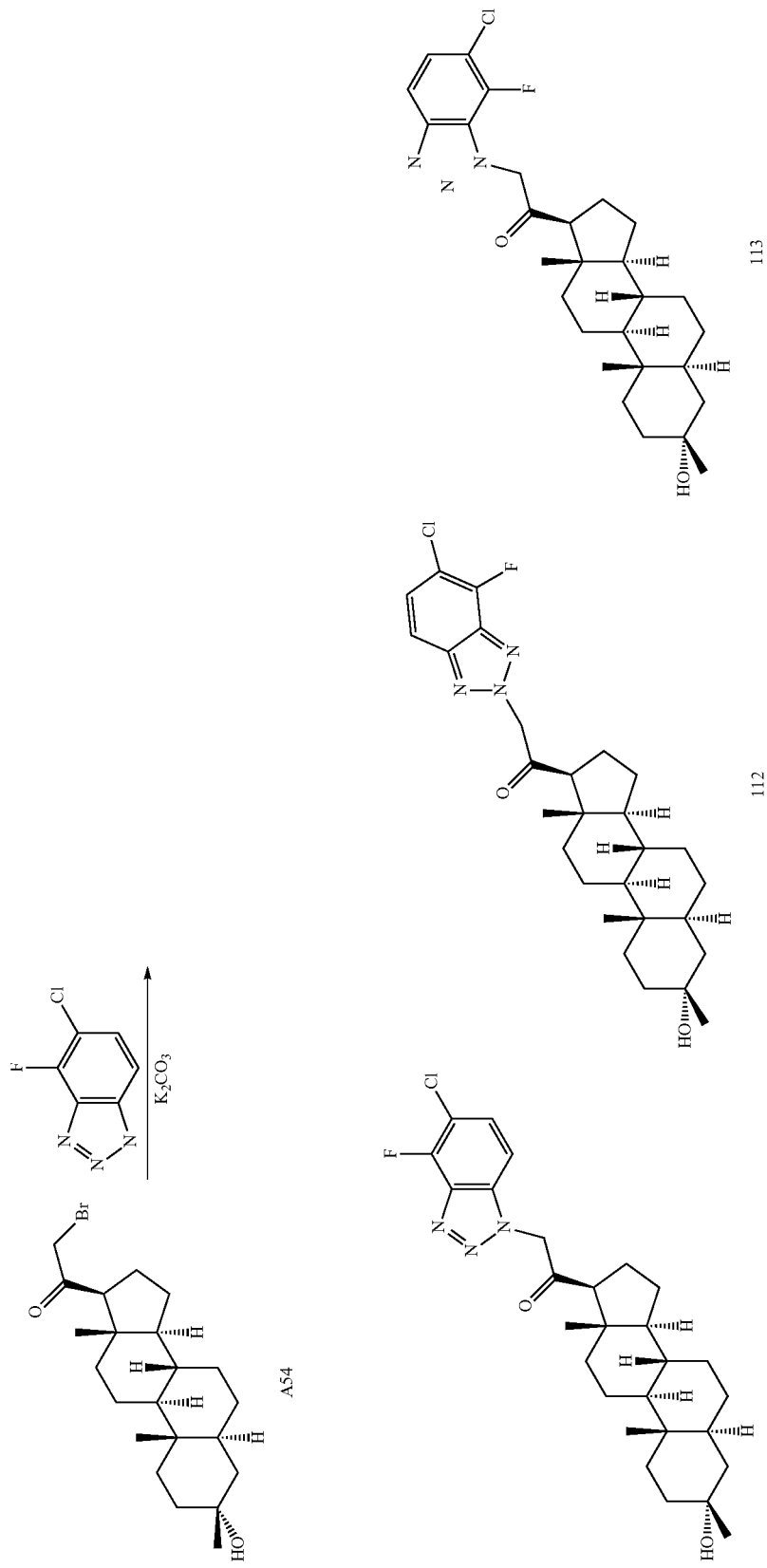

The title compounds were prepared according to Example 47, step 7.

Compound 111: ¹H NMR: (400 MHz, CDCl₃) δ7.48-7.45 (m, 1H), 7.07-7.05 (m, 1H), 5.46-5.34 (m, 2H), 2.73-2.68 (m, 1H), 2.21-2.17 (m, 2H), 1.87-1.11 (m, 21H), 1.07-0.70 (m, 9H).
LCMS: Rt=1.460 min in 2 min Chromatography, MS ESI calcd. for $C_{28}H_{38}FClN_3O_2$[M+H]502, found 502.

Compound 112: ¹H NMR: (400 MHz, CDCl₃) δ7.62 (d, J=8.8 Hz, 1H), 7.37 (d, J=6.8 Hz, 1H), 5.52 (d, J=5.3 Hz, 2H), 2.75-2.58 (m, 1H), 2.33-2.06 (m, 2H), 1.87-1.11 (m, 21H), 1.06-0.64 (m, 9H). LCMS: Rt=1.525 min in 2 min Chromatography, MS ESI calcd. for $C_{28}H_{38}FClN_3O_2$ [M+H]⁺ 502, found 484 [M+H–18]⁺.

Compound 113: ¹H NMR: (400 MHz, CDCl₃) δ7.82-7.74 (m, 1H), 7.38-7.30 (m, 1H), 5.52 (s, 2H), 2.79-2.63 (m, 1H), 2.28-2.07 (m, 2H), 1.90-1.13 (m, 21H), 1.10-0.63 (m, 9H). LCMS: Rt=1.482 min in 2 min Chromatography, MS ESI calcd. for $C_{28}H_{38}FClN_3O_2$[M+H]⁺ 502. found 484 [M+H–18]⁺.

Example 50

Synthesis of 114

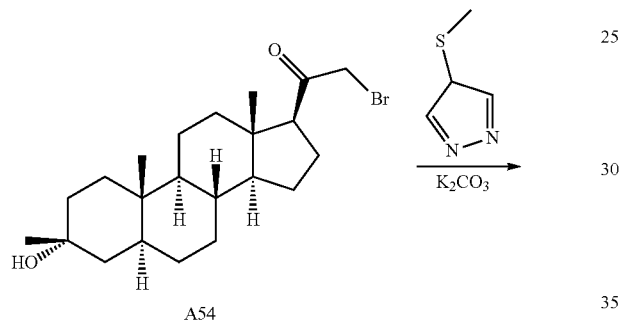

A54

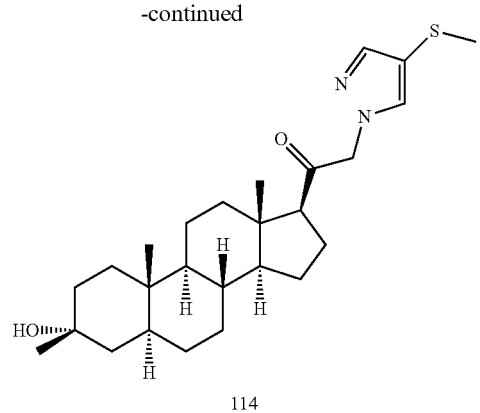

114

The title compound was prepared according to Example 47, step 7.

Compound 114: ¹H NMR (400 MHz, CDCl₃) δ7.52 (s, 1H), 7.41 (s, 1H), 4.93-4.79 (m, 2H), 2.57 (t, J=8.8 Hz, 1H), 2.34 (s, 3H), 2.17-1.95 (m, 2H), 1.80-1.10 (m, 21H), 1.05-0.65 (m, 9H).
LCMS: Rt=1.369 min in 2 min Chromatography, MS ESI calcd. for $C_{26}H_{41}SN_2O_2$[M+H]⁺ 445, found 445.

Example 51

Synthesis of 115, 116, and 117

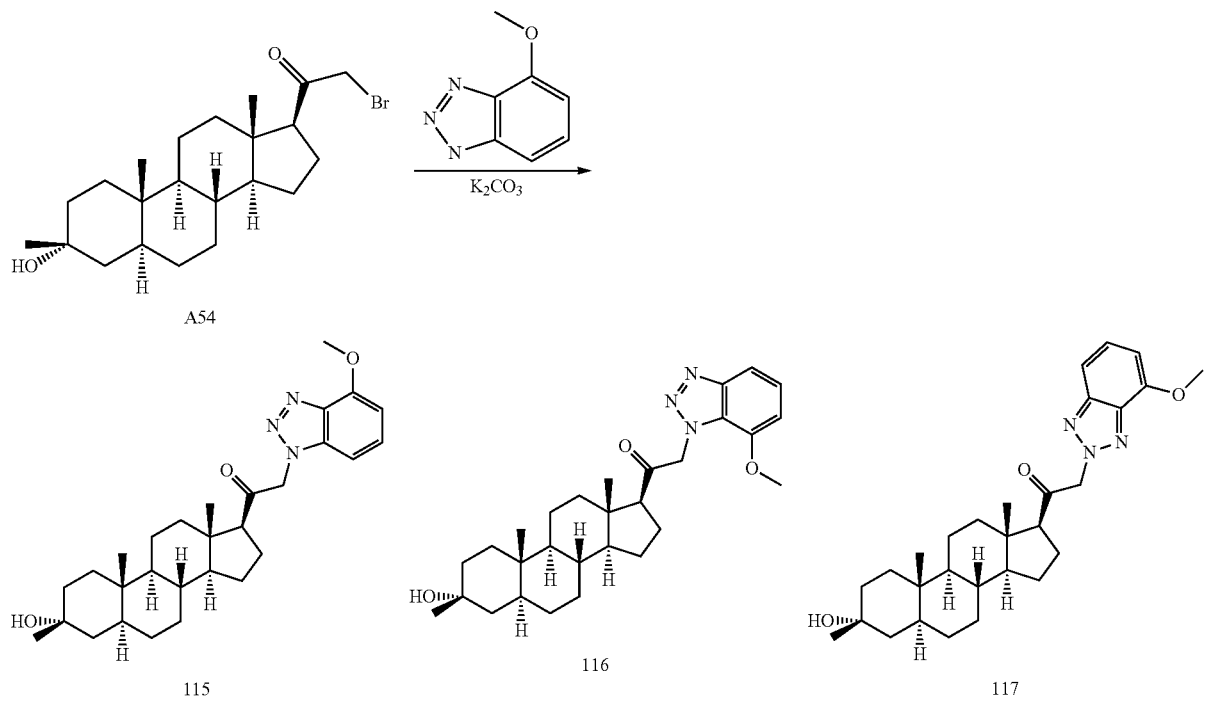

The title compounds were prepared according to Example 47, step 7.

Compound 115: $^1$H NMR (400 MHz, CDCl$_3$) δ7.40-7.36 (m, 1H), 6.87-6.85 (m, 1H), 6.70-6.68 (m, 1H), 5.37-5.35 (m, 2H), 4.12 (s, 3H), 2.69-2.65 (m, 1H), 2.21-2.17 (m, 2H), 1.87-1.11 (m, 21H), 1.07-0.70 (m, 9H). LCMS: Rt=1.384 min in 2 min Chromatography, MS ESI calcd. for C$_{29}$H$_{42}$N$_3$O$_3$ [M+H]$^+$ 480, found 480.

Compound 116: $^1$H NMR (400 MHz, CDCl$_3$) δ7.66-7.59 (m, 1H), 7.25-7.20 (m, 1H), 6.79-6.73 (m, 1H), 5.64-5.52 (m, 2H), 3.89 (s, 3H), 2.7-2.63 (m, 1H), 2.25-2.10 (m, 2H), 1.82-1.14 (m, 22H), 1.04-0.79 (m, 2H), 0.79-0.68 (m, 6H). LCMS: Rt=1.373 min in 2 min Chromatography, MS ESI calcd. for C$_{29}$H$_{42}$N$_3$O$_3$ [M+H]$^+$ 480, found 480.

Compound 117: $^1$H NMR (400 MHz, CDCl$_3$) δ7.44-7.42 (m, 1H), 7.31-7.27 (m, 1H), 6.64-6.63 (m, 1H), 5.54-5.45 (m, 2H), 4.02 (s, 3H), 2.65-2.60 (m, 1H), 2.21-2.10 (m, 2H), 1.87-1.11 (m, 21H), 1.07-0.70 (m, 9H). LCMS: Rt=1.397 min in 2 min Chromatography, MS ESI calcd. for C$_{29}$H$_{42}$N$_3$O$_3$ [M+H]$^+$ 480, found 480.

Example 52

Synthesis of 118

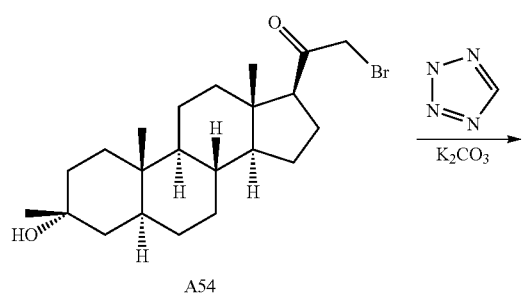

A54

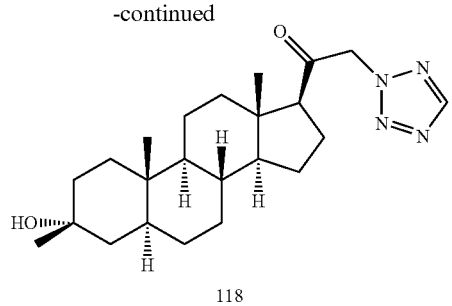

118

The title compound was prepared according to Example 47, step 7.

Compound 118: $^1$H NMR (400 MHz, CDCl$_3$) δ 8.56 (s, 1H), 5.49-5.30 (m, 2H), 2.64 (t, J=8.8 Hz, 1H), 2.22-2.06 (m, 2H), 1.80-1.10 (m, 19H), 1.05-0.70 (m, 9H). LCMS: R$_t$=1.305 min in 2 min Chromatography, MS ESI calcd. for C$_{23}$H$_{37}$N$_4$O$_2$ [M+H]$^+$ 401, found 401.

Example 53

Synthesis of 119 and 120

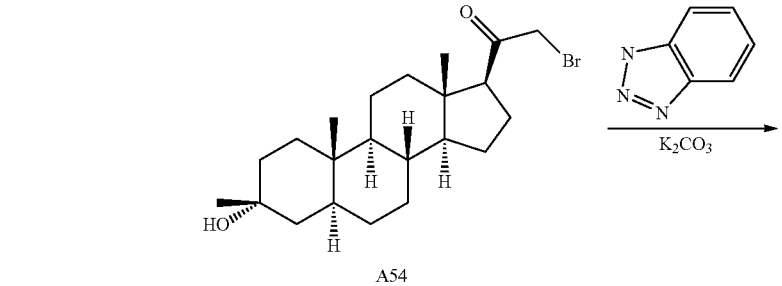

A54

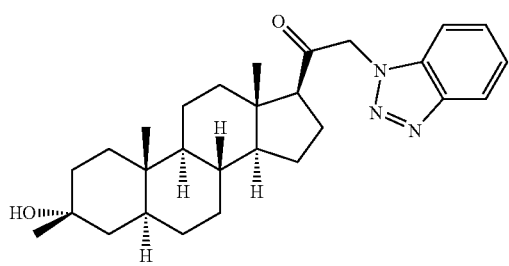

119

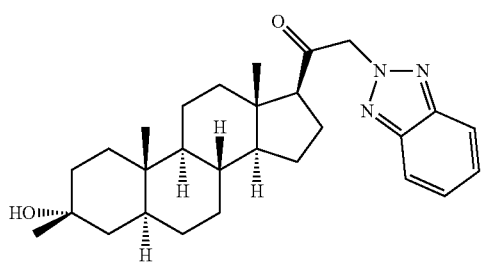

120

The title compounds were prepared according to Example 47, step 7.

Compound 119: $^1$H NMR (400 MHz, CDCl$_3$) δ 8.09-8.06 (m, 1H), 7.50-7.32 (m, 3H), 5.46-5.36 (m, 2H), 2.70 (t, J=8.8 Hz, 1H), 2.24-2.16 (m, 2H), 1.80-1.10 (m, 21H), 1.05-0.72 (m, 9H).

LCMS Rt=1.360 min in 2 min Chromatography, MS ESI calcd. for C$_{28}$H$_{40}$N$_3$O$_2$ [M+H]$^+$ 450, found 450.

Compound 120: $^1$H NMR (400 MHz, CDCl$_3$) δ7.88-7.86 (m, 2H), 7.40-7.37 (m, 2H), 5.56-5.46 (m, 2H), 2.65 (t, J=8.8 Hz, 1H), 2.21-2.10 (m, 2H), 1.80-1.10 (m, 21H), 1.17-0.74 (m, 9H).

LCMS: Rt=1.008 min in 1.5 min Chromatography, MS ESI calcd. for C$_{28}$H$_{40}$N$_3$O$_2$ [M+H]$^+$450, found 450.

Example 54

Synthesis of 121

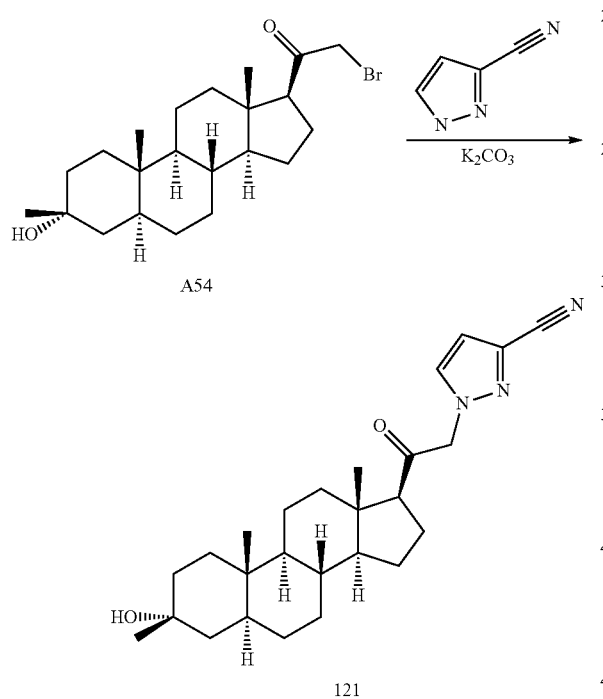

121

The title compounds were prepared according to Example 47, step 7.

Compound 121: $^1$H NMR (400 MHz, CDCl$_3$) δ7.48-7.47 (m, 1H), 6.73-6.72 (m, 1H), 5.05-4.88 (m, 2H), 2.59 (t, J=8.8 Hz, 1H), 2.17-1.95 (m, 2H), 1.80-1.10 (m, 21H), 1.05-0.65 (m, 9H).

LCMS Rt=0.949 min in 1.5 min Chromatography, MS ESI calcd. for C$_{26}$H$_{38}$N$_3$O$_2$ [M+H]$^+$ 424. found 406[M+H–18]$^+$.

Compound 122: $^1$H NMR (400 MHz, CDCl$_3$) δ7.50-7.44 (m, 1H), 6.77-6.71 (m, 1H), 5.12-4.86 (m, 2H), 2.78-2.72 (m, 1H), 1.94-1.10 (m, 58H), 1.06-0.69 (m, 15H). LCMS: Rt=1.373 min in 2 min Chromatography, MS ESI calcd. for C$_{26}$H$_{37}$N$_3$O$_2$ Na [M+Na]$^+$ 446, found 446.

Example 55

Synthesis of 124

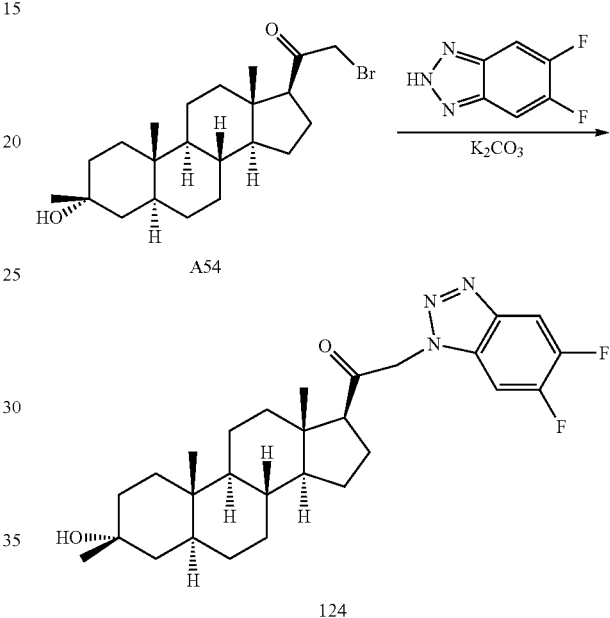

124

The title compounds were prepared according to Example 47, step 7.

Compound 124: $^1$H NMR (400 MHz, CDCl$_3$) δ 7.84-7.80 (m, 1H), 7.14-7.10 (m, 1H), 5.44-5.31 (m, 2H), 2.73-2.69 (m, 1H), 2.25-2.05 (m, 2H), 1.80-1.10 (m, 22H), 1.05-0.90 (m, 2H), 0.77 (s, 3H), 0.71 (s, 3H). LCMS Rt=1.404 min in 2 min Chromatography, MS ESI calcd. for C$_{28}$H$_{38}$F$_2$N$_3$O$_2$ [M+H]$^+$ 486, found 486.

Example 56

Synthesis of 125, 126, and 127

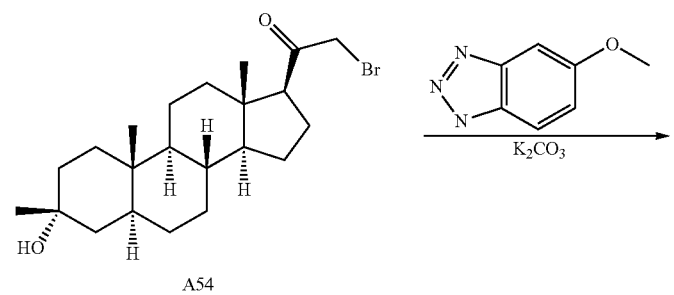

A54

-continued

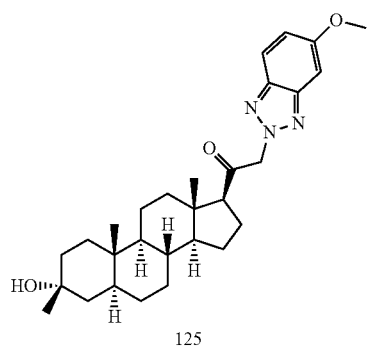
125

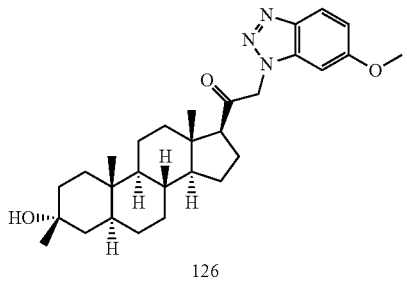
126

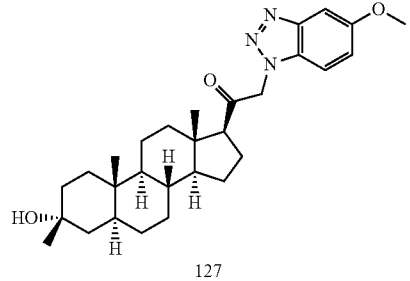
127

The title compounds were prepared according to Example 47, step 7.

Compound 125: $^1$H NMR: (400 MHz, CDCl$_3$) δ7.77-7.73 (m, 1H), 7.13-7.06 (m, 1H), 5.53-5.40 (m, 2H), 3.90 (s, 3H), 2.72-2.61 (m, 1H), 2.35-2.12 (m, 3H), 1.90-0.72 (m, 30H). LCMS: R$_t$=1.422 min in 2 min Chromatography, MS ESI calcd. for C$_{29}$H$_{42}$N$_3$O$_3$ [M+H]$^+$ 480, found 480.

Compound 126: $^1$H NMR: (400 MHz, CDCl$_3$) δ7.96-7.87 (m, 1H), 7.01 (dd, J=2.0, 9.0 Hz, 1H), 6.60 (d, J=2.0 Hz, 1H), 5.33 (d, J=5.8 Hz, 2H), 3.86 (s, 3H), 2.76-2.65 (m, 1H), 2.28-2.10 (m, 2H), 1.83-1.12 (m, 21H), 0.75 (d, J=17.6 Hz, 9H). LCMS: R$_t$=1.362 min in 2 min Chromatography, MS ESI calcd. for C$_{29}$H$_{42}$N$_3$O$_3$ [M+H]$^+$ 480, found 480.

Compound 127: $^1$H NMR: (400 MHz, CDCl$_3$) δ7.95-7.89 (m, 1H), 7.43-7.34 (m, 1H), 7.18 (d, J=17.3 Hz, 2H), 7.0-6.98 (m, 1H), 6.63-6.58 (m, 1H), 5.59-5.19 (m, 2H), 3.89 (s, 3H), 2.73-2.62 (m, 1H), 2.26-2.07 (m, 2H), 1.82-1.11 (m, 18H), 1.07-0.65 (m, 9H) LCMS: R$_t$=1.359 min in 2 min Chromatography, MS ESI calcd. for C$_{29}$H$_{42}$N$_3$O$_3$ [M+H]$^+$ 480, found 480.

Example 57

Synthesis of 128

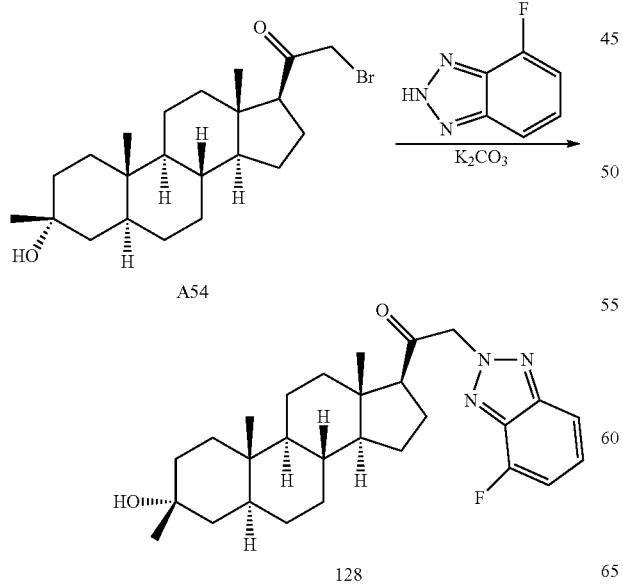

The title compound was prepared according to Example 47, step 7.

Compound 128: $^1$H NMR (400 MHz, CDCl$_3$) δ 7.67 (d, J=8.8 Hz, 1H), 7.37-7.28 (m, 1H), 7.09-6.98 (m, 1H), 5.54 (d, J=5.5 Hz, 2H), 2.66 (s, 1H), 2.27-2.09 (m, 3H), 1.87-1.09 (m, 20H), 0.75 (d, J=11.3 Hz, 9H). LCMS: Rt=1.446 min in 2 min chromatography, MS ESI calcd. for C$_{28}$H$_{39}$FN$_3$O$_2$ [M+H]$^+$ 468, found 450 [M+H−18]$^+$.

Example 58

Synthesis of 129

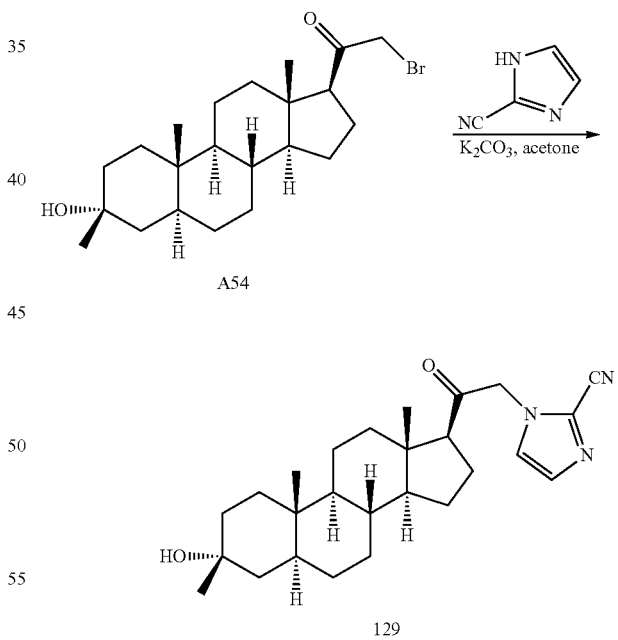

The title compound was prepared according to Example 47, step 7.

Compound 129: $^1$H NMR (400 MHz, CDCl$_3$): δ 7.28 (s, 1H), 7.06 (s, 1H), 5.00-4.84 (m, 2H), 2.64 (t, J=8.4 Hz, 1H), 2.22-2.06 (m, 2H), 1.79-1.53 (m, 4H), 1.50-1.20 (m, 19H), 1.02-0.85 (m, 19H), 0.78 (s, 3H), 0.72 (s, 3H). LCMS: R$_t$=0.901 min in 1.5 min Chromatography, MS ESI calcd. for C$_{26}$H$_{37}$N$_3$O$_2$ [M+H]$^+$ 424, found 424.

Example 59

Synthesis of 130

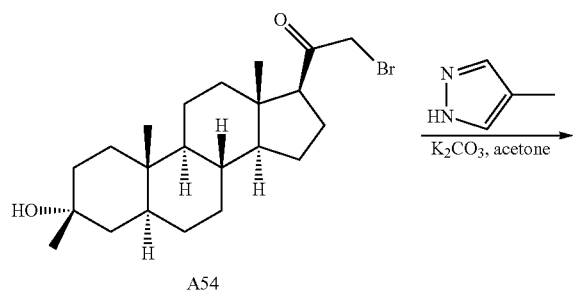

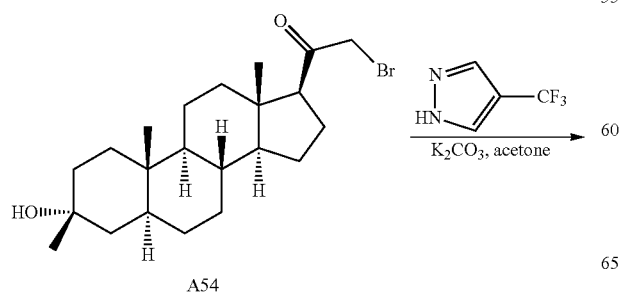

The title compound was prepared according to Example 47, step 7.

Compound 130: $^1$H NMR (400 MHz, CDCl$_3$): δ 7.33 (s, 1H), 7.16 (s, 1H), 4.90-4.77 (m, 2H), 2.56 (t, J=8.4 Hz, 1H), 2.17-2.08 (m, 5H), 1.72-1.50 (m, 6H), 1.40-1.20 (m, 15H), 0.80-0.79 (m, 3H), 0.75 (s, 3H), 0.70 (s, 3H). LCMS: Rt=0.927 min in 1.5 min Chromatography, MS ESI calcd. for C$_{26}$H$_{40}$N$_2$O$_2$ [M+H]$^+$ 413, found 413.

Example 60

Synthesis of 131

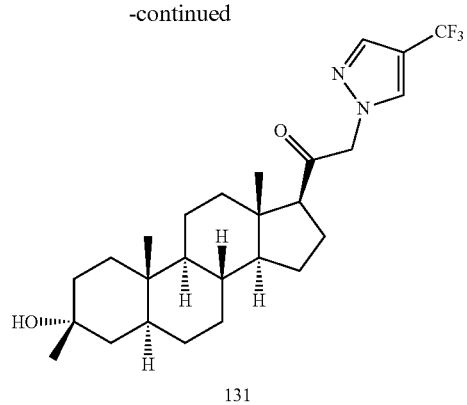

The title compound was prepared according to Example 47, step 7.

Compound 131: $^1$H NMR (400 MHz, CDCl$_3$): δ 7.72 (s, 2H), 5.02-4.86 (m, 2H), 2.60 (t, J=8.4 Hz, 1H), 2.19-2.03 (m, 5H), 1.73-1.51 (m, 6H), 1.37-1.20 (m, 16H), 0.85-0.82 (m, 3H), 0.76 (s, 3H), 0.67 (s, 3H). LCMS: Rt=0.983 min in 1.5 min Chromatography, MS ESI calcd. for C$_{26}$H$_{37}$F$_3$N$_2$O$_2$ [M+H]$^+$ 467, found 467.

Example 62

Synthesis of 133

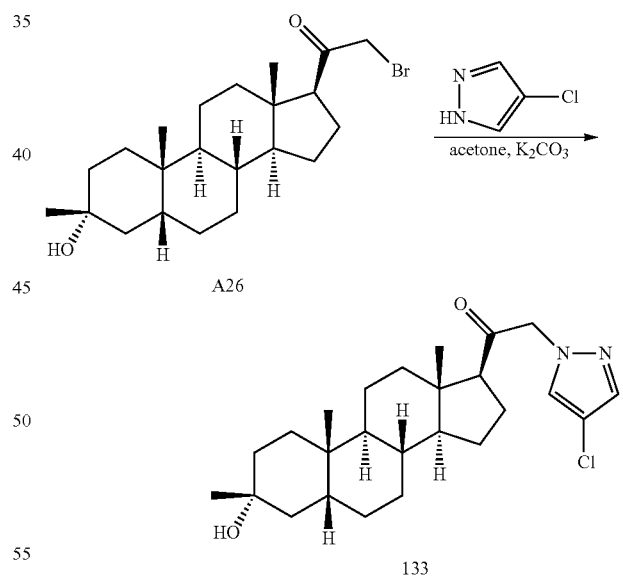

The title compound was prepared according to Example 5, step 4.

Compound 133: $^1$H NMR (400 MHz, CDCl$_3$) δ 7.43 (d, J=18.1 Hz, 1H), 4.94-4.76 (m, 1H), 2.61-2.53 (m, 1H), 2.25-2.13 (m, 1H), 2.08-1.80 (m, 3H), 1.79-1.66 (m, 3H), 1.63-1.35 (m, 11H), 1.34-1.18 (m, 9H), 1.17-1.01 (m, 2H), 0.95 (s, 3H), 0.65 (s, 3H). LCMS: R$_f$=1.127 min in 2 min Chromatography, MS ESI calcd. for C$_{25}$H$_{37}$ClN$_2$O$_2$[M+H]$^+$ 433, found 433.

Example 63

Synthesis of 134

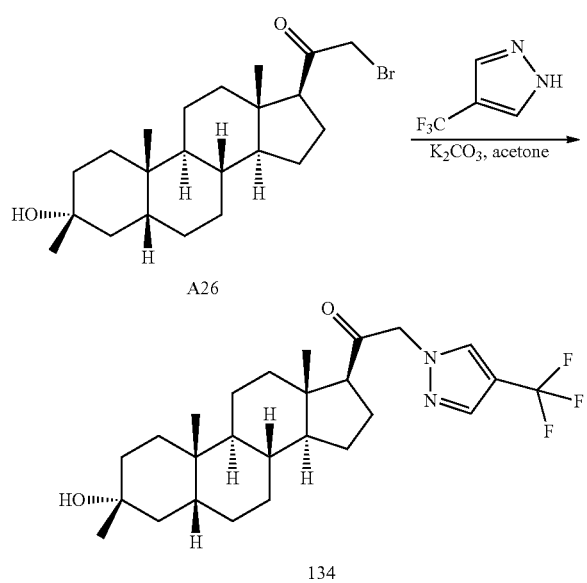

The title compound was prepared according to Example 5, step 4.

Compound 134: $^1$H NMR (400 MHz, CDCl$_3$) δ 7.72 (s, 1H), 5.03-4.84 (m, 1H), 2.64-2.55 (m, 1H), 2.27-1.02 (m, 28H), 0.95 (s, 3H), 0.66 (s, 3H). LCMS: Rt=1.332 min in 2 min chromatography, MS ESI calcd. For C26H37F3N2O2 [M+H]$^+$ 467, found 467.

Example 64

Synthesis of 135 and 136

The title compounds were prepared according to Example 47, step 7.

Compound 135: $^1$H NMR (400 MHz, CDCl$_3$) δ 7.29 (s, 1H), 6.55 (s, 1H), 4.66-4.54 (m, 2H), 2.55 (t, J=8.4 Hz, 1H), 2.27-2.00 (m, 5H), 1.70-1.51 (m, 5H), 1.47-1.21 (m, 18H), 0.84-0.80 (m, 3H), 0.76 (s, 3H), 0.65 (s, 3H). LCMS: Rt=0.795 min in 1.5 min Chromatography, MS ESI calcd. for C$_{26}$H$_{40}$N$_2$O$_2$ [M+H]$^+$ 413, found 413.

Compound 136: $^1$H NMR (400 MHz, DMSO-d$_6$) δ 7.42 (s, 1H), 6.62 (s, 1H), 5.03-4.77 (m, 2H), 3.88 (s, 1H), 2.68 (t, J=10 Hz, 3H), 2.34 (s, 1H) 2.04-1.63 (m, 5H), 1.44-1.15 (m, 27H), 1.07-0.75 (m, 4H), 0.72 (s, 3H), 0.59 (s, 3H). LCMS: Rt=1.087 min in 1.5 min Chromatography, MS ESI calcd. for C$_{26}$H$_{40}$N$_2$O$_2$ [M+H]$^+$ 413, found 413.

Example 65

Synthesis of 137

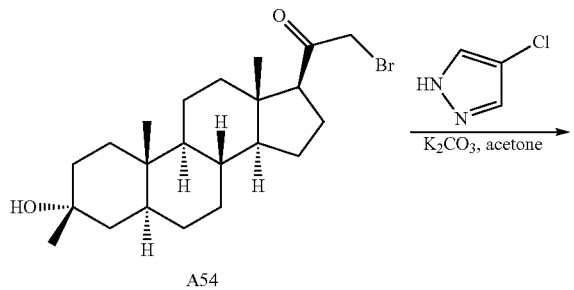

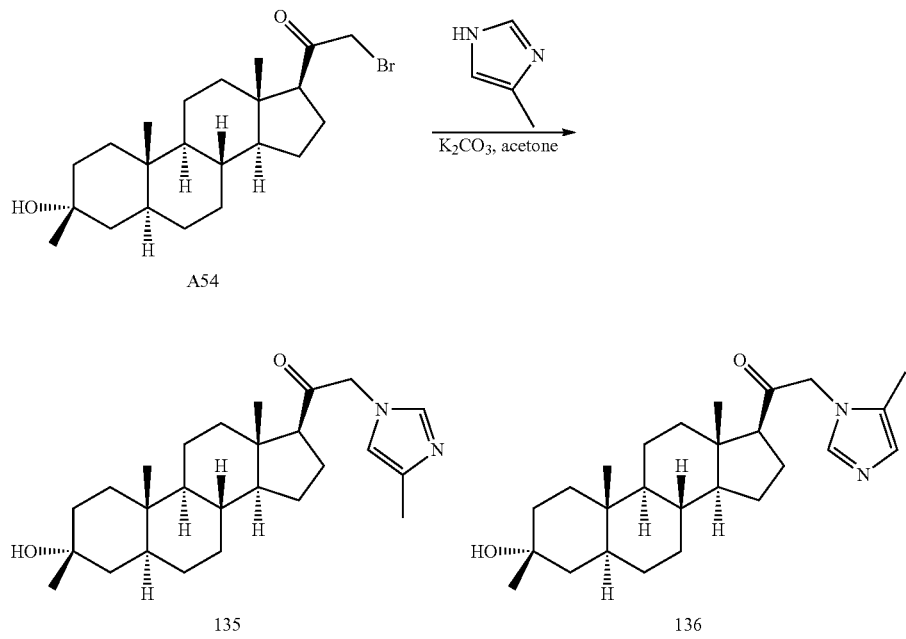

Example 66

Synthesis of 138

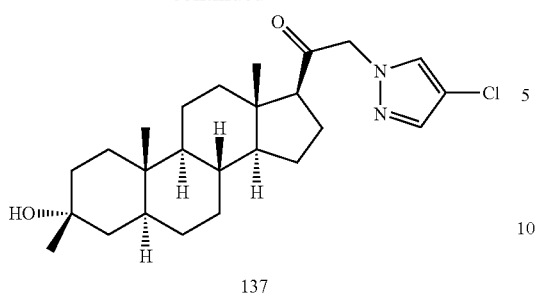

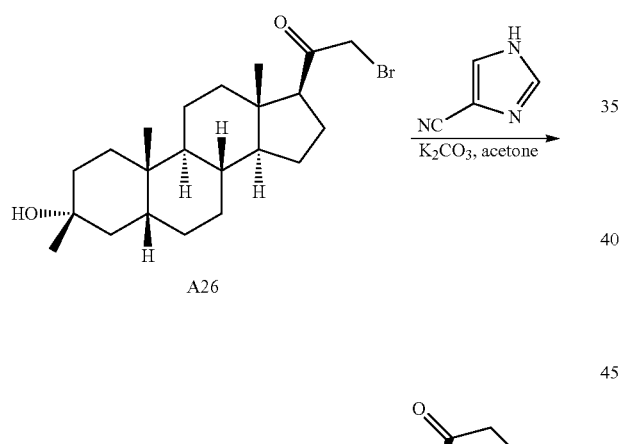

The title compound was prepared according to Example 5, step 4.

Compound 138: $^1$H NMR (400 MHz, CDCl$_3$) δ 7.43 (d, J=6.0 Hz, 1H), 4.79-4.68 (m, 1H), 2.65-2.53 (m, 1H), 2.20 (d, J=9.3 Hz, 1H), 2.04-1.02 (m, 29H), 0.96 (s, 3H), 0.70-0.59 (m, 3H).

LCMS: Rt=0.891 min in 1.5 min Chromatography, MS ESI calcd. for C26H37N3O2 [M+H]$^+$424, found 424.

Example 67

Synthesis of 139

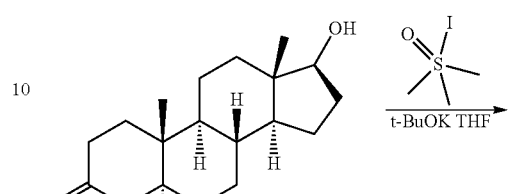

The title compound was prepared according to Example 47, step 7.

Compound 137: $^1$H NMR (400 MHz, CDCl$_3$) δ 7.45 (s, 1H), 7.41 (s, 1H), 4.93-4.78 (m, 2H), 2.57 (t, J=8.8 Hz, 1H), 2.18-2.04 (m, 2H), 1.73-1.50 (m, 4H), 1.27-1.17 (m, 18H), 0.81-0.80 (m, 3H) 0.75 (s, 3H), 0.66 (s, 3H). LCMS: Rt=0.953 min in 1.5 min chromatography MS ESI calcd. For C$_{25}$H$_{37}$ClN$_2$O$_2$[M+Na]$^+$ 433, found 433.

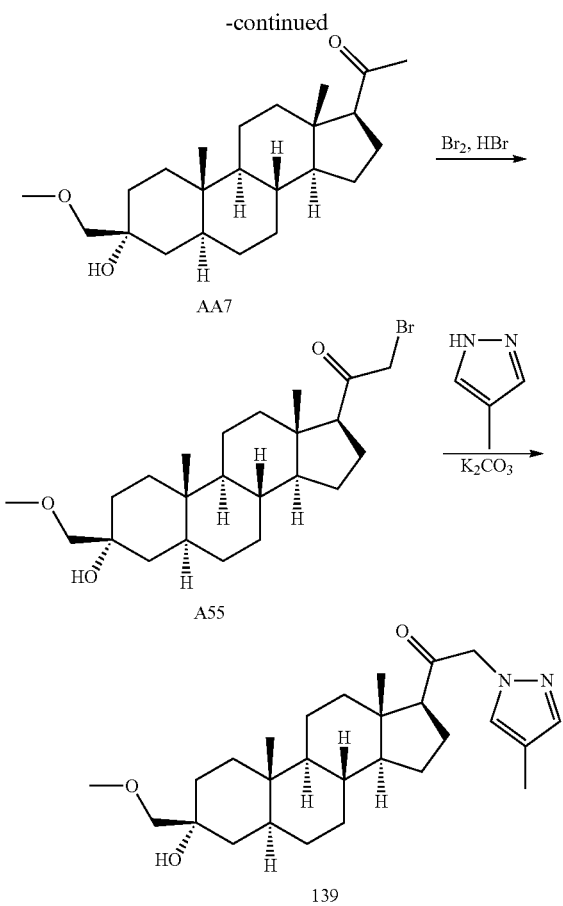

Step 1. Synthesis of AA2: To a solution of Me₃SOI (30.1 g, 137 mmol) in THF (200 mL) in a flask was added t-BuOK (15.3 g, 137 mmol), and the reaction mixture was stirred at 25° C. for 0.5 h. (5S,8R,9S,10S,13S,14S,17S)-17-hydroxy-10,13-dimethyltetradecahydro-1H-cyclopenta[a]phenanthren-3(2H)-one (AA1, 20 g, 68.8 mmol) was added, and the reaction was stirred for 2 h at 25° C. After TLC (PE/EA=3:1) showed the reaction was complete, the reaction was quenched with aq.NH₄Cl (300 mL). The reaction was extracted with EtOAc (200 mL×2), washed with brine (200 mL), dried over Na₂SO₄ and evaporated in vacuum to afford crude product (5S,8R,9S,10S,13S,14S,17S)-10,13-dimethylhexadecahydrospiro-[cyclopenta[a]phenanthrene-3,2'-oxiran]-17-ol (AA2, 23 g) as white solid, which was used directly in the next step without further purification.

Step 2. Synthesis of AA3. To a solution of (5S,8R,9S,10S,13S,14S,17S)-10,13-dimethylhexadecahydrospiro[cyclopenta[a]phenanthrene-3,2'-oxiran]-17-ol (AA2, 23 g, 75.5 mmol) in MeOH (200 mL) in a flask was added MeONa (12.2 g, 226 mmol), and the reaction mixture was heated to 60° C. and stirred for 4 h. Once TLC (PE:EtOAc=3:1) showed the reaction was complete, the reaction was quenched with aq.NH₄Cl (300 mL). The reaction was extracted with EtOAc (200 mL×2), washed with brine (200 mL), dried over Na₂SO₄ and evaporated in vacuum to afford crude product (3R,5S,8R,9S,10S,13S,14S,17S)-3-(methoxymethyl)-10,13-dimethylhexadecahydro-1H-cyclopenta[a]phenanthrene-3,17-diol (AA3, 25 g) as yellow solid, which was used directly in the next step without further purification. $^1$HNMR (CDCl3, 400 MHz): δδ=3.78-3.63 (m, 1H), 3.40 (s, 3H), 3.20 (s, 2H), 2.09-2.02 (m, 3H), 1.89-1.32 (m, 26H), 1.29-0.75 (m, 14H).

Step 3. Synthesis of AA4. To a solution of (3R,5S,8R,9S,10S,13S,14S,17S)-3-(methoxymethyl)-10,13-dimethyl-hexadecahydro-1H-cyclopenta[a]phenanthrene-3,17-diol (AA3, 25 g, 74.2 mmol) in dry DCM (200 mL) was added Dess-Martin reagent (47.0 g, 111 mmol) in portions at 0° C. The reaction mixture was stirred at 30° C. for 2 h. TLC (PE/EA=3:1) showed the starting material was consumed completely. The mixture was quenched with saturated NaHCO₃/Na₂S₂O₃=1:3 (200 ml) and extracted with EtOAc (200 mL×2). The organic phase was washed with brine (200 mL) and dried over Na₂SO₄, and the solvent was evaporated at 40° C. to afford crude product (3R,5S,8R,9S,10S,13S,14S)-3-hydroxy-3-(methoxymethyl)-10,13-dimethyltetradecahydro-1H-cyclopenta[a]phenanthren-17(2H)-one (AA4, 26 g), which was directly used in the next step without further purification. $^1$HNMR (CDCl3, 400 MHz): δδ=3.39 (s, 3H), 3.18 (s, 2H), 2.69-2.65 (m, 1H), 2.44-2.40 (m, 1H), 2.09-1.41 (m, 28H), 1.38-1.31 (m, 11H).

Step 4. Synthesis of AA5. To a suspension of EtPPh₃Br (144 g, 388 mmol) in THF (500 mL) was added t-BuOK (43.5 g, 388 mmol). After stirring at 60° C. for 1 h, (3R,5S,8R,9S,10S,13S,14S)-3-hydroxy-3-(methoxymethyl)-10,13-dimethyltetradecahydro-1H-cyclopenta[a]phenanthren-17(2H)-one (AA4, 26 g, 77.7 mmol) was added in portions at 60° C. The reaction mixture was stirred at the same temperature for 8 h. TLC (PE/EtOAc=3/1) showed the reaction was complete, and a main product was found with lower polarity. The reaction mixture was quenched with aq.NH₄Cl (500 mL) and extracted with EtOAc (500 mL) for three times. The combined organic layer was washed with brine (500 mL), dried over Na₂SO₄ and concentrated in vacuum to give the crude product. The crude product was purified by column chromatography (PE:EA=10:1-6:1) to give (3R,5S,8R,9S,10S,13S,14S,Z)-17-ethylidene-3-(methoxymethyl)-10,13-dimethylhexadecahydro-1H-cyclopenta[a]phenanthren-3-ol (AA5, 20 g) as white solid. $^1$HNMR (CDCl3, 400 MHz): δδ=5.12-5.10 (m, 1H), 3.39 (s, 3H), 3.18 (s, 2H), 2.40-2.12 (m, 3H), 1.66-1.16 (m, 25H), 1.10-0.70 (m, 9H).

Step 5. Synthesis of AA6. To a solution of (3R,5S,8R,9S,10S,13S,14S,Z)-17-ethylidene-3-(methoxymethyl)-10,13-dimethylhexadecahydro-1H-cyclopenta[a]phenanthren-3-ol (AA5, 20 g, 57.7 mmol) in THF (200 mL) was added dropwise a solution of BH₃-Me₂S (57.6 mL, 10 M) at 0° C. The solution was stirred at 25° C. for 8 h. TLC (PE:EtOAc=3:1) showed the reaction was almost complete, and a main product was found with higher polarity. After cooling to 0° C., a solution of NaOH (230 mL, 3M) was added very slowly. After the addition was complete, H₂O₂ (104 mL, 33%) was added slowly and the inner temperature was maintained below 10° C. The resulting solution was stirred at 25° C. for 2 h. The resulting solution was extract with EtOAc (200 mL×3). The combined organic solution was washed with saturated Na₂S₂O₃ (200 mL×2), brine (200 mL), dried over Na₂SO₄ and concentrated in vacuum to give the crude product (AA6, 25 g) as yellow solid. The crude product was used for the next step without further purification.

Step 6. Synthesis of AA7. A mixture of (3R,5S,8R,9S,10S,13S,14S,17S)-17-((R)-1-hydroxyethyl)-3-(methoxymethyl)-10,13-dimethylhexadecahydro-1H-cyclopenta[a]phenanthren-3-ol (AA6, 25 g, 68.5 mmol), PCC (21.9 g, 102 mmol) and silica gel (24 g, w/w=1/1.1) in DCM (200 mL) was stirred at 25° C. for 2 h. The reaction mixture color became brown. TLC (PE/EtOAc=3/1) showed the reaction was complete, and a main product was found with lower polarity. The solution was filtered and the filter cake was washed with DCM (200 mL). The combined filtrate was concentrated in vacuum. The residue was purified by silica gel column eluted with PE/EtOAc=15/1 to 6/1 to give 1-((3R,5S,8R,9S,10S,13S,14S,17S)-3-hydroxy-3-(methoxymethyl)-10,13-dimethylhexadecahydro-1H-cyclopenta[a]phenanthren-17-yl)ethanone (AA7, 16 g) as white solid. $^1$HNMR (CDCl3, 400 MHz): δδ=3.41 (s, 3H), 3.40 (s, 2H), 2.58-2.53 (m, 1H), 2.18-2.13 (m, 4H), 2.03-1.99 (m, 2H), 1.71-1.30 (m, 23H), 1.10-10.70 (m, 6H), 0.67 (s, 3H).

Step 7. Synthesis of A55. To a solution of 1-((3R,5S,8R, 9S,10S,13S,14S,17S)-3-hydroxy-3-(methoxymethyl)-10,13-dimethyihexadecahydro-1H-cyclopenta[a]phenanthren-17-yl)ethanone (AA7, 15 g, 41.3 mmol) and a catalytic amount of HBr (167 mg, 40% in water) in MeOH (150 mL) was added dropwise dibromine (2.32 mL, 45.4 mmol) at 0° C. The reaction mixture was stirred at 25° C. for 2 h. TLC (PE:EtOAc=3:1) showed the reaction was complete. The reaction was quenched by saturated NaHCO$_3$ and the pH was adjusted to 7~8. The reaction mixture was extracted with DCM (200 mL×2). The combined organic layer was washed with brine (200 mL), dried over Na$_2$SO$_4$, filtered and concentrated to give the crude product 2-bromo-1-((3R, 5S,8R,9S,10S,13S,14S,17S)-3-hydroxy-3-(methoxymethyl)-10,13-dimethylhexadecahydro-1H-cyclopenta[a]phenanthren-17-yl)ethanone (A55, 16 g) as yellow oil. $^1$HNMR (CDCl3, 400 MHz): δδ=3.92-3.91 (m, 2H), 3.50 (s, 5H), 3.39 (S, 5H), 3.18 (s, 3H), 2.82-3.72 (m, 1H), 2.30-2.10 (m, 1H), 1.72-1.12 (m, 34H), 1.08-0.70 (m, 9H), 0.67 (s, 3H).

Step 8. Synthesis of 139. K$_2$CO$_3$ (125 mg, 906 umol) was added to a solution of A55 (200 mg, 453 umol) and 4-methyl-1H-pyrazole (48 mg, 588 umol) in acetone (3 mL) at 25° C. The resulting mixture was stirred at 25° C. for 12 hours, at which point TLC indicated the reaction was complete. The reaction mixture was diluted with water (10 mL) and extracted with EtOAc (10 mL*3). The combined organic layers were washed with brine (10 mL), dried over Na$_2$SO$_4$, filtered, and evaporated to afford crude product (200 mg). The reaction mixture was purified by HPLC (column: Waters Xbridge Prep OBD C18 150*30 5 u, gradient: 44-74% B (A=0.05% ammonia-ACN, B=acetonitrile), flow rate: 25 mL/min) to obtain Compound 139 (53.6 mg) as a white solid. $^1$HNMR (Chloroform-d, 400 MHz) δ=7.34 (s, 1H), 7.17 (s, 1H), 4.77-4.91 (m, 2H), 3.39 (s, 3H), 3.18 (s, 2H), 2.57 (t, J=8.8 Hz, 1H), 2.14-2.23 (m, 1H), 2.09 (s, 3H), 1.98-2.06 (m, 2H), 1.63-1.74 (m, 4H), 1.50-1.55 (m, 2H), 1.10-1.50 (m, 12H), 0.94-1.02 (m, 1H), 0.80-0.87 (m, 1H), 0.75 (s, 3H), 0.67 ppm (s, 3H). LCMS Rt=2.848 min in 4 min chromatography, MS ESI calcd. for C27H42N2O3 [M+Na]+ 465.3, found 465.1 ([M+H−18]+).

Example 68

Synthesis of 140

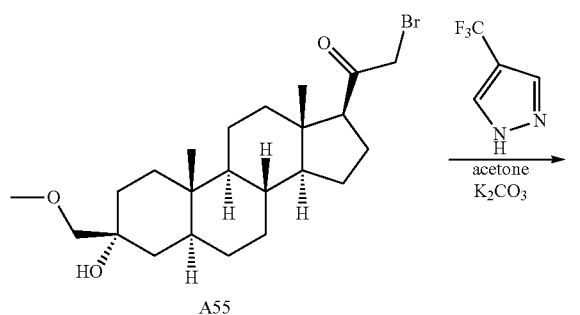

-continued

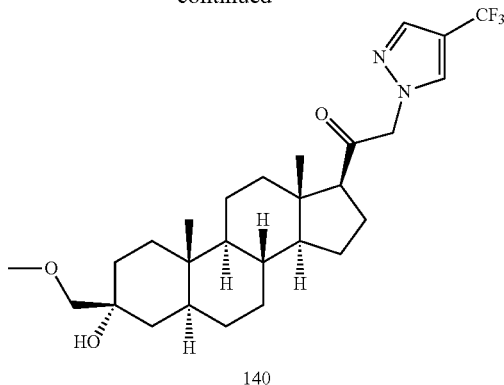

140

The title compound was prepared according to Example 67.

Compound 140 (64.3 mg): $^1$HNMR (Chloroform-d, 400 MHz) δ=7.72 (s, 2H), 4.86-5.02 (m, 2H), 3.33-3.43 (m, 3H), 3.19 (s, 2H), 2.61 (t, J=8.8 Hz, 1H), 2.16-2.25 (m, 1H), 1.99-2.08 (m, 2H), 1.63-1.78 (m, 4H), 1.06-1.55 (m, 14H), 0.94-1.03 (m, 1H), 0.82-0.89 (m, 1H), 0.72-0.80 (m, 3H), 0.67 (s, 3H). LCMS: Rt=3.106 min in 4 min chromatography, MS ESI calcd. for C27H39F3N2O3 [M+H]+ 497.3, found 497.1 ([M+H]+).

Example 69

Synthesis of 141

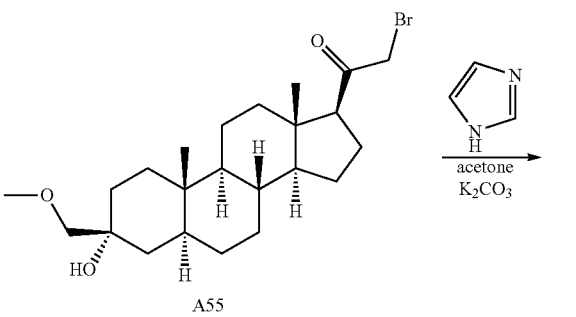

A55

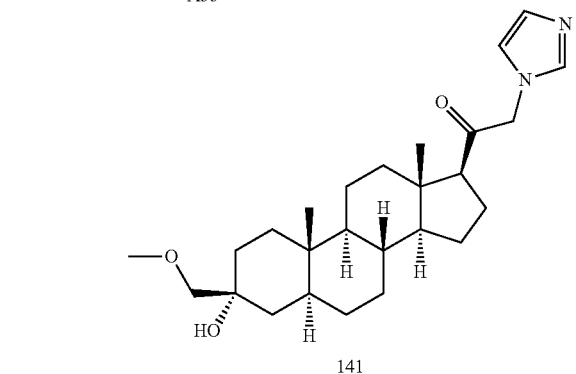

141

The title compound was prepared according to Example 67.

Compound 141 (59.4 mg): $^1$HNMR (Chloroform-d, 400 MHz): δ=9.65 (br. s., 1H), 7.32 (s, 1H), 7.06 (s, 1H), 5.44 (d, J=17.6 Hz, 1H), 5.26 (d, J=18.2 Hz, 1H), 3.39 (s, 3H), 3.19 (s, 2H), 2.72 (t, J=9.0 Hz, 1H), 2.20 (d, J=10.6 Hz, 1H), 2.11

(d, J=11.6 Hz, 2H), 1.49-1.80 (m, 10H), 1.22-1.42 (m, 8H), 0.94-1.04 (m, 1H), 0.85 (t, J=9.6 Hz, 1H), 0.76 (s, 3H), 0.69 (s, 3H). LCMS: Rt=2.074 min in 4 min chromatography, MS ESI calcd. for C26H40N2O3 [M+Na]+ 451.3, found 451.2 ([M+Na]+.

Example 70

Synthesis of 142

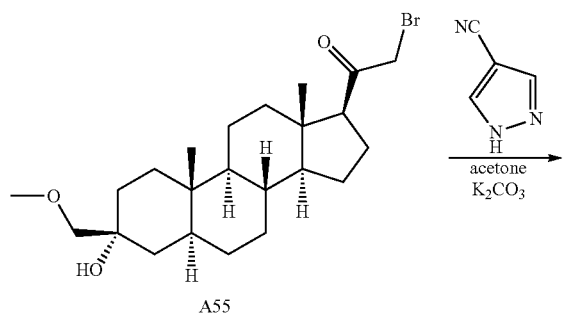

The title compound was prepared according to Example 67.

Compound 141 (59.4 mg): ¹HNMR (Chloroform-d, 400 MHz) δ=7.86 (s, 1H), 7.82 (s, 1H), 4.87-5.05 (m, 2H), 3.40 (s, 3H), 3.19 (s, 2H), 2.61 (t, J=8.8 Hz, 1H), 2.16-2.26 (m, 1H), 2.01-2.08 (m, 2H), 1.66-1.77 (m, 4H), 1.14-1.55 (m, 14H), 0.94-1.04 (m, 1H), 0.82-0.89 (m, 1H), 0.76 (s, 3H), 0.66 (s, 3H). LCMS Rt=2.827 min in 4 min chromatography, MS ESI calcd. for C27H39N3O3 [M+H]+ 454.3, found 454.2 ([M+H]+.

Example 71

Synthesis of 143

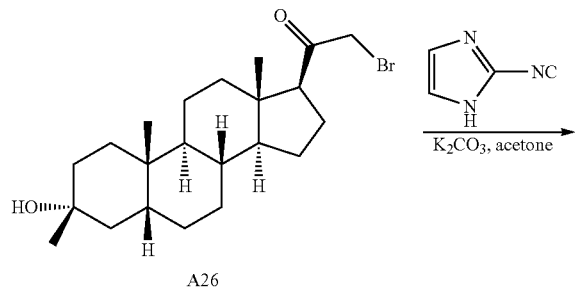

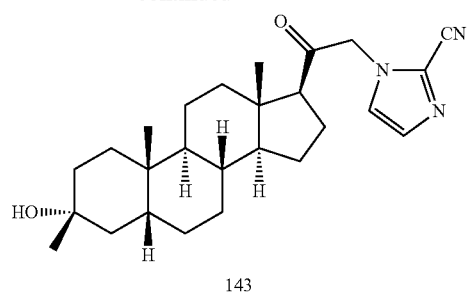

The title compound was prepared according to Example 5, step 4.

Compound 143: ¹H NMR (400 MHz, CDCl₃) δ 7.25 (d, J=1.0 Hz, 1H), 7.04 (d, J=1.0 Hz, 1H), 5.00-4.81 (m, 2H), 2.69-2.57 (m, 1H), 2.29-1.02 (m, 27H), 0.99-0.89 (m, 3H), 0.69 (s, 3H).

LCMS: Rt=1.367 min in 2 min chromatography, MS ESI calcd. For C27H42N2O3 [M+H+Na]⁺ 424, found 424.

Example 73

Synthesis of 145

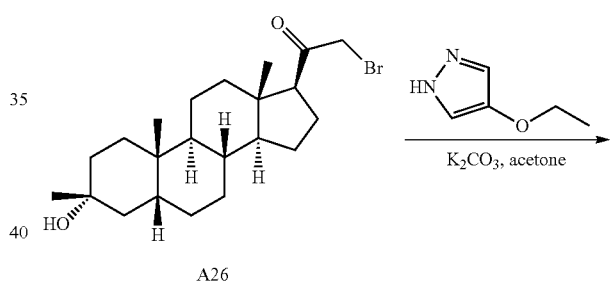

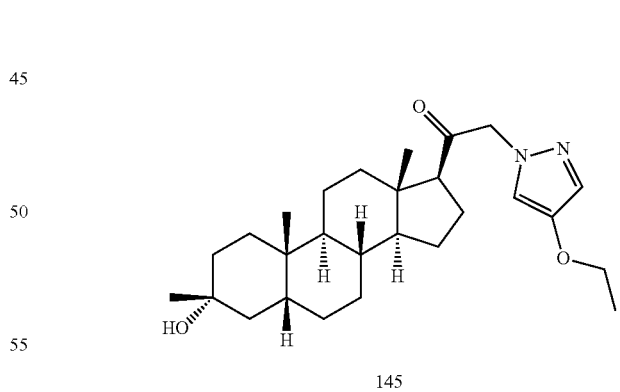

The title compound was prepared according to Example 5, step 4.

Compound 145: ¹H NMR (400 MHz, CDCl₃) δ 7.28 (s, 1H), 7.07 (s, 1H), 4.86-4.73 (m, 2H), 3.97-3.92 (m, 2H), 2.54 (t, J=8.8 Hz, 1H), 2.19-1.70 (m, 9H), 1.43-1.07 (m, 22H), 0.94 (s, 3H), 0.65 (s, 3H). LCMS: Rt=0.918 min in 1.5 min chromatography, MS ESI calcd. for C₂₇H₄₂N₂O₃ [M+H]⁺ 443, found 443.

Example 74

Synthesis of 146

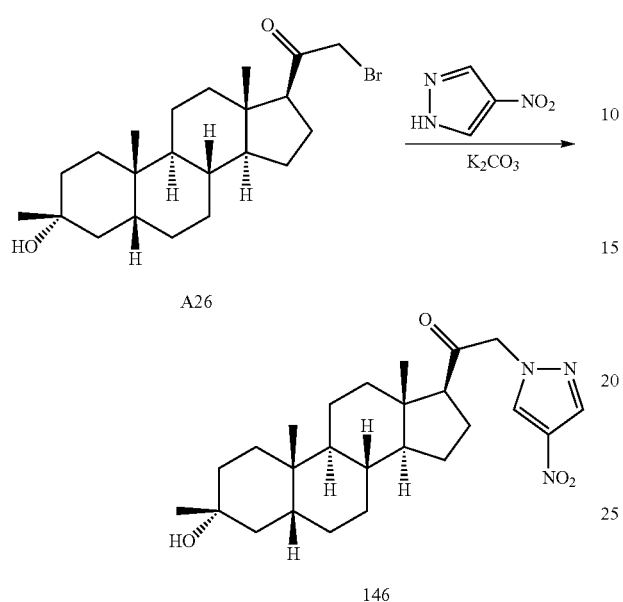

The title compound was prepared according to Example 5, step 4.

Compound 146: ¹H NMR (400 MHz, CDCl₃) δ 8.17 (s, 1H), 8.08 (s, 1H), 5.05-4.83 (m, 2H), 2.67-2.55 (m, 1H), 2.28-1.01 (m, 28H), 0.95 (s, 3H), 0.66 (s, 3H). LCMS: Rt=1.330 min in 2 min chromatography, MS ESI calcd. For C25H37N3O4 [M+H−H2O]⁺ 426, found 426.

Example 75

Synthesis of 147

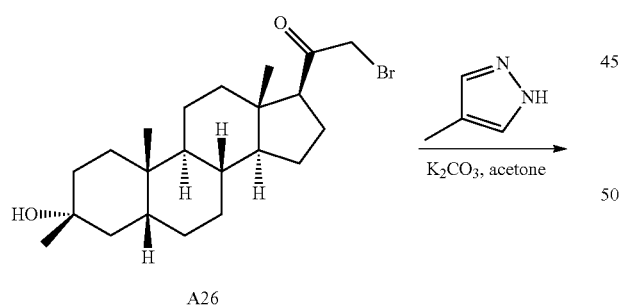

The title compound was prepared according to Example 5, step 4.

Compound 147: ¹H NMR (400 MHz, CDCl₃) δ 7.34 (s, 1H), 7.16 (s, 1H), 4.91-4.75 (m, 2H), 2.60-2.49 (m, 1H), 2.27-1.00 (m, 31H), 0.94 (s, 3H), 0.65 (s, 3H). LCMS Rt=1.264 min in 2 min chromatography, MS ESI calcd. For C26H40N2O2 [M+H]⁺ 413, found 413.

Example 76

Synthesis of 148

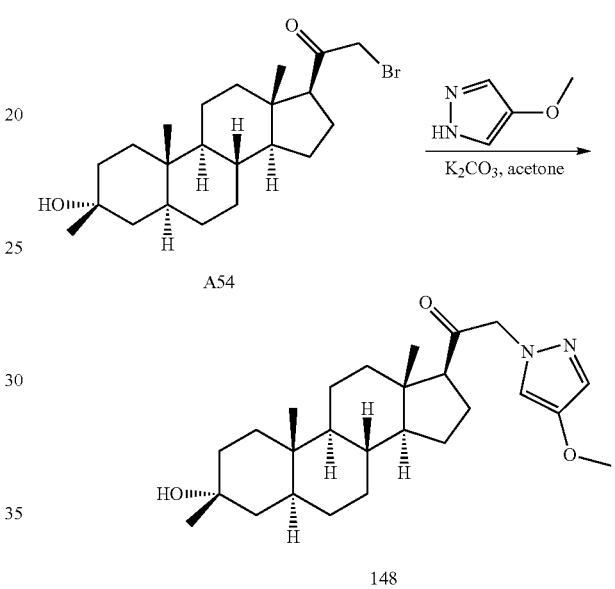

The title compound was prepared according to Example 47, step 7.

Compound 148: ¹H NMR (400 MHz, CDCl₃) δ 7.27 (s, 1H), 7.07 (s, 1H), 4.86-4.72 (m, 2H), 3.75 (s, 3H), 2.55 (t, J=9.2 Hz, 1H), 2.22-2.17 (m, 2H), 1.72-1.50 (m, 4H), 1.37-1.20 (m, 17H), 0.80-0.79 (m, 3H) 0.75 (s, 3H), 0.66 (s, 3H). LCMS Rt=1.306 min in 2 min chromatography, MS ESI calcd. For C26H40N2O3 [M+Na]⁺ 429, found 429.

Example 77

Synthesis of 149

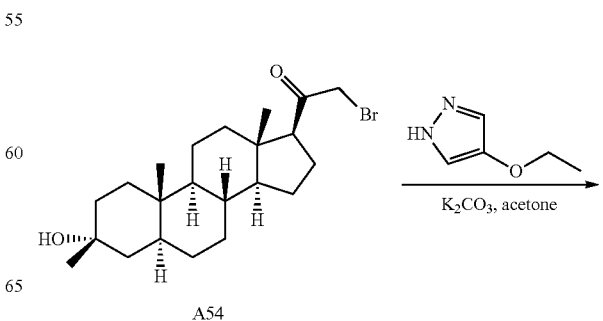

-continued

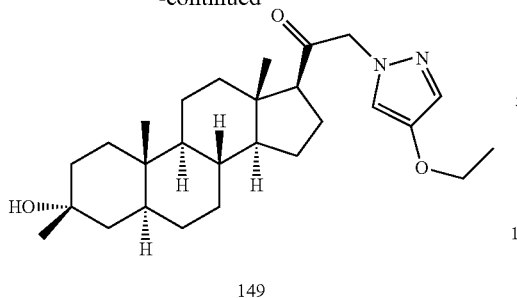

149

The title compound was prepared according to Example 47, step 7.

Compound 149: $^1$H NMR (400 MHz, CDCl$_3$) δ 7.24 (s, 1H), 7.05 (d, J=6.8 Hz, 1H), 4.83-4.69 (m, 2H), 3.94-3.89 (m, 2H), 2.53 (t, J=8.8 Hz, 1H), 2.17-1.99 (m, 2H), 1.67-1.18 (m, 24H), 0.78-0.77 (m, 3H) 0.73 (s, 3H), 0.64 (s, 3H). LCMS Rt=1.334 min in 2 min chromatography, MS ESI calcd. For C$_{27}$H$_{42}$N$_2$O$_3$ [M+Na]$^+$ 443, found 443.

Example 78

Synthesis of 150

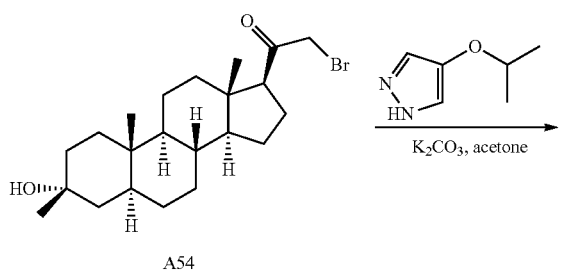

150

The title compound was prepared according to Example 47, step 7.

Compound 149: $^1$H NMR (400 MHz, CDCl$_3$) δ 7.25 (s, 1H), 7.06 (s, 1H), 4.84-4.71 (m, 2H), 4.14-4.13 (m, 1H), 2.54 (t, J=8.8 Hz, 1H), 2.18-2.00 (m, 2H), 1.69-1.50 (m, 24H), 1.36-1.19 (m, 22H), 0.79-0.78 (m, 2H) 0.74 (s, 3H), 0.65 (s, 3H). LCMS Rt=0.957 min in 1.5 min chromatography, MS ESI calcd. For C$_{28}$H$_{44}$N$_2$O$_3$ [M+Na]$^+$ 479, found 479.

Example 79

Synthesis of 151, 152, and 153

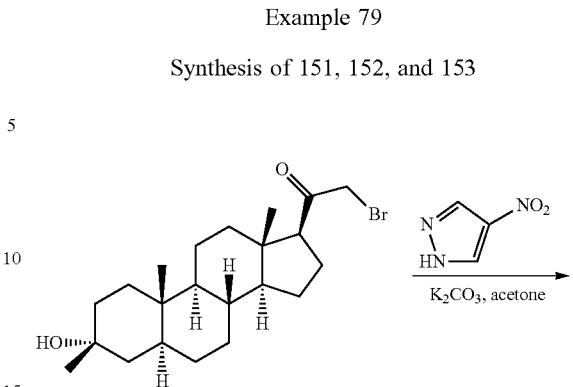

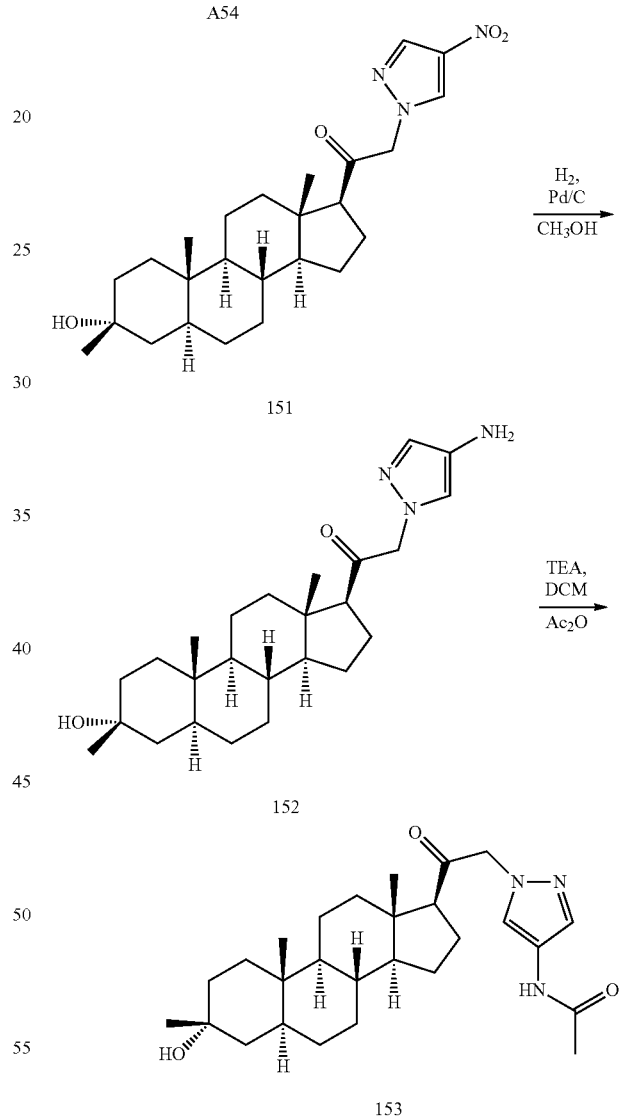

Compound 151 was prepared according to Example 47, step 7.

Compound 151: $^1$H NMR (400 MHz, CDCl$_3$) δ 8.17 (s, 1H), 8.08 (s, 1H), 5.03-4.86 (m, 2H), 2.61 (t, J=8.8 Hz, 1H), 2.20-2.05 (m, 2H), 1.75-1.51 (m, 4H), 1.50-1.21 (m, 16H), 0.99-0.82 (m, 2H) 0.76 (s, 3H), 0.66 (s, 3H). LCMS Rt=0.940 min in 1.5 min chromatography, MS ESI calcd. For C$_{25}$H$_{37}$N$_3$O$_4$ [M+H−H$_2$O]$^+$ 426, found 426.

Synthesis of Compound 152: To a solution of Compound 151 (400 mg, 0.901 mmol) in MeOH (5 mL) was added Pd/C (wet, 10%, 40 mg). After degassing three times with $H_2$, the reaction mixture was stirred for 6 h at 25° C. in $H_2$ (15 psi). When TLC (PE:EA) showed the starting material was consumed, and the reaction mixture was filtered to remove Pd/C, the filtrate was concentrated to give 2-(4-amino-1H-pyrazol-1-yl)-1-((3R,5S,8R,9S,10S,13S,14S,17S)-3-hydroxy-3,10,13-trimethylhexadecahydro-1H-cyclopenta[a]phenanthren-17-yl)ethanone (200 mg). Compound 152: $^1$H NMR (400 MHz, CDCl$_3$) δ 7.20 (s, 1H), 7.01 (s, 1H), 4.83-4.70 (m, 2H), 2.54 (t, J=8.8 Hz, 1H), 2.18-2.00 (m, 2H), 1.69-1.50 (m, 4H), 1.40-1.20 (m, 15H), 0.79-0.78 (m, 2H) 0.75 (s, 3H), 0.65 (s, 3H). LCMS Rt=0.754 min in 1.5 min chromatography, MS ESI calcd. For $C_{25}H_{39}N_3O_2$ [M+Na]$^+$ 436, found 436.

Synthesis of Compound 153: To a solution of 2-(4-amino-1H-pyrazol-1-yl)-1-((3R,5S,8R,9S,10S,13S,14S,17S)-3-hydroxy-3,10,13-trimethylhexadecahydro-1H-cyclopenta[a]phenanthren-17-yl)ethanone (150 mg, 0.362 mmol) in DCM (2 mL) was added acetic anhydride (44.3 mg, 0.434 mmol), followed by TEA (0.15 mL, 0.362 mmol). The resulting reaction mixture was stirred at 25° C. for 12 hours. LCMS indicated the starting material was consumed completely. To the mixture was added water (10 mL) and then extracted with EtOAc (8 mL*3). The combined organic phases was concentrated to give a residue, which was purified by prep-HPLC to give N-(1-(2-((3R,5S,8R,9S,10S,13S,14S,17S)-3-hydroxy-3,10,13-trimethylhexadecahydro-1H-cyclopenta[a]phenanthren-17-yl)-2-oxoethyl)-1H-pyrazol-4-yl)acetamide (13 mg). Compound 153: $^1$H NMR (400 MHz, CDCl$_3$) δ 7.90 (s, 1H), 7.42 (s, 1H), 7.09 (s, 1H), 4.91-4.78 (m, 2H), 2.54 (t, J=8.4 Hz, 1H), 2.19-2.01 (m, 5H), 1.67-1.51 (m, 5H), 1.40-1.17 (m, 19H), 0.97-0.79 (m, 3H), 0.75 (s, 3H), 0.66 (s, 3H). LCMS Rt=1.205 min in 2 min chromatography, MS ESI calcd. For $C_{27}H_{41}N_3O_3$ [M+H]$^+$ 456, found 456.

Example 80

Synthesis of 154

The title compound was prepared according to Example 47, step 7.

Compound 154: $^1$H NMR (400 MHz, CDCl$_3$) δ 7.42 (d, J=6 Hz, 1H), 4.79-4.69 (m, 2H), 2.59 (t, J=8.8 Hz, 1H), 2.21-1.92 (m, 2H), 1.72-1.50 (m, 4H), 1.38-1.21 (m, 22H), 0.85-0.83 (m, 4H), 0.76 (s, 3H), 0.65 (s, 3H). LCMS Rt=0.888 min in 1.5 min chromatography, MS ESI calcd. for $C_{26}H_{37}N_3O_2$ [M+H]$^+$ 424, found 424.

Example 81

Synthesis of 155

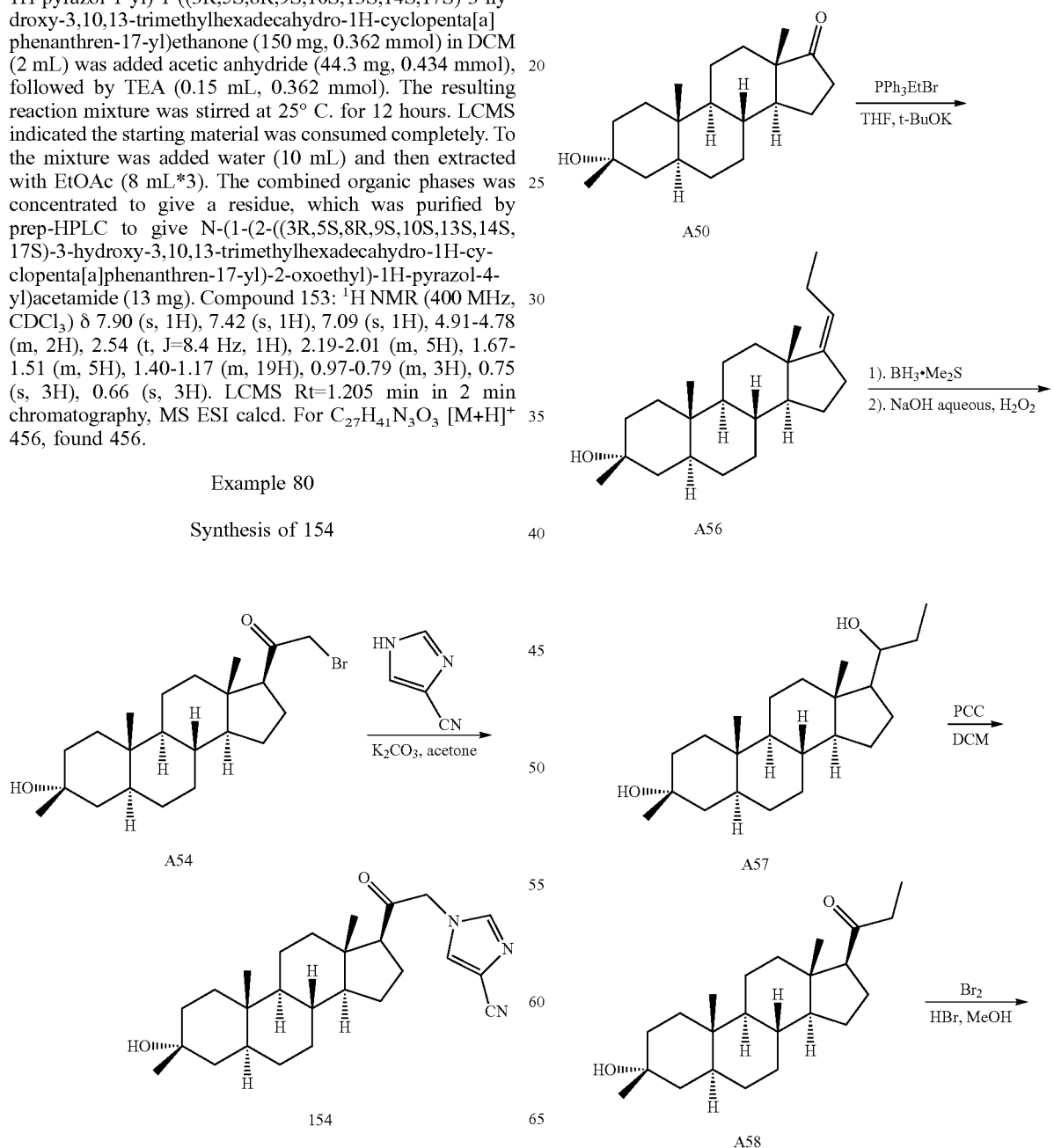

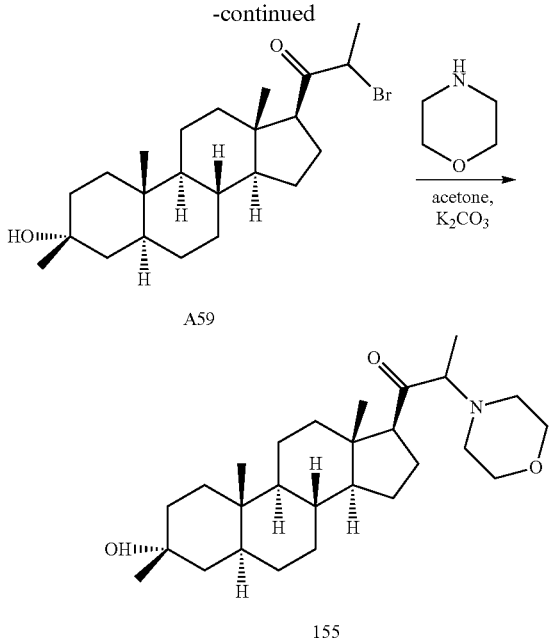

Compound A50 was prepared according to Example 47, step 2.

Synthesis of A56. To a suspension of bromotriphenyl (propyl)phosphorane (11.6 g, 30.3 mmol) in anhydrous THF (160 mL) was added potassium 2-methylpropan-2-olate (3.40 g, 30.3 mmol) at 25° C. under a $N_2$ atmosphere. The resulting mixture was stirred at 65° C. for 1 hour, at which point A50 (3.1 g, 10.1 mmol) in anhydrous THF (40 mL) was added at 65° C. The mixture was stirred at 65° C. for 16 hours, at which point TLC (PE:EA=2:1) indicated the starting material was consumed. The reaction was quenched with water (100 mL) and extracted with ethyl acetate (150 mL×3), and the combined organic phase was washed with brine (150 mL), dried over $Na_2SO_4$, and concentrated to provide a residue that was purified by chromatography on silica gel (PE:EtOAc=6:1) to give A56 (2.2 g) as a white solid. $^1$H NMR (400 MHz, CDCl$_3$) δ 5.09-4.90 (m, 1H), 2.37 (dd, J=6.8, 16.3 Hz, 1H), 2.24-1.99 (m, 4H), 1.77-1.10 (m, 23H), 1.04-0.67 (m, 13H).

Synthesis of A57. To a solution of A56 in THF (30 mL) was added dropwise a solution of BH$_3$-Me$_2$S (7.01 mL, 70.01 mmol) at 0° C. The solution was stirred at 25° C. for 12 hours, at which point TLC (PE:EA=3:1) showed the reaction was complete. After cooling to 0° C., a solution of NaOH (23.3 mL, 3M, 70.01 mmol) was added slowly, followed by the addition of H$_2$O$_2$(8.06 g, 33% w/w in water, 70.1 mmol) while maintaining the temperature below 10° C. The resulting solution was stirred at 25° C. for 2 hours, then extracted with EtOAc (40 mL×3). The combined organic phase was washed with saturated aqueous Na$_2$S$_2$O$_3$ (20 mL×2), brine (30 mL), dried over Na$_2$SO$_4$ and concentrated to give A57 as a white solid. The crude product was used for the next step without further purification.

Synthesis of A58. A mixture of A57, PCC (2.32 g, 10 mmol) and silica gel (2.5 g) in DCM (30 mL) was stirred at 25° C. for 1 hour, after which TLC (PE:EA=3:1) showed the reaction was complete. The solution was concentrated in vacuum to give the crude product, which was purified by chromatography on silica gel (PE:EA=5:1) to afford A58 (1.05 g) as a yellow solid.

Synthesis of A59. To a solution of A58 (200 mg, 577 µmol) and concentrated HBr (9.7 mg, 57.6 µmol) in MeOH (5 mL) was added dropwise bromine (138 mg, 865 µmol). The reaction mixture was stirred at 25° C. for 8 hours and then heated to 50° C. for 8 hours, at which point TLC (PE:EA=3:1) showed the reaction was complete. The reaction was quenched by saturated aqueous NaHCO$_3$ (4 mL) and the pH adjusted to 7-8. The solution was extracted with EtOAc (8 mL×3), and the combined organic phase was dried over Na$_2$SO$_4$ and concentrated to give A59 (210 mg).

Synthesis of 155. To a solution of A59 (250 mg, 587 µmol) in acetone (6 mL) was added potassium carbonate (243 mg, 1.76 mmol) and morpholine (255 mg, 2.93 mmol) at 25° C. and the mixture was stirred at 50° C. for 8 hours. TLC (PE:EA=1:1) analysis showed the reaction was complete, at which point the mixture was extracted with water (8 mL) and EA (12 mL×3). The combined organic phase was dried over Na$_2$SO$_4$ and concentrated to give 155 (220 mg, crude) as a yellow solid. The crude solid was purified by preparative HPLC (0.05% HCl-ACN) to afford 155 (42.0 mg) as white solid. $^1$H NMR (400 MHz, Methanol-d4) δ 3.80-3.60 (m, 4H), 3.28-3.17 (m, 1H), 2.81-2.48 (m, 4H), 2.18-1.83 (m, 2H), 1.79-1.13 (m, 22H), 1.11-0.77 (m, 7H), 0.75-0.58 (m, 3H). LCMS R$_t$=1.013 min in 2 min chromatography, MS ESI calcd. for C$_{27}$H$_{45}$NO$_3$ [M+H]$^+$ 432, found 432 ([M+H]$^+$).

Example 82

Synthesis of 156 and 157

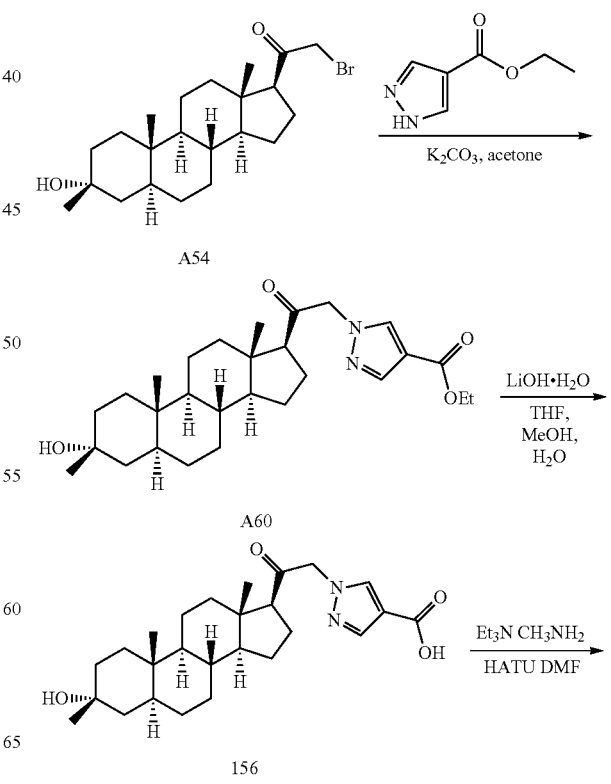

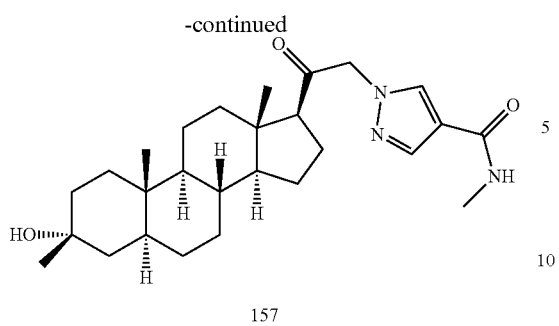

157

Compound A60 was prepared according to Example 47, step 7.

Synthesis of 156. To a solution of A60 (450 mg, 0.956 mmol) in THF (5 mL), CH$_3$OH (2 mL) and H$_2$O (5 mL) was added lithium hydroxide hydrate (80.1 mg, 1.91 mmol). The resulting reaction mixture was stirred at 25° C. for 16 hours, at which point TLC (PE:EA=1:1) indicated the starting material was completely consumed. The mixture was then diluted with water (10 mL) and then extracted with EtOAc (8 mL×3). The combined organic phase was concentrated to give a crude (400 mg) residue, which was purified by prep-HPLC to afford 16 mg of 156. $^1$H NMR (400 MHz, CDCl$_3$) δ 7.98 (s, 1H), 7.97 (s, 1H), 5.02-4.87 (m, 2H), 2.60 (t, J=8.8 Hz, 1H), 2.12-2.03 (m, 3H), 1.73-1.51 (m, 5H), 1.45-1.21 (m, 14H), 0.99-0.81 (m, 3H), 0.76 (s, 3H), 0.67 (s, 3H). LCMS: Rt=0.862 min in 1.5 min chromatography, MS ESI calcd. For C$_{26}$H$_{38}$N$_2$O$_4$ [M+H]$^+$ 443, found 443.

Synthesis of 157. To a solution of 156 in DMF (2 mL) was added HATU (170 mg, 0.450 mmol) and TEA (45.5 mg) followed by methanamine (10.4 mg, 0.337 mmol). The resulting reaction mixture was stirred at 25° C. for 16 hours, after which TLC (DCM:MeOH=10:1) indicated the starting material was completely consumed. The mixture was then diluted with water (10 mL) and then extracted with EtOAc (8 mL×3). The combined organic phase was concentrated then purified by prep-HPLC to afford 157 (5.5 mg) as a white solid. $^1$H NMR (400 MHz, CDCl$_3$) δ 7.88 (s, 1H), 7.78 (s, 1H), 5.00-4.87 (m, 2H), 2.96 (s, 3H), 2.60 (t, J=8.4 Hz, 1H), 2.14-2.02 (m, 2H), 1.77-1.20 (m, 18H), 0.98-0.81 (m, 3H), 0.75 (s, 3H), 0.66 (s, 3H). LCMS Rt=0.839 min in 1.5 min chromatography, MS ESI calcd. For C$_{27}$H$_{41}$N$_3$O$_3$ [M+Na]$^+$ 455, found 478.

Example 83

Synthesis of 158

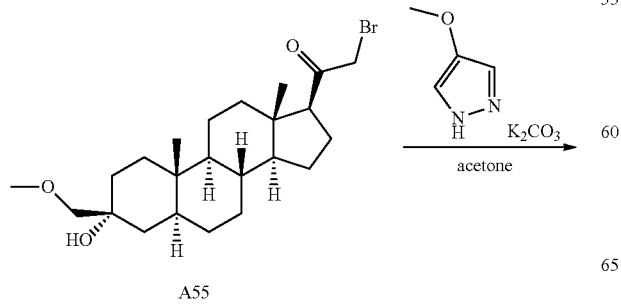

A55

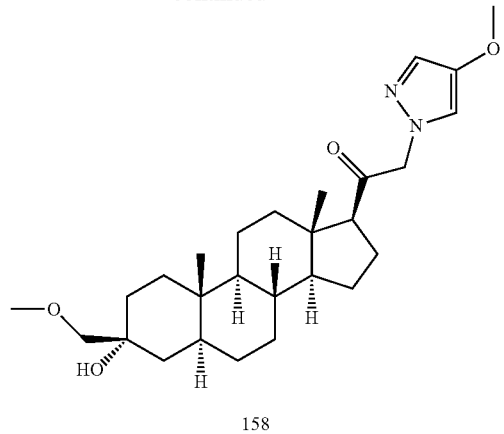

158

The title compound was prepared according to Example 67.

Compound 158 (34 mg): $^1$H NMR (400 MHz, CDCl$_3$) δ 7.32 (s, 1H), 7.12 (s, 1H), 4.81-4.97 (m, 2H), 3.70-3.84 (m, 3H), 3.39 (s, 3H), 3.19 (s, 2H), 2.58 (t, J=8.7 Hz, 1H), 2.13-2.25 (m, 1H), 2.05 (d, J=11.3 Hz, 1H), 1.62-1.77 (m, 4H), 1.11-1.61 (m, 15H), 0.94-1.03 (m, 1H), 0.80-0.88 (m, 1H), 0.76 (s, 3H), 0.67 (s, 3H). LCMS: Rt=2.776 min in 4 min chromatography, MS ESI calcd. for C27H42N2O4 [M+H]+ 459.3, found 459.2 [M+H]+.

Example 84

Synthesis of 159

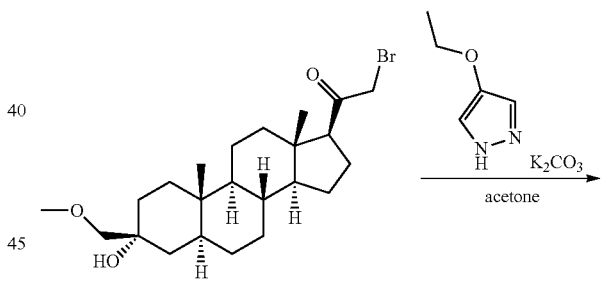

A55

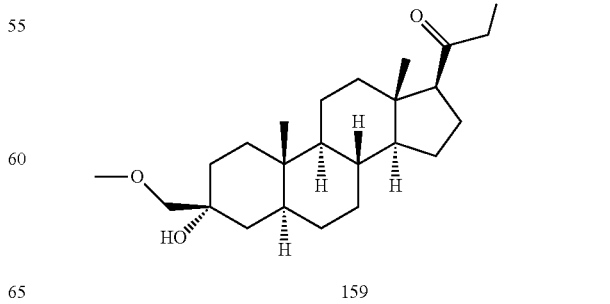

159

The title compound was prepared according to Example 67.

Compound 159 (33.2 mg): $^1$H NMR (DMSO-d$_6$, 400 MHz): δ=7.36 (s, 1H), 7.18 (s, 1H), 4.80-5.00 (m, 2H), 4.01 (s, 1H), 3.86 (q, J=7.0 Hz, 2H), 3.24 (s, 3H), 3.03 (s, 2H), 2.59-2.67 (m, 1H), 2.33 (br. s., 1H), 2.01 (d, J=11.0 Hz, 2H), 1.62 (br. s., 4H), 1.17-1.54 (m, 12H), 1.15 (d, J=10.0 Hz, 4H), 1.04 (d, J=13.2 Hz, 1H), 0.82-0.95 (m, 1H), 0.69 (s, 3H), 0.55 (s, 3H). LCMS: Rt=2.869 min in 4 min chromatography, MS ESI calcd. for C28H44N2O4 [M+H]+ 473.3, found 473.6 ([M+H]+.

Example 85

Synthesis of 160

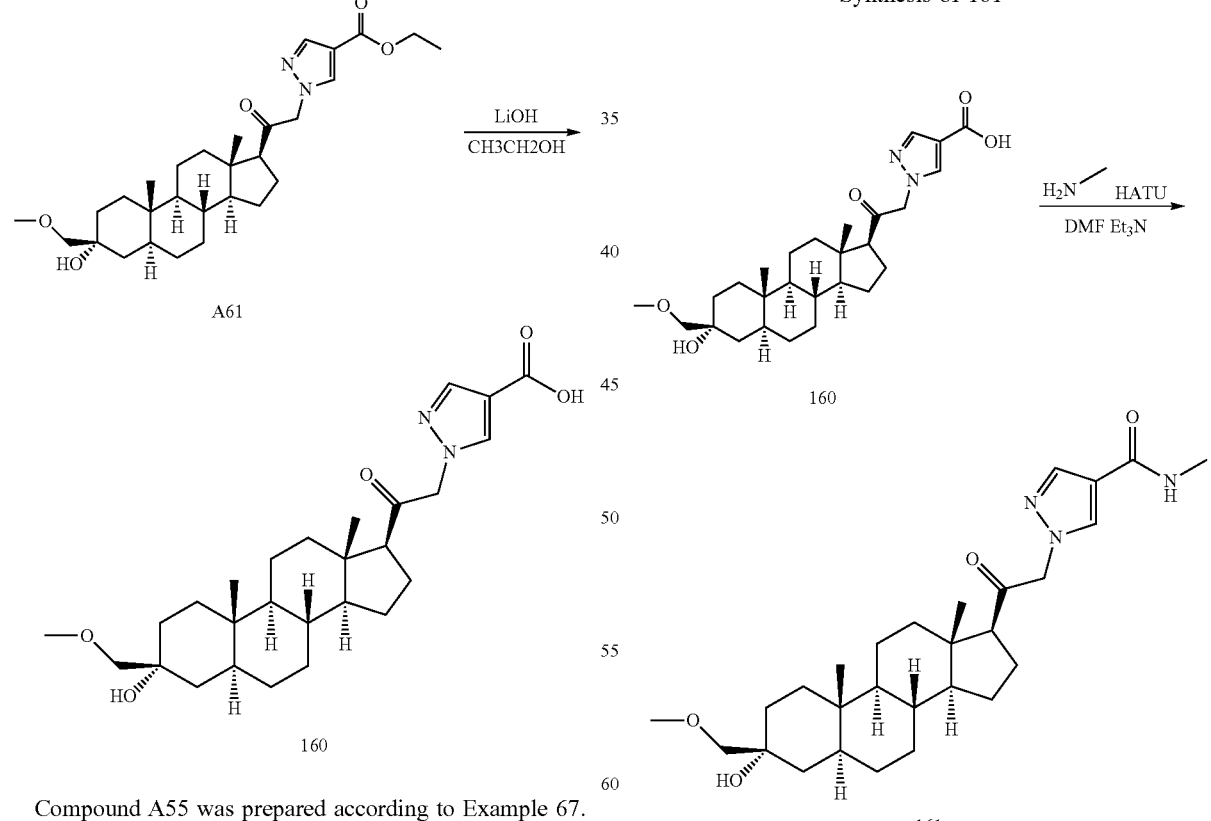

Compound A55 was prepared according to Example 67.

Synthesis of A61. K$_2$CO$_3$ (937 mg, 6.78 mmol) was added to A55 (1.5 g, 3.39 mmol) and ethyl 1H-pyrazole-4-carboxylate (616 mg, 4.4 mmol) in acetone (15 mL) at 25° C. The resulting mixture was stirred at 25° C. for 12 hours, at which point TLC indicated the reaction was complete. The reaction mixture was diluted with water (50 mL), then extracted with EtOAc (50 mL*3), and the combined organic layers were washed with brine (50 mL). The organic layer was dried over Na$_2$SO$_4$, filtered and purified by chromatography (silica gel: EtOAc in PE 20-50%) to afford A61 (1.4 g, 82.8%) as a white solid. $^1$H NMR (400 MHz, CDCl$_3$) δ 8.06 (s, 1H), 7.91 (s, 1H), 4.81-5.04 (m, 2H), 4.28-4.33 (m, 2H), 3.33-3.46 (m, 3H), 3.12-3.24 (m, 2H), 2.60 (t, J=8.8 Hz, 1H), 2.15-2.26 (m, 1H), 1.63-1.76 (m, 4H), 1.15-1.55 (m, 19H), 0.99 (td, J=12.2, 4.8 Hz, 1H), 0.82-0.89 (m, 1H), 0.74-0.79 (m, 3H), 0.47-0.73 (m, 3H). LCMS: Rt=0.911 min in 1.5 min chromatography, MS ESI calcd. for C29H44N2O5 [M+H]+ 501.3, found 501.7 ([M+H]+.

Synthesis of 160. LiOH (200 mg, 906 umol) was added to A61 (1.4 g, 2.79 mol) in EtOH (10 mL) at 25° C. The resulting mixture was stirred at 25° C. for 5 hours, at which point TLC analysis indicated the reaction was complete. The reaction mixture was acidified to pH=4-5 with 1 M HCl, then filtered to afford a precipitate (1.4 g) that was purified by HPLC afford 160 (1.2 g) as a white solid. $^1$H NMR (400 MHz, CDCl$_3$) δ=7.87-8.10 (m, 2H), 4.83-5.07 (m, 2H), 3.39 (s, 3H), 3.20 (s, 2H), 2.61 (br. s., 1H), 2.12-2.27 (m, 1H), 1.99-2.07 (m, 1H), 1.63-1.80 (m, 4H), 1.12-1.60 (m, 14H), 0.94-1.05 (m, 1H), 0.85 (t, J=9.6 Hz, 1H), 0.76 (s, 3H), 0.67 (s, 3H). LCMS: Rt=2.542 min in 4 min chromatography, MS ESI calcd. for C27H40N2O5 [M+H]+ 473.2, found 473.3 ([M+H]+.

Example 86

Synthesis of 161

Compound 160 was prepared according to Example 85. Methylamine (1.26 mL, 1.26 mmol) was added to A61 (300 mg, 634 umol), followed by triethylamine (192 mg, 1.9 mmol) and HATU (288 mg, 760 umol) in DMF (3 mL) at 25° C. The resulting mixture was stirred at 25° C. for 3 hours, at which point LCMS showed the reaction was complete. The reaction mixture was diluted with water (10 mL) and extracted with EtOAc (10 mL×3). The combined organic layers were washed with brine (10 mL), dried over Na$_2$SO$_4$, filtered, and concentrated to afford crude product (300 mg), which was purified by HPLC to obtain 161 (110 mg) as a white solid. $^1$H NMR (CDCl$_3$, 400 MHz): δ 7.85 (s, 1H), 7.76 (s, 1H), 5.78 (br. s., 1H), 4.84-5.00 (m, 2H), 3.39 (s, 3H), 3.19 (s, 2H), 2.96 (br. s., 3H), 2.59 (t, J=8.8 Hz, 1H), 2.14-2.24 (m, 1H), 2.04 (d, J=11.6 Hz, 1H), 1.82 (br. s., 2H), 1.62-1.78 (m, 4H), 1.12-1.59 (m, 13H), 0.95-1.03 (m, 1H), 0.81-0.89 (m, 1H), 0.76 (s, 3H), 0.66 (s, 3H). LCMS: Rt=2.487 min in 4 min chromatography, MS ESI calcd. For C28H43N3O4 [M+H]+ 486.3, found 486.2 ([M+H]+.

Example 87

Synthesis of 162

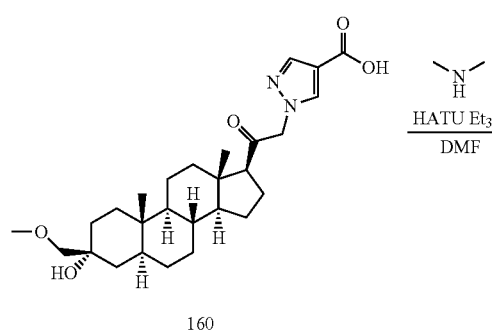

160

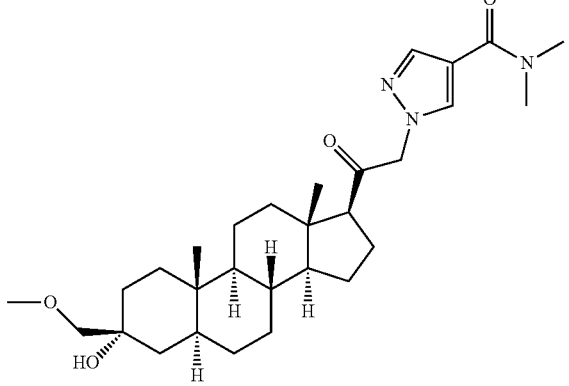

162

The title compound was prepared according to Example 87.

Compound 162 (83.2 mg): $^1$H NMR (CDCl$_3$, 400 MHz): δ 7.72-7.81 (m, 2H), 4.84-5.00 (m, 2H), 3.39 (s, 3H), 3.18 (s, 8H), 2.60 (t, J=8.6 Hz, 1H), 2.15-2.24 (m, 1H), 2.05 (d, J=11.6 Hz, 1H), 1.62-1.78 (m, 5H), 1.13-1.56 (m, 14H), 0.94-1.03 (m, 1H), 0.80-0.88 (m, 1H), 0.76 (s, 3H), 0.67 ppm (s, 3H). LCMS Rt=2.572 min in 4 min chromatography, MS ESI calcd. For C29H45N3O4 [M+H]+ 500.3, found 500.2 ([M+H]+.

Example 88

Synthesis of 163

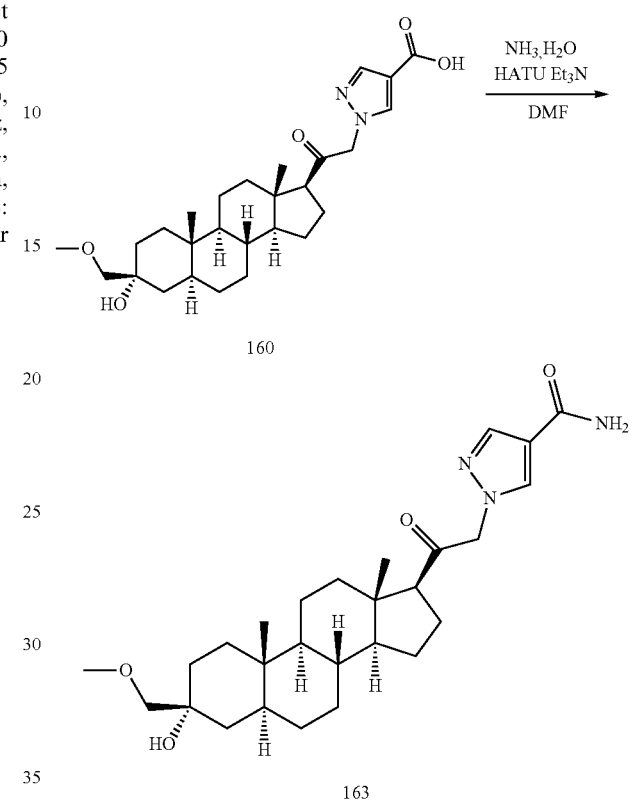

The title compound was prepared according to Example 86.

Compound 163 (102 mg): $^1$H NMR (CDCl$_3$, 400 MHz): δ 7.89 (br. s., 1h), 7.80 (br. s., 1H), 5.78 (br. s., 2H), 4.94 (d, J=19.2 Hz, 2H), 3.39 (s, 3H), 3.19 (s, 2h), 2.61 (br. s., 1H), 2.19 (br. s., 1h), 2.01-2.07 (m, 1H), 1.90 (br. s., 2H), 1.63-1.82 (m, 4H), 1.12-1.60 (m, 13H), 0.98 (d, J=11.6 Hz, 1H), 0.84 (t, J=9.8 Hz, 1H), 0.76 (s, 3H), 0.66 (br. s., 3H). LCMS: Rt=2.293 min in 4 min chromatography, MS ESI calcd. For C27H41N3O4 [M+H]+ 472.3, found 472.2 ([M+H]+.

Example 89

Synthesis of 164

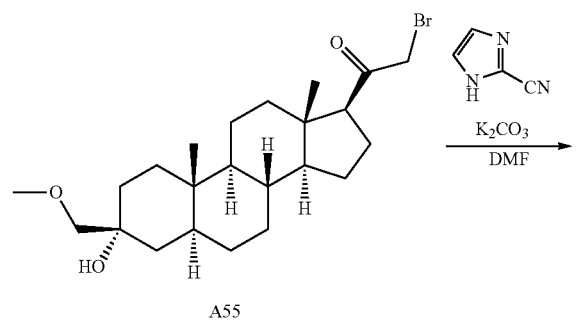

A55

-continued

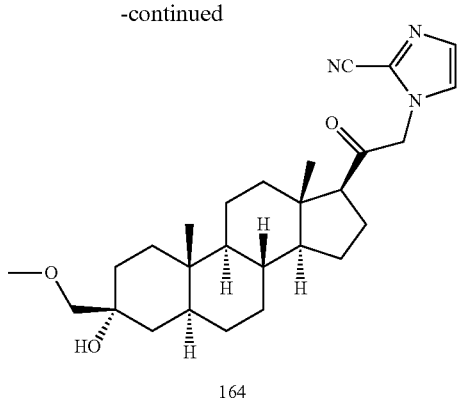

164

The title compound was prepared according to Example 67.

Compound 164 (8.2 mg): $^1$H NMR (CDCl$_3$, 400 MHz): δ 7.25 (s, 1H), 7.05 (s, 1H), 4.82-5.00 (m, 2H), 3.40 (s, 3H), 3.19 (s, 2H), 2.63 (t, J=8.4 Hz, 1H), 2.18-2.27 (m, 1H), 2.07 (d, J=11.6 Hz, 1H), 1.65-1.78 (m, 4H), 1.09-1.58 (m, 15H), 0.96-1.05 (m, 1H), 0.86 (t, J=9.8 Hz, 1H), 0.76 (s, 3H), 0.71 (s, 3H). LCMS: Rt=2.760 min in 4 min chromatography, MS ESI calcd. for C27H39N3O3 [M+H]+ 454.4, found 454.1 ([M+H]+.

Example 90

Synthesis of 165

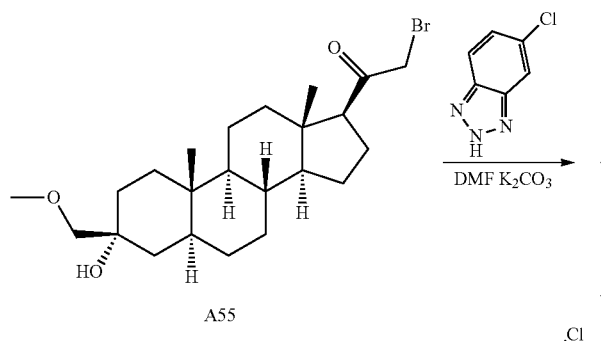

165

The title compound was prepared according to Example 67.

Compound 165 (15.6 mg): $^1$H NMR (CDCl$_3$, 400 MHz): δ 7.87 (s, 1H), 7.82 (d, J=9.0 Hz, 1H), 7.35 (dd, J=9.0, 2.0 Hz, 1H), 5.44-5.55 (m, 2H), 3.40 (s, 3H), 3.19 (s, 2H), 2.66 (t, J=8.6 Hz, 1H), 2.18-2.28 (m, 1H), 2.14 (d, J=11.6 Hz, 1H), 2.02 (br. s., 1H), 1.65-1.81 (m, 4H), 1.12-1.54 (m, 14H), 0.95-1.04 (m, 1H), 0.82-0.89 (m, 1H), 0.77 (s, 3H), 0.73 ppm (s, 3H). LCMS: Rt=3.012 min in 4 min chromatography, MS ESI calcd. for C29H40ClN3O3 [M+H]+ 514.2, found 514.1 ([M+H]+.

Example 91

Synthesis of 166

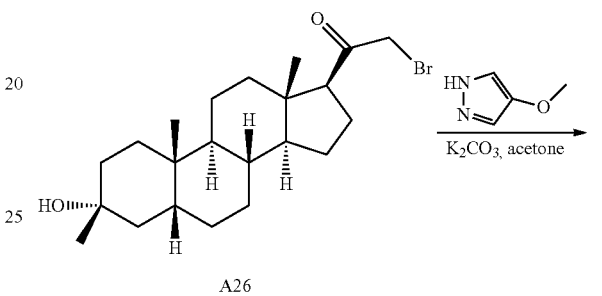

166

The title compound was prepared according to Example 5, step 4.

Compound 166: $^1$H NMR (CDCl$_3$, 400 MHz): δ 7.28 (s, 1H), 7.08 (s, 1H), 4.87-4.71 (m, 2H), 3.76 (s, 3H), 2.55 (t, J=8.9 Hz, 1H), 2.25-1.01 (m, 31H), 0.95 (s, 3H), 0.66 (s, 3H). LCMS: R$_t$=1.263 min in 2 min chromatography, MS ESI calcd. For C26H40N2O3 [M+H]$^+$ 429, found 429.

Example 92

Synthesis of 167

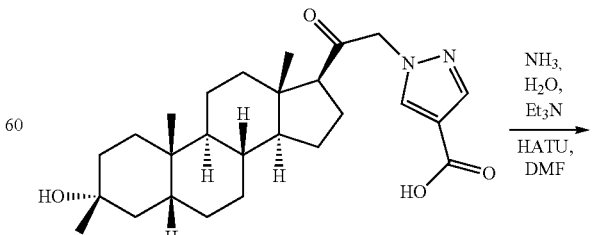

A62

205
-continued

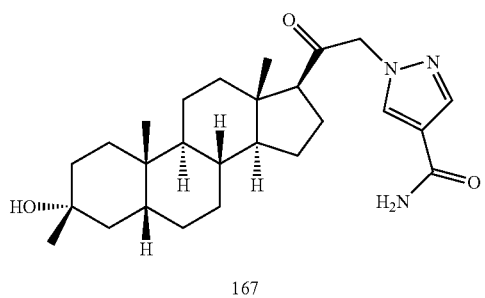

167

The title compound was prepared according to Example 86.

Compound 167: $^1$H NMR (MeOD, 400 MHz): δ 8.07 (s, 1H), 7.93 (s, 1H), 5.11 (d, J=4.3 Hz, 2H), 2.79-2.72 (m, 1H), 2.27-1.06 (m, 27H), 1.00 (s, 3H), 0.69 (s, 3H). LCMS: Rt=1.166 min in 1.5 min chromatography, MS ESI calcd. for C26H39N3O3 [M+H−H2O]$^+$ 424, found 424.

Example 93

Synthesis of 168

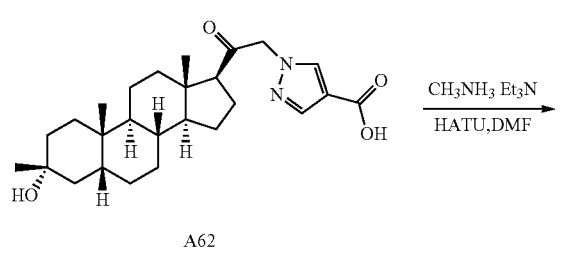

A62

168

The title compound was prepared according to Example 86.

Compound 168: $^1$H NMR (CDCl3, 400 MHz): Δ 8.01-7.76 (m, 2H), 6.10 (br. s., 1h), 4.96 (br. s., 2h), 2.97 (br. s., 3H), 2.60 (br. s., 1H), 2.28-1.00 (m, 31H), 0.95 (s, 3H), 0.66 (s, 3H).

LCMS: Rt=0.818 min in 1.5 min chromatography, MS ESI calcd. For C26H40N2O3 [M+H−H2O]$^+$ 438, found 438.

206

Example 94

Synthesis of 169

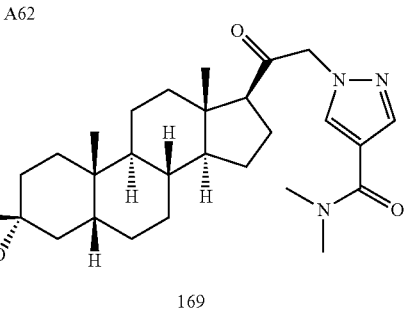

A62

169

The title compound was prepared according to Example 86.

Compound 169: $^1$H NMR (CDCl$_3$, 400 MHz): δ7.80-7.72 (m, 1H), 5.05-4.81 (m, 1H), 3.12 (br. s., 3H), 2.71-2.53 (m, 1H), 2.26-0.99 (m, 28H), 0.95 (s, 3H), 0.66 (s, 3H). LCMS: Rt=1.194 min in 2 min chromatography, MS ESI calcd. For C28H43N3O3 [M+H−H2O]$^+$ 452, found 452.

Example 95

Synthesis of 170

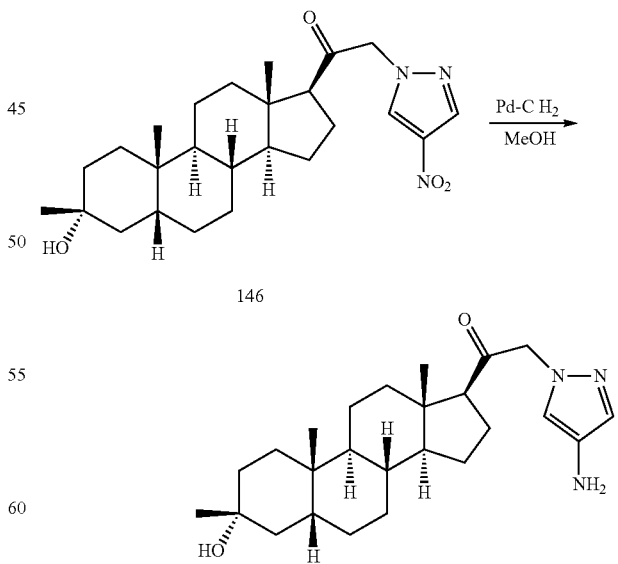

146

170

Compound 146 was prepared as described in Example 74.
To a solution of 146 (50 mg, 0.112 mmol) in MeOH (5 mL)

was added Pd—C (11.8 mg, 0.112 mmol) under N₂ at 25° C., and the reaction was stirred at 25° C. for 3 h under H₂. TLC (PE:EA=1:1) analysis showed that the reaction was complete, and the mixture was filtered and concentrated to give a crude residue which was purified by HPLC to give 170 (149 mg) as a red solid. ¹H NMR (CDCl₃, 400 MHz): δ7.21 (s, 1H), 7.01 (s, 1H), 4.85-4.68 (m, 2H), 2.53 (t, J=9.0 Hz, 1H), 2.22-0.99 (m, 29H), 0.94 (s, 3H), 0.65 (s, 3H). LCMS: Rt=1.019 min in 2 min chromatography, MS ESI calcd. For C25H39N3O2 [M+H−H2O]⁺ 396, found 396.

Example 96

Synthesis of 171

Example 97

Synthesis of 172

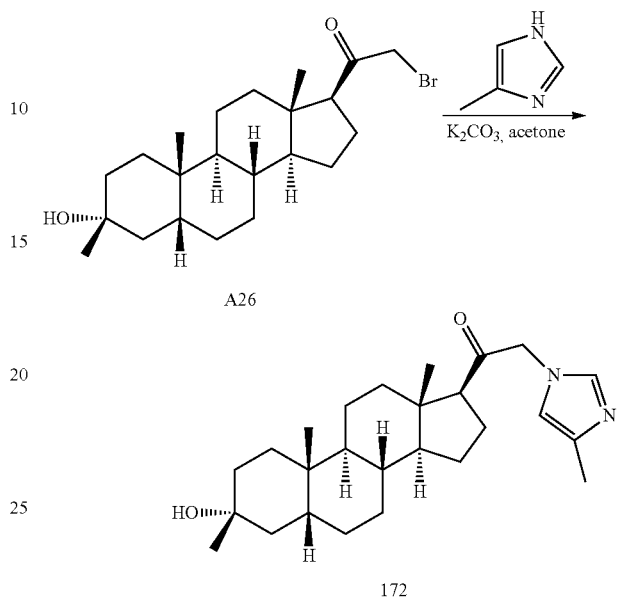

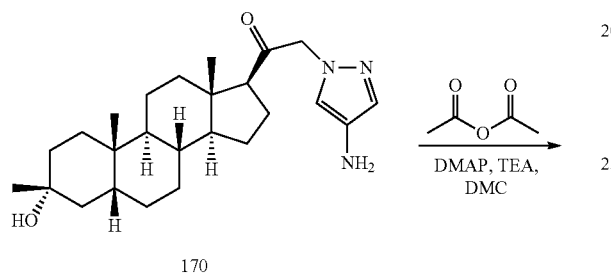

Compound 170 was prepared as described in Example 96. To a solution of 170 (140 mg, 0.338 mmol) in DCM (5 mL) was added DMAP (41.2 mg, 0.338 mmol), acetic anhydride (69.0 mg, 0.676 mmol) and triethylamine (68.4 mg, 0.676 mmol). The mixture was stirred at 25° C. for 16 h, at which point LCMS showed that starting material was consumed completely. The mixture was diluted with water (6 mL) and EtOAc (8 mL), and extracted with EtOAc (9 mL*2). The combined organic phase was washed with aq. HCl (20 mL*2, 4 M), sat. aq, NaCl (20 mL*2), dried over Na₂SO₄, and concentrated to give a residue which was purified by HPLC to give 171 (33 mg) as a white solid. ¹H NMR (CDCl₃, 400 MHz): δ7.93 (br. s., 1h), 7.44 (br. s., 1H), 7.35 (br. s., 1H), 4.97-4.79 (m, 2H), 2.61-2.51 (m, 1H), 2.22-0.98 (m, 32H), 0.94 (s, 3H), 0.65 (s, 3H). LCMS: Rt=1.180 min in 2 min chromatography, MS ESI calcd. for C27H41N3O3 [M+H−H2O]⁺ 438, found 438.

The title compound was prepared according to Example 5, step 4.

Compound 172: ¹H NMR (CDCl₃, 400 MHz): δ7.30 (br. s., 1H), 6.54 (s, 1H), 4.67-4.51 (m, 2H), 2.54 (t, J=8.8 Hz, 1H), 2.28-1.00 (m, 32H), 0.95 (s, 3H), 0.64 (s, 3H).

LCMS Rt=1.072 min in 1.5 min chromatography, 5-95AB, MS ESI calcd. For C26H40N2O2 [M+H]⁺ 413, found 413.

Example 98

Synthesis of 173

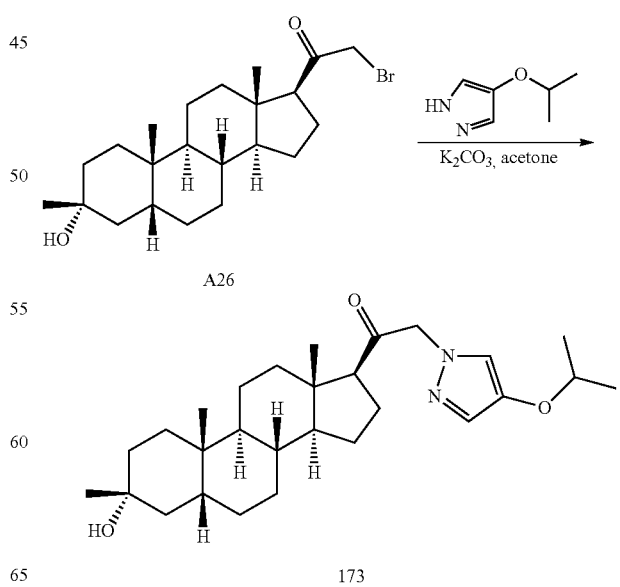

The title compound was prepared according to Example 5, step 4.

Compound 173: $^1$H NMR (CDCl3, 400 MHz): δ7.07 (br. s., 1H), 4.89-4.64 (m, 2H), 4.17 (td, J=6.0, 12.0 Hz, 1H), 2.65-2.47 (m, 1H), 2.25-1.00 (m, 31H), 0.94 (s, 3H), 0.75-0.56 (m, 3H).

LCMS Rt=1.338 min in 2 min chromatography, MS ESI calcd. For C28H44N2O3 [M+H]$^+$457, found 457.

Example 99

Synthesis of 174

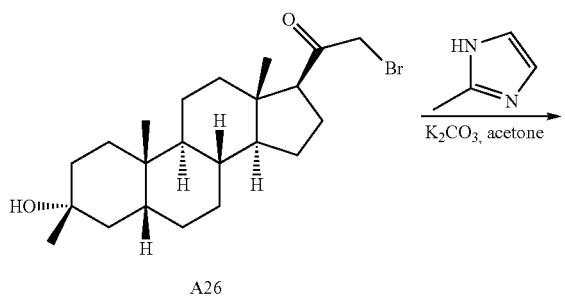

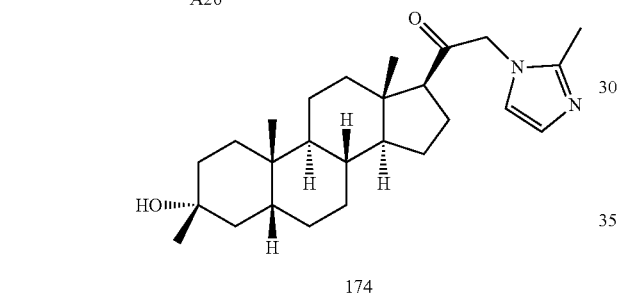

The title compound was prepared according to Example 5, step 4.

Compound 174: $^1$H NMR (CDCl$_3$, 400 MHz): δ7.23 (br. s., 1H), 6.99-6.97 (m, 1H), 7.00 (br. s., 1H), 5.12-4.77 (m, 2H), 2.65 (br. s., 3H), 2.27-1.01 (m, 28H), 0.99-0.87 (m, 3H), 0.66 (s, 3H). LCMS: Rt=1.065 min in 2 min chromatography, MS ESI calcd. For C26H40N2O2 [M+H]$^+$ 413, found 413.

Example 100

Synthesis of 175

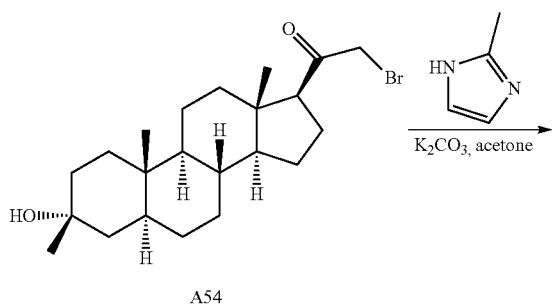

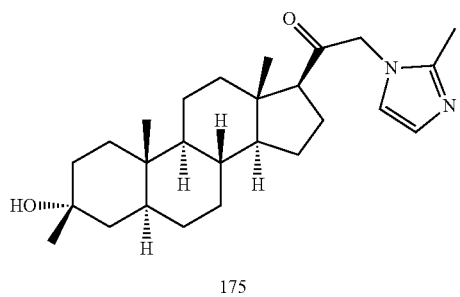

The title compound was prepared according to Example 47, step 7.

Compound 175: $^1$H NMR (CDCl$_3$, 400 MHz): δ7.56 (d, J=2 Hz, 1H), 7.48 (s, 1H), 5.37-5.10 (m, 2H), 3.86 (s, 1H), 2.74 (t, J=8.8 Hz, 1H), 2.41 (s, 3H), 2.32-2.03 (m, 3H), 1.72-1.10 (m, 20H), 1.05-0.74 (m, 2H), 0.70 (s, 3H), 0.58 (s, 3H). LCMS Rt=0.775 min in 1.5 min chromatography, MS ESI calcd. for C$_{26}$H$_{40}$N$_2$O$_2$ [M+H]$^+$ 413, found 413.

Example 101

Synthesis of 176

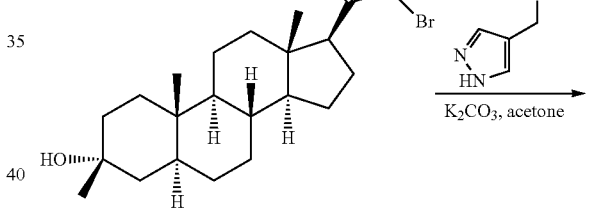

The title compound was prepared according to Example 47, step 7.

Compound 176: $^1$H NMR (CDCl$_3$, 400 MHz): δ7.56 (s, 1H), 7.43 (s, 1H), 4.99-4.86 (m, 2H), 4.61 (s, 3H), 2.59 (t, J=9.2 Hz, 1H), 2.17-2.04 (m, 3H), 1.54-1.20 (m, 19H), 0.98-0.81 (m, 3H), 0.75 (s, 1H), 0.66 (s, 1H). LCMS Rt=1.200 min in 2 min chromatography, MS ESI calcd. for C$_{26}$H$_{40}$N$_2$O$_3$ [M+H]$^+$ 429, found 429.

Example 102

Synthesis of 177

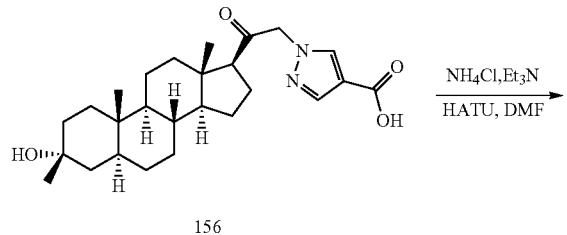

156

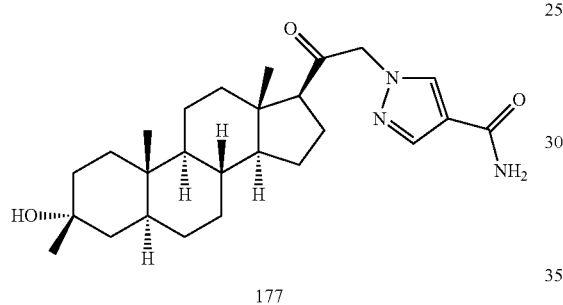

177

The title compound was prepared according to Example 82.

Compound 177: $^1$H NMR (CDCl$_3$, 400 MHz): δ7.88 (s, 1H), 7.79 (s, 1H), 5.54 (s, 2H), 5.01-4.85 (m, 2H), 2.60 (t, J=8.4 Hz, 1H), 2.24-2.02 (m, 2H), 1.72-1.51 (m, 4H), 1.41-1.21 (m, 2H), 0.98-0.82 (m, 2H), 0.76 (s, 3H), 0.66 (s, 3H). LCMS Rt=1.172 min in 2 min chromatography, MS ESI calcd. for C$_{26}$H$_{39}$N$_3$O$_3$ [M+H]$^+$ 442, found 442.

Example 103

Synthesis of 178

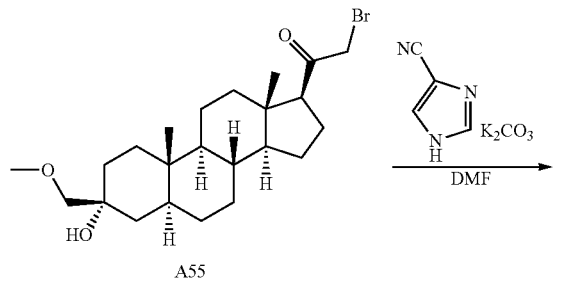

A55

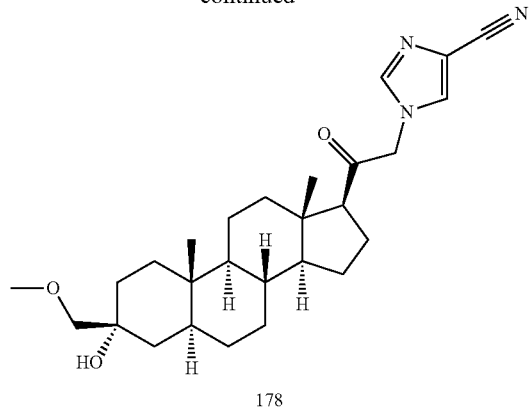

178

The title compound was prepared according to Example 67.

Compound 178: $^1$H NMR (CDCl$_3$, 400 MHz): δ7.86 (s, 1H), 7.82 (s, 1H), 4.87-5.05 (m, 2H), 3.40 (s, 3H), 3.19 (s, 2H), 2.61 (t, J=8.8 Hz, 1H), 2.16-2.26 (m, 1H), 2.01-2.08 (m, 2H), 1.66-1.77 (m, 4H), 1.14-1.55 (m, 14H), 0.94-1.04 (m, 1H), 0.82-0.89 (m, 1H), 0.76 (s, 3H), 0.66 (s, 3H).

LCMS: Rt=2.827 min in 4 min chromatography, MS ESI calcd. for C27H39N3O3 [M+H]+ 454.3, found 454.2 ([M+H]+.

Example 104

Synthesis of 179

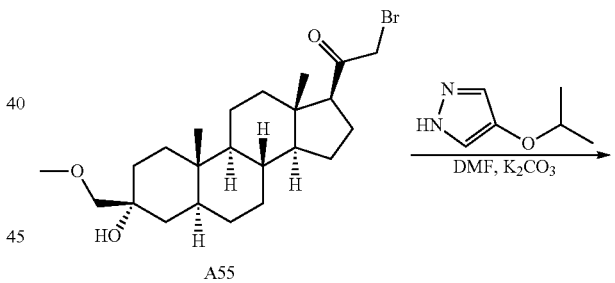

A55

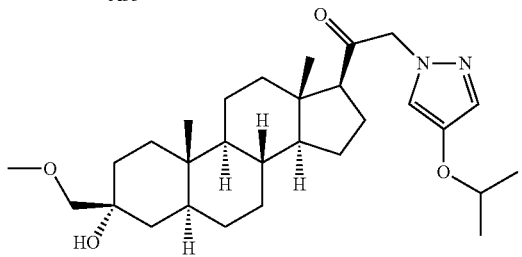

179

The title compound was prepared according to Example 67.

Compound 179: $^1$H NMR (CDCl$_3$, 400 MHz): δ7.26-7.25 (m, 1H), 7.07 (s, 1H), 4.78 (d, J=19.6 Hz, 2H), 4.21-4.13 (m, 1H), 3.39 (s, 3H), 3.18 (s, 2H), 2.58-2.52 (m, 1H), 2.23-2.12 (m, 1H), 2.06-1.97 (m, 2H), 1.69 (d, J=3.3 Hz, 5H), 1.59-1.49 (m, 4H), 1.49-1.35 (m, 4H), 1.31 (d, J=6.0 Hz, 11H), 1.25-1.12 (m, 4H), 1.02-0.91 (m, 1H), 0.87-0.79 (m, 1H), 0.75 (s, 3H), 0.66 (s, 3H). LCMS Rt=1.046 min in 2 min chromatography, MS ESI calcd. for $C_{29}H_{46}N_2O_4$ [M+H]$^+$ 487, found 487.

Example 105

Synthesis of 180, 181, and 182

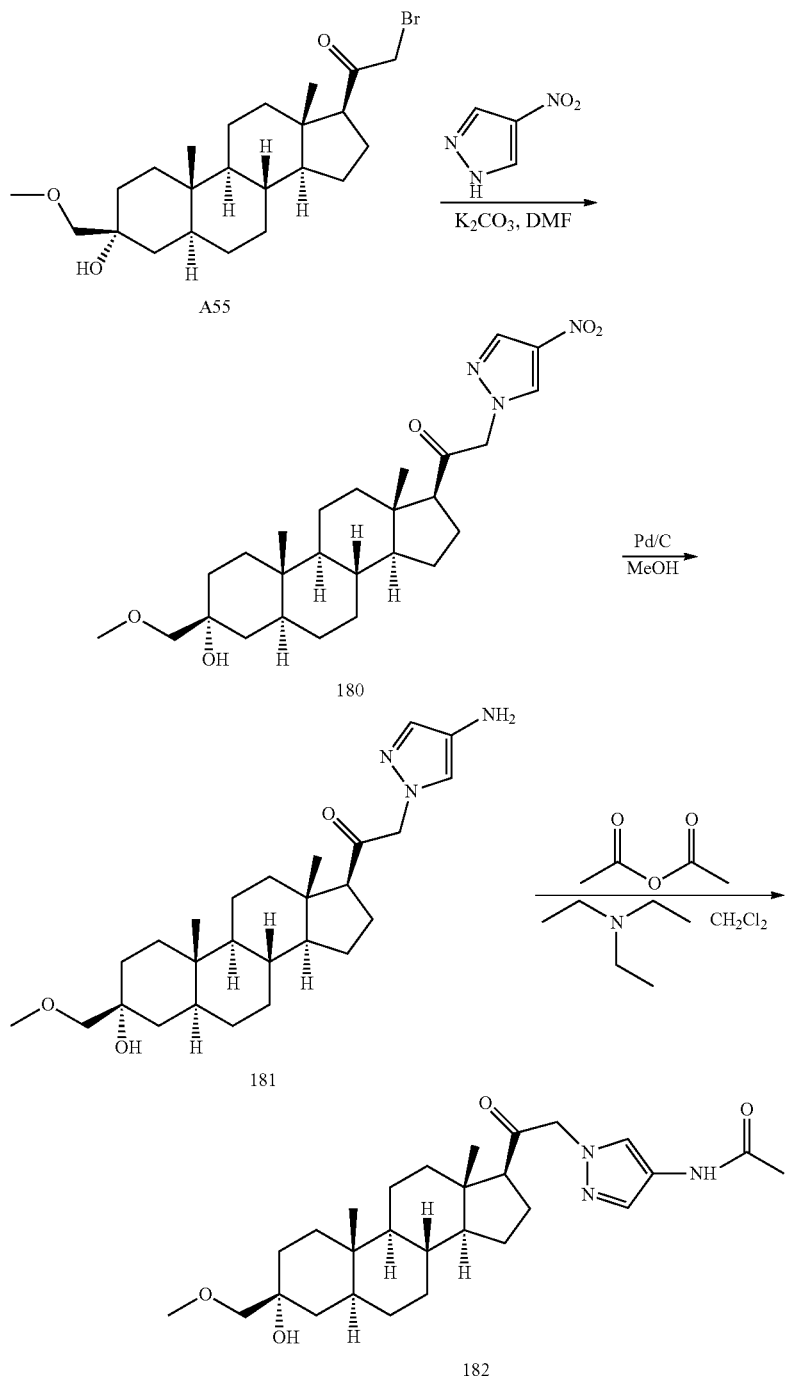

Compound 180 was prepared according to Example 67. $^1$H NMR (CDCl$_3$, 400 MHz): δ 8.20-8.06 (m, 1H), 5.05-4.82 (m, 1H), 3.39 (s, 1H), 3.19 (s, 1H), 2.65-2.58 (m, 1H), 2.26-2.16 (m, 1H), 2.08-1.99 (m, 2H), 1.81-1.64 (m, 4H), 1.56-1.13 (m, 13H), 1.05-0.92 (m, 1H), 0.90-0.81 (m, 1H), 0.76 (s, 3H), 0.67 (s, 3H). LCMS Rt=1.042 min in 2 min chromatography, MS ESI calcd. for $C_{26}H_{39}N_3O_5$ [M+H]$^+$ 456, found 456 ([M+H]$^+$).

Synthesis of 181. To a solution of 180 (846 mg, 1.78 mmol) in MeOH (10 mL) was added Pd/C (300 mg) at 25° C. The mixture was stirred under a H$_2$ balloon at 25° C. for 3 hours, at which point LCMS indicated the reaction was complete. The reaction mixture was filtered through a pad of Celite and washed with MeOH (5 mL×2), and the combined filtrate was concentrated to give a crude residue, which was purified by HPLC to give afford 181 (9.4 mg) as a white solid.

1H NMR (CDCl3 400 MHz) δ 7.20 (s, 1H), 7.01 (s, 1H), 4.85-4.69 (m, 2H), 3.39 (s, 3H), 3.18 (s, 2H), 2.91 (br. s., 1H), 2.58-2.52 (m, 1H), 2.22-2.12 (m, 1H), 2.06-1.98 (m, 2H), 1.74-1.62 (m, 4H), 1.59-1.56 (m, 1H), 1.54-1.50 (m, 2H), 1.49-1.33 (m, 4H), 1.32-1.12 (m, 7H), 1.03-0.93 (m, 1H), 0.87-0.78 (m, 1H), 0.75 (s, 3H), 0.66 (s, 3H). LCMS Rt=0.446 min in 2 min chromatography, MS ESI calcd, for $C_{26}H_{41}N_3O_3$ [M+H]=444.

Synthesis of 182. To a solution of 181 (450 mg, 1.01 mmol) in $CH_2Cl_2$ (5 mL) was added triethylamine (204 mg, 2.02 mmol) and acetic anhydride (206 mg, 2.02 mmol) at 25° C. for 2 hours, at which point LCMS indicated the reaction was complete. The mixture was poured into water (10 mL) and extracted with $CH_2Cl_2$ (20 mL×2). The combined organic solution was washed with brine (10 mL), dried over $Na_2SO_4$, and the organic layer was filtered and concentrated under reduced pressure to provide a residue that was purified by HPLC to afford 182 (115 mg) as a white solid. $^1$H NMR (CDCl$_3$ 400 MHz) δ 7.92-7.87 (m, 1H), 7.46-7.38 (m, 1H), 7.14-7.07 (m, 1H), 4.93-4.76 (m, 2H), 3.39 (s, 3H), 3.18 (s, 2H), 2.61-2.52 (m, 1H), 2.14 (s, 4H), 2.06-1.97 (m, 2H), 1.76-1.62 (m, 5H), 1.55-1.49 (m, 3H), 1.30 (s, 15H), 1.04-0.92 (m, 1H), 0.88-0.79 (m, 1H), 0.76 (s, 3H), 0.66 (s, 3H). LCMS Rt=0.898 min in 2 min chromatography, MS ESI calcd, for $C_{28}H_{43}N_3O_4$ [M+H]$^+$ 486, found 486 ([M+H]$^+$).

Example 106

Synthesis of 183 and 184

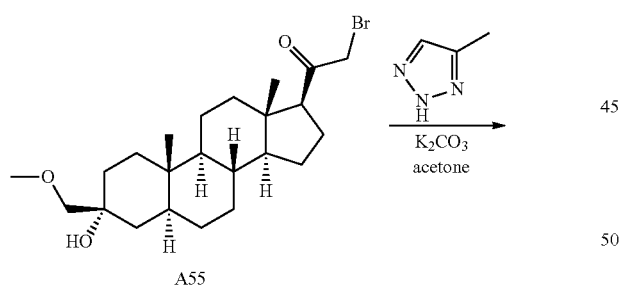

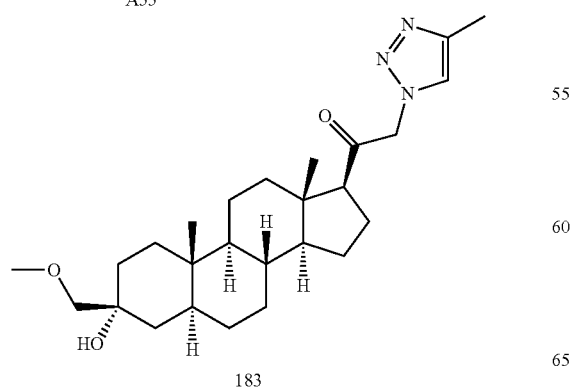

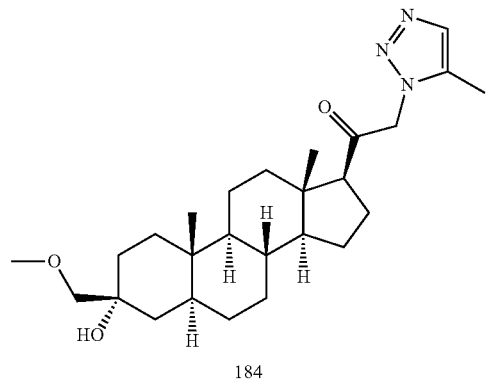

The title compounds were prepared according to Example 67.

Compound 183: $^1$H NMR (CDCl$_3$, 400 MHz): δ7.35 (s, 1H), 5.03-5.21 (m, 2H), 3.39 (s, 3H), 3.19 (s, 2H), 2.63 (t, J=8.8 Hz, 1H), 2.38 (s, 3H), 2.15-2.25 (m, 1H), 1.99-2.10 (m, 2H), 1.63-1.77 (m, 4H), 1.10-1.58 (m, 14H), 0.95-1.04 (m, 1H), 0.81-0.89 (m, 1H), 0.76 (s, 3H), 0.66 (s, 3H). LCMS Rt=2.657 min in 4 min chromatography, MS ESI calcd. for C26H41N3O3 [M+H]+ 444.3, found 444.1 ([M+H]+.

Compound 184: $^1$H NMR (DMSO-d$_6$, 400 MHz): δ7.49 (s, 1H), 5.46 (d, J=18.6 Hz, 1H), 5.23 (d, J=18.6 Hz, 1H), 4.02 (s, 1H), 3.24 (s, 3H), 3.04 (s, 2H), 2.80 (t, J=9.0 Hz, 1h), 2.67 (br. s., 1H), 2.33 (br. s., 1H), 2.13 (s, 3H), 2.04 (d, J=8.0 Hz, 1H), 1.64 (d, J=16.6 Hz, 4H), 1.49 (d, J=9.0 Hz, 13H), 0.93 (d, J=9.6 Hz, 1H), 0.76 (d, J=9.6 Hz, 1H), 0.70 (s, 3H), 0.58 (s, 3H).

LCMS Rt=2.683 min in 4 min chromatography, MS ESI calcd. for C26H41N3O3 [M+H]+ 444.3, found 444.1 ([M+H]+.

Example 107

Synthesis of 185

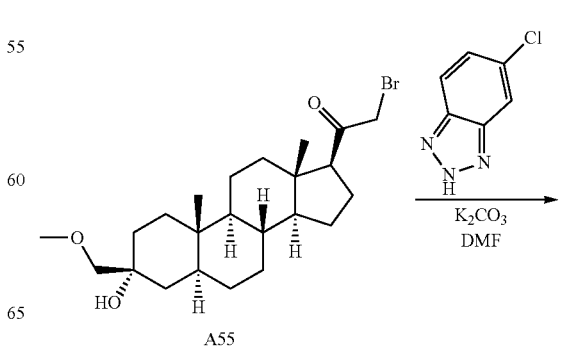

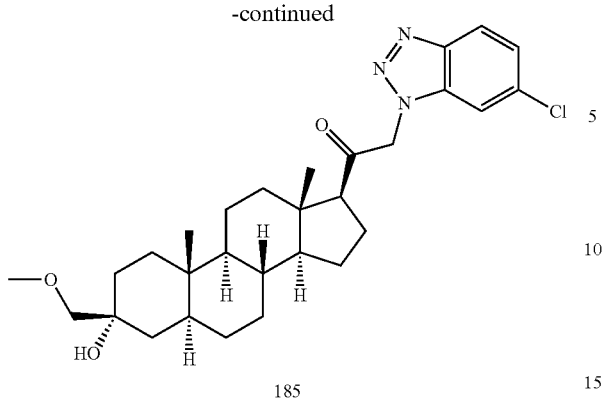

185

The title compound was prepared according to Example 67.

Compound 185: $^1$H NMR (CDCl$_3$, 400 MHz): δ8.00 (d, J=9.6 Hz, 1H), 7.29-7.38 (m, 2H), 5.38 (q, J=18.2 Hz, 2H), 3.40 (s, 3H), 3.19 (s, 2H), 2.73 (t, J=8.6 Hz, 1H), 2.13-2.26 (m, 2H), 2.03 (s, 1H), 1.67-1.82 (m, 4H), 1.13-1.56 (m, 14H), 0.97-1.06 (m, 1H), 0.84-0.91 (m, 1H), 0.78 (s, 3H), 0.72 (s, 3H). LCMS Rt=3.150 min in 4.0 min chromatography, MS ESI calcd. for C29H40ClN3O3 [M+H]+ 514.1, found 514.1 ([M+H]+.

Example 108

Synthesis of 186

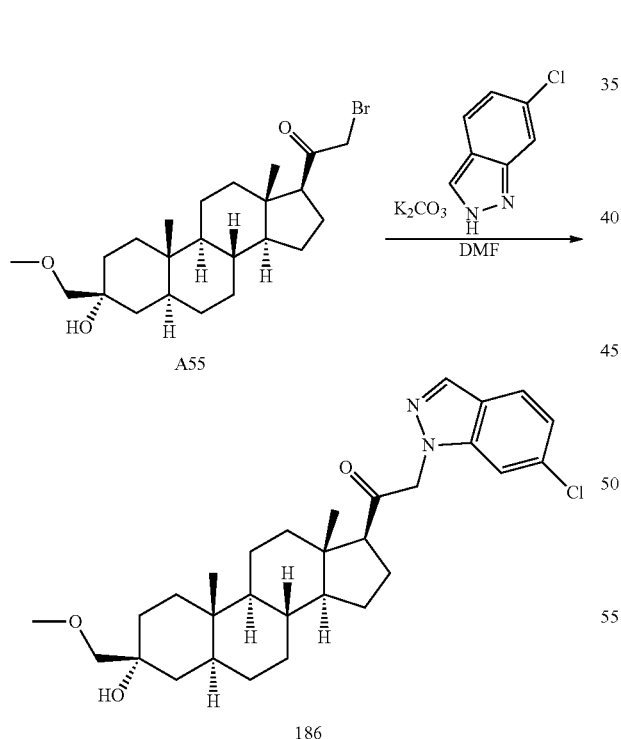

186

The title compound was prepared according to Example 67.

Compound 186: $^1$H NMR (CDCl$_3$, 400 MHz): δ8.01 (s, 1H), 7.66 (d, J=8.6 Hz, 1H), 7.20 (s, 1H), 7.08-7.16 (m, 1H), 5.04-5.16 (m, 2H), 3.39 (s, 3H), 3.19 (s, 2H), 2.65 (t, J=9.0 Hz, 1H), 2.10-2.24 (m, 2H), 2.01 (s, 1H), 1.66-1.75 (m, 4H), 1.13-1.54 (m, 14H), 0.94-1.03 (m, 1H), 0.82-0.90 (m, 1H), 0.77 (s, 3H), 0.71 (s, 3H). LCMS Rt=3.269 min in 4.0 min chromatography, MS ESI calcd. for C30H41ClN2O3 [M+H]+ 513.3, found 513.0 ([M+H]+.

Example 109

Synthesis of 187

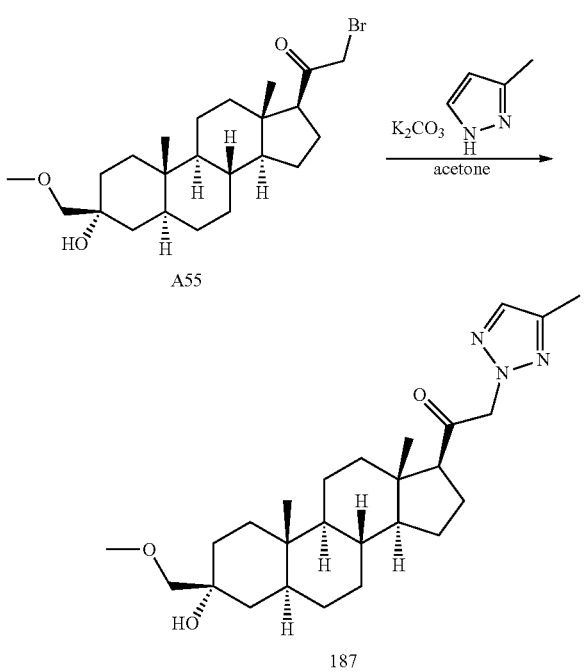

187

The title compound was prepared according to Example 67.

Compound 187: $^1$H NMR (CDCl$_3$, 400 MHz): δ7.43 (s, 1H), 5.15 (d, J=4.6 Hz, 2H), 3.40 (s, 3H), 3.19 (s, 2H), 2.58 (t, J=8.8 Hz, 1H), 2.34 (s, 3H), 2.15-2.23 (m, 1H), 2.00-2.09 (m, 2H), 1.63-1.76 (m, 4H), 1.09-1.56 (m, 14H), 0.94-1.03 (m, 1H), 0.81-0.87 (m, 1H), 0.76 (s, 3H), 0.70 ppm (s, 3H). LCMS: Rt=2.873 min in 4.0 min chromatography, MS ESI calcd. for C26H41N3O3 [M+H]+ 444.3, found 444.2 ([M+H]+.

Example 110

Synthesis of 188

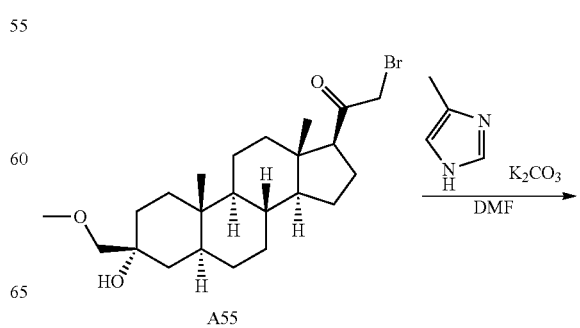

-continued

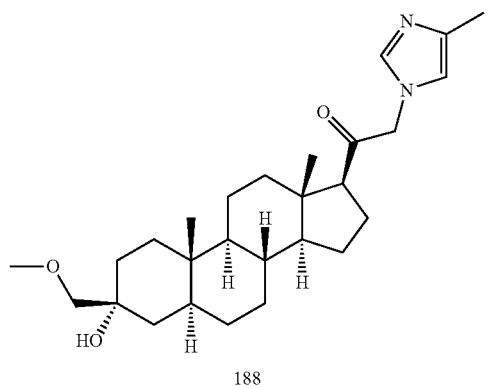
188

The title compound was prepared according to Example 67.

Compound 188: $^1$H NMR (CDCl$_3$, 400 MHz): δ7.30 (s, 1H), 6.56 (s, 1H), 4.55-4.67 (m, 2H), 3.39 (s, 3H), 3.19 (s, 2H), 2.56 (t, J=8.8 Hz, 1H), 2.23 (s, 3H), 2.13-2.21 (m, 1H), 2.00-2.08 (m, 1H), 1.95 (d, J=11.6 Hz, 1H), 1.66-1.75 (m, 4H), 1.14-1.58 (m, 14H), 0.94-1.04 (m, 1H), 0.81-0.88 (m, 1H), 0.76 (s, 3H), 0.65 (s, 3H). LCMS: Rt=2.194 min in 4.0 min chromatography, MS ESI calcd. for C27H42N2O3 [M+H]+ 443.3, found 443.2 ([M+H]+.

Example 111

Synthesis of 189

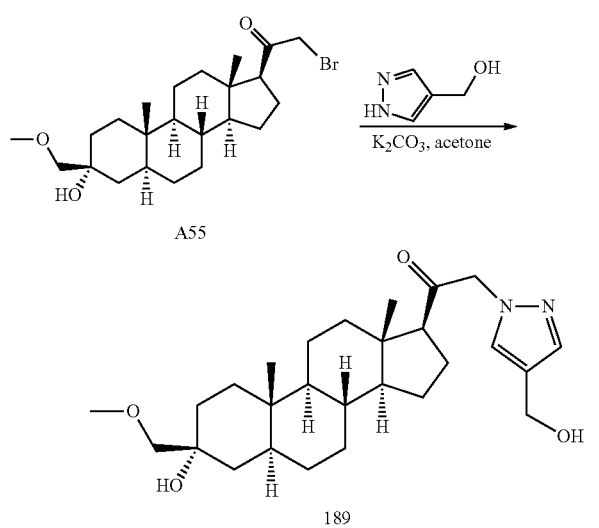
189

The title compound was prepared according to Example 67.

Compound 189: $^1$H NMR (CDCl$_3$, 400 MHz): δ7.54 (s, 1H), 7.41 (s, 1H), 4.96-4.82 (m, 1H), 4.61 (s, 3H), 3.39 (s, 3H), 3.18 (s, 3H), 2.59 (t, J=8.8 Hz, 1H), 2.20-2.01 (m, 4H), 1.71-1.22 (m, 22H), 0.99-0.84 (m, 2H), 0.75 (s, 3H), 0.66 (s, 3H). LCMS Rt=0.818 min in 1.5 min chromatography, MS ESI calcd. for C$_{27}$H$_{42}$N$_2$O$_4$ [M+Na]$^+$ 481, found 481.

Example 112

Synthesis of 190

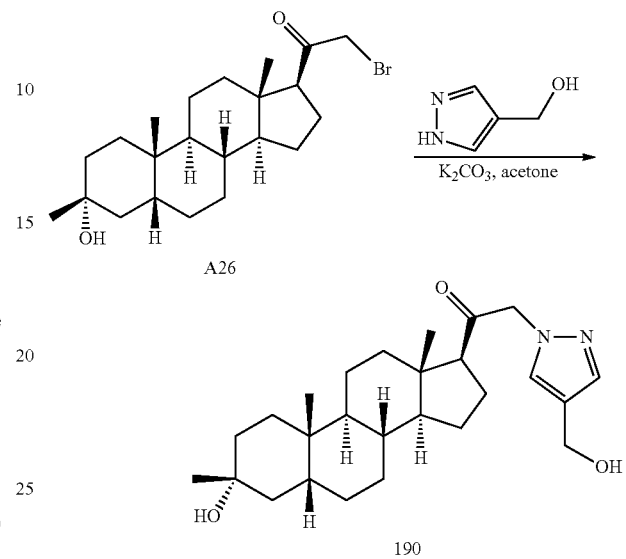
190

The title compound was prepared according to Example 5, step 4.

Compound 190: $^1$H NMR (CDCl3, 400 MHz): δ7.54 (s, 1H), 7.42 (s, 1H), 4.96-4.82 (m, 1H), 4.61 (s, 3H), 2.58 (t, J=8.8 Hz, 1H), 2.07-1.71 (m, 8H), 1.57-1.11 (m, 23H), 0.95 (s, 1H), 0.66 (s, 1H). LCMS Rt=0.823 min in 1.5 min chromatography, MS ESI calcd. for C$_{26}$H$_{40}$N$_2$O$_3$ [M+H]$^+$ 429, found 429.

Example 113

Synthesis of 191 and 192

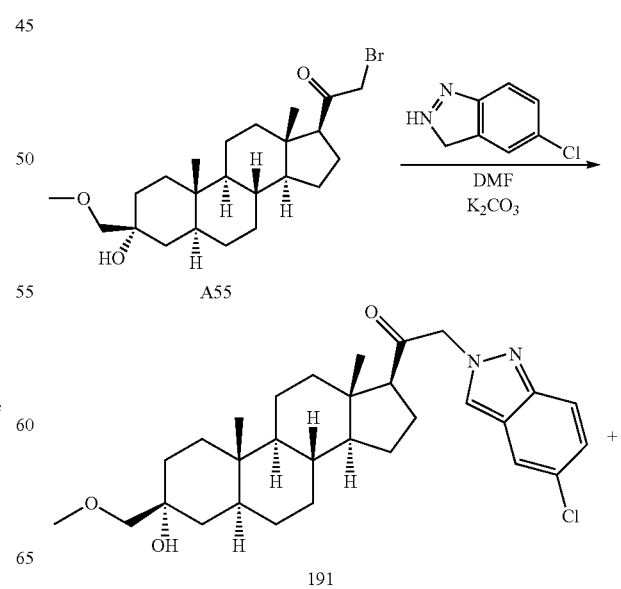
191

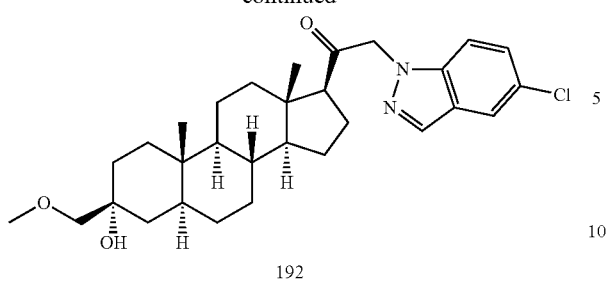

192

The title compounds were prepared according to Example 67.

Compound 191: $^1$H NMR (CDCl$_3$, 400 MHz): δ 7.90 (s, 1H), 7.71-7.61 (m, 2H), 7.23 (dd, J=2.0, 9.0 Hz, 1H), 5.28-5.12 (m, 2H), 3.41 (s, 3H), 3.21 (s, 2H), 2.66 (t, J=8.7 Hz, 1H), 2.29-2.18 (m, 1H), 2.12 (d, J=12.0 Hz, 1H), 2.03 (s, 1H), 1.81-1.67 (m, 4H), 1.57 (br. s., 2H), 1.50-1.36 (m, 4H), 1.35-1.17 (m, 8H), 1.05-0.96 (m, 1H), 0.91-0.84 (m, 1H), 0.78 (s, 3H), 0.72 (s, 3H). LCMS Rt=1.217 min in 2 min chromatography, MS ESI calcd. for C30H41ClN2O3 [M+H]$^+$ 513, found 513.

Example 114

Synthesis of 193 and 194

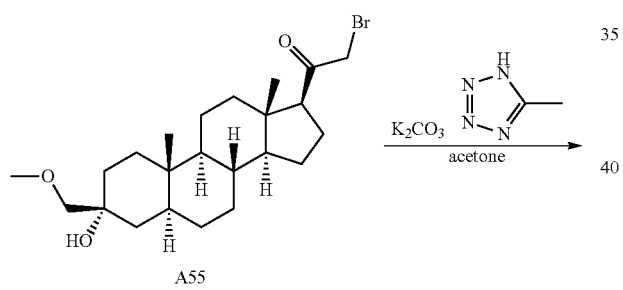

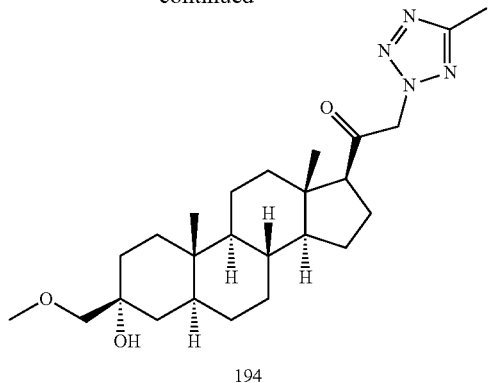

194

The title compounds were prepared according to Example 67.

Compound 193: $^1$H NMR (CDCl$_3$, 400 MHz): δ5.20-5.03 (m, 1H), 3.41 (s, 3H), 3.21 (s, 2H), 2.72-2.64 (m, 1H), 2.49 (s, 3H), 2.27-2.17 (m, 1H), 2.11-2.05 (m, 1H), 2.04 (s, 1H), 1.84-1.67 (m, 1H), 1.66-1.60 (m, 1H), 1.57-1.15 (m, 13H), 1.08-0.94 (m, 1H), 0.94-0.84 (m, 1H), 0.79 (s, 3H), 0.69 (s, 3H). LCMS Rt=0.999 min in 2 min chromatography, MS ESI calcd. for C$_{25}$H$_{40}$N$_4$O$_3$ [M+H]$^+$ 445, found 445.

Compound 194: $^1$H NMR (CDCl$_3$, 400 MHz): δ5.45-5.29 (m, 2H), 3.41 (s, 3H), 3.20 (s, 2H), 2.65 (t, J=8.8 Hz, 1H), 2.58 (s, 3H), 2.29-2.18 (m, 1H), 2.13-1.99 (m, 2H), 1.83-1.66 (m, 4H), 1.58-1.14 (m, 14H), 1.06-0.94 (m, 1H), 0.92-0.82 (m, 1H), 0.78 (s, 3H), 0.72 (s, 3H).

LCMS: Rt=1.056 min in 2 min chromatography, MS ESI calcd. for C$_{25}$H$_{40}$N$_4$O$_3$ [M+H]$^+$ 445, found 445.

Example 115

Synthesis of 195

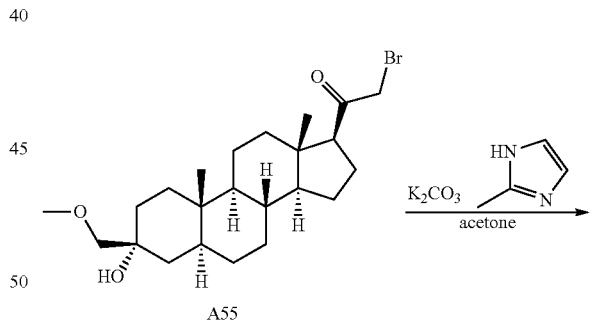

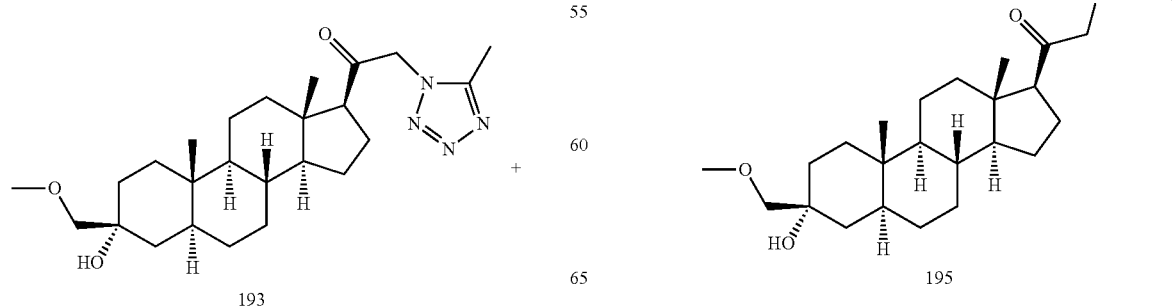

The title compound was prepared according to Example 67.
Compound 195: $^1$H NMR (CDCl3, 400 MHz): δ7.24 (S, 1H), 6.95 (br. s., 1H), 5.05-4.73 (m, 2H), 3.41 (s, 3H), 3.20 (s, 2h), 2.68 (br. s., 3h), 2.20 (br. s., 1H), 1.96 (br. s., 1H), 1.90-1.63 (m, 6H), 1.59-1.16 (m, 14H), 1.06-0.95 (m, 1H), 0.93-0.82 (m, 1H), 0.77 (s, 3H), 0.68 (s, 3H).
LCMS Rt=0.681 min in 2 min chromatography, MS ESI calcd. for C27H42N2O3 [M+H]$^+$ 443, found 443.
Example 116
Synthesis of 196
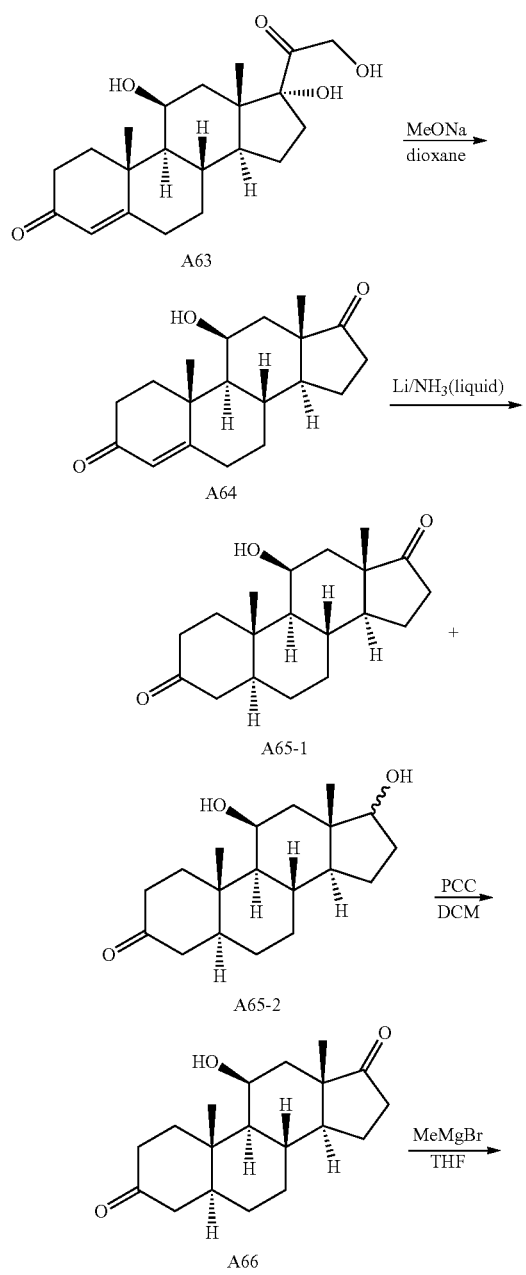
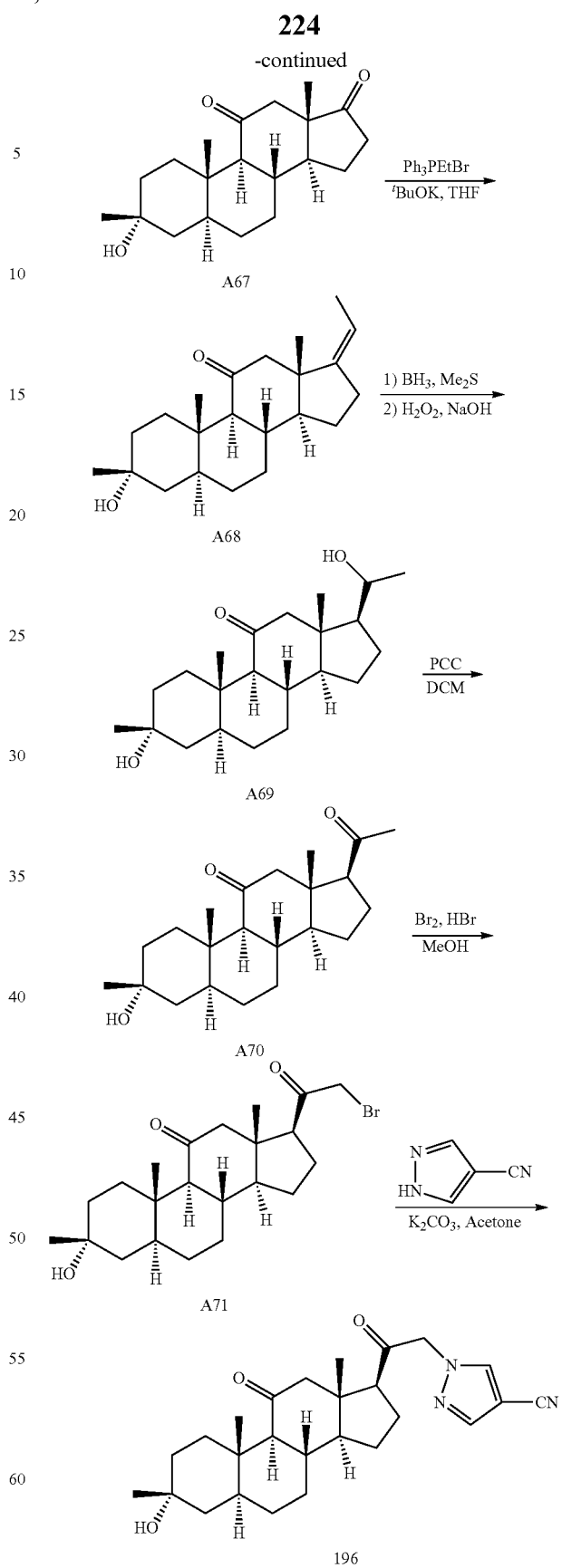
Synthesis of A64. To solution of A63 in dry dioxane (1000 mL) under N$_2$ was added sodium methoxide (74.0 g, 1.37 mol). The mixture was stirred at 110° C. for 16 hours, at which point TLC analysis (PE:EA=1:1) indicated the reaction was complete. The solvent was reduced to ⅓ volume and mixture was acidified with 2 M HCl to pH=5~6, extracted with DCM (1000 mL*2), washed with aqueous sodium bicarbonate (1000 mL) and brine (1000 mL), dried over sodium sulfate and concentrated. The residue was purified by column chromatography on silica gel (PE:EA:MeOH=3:1:0.1) to give A64 (20 g) as a white solid.

Synthesis of A65-1 and A65-2. Li (4.62 g, 660 mmol) was added to liquid ammonium (1500 mL, prepared in 13-601 over 30 mins) at −70° C. in small portions, and the mixture was stirred at −70° C. for 10 mins until all of Li was dissolved. A solution of A64 (20 g, 66.1 mmol) and tert-BuOH (14.6 g, 198 mmol) in 200 ml of anhydrous tetrahydrofuran was added dropwise and stirred for 90 mins until the reaction mixture turned light yellow, at which point TLC analysis (PE:EA=1:1, PMA) indicated the reaction was complete. Ammonium chloride (40 g) was added and excess ammonia was left to evaporate. The residue was extracted with 0.5N HCl (1000 mL) and dichloromethane (1000 mL×2), and the combined organic layers were washed with saturated NaHCO$_3$ solution, dried over Na$_2$SO$_4$, filtered and concentrated to give a mixture of A65-1 and A65-2 (18 g, impure) which was directly used in the next step without further purification.

Synthesis of A66. To a solution of A65-1 and A65-2 (18 g, 59.1 mmol) in 300 mL of anhydrous dichloromethane was added PCC (25.3 g, 118 mmol) and silica gel (25.3 g). After stirring at 15° C. for 2 h, TLC analysis (PE:EA=1:1, PMA) showed the reaction was complete. The resulting solution was concentrated and purified by chromatography on silica gel (petroleum ether/ethyl acetate=5:1 to 2:1) to A66 (7.5 g, 42.1%) as a white solid. $^1$H NMR (400 MHz, CDCl$_3$) δ 2.80-2.70 (m, 1H), 2.60-2.40 (m, 3H), 2.35-2.20 (m, 4H), 2.15-1.85 (m, 6H), 1.75-1.15 (m, 9H), 0.84 (s, 3H).

Synthesis of A67. To a solution of A66 (5 g, 16.5 mmol) in THF (80 mL) was added MeMgBr (16.5 mL, 49.5 mmol, 3M in ether) at −70° C. under N$_2$. The reaction mixture was stirred at −70° C. for 30 minutes, after which TLC (PE:EA=1:1, PMA) indicated the reaction was complete. The reaction was quenched with saturated NH$_4$Cl (100 mL) and extracted with EtOAc (100 mL*2). The organic layers were combined, dried, filtered, and concentrated to give 5 g of A67.

Synthesis of A68. To a slurry of bromo(ethyl)triphenylphosphorane (29.1 g, 78.4 mmol) in THF (50 mL) was added a solution of t-BuOK (8.78 g, 78.4 mmol) in THF (30 mL) under N$_2$. After addition, the mixture was stirred at 60° C. for 30 minutes, at which point A67 (5 g, 15.7 mmol) in THF (20 mL) was added. The final reaction mixture was stirred at 60° C. for 2 hours until TLC (PE:EA=1:1, PMA) indicated the reaction was finished. The mixture was diluted with saturated NH$_4$Cl solution (100 mL) then extracted with EtOAc (50 mL*2), and then the combined organic phase was dried, filtered, concentrated and purified by combi-flash (PE:EA=100%-80%) to give A68 (2.2 g) as a white solid. $^1$H NMR (400 MHz, CDCl$_3$) δ 5.18-5.14 (m, 2H), 2.86-2.83 (m, 1H), 2.58-2.55 (m, 1H), 2.39-2.32 (m, 4H), 1.80-1.10 (m, 20H), 0.82 (s, 3H), 0.69 (s, 3H).

Synthesis of A69. To a solution of A68 (2.2 g, 6.65 mmol) in THF (50 mL) was added dropwise a solution of BH$_3$-Me$_2$S (6.65 mL, 66.5 mmol, 10M in THF) at 0° C. The solution was stirred at 15° C. for 3 h, at which point TLC (PE/EtOAc=1/1) indicated the reaction was complete. After cooling to 0° C., a solution of NaOH solution (39.9 mL, 2M) was added very slowly, followed by addition of H$_2$O$_2$(15 g, 133 mmol, 30% in water). The reaction mixture was cooled to 10° C. and stirred for 2 h. The mixture was then diluted with saturated aqueous Na$_2$S$_2$O$_3$ (500 mL) until the reaction solution became clear, then extracted with EtOAc (50 mL×3). The combined organic solution was washed with saturated aqueous Na$_2$S$_2$O$_3$ (100 mL×2), brine (100 mL), dried over Na$_2$SO$_4$ and concentrated under vacuum to give the crude product A69 (2.0 g) as a white solid, which was used in next step without further purification.

Synthesis of A70. To a solution of A69 (2.0 g, 5.73 mmol) in 50 mL of anhydrous dichloromethane was added PCC (2.45 g, 11.3 mmol) and silica gel (2.45 g). After stirring at 15° C. for 2 h, TLC (PE:EA=1:1, PMA) indicated complete consumption of the starting material. The resulting solution was concentrated and purified by chromatography on silica gel (PE:EA=5:1 to 2:1) to afford A70 (1.0 g, 51.2%) as a white solid. $^1$H NMR (400 MHz, CDCl$_3$) δ 2.80-2.60 (m, 1H), 2.57-2.45 (m, 2H), 2.35-2.20 (m, 2H), 2.17 (s, 3H), 1.85-1.10 (m, 20H), 0.96 (s, 3H), 0.57 (s, 3H).

Synthesis A71. To a solution of A70 (1.0 g, 2.88 mmol) in MeOH (20 mL) was added HBr (11.6 mg, 0.144 mmol) and Br$_2$ (552 mg, 3.45 mmol). The reaction mixture was stirred at 15° C. for 2 hours, at which point LCMS indicated the reaction was complete. The mixture was diluted with saturated NaHCO$_3$ solution (10 mL) to form a white precipitate, which was filtered to afford A71 (1.2 g, 98.3%). $^1$H NMR (400 MHz, CDCl$_3$) δ 3.83 (s, 2H), 3.10-3.05 (m, 1H), 2.55-2.45 (m, 2H), 2.30-2.20 (m, 2H), 1.95-1.05 (m, 20H), 0.96 (s, 3H), 0.56 (s, 3H).

Synthesis of 196. To a solution of A71 (0.1 g, 0.235 mmol) in acetone (2 mL) was added K$_2$CO$_3$ (63.9 mg, 0.47 mmol) and 1H-pyrazole-4-carbonitrile (43.7 mg, 0.47 mmol). The mixture was stirred at 15° C. for 2 hours, at which point LCMS indicated the reaction was complete. The mixture was filtered, concentrated and purified by prep-HPLC to give 196. $^1$H NMR (400 MHz, CDCl$_3$) δ 7.84-7.81 (m, 2H), 1.90 (s, 2H), 2.79 (t, J=8.6 Hz, 1H), 2.60-2.45 (m, 2H), 2.30-2.20 (m, 2H), 1.95-1.10 (m, 20H), 0.96 (s, 3H), 0.63 (s, 3H). LCMS Rt=1.205 min in 2 min chromatography, MS ESI calcd. for C$_{26}$H$_{36}$N$_3$O$_3$ [M+H]$^+$ 437, found 420[M−18]$^+$.

Example 117

Synthesis of 197 and 198

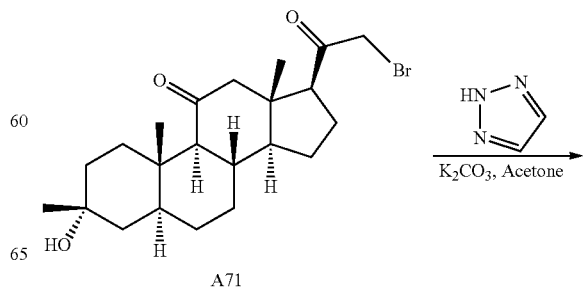

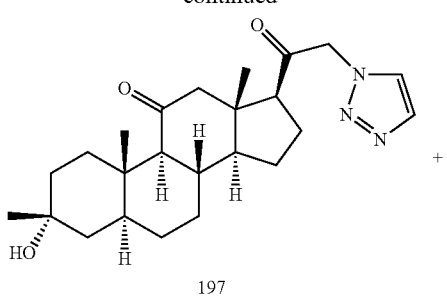

197

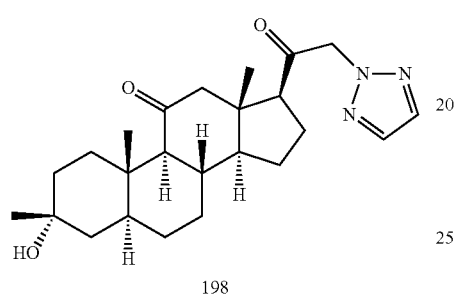

198

The title compounds were prepared according to Example 116.

Compound 197: ¹H NMR (CDCl₃, 400 MHz): δ7.77 (s, 1H), 7.62 (s, 1H), 5.24-5.08 (m, 2H), 2.85-2.82 (m, 1H), 2.58-2.45 (m, 2H), 2.30-2.20 (m, 2H), 1.95-1.15 (m, 20H), 0.97 (s, 3H), 0.65 (s, 3H). LCMS Rt=1.142 min in 2 min chromatography, MS ESI calcd. for $C_{24}H_{36}N_3O_3$ $[M+H]^+$ 414, found 414.

Compound 198: ¹H NMR (CDCl₃, 400 MHz): δ7.68 (s, 2H), 5.23-5.13 (m, 2H), 2.76-2.71 (m, 1H), 2.61-2.40 (m, 2H), 2.30-2.20 (m, 2H), 1.95-1.15 (m, 20H), 0.96 (s, 3H), 0.67 (s, 3H).

LCMS Rt=1.180 min in 2 min chromatography, MS ESI calcd. for $C_{24}H_{36}N_3O_3$ $[M+H]^+$ 420. found 420.

Example 118

Synthesis of 199

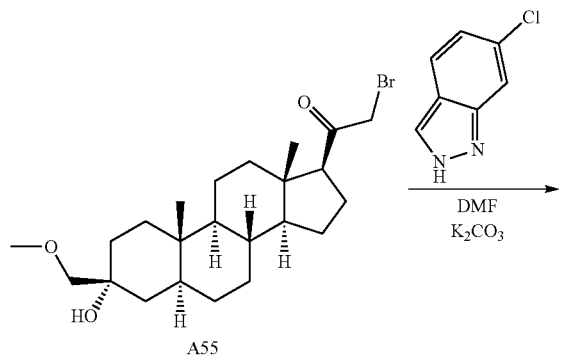

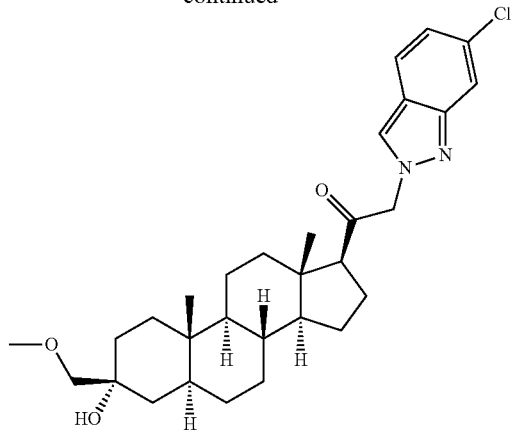

199

The title compound was prepared according to Example 67.

Compound 199: ¹H NMR (CDCl₃, 400 MHz): δ7.93 (s, 1H), 7.68 (s, 1H), 7.60 (d, J=9.0 Hz, 1H), 7.04 (d, J=7.6 Hz, 1H), 5.10-5.26 (m, 2H), 3.39 (s, 3H), 3.13-3.25 (m, 2H), 2.59-2.71 (m, 1H), 2.17-2.26 (m, 1H), 2.11 (d, J=12.0 Hz, 1H), 2.02 (br. s., 1H), 1.65-1.76 (m, 4H), 1.06-1.55 (m, 14H), 0.93-1.03 (m, 1H), 0.82-0.89 (m, 1H), 0.77 (s, 3H), 0.70 (s, 3H). LCMS Rt=3.190 min in 4.0 min chromatography MS ESI calcd. for C30H44O3 [M+H]+ 513.11, found 513.1 ([M+H]+.

Example 119

Synthesis of 200

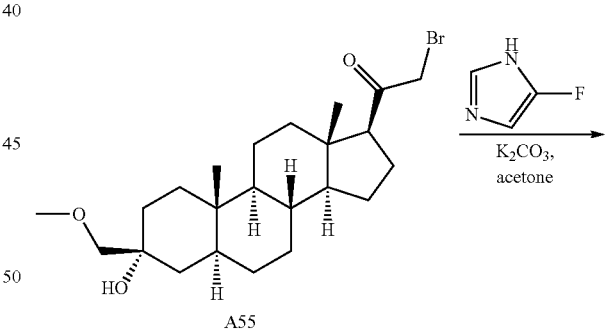

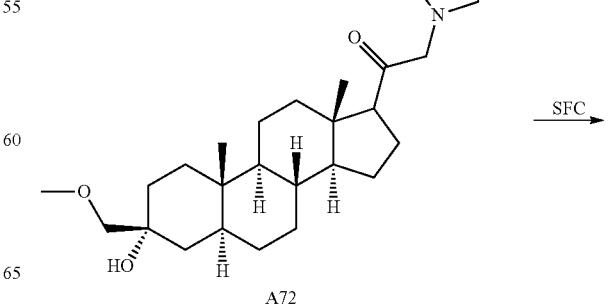

-continued

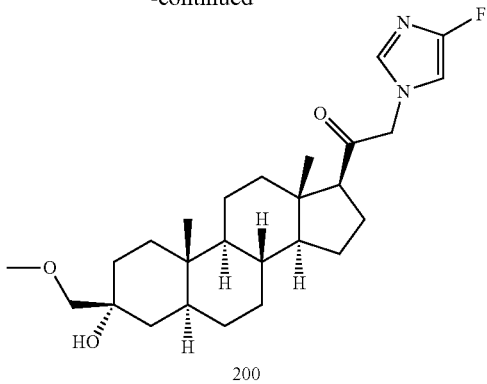

200

The title compounds were prepared according to Example 67.

Synthesis of A72: $^1$H NMR (CDCl$_3$, 400 MHz): δ7.00 (s, 1H), 6.33-6.41 (m, 1H), 4.52-4.64 (m, 2H), 3.34-3.41 (m, 3H), 3.06-3.25 (m, 3H), 2.56 (t, J=8.8 Hz, 1H), 2.13-2.25 (m, 1H), 2.01 (s, 1H), 1.90-1.96 (m, 1H), 1.64-1.75 (m, 4H), 1.15-1.50 (m, 13H), 0.93-1.01 (m, 1H), 0.81-0.89 (m, 1H), 0.73-0.79 (m, 3H), 0.65 (s, 3H). LCMS S Rt=1.942 min in 4.0 min chromatography, MS ESI calcd. for C$_{26}$H$_{39}$FN$_2$O$_3$ [M+H]$^+$ 447, found 447.

Purification of Compound 200 was carried out by SFC. Compound 200: $^1$H NMR (CDCl$_3$, 400 MHz): δ 7.00 (s, 1H), 6.37 (d, J=8.0 Hz, 1H), 4.52-4.66 (m, 2H), 3.39 (s, 3H), 3.18 (s, 2H), 2.56 (t, J=8.8 Hz, 1H), 2.11-2.25 (m, 2H), 2.01 (s, 1H), 1.93 (d, J=12.0 Hz, 1H), 1.63-1.77 (m, 4H), 1.10-1.54 (m, 13H), 0.97 (dd, J=12.0, 4.5 Hz, 1H), 0.81-0.88 (m, 1H), 0.76 (s, 3H), 0.65 (s, 3H). LCMS Rt=1.949 min in 4.0 min chromatography, MS ESI calcd. for C$_{26}$H$_{39}$FN$_2$O$_3$[M+H]$^+$ 447, found 447.

Example 120

Synthesis of 202

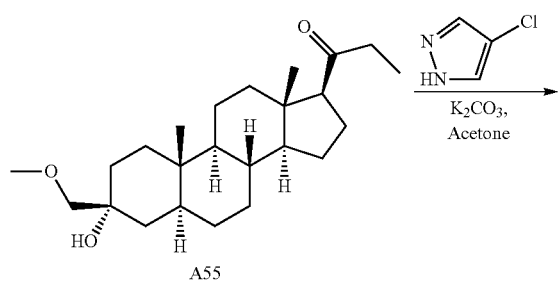

A55

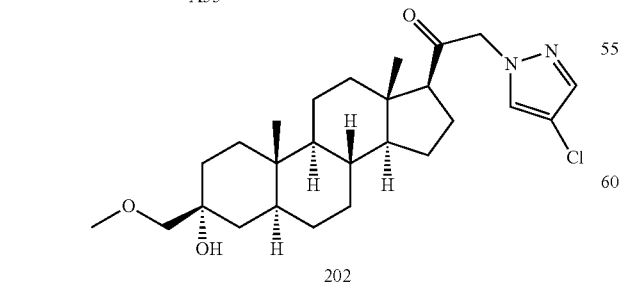

202

The title compound was prepared according to Example 67.

Compound 202: $^1$H NMR (CDCl$_3$, 400 MHz): δ0.66 (s, 3 H), 0.75 (s, 3 H), 0.78-1.03 (m, 3 H), 1.55 (s, 27 H), 2.00 (s, 1 H), 2.04 (br. s., 1 H), 2.03-2.03 (m, 1 H), 2.13-2.23 (m, 1 H), 2.57 (t, J=8.78 Hz, 1 H), 3.18 (s, 2 H), 3.39 (s, 3 H), 4.82 (s, 1 H), 4.87-4.94 (m, 1 H), 7.38-7.43 (m, 1 H), 7.45 (s, 1 H). LCMS Rt=1.283 min in 2.0 min chromatography, MS ESI calcd. for C$_{24}$H$_{36}$N$_2$O$_2$ [M+H]$^+$ 463, found 463.

Example 121

Synthesis of 203

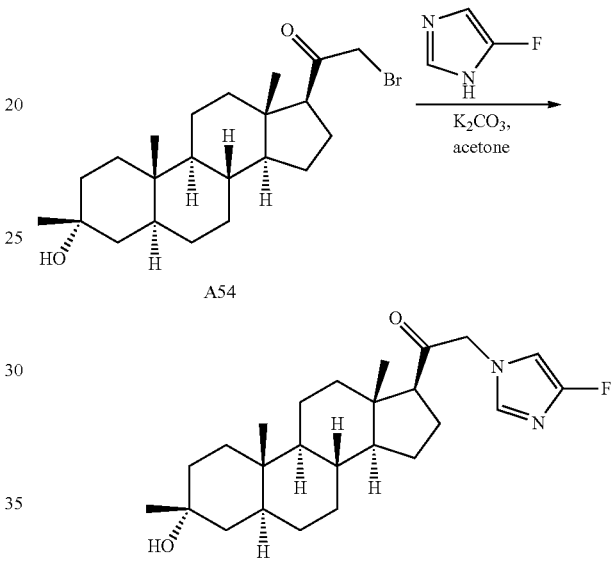

A54

203

The title compound was prepared according to Example 47, step 7.

Compound 203: $^1$H NMR (CDCl$_3$, 400 MHz): δ7.00 (s, 1 H), 6.37 (dd, J=8.16, 1.63 Hz, 1 H), 4.48-4.68 (m, 2 H), 2.56 (t, J=8.78 Hz, 1 H), 2.13-2.30 (m, 1 H), 1.89-1.98 (m, 1 H), 1.63-1.81 (m, 4 H), 1.10-1.61 (m, 18 H), 0.89-1.03 (m, 1 H), 0.71-0.86 (m, 4 H), 0.65 (s, 3 H). LCMS: MS Calcd. for: C$_{25}$H$_{37}$FN$_2$O$_2$[M+H]$^+$) 417; Found: 417.

Example 122

Synthesis of 204

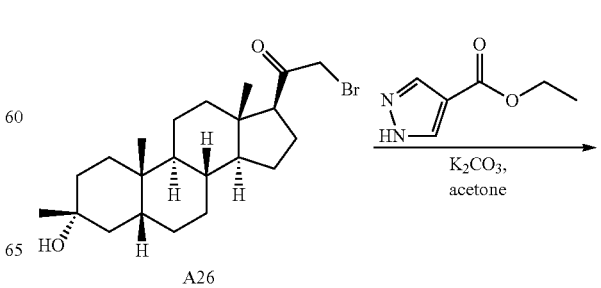

A26

-continued

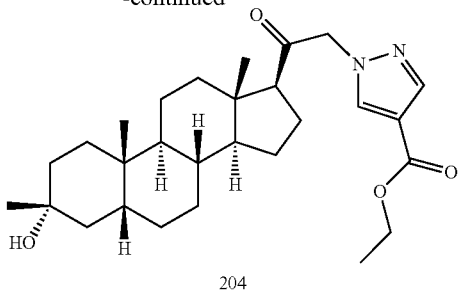

204

The title compound was prepared according to Example 5, step 4.

Compound 204: $^1$H NMR (CDCl$_3$, 400 MHz): δ7.92 (d, J=8.8 Hz, 2H), 5.01-4.82 (m, 2H), 4.29 (q, J=7.3 Hz, 2H), 2.63-2.55 (m, 1H), 2.26-2.14 (m, 1H), 2.06 (d, J=11.0 Hz, 1H), 1.96 (t, J=13.2 Hz, 1H), 1.90-1.80 (m, 1H), 1.79-1.68 (m, 3H), 1.53-1.38 (m, 8H), 1.37-1.31 (m, 4H), 1.30-1.20 (m, 8H), 1.18-1.00 (m, 2H), 0.95 (s, 3H), 0.66 (s, 3H). LCMS Rt=1.088 min in 2 min chromatography, MS ESI calcd. for C$_{28}$H$_{42}$N$_2$O$_4$ [M+H]$^+$ 471, found 471.

Example 123

Synthesis of 205 and 206

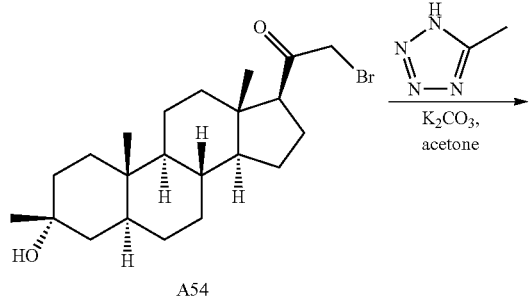

The title compounds were prepared according to Example 47, step 7.

Compound 205: $^1$H NMR (CDCl$_3$, 400 MHz): δ5.17-5.04 (m, 2H), 2.68-2.64 (m, 1H), 2.47 (s, 3H), 2.06-2.04 (m, 2H), 1.76-1.24 (m, 23H), 0.84-0.83 (m, 2H), 0.76 (s, 3H), 0.67 (s, 3H).

LCMS Rt=1.241 min in 2.0 min chromatography, MS ESI calcd. for C$_{24}$H$_{38}$N$_4$O$_2$ [M+H]$^+$ 415, found 415.

Compound 206: $^1$H NMR (CDCl$_3$, 400 MHz): δ5.40-5.31 (m, 2H), 2.65-2.56 (m, 1H), 2.24 (s, 3H), 2.08-2.06 (m, 2H), 1.76-1.24 (m, 23H), 0.84-0.83 (m, 2H), 0.76 (s, 3H), 0.70 (s, 3H).

LCMS Rt=1.290 min in 2.0 min chromatography, MS ESI calcd. for C$_{24}$H$_{38}$N$_4$O$_2$ [M+H]$^+$ 415, found 415.

Example 124

Synthesis of 207 and 208

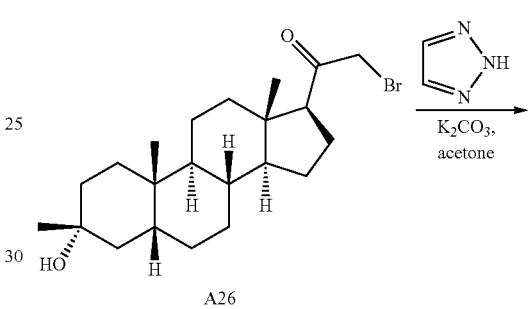

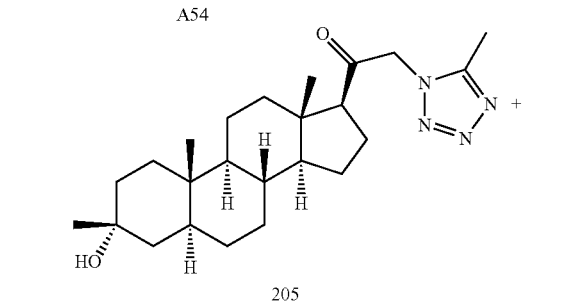

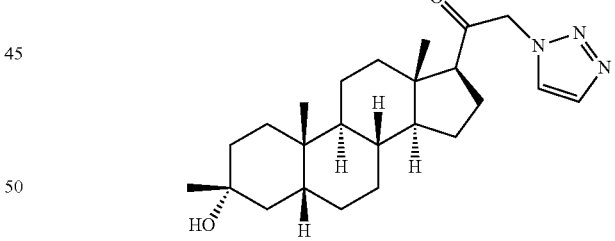

The title compounds were prepared according to Example 5, step 4.

Compound 207: $^1$H NMR (CDCl$_3$, 400 MHz): δ7.69 (s, 2H), 5.30-5.17 (m, 2H), 2.61-2.52 (m, 1H), 2.26-1.01 (m, 31H), 0.95 (s, 3H), 0.69 (s, 3H). LCMS R$_t$=0.904 min in 1.5 min chromatography, ESI calcd. for C$_{24}$H$_{37}$N$_3$O$_2$ [M+H−H$_2$O]$^+$ 382, found 382.

Compound 208: $^1$H NMR (CDCl$_3$, 400 MHz): δ7.78 (s, 1H), 7.66 (s, 1H), 5.32-5.24 (m, 1H), 5.18-5.10 (m, 1H), 2.70-2.60 (m, 1H), 2.28-1.03 (m, 32H), 0.96 (s, 3H), 0.66 (s, 3H). LCMS R$_t$=0.864 min in 1.5 min chromatography, MS ESI calcd. for C$_{24}$H$_{37}$N$_3$O$_2$ [M+H]$^+$ 400, found 400.

Example 125

Synthesis of 209 and 210

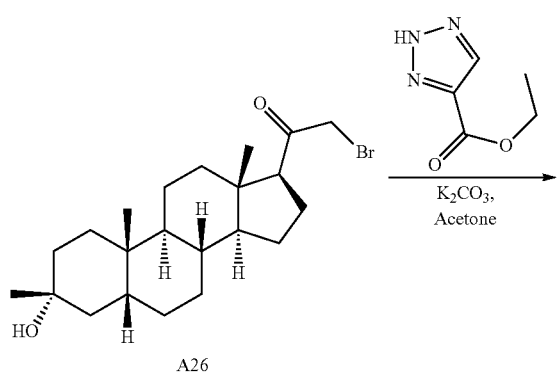

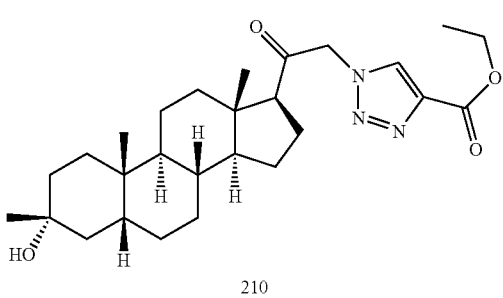

The title compounds were prepared according to Example 5, step 4.

Compound 209: ¹H NMR (CDCl₃, 400 MHz): δ8.10 (s, 1H), 5.33-5.23 (m, 2H), 4.42 (q, J=7.0 Hz, 2H), 3.47 (br. s., 1H), 2.62-2.52 (m, 1H), 2.25-1.00 (m, 31H), 0.95 (s, 3H), 0.68 (s, 3H). LCMS $R_f$=1.342 min in 2 min chromatography, 10-80AB, MS ESI calcd. For $C_{27}H_{41}N_3O_4$[M+Na]⁺ 494, found 494.

Compound 210: ¹H NMR (CDCl₃, 400 MHz): δ8.17 (s, 1H), 5.32-5.12 (m, 2H), 4.44 (q, J=7.0 Hz, 2H), 2.69-2.60 (m, 1H), 2.29-1.02 (m, 33H), 0.96 (s, 3H), 0.66 (s, 3H). LCMS $R_f$=1.278 min in 2 min chromatography, MS ESI calcd. For $C_{27}H_{41}N_3O_4$ [M+H–H₂O]⁺454, found 454.

Example 126

Synthesis of 211

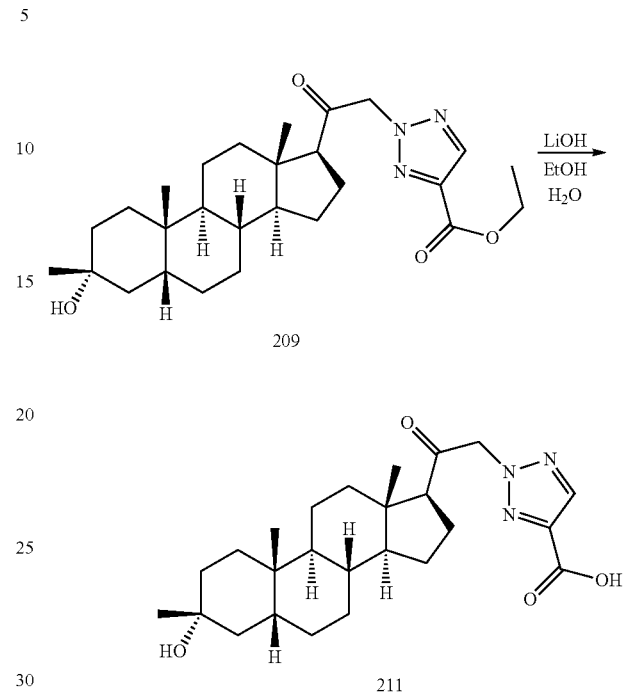

Compound 209 was prepared according to Example 127. To a solution of 209 (3.9 g, 8.26 mmol) in EtOH (50 mL) and H₂O (12 mL) was added LiOH (989 mg, 41.3 mmol) at 25° C. The reaction was stirred at 25° C. for 1 h, at which point LCMS showed that the reaction was complete. The reaction mixture was concentrated to provide a residue, which was then extracted with EtOAc (100 mL*2) and water (100 mL). The combined organic layers were dried over Na₂SO₄, filtered, and concentrated to give crude product that was washed with MeOH (100 mL) to afford 211 (2.9 g, 79.2%) as a white solid. ¹H NMR (400 MHz, CDCl3) δ 8.18 (s, 1H), 5.31 (s, 2H), 2.65-2.54 (m, 1H), 2.25-1.00 (m, 25H), 0.96 (s, 3H), 0.70 (s, 3H). LCMS $R_f$=0.874 min in 1.5 min chromatography, MS ESI calcd. For $C_{25}H_{37}N_3O_4$ [M+Na]⁺ 446, found 446.

Example 127

Synthesis of 212

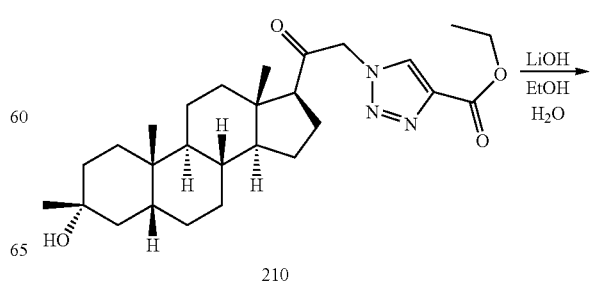

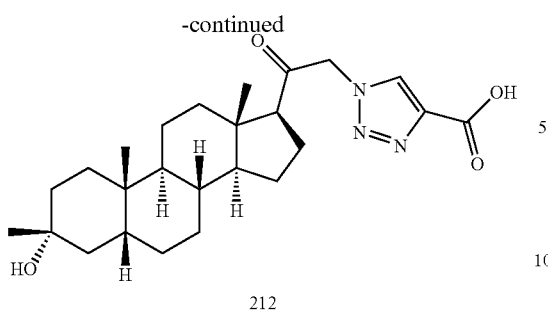

212

The title compound was prepared according to Example 126.

Compound 212: $^1$H NMR (DMSO-d$_6$, 400 MHz): δ8.58 (s, 1H), 5.60-5.53 (m, 1H), 5.41-5.34 (m, 1H), 4.27 (brs., 1H), 2.84-2.74 (m, 1H), 2.20-1.00 (m, 26H), 0.92 (s, 3H), 0.59 (s, 3H).

LCMS Rt=0.837 min in 1.5 min chromatography, MS ESI calcd. For $C_{25}H_{37}N_3O_4$ [M+H–H$_2$O]+425, found 425.

Example 128. Synthesis of 213

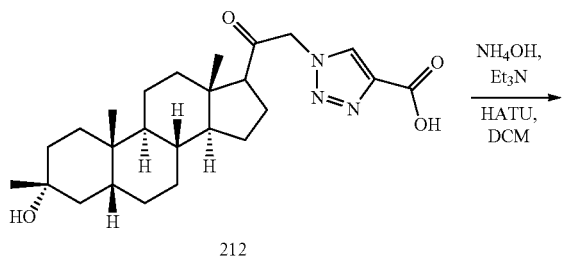

Compound 212 was prepared according to Example 127. To a solution of 212 (500 mg, 1.12 mmol) in DCM (5 mL) was added HATU (638 mg, 1.68 mmol) and Et$_3$N (226 mg, 2.24 mmol) at 25° C. After stirring at 25° C. for 1 h, ammonia hydrate (0.5 mL, 2.24 mmol) was added to the solution at 25° C. and the reaction was stirred at 25° C. for 2 h, at which point LCMS indicated that the reaction was complete. The reaction mixture was filtered and concentrated, and the residue was purified by HPLC to afford 213 (100 mg) as a white solid. $^1$H NMR (400 MHz, CDCl$_3$) δ 8.13 (s, 1h), 7.04 (br. s., 1H), 5.51 (br. s., 1H), 5.28-5.12 (m, 2H), 2.67-2.62 (m, 1H), 1.76-0.75 (m, 29H), 0.66 (s, 3H). LCMS Rt=0.827 min in 1.5 min chromatography MS ESI calcd. For $C_{25}H_{38}N_4O_3$ [M+Na]$^+$ 465, found 465.

Example 129

Synthesis of 214

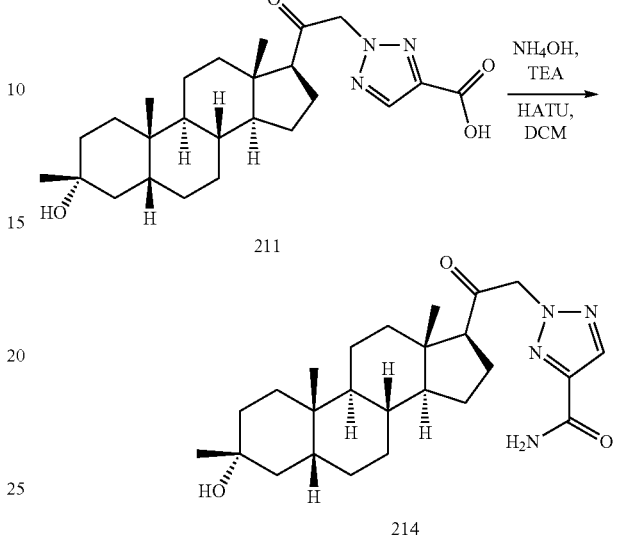

The title compound was prepared according to Example 128.

Compound 214: $^1$H NMR (CDCl$_3$, 400 MHz): δ8.13 (s, 1h), 6.58 (br. s., 1H), 5.51 (br. s., 1H), 5.31-5.17 (m, 2H), 2.64-2.56 (m, 1H), 2.30-1.03 (m, 26H), 0.96 (s, 3H), 0.70 (s, 3H). LCMS Rt=1.189 min in 2 min chromatography, MS ESI calcd. For $C_{25}H_{38}N_4O_3$ [M+Na]$^+$ 465, found 465.

Example 130

Synthesis of 215

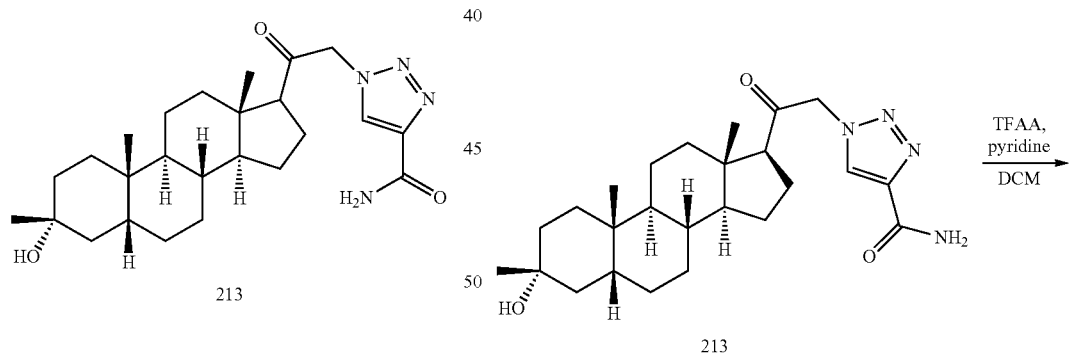

Compound 213 was prepared according to Example 128. To a solution of 213 (50 mg, 0.112 mmol) in DCM (5 mL)

was added pyridine (70.8 mg, 0.896 mmol) and trifluoroacetic anhydride (141 mg, 0.672 mmol) at 25° C. under N₂. The reaction was stirred at 25° C. for 16 h, at which point LCMS showed that the starting material was consumed. The mixture was concentrated and the residue purified by to give 215 (8 mg) as a white solid. ¹H NMR (400 MHz, CDCl₃) δ 8.12 (s, 1H), 5.35-5.13 (m, 2H), 2.71-2.67 (m, 1H), 2.32-1.06 (m, 26H), 0.97 (s, 3H), 0.65 (s, 3H).

LCMS R$_t$=1.073 min in 1.5 min chromatography MS ESI calcd. For C$_{25}$H$_{36}$N$_4$O$_2$ [M+H−H$_2$O]$^+$407, found 407.

Example 131

Synthesis of 216

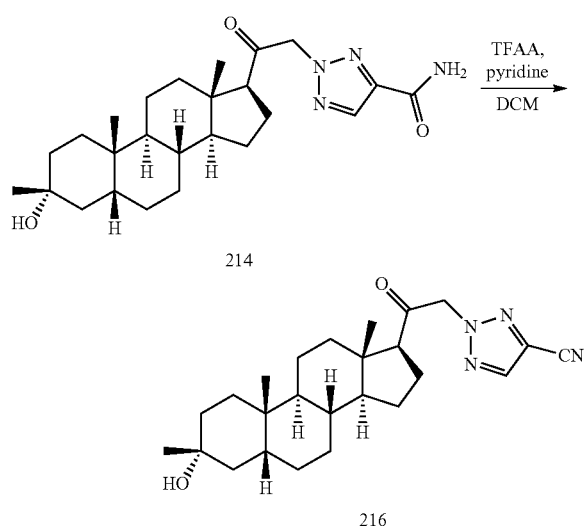

The title compound was prepared according to Example 130.

Compound 216: ¹H NMR (CDCl₃, 400 MHz): δ8.02 (s, 1H), 5.34-5.24 (m, 2H), 2.66-2.60 (m, 1H), 2.32-1.07 (m, 25H), 0.98 (s, 3H), 0.70 (s, 3H). LCMS R$_t$=1.532 min in 2 min chromatography, MS ESI calcd. For C$_{25}$H$_{36}$N$_4$O$_2$ [M+H−H$_2$O]$^+$ 407, found 407.

Example 132

Synthesis of 217 and 218

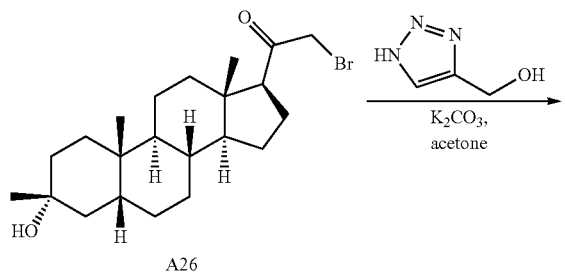

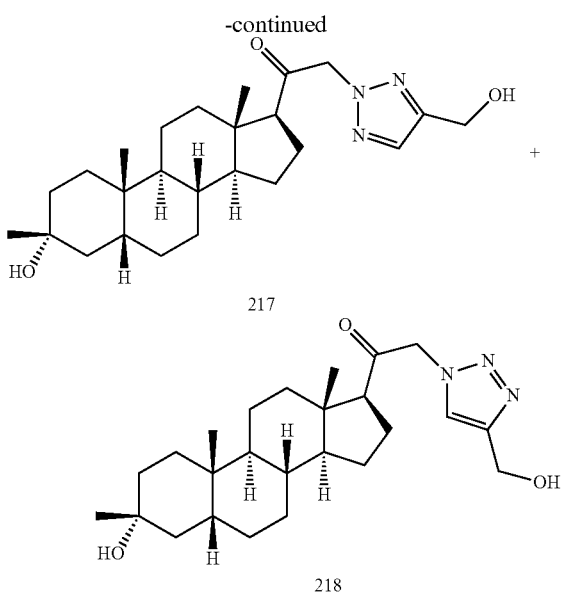

The title compounds were prepared according to Example 5, step 4.

Compound 217: ¹H NMR (CDCl₃, 400 MHz): δ7.66 (s, 1H), 5.23-5.14 (m, 2H), 4.80 (s, 2H), 2.62-2.53 (m, 1H), 2.26-1.01 (m, 27H), 0.96 (s, 3H), 0.69 (s, 3H). LCMS Rt=1.165 min in 2 min chromatography, MS ESI calcd. For C$_{25}$H$_{39}$N$_3$O$_3$ [M+Na]$^+$ 452, found 452.

Compound 218: ¹H NMR (CDCl₃, 400 MHz): δ7.62 (s, 1H), 5.30-5.05 (m, 2H), 4.84 (s, 2H), 2.64-2.62 (m, 1H), 2.33-1.00 (m, 27H), 0.95 (s, 3H), 0.65 (s, 3H). LCMS R$_t$=1.138 min in 2 min chromatography, MS ESI calcd. For C$_{25}$H$_{39}$N$_3$O$_3$ [M+H]$^+$ 430, found 430.

Example 133

Synthesis of 219 and 220

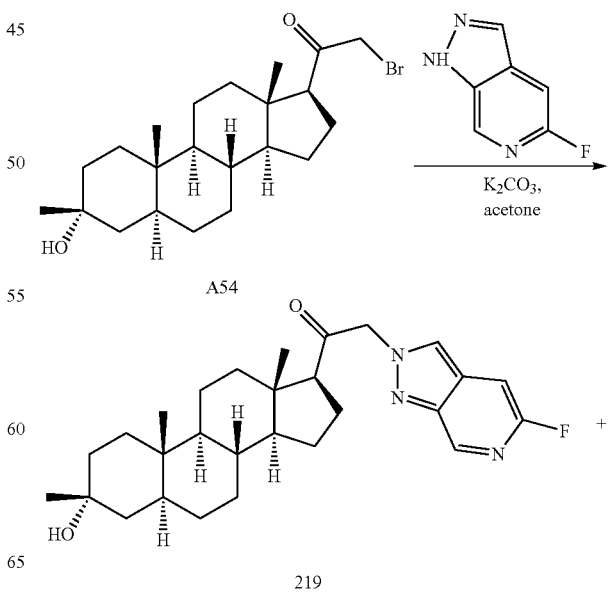

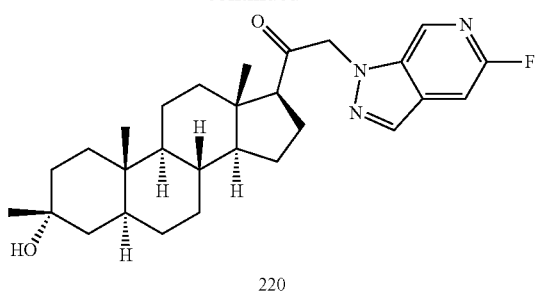

220

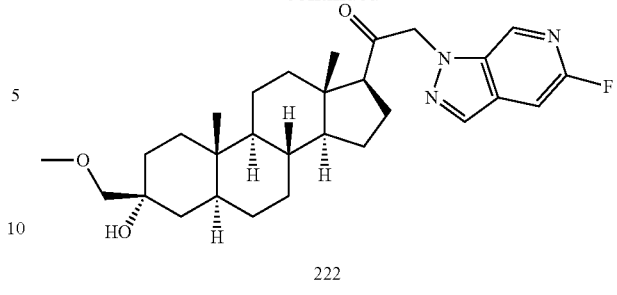

222

The title compounds were prepared according to Example 47, step 7.

Compound 219: $^1$H NMR (CDCl$_3$, 400 MHz): δ8.93 (s, 1H), 7.97 (s, 1H), 7.07 (s, 1H), 5.38-5.12 (m, 2H), 2.67 (t, J=8.8 Hz, 1H), 2.30-2.07 (m, 2H), 1.83-1.64 (m, 4H), 1.62-1.10 (m, 35H), 1.05-0.90 (m, 1H), 0.89-0.79 (m, 1H), 0.77 (s, 3H), 0.70 (s, 3H). LCMS R$_t$=2.135 min in 4 min chromatography, 30-90AB, MS ESI calcd. For C$_{28}$H$_{38}$FN$_3$O$_2$[M+H]$^+$ 468, found 468.

$^{19}$F NMR (CDCl$_3$, 400 MHz): δ −85.326.

Compound 220: $^1$H NMR (CDCl$_3$, 400 MHz): δ8.35 (s, 1H), 8.07 (s, 1H), 7.19 (s, 1H), 5.29-5.15 (m, 2H), 2.68 (t, J=8.8 Hz, 1H), 2.26-2.08 (m, 2H), 1.81-1.64 (m, 4H), 1.63-1.12 (m, 21H), 0.97 (dq, J=5.5, 12.0 Hz, 1H), 0.89-0.79 (m, 1H), 0.77 (s, 3H), 0.70 (s, 3H). LCMS R$_t$=2.631 min in 4 min chromatography, MS ESI calcd. For C$_{28}$H$_{38}$FN$_3$O$_2$ [M+H]$^+$ 468, found 468.

$^{19}$F NMR (CDCl$_3$, 400 MHz): δ −84.137.

The title compounds were prepared according to Example 67.

Compound 221: $^1$H NMR (CDCl$_3$, 400 MHz): δ8.95 (s, 1H), 7.99 (s, 1H), 7.11-7.07 (m, 1H), 5.38-5.19 (m, 2H), 3.41 (s, 3H), 3.21 (s, 2H), 2.70 (t, J=8.8 Hz, 1H), 2.30-2.11 (m, 2H), 2.08-2.01 (m, 1H), 1.85-1.68 (m, 4H), 1.56-1.14 (m, 14H), 1.08-0.84 (m, 2H), 0.79 (s, 3H), 0.73 (s, 3H). LCMS Rt=0.928 min in 1.5 min chromatography, MS ESI calcd. for C$_{29}$H$_{40}$FN$_3$O$_3$ [M+H]$^+$ 498, found 498.

Compound 222: $^1$H NMR (CDCl$_3$, 400 MHz): δ8.37 (s, 1H), 8.09 (s, 1H), 7.21 (d, J=1.0 Hz, 1H), 5.33-5.17 (m, 2H), 3.41 (s, 3H), 3.21 (s, 2H), 2.70 (t, J=8.9 Hz, 1H), 2.28-1.99 (m, 3H), 1.83-1.65 (m, 4H), 1.59-1.15 (m, 14H), 1.08-0.83 (m, 2H), 0.79 (s, 3H), 0.73 (s, 3H). LCMS Rt=0.950 min in 1.5 min chromatography, MS ESI calcd. for C$_{29}$H$_{40}$FN$_3$O$_3$ [M+H]$^+$ 498, found 498.

Example 135

Synthesis of 223

Example 134

Synthesis of 221 and 222

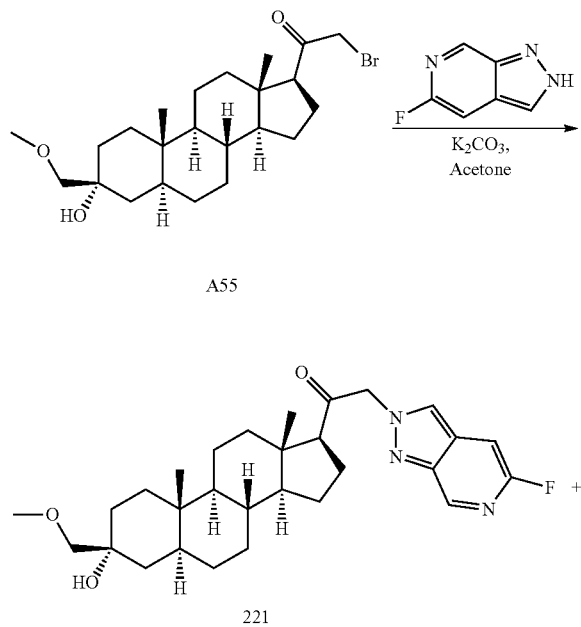

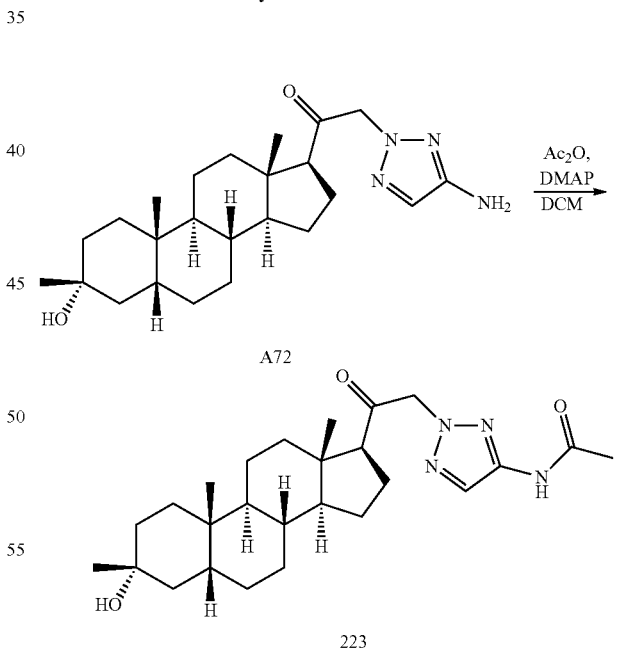

To a solution of A72 (20 mg, 0.048 mmol) in DCM (2 mL) was added 4-(dimethylamino)pyridine (6.47 mg, 0.053 mmol) and acetic anhydride (7.38 mg, 0.072 mmol) at 25° C. The reaction was stirred at 25° C. for 16 h, at which point LCMS indicated the reaction was complete. The reaction was quenched by water (5 mL) and extracted with DCM (10 mL×3), and the combined organic layers were dried over Na₂SO₄, filtered, concentrated and purified by HPLC to give 223 (3 mg) as a white solid. ¹H NMR (400 MHz, CDCl3) δ 8.07-s, 1H), 7.78 (br. s., 1H), 5.13-5.01 (m, 2H), 2.55-2.52 (m, 1H), 2.18 (s, 3H), 2.10-1.01 (m, 26H), 0.95 (s, 3H), 0.67 (s, 3H). LCMS Rt=1.209 min in 2 min chromatography, MS ESI calcd. For $C_{26}H_{40}N_4O_3$ [M+Na]$^+$ 479, found 479.

Example 134

Synthesis of 224

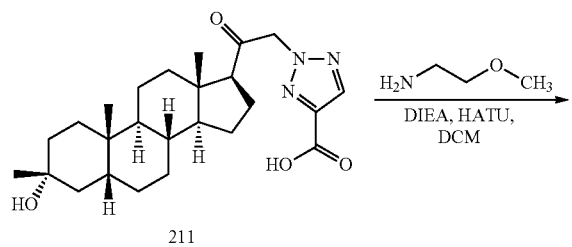

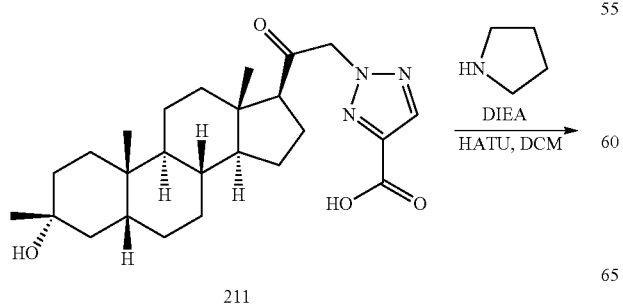

The title compound was prepared according to Example 128.

Compound 224: ¹H NMR (CDCl₃, 400 MHz): δ8.10 (s, 1H), 7.01 (br. s., 1H), 5.28-5.15 (m, 2H), 3.65-3.61 (m, 2H), 3.57-3.51 (m, 2H), 3.38 (s, 3H), 2.63-2.55 (m, 1H), 2.27-0.99 (m, 26H), 0.96 (s, 3H), 0.70 (s, 3H). LCMS Rt=0.891 min in 1.5 min chromatography, MS ESI calcd. For $C_{28}H_{44}N_4O_4$ [M+Na]+ 523. found 523.

Example 135

Synthesis of 225

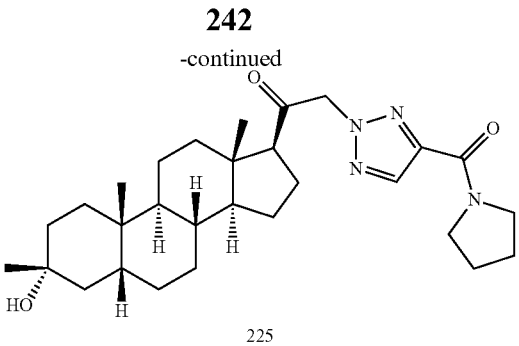

The title compound was prepared according to Example 128.

Compound 225: ¹H NMR (CDCl₃, 400 MHz): δ8.12 (s, 1H), 5.30-5.15 (m, 2H), 4.06-3.56 (m, 4H), 2.65-2.50 (m, 1H), 2.25-1.01 (m, 30H), 0.95 (s, 3H), 0.69 (s, 3H). LCMS R$_t$=1.263 min in 2 min chromatography, MS ESI calcd. For $C_{29}H_{44}N_4O_3$ [M+Na]$^+$ 519, found 519.

Example 136

Synthesis of 226 and 227

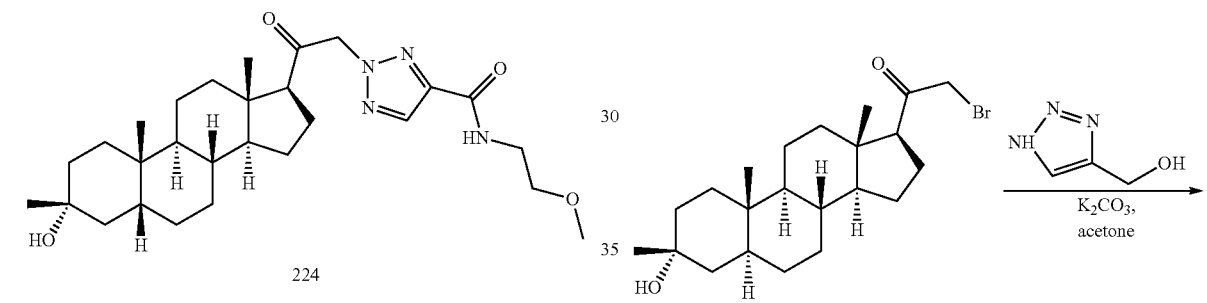

The title compounds were prepared according to Example 47, step 7.

Compound 226: ¹H NMR (CDCl₃, 400 MHz): δ7.64 (s, 1H), 5.25-5.11 (m, 2H), 4.76 (s, 2H), 2.58 (t, J=8.9 Hz, 1H), 2.24-2.13 (m, 1H), 2.10-2.00 (m, 1H), 1.79-1.10 (m, 23H), 1.05-0.90 (m, 1H), 0.85-0.78 (m, 1H), 0.75 (s, 3H), 0.68 (s, 3H). LCMS Rt=1.211 min in 2.0 min chromatography, MS ESI calcd. for C25H39N3O3 [M+H]+ 430, found 430.

Compound 227: ¹H NMR (CDCl₃, 400 MHz): δ7.63 (s, 1H), 5.31-5.04 (m, 2H), 4.84 (s, 2H), 2.70-2.55 (m, 1H), 2.25-2.15 (m, 1H), 2.10-2.00 (m, 1H), 1.88-1.13 (m, 30H), 1.04-0.90 (m, 1H), 0.89-0.78 (m, 1H), 0.76 (s, 3H), 0.66 (s, 3H). LCMS Rt=1.167 min in 2.0 min chromatography, MS ESI calcd. for C25H39N3O3 [M+H]+ 430, found 430.

Example 137

Synthesis of 228

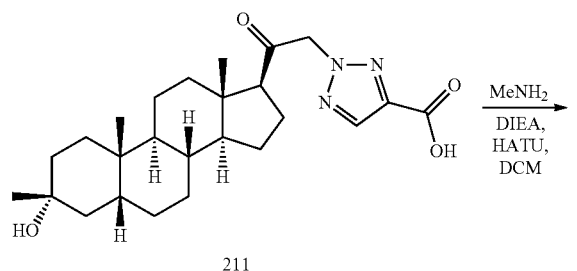

The title compound was prepared according to Example 128.

Compound 225: ¹H NMR (DMSO-d₆, 400 MHz): δ8.40-8.35 (m, 1H), 8.15 (s, 1H), 5.66-5.34 (m, 2H), 4.27 (s, 1H), 2.81-2.70 (m, 4H), 2.10-1.99 (m, 2H), 1.93-1.58 (m, 5H), 1.54-1.31 (m, 7H, 1.29-1.08 (m, 10H), 1.08-0.95 (m, 2H), 0.92 (s, 3H), 0.60 (s, 3H). LCMS Rt=0.922 min in 1.5 min chromatography, MS ESI calcd. for C26H40N4O3 [M+Na]+ 479, found 479.

Example 138

Synthesis of 229

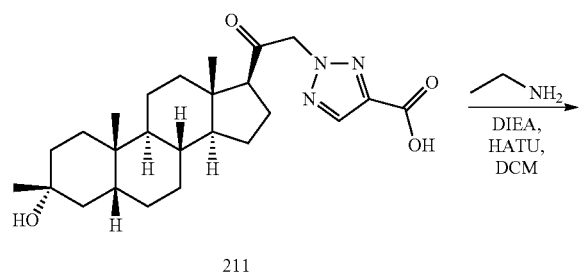

-continued

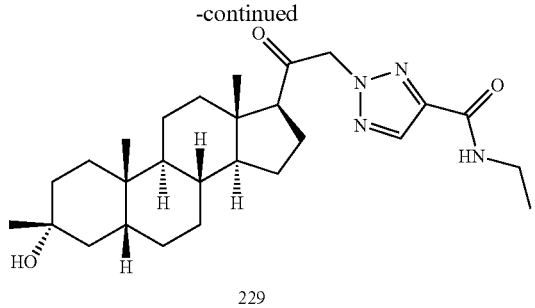

The title compound was prepared according to Example 128.

Compound 229: ¹H NMR (DMSO-d₆, 400 MHz): δ8.50-8.40 (m, 1H), 8.14 (s, 1H), 5.62-5.36 (m, 2H), 3.22-3.22 (m, 1H), 3.28-3.22 (m, 2H), 2.77-2.73 (m, 1H), 2.05-2.02 (m, 2H), 1.91-1.78 (m, 2H), 1.71-1.69 (m, 1H), 1.69-1.61 (m, 2H), 1.51-1.32 (m, 7H), 1.26-0.98 (m, 15H), 0.91 (s, 3H), 0.59 (s, 3H). LCMS Rt=1.123 min in 1.5 min chromatography, MS ESI calcd. for C27H42N4O3 [M+Na]+ 493, found 493.

Example 139

Synthesis of 230

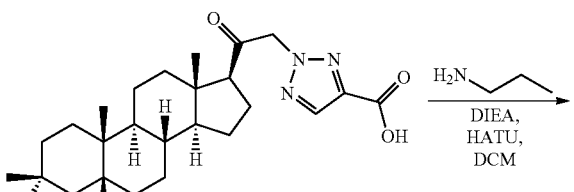

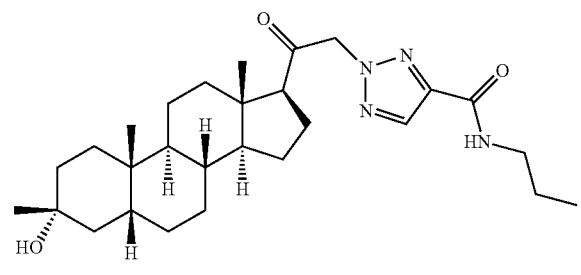

The title compound was prepared according to Example 128.

Compound 230: ¹H NMR (DMSO-d₆, 400 MHz): δ8.43 (t, J=5.8 Hz, 1H), 8.15 (s, 1H), 5.64-5.35 (m, 2H), 3.23-3.14 (m, 2H), 2.80-2.71 (m, 1H), 2.10-2.00 (m, 2H), 1.91-1.61 (m, 5H), 1.57-1.31 (m, 10H), 1.26-0.95 (m, 11H), 0.91 (s, 3H), 0.86 (t, J=7.4 Hz, 3H), 0.59 (s, 3H). LCMS Rt=1.186 min in 1.5 min chromatography, MS ESI calcd. for C28H44N4O3 [M+Na]+ 507, found 507.

Example 140

Synthesis of 231

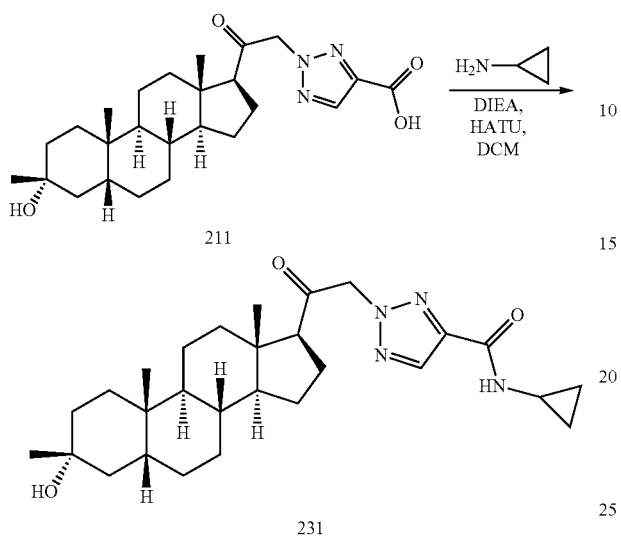

The title compound was prepared according to Example 128.

Compound 231: $^1$H NMR (DMSO-d$_6$, 400 MHz): δ8.51 (d, J=4.4 Hz, 1H), 8.15 (s, 1H), 5.59 (d, J=18.1 Hz, 1H), 5.38 (d, J=17.8 Hz, 1H), 4.28 (s, 1H), 2.82-2.80 (m, 1H), 2.75-2.72 (m, 1H), 2.10-0.95 (m, 26H), 0.91 (s, 3H), 0.75-0.47 (m, 6H). LCMS R$_t$=1.337 min in 2 min chromatography, MS ESI calcd. For C$_{28}$H$_{42}$N$_4$O$_3$ [M+Na]$^+$ 505, found 505.

Example 141

Synthesis of 232

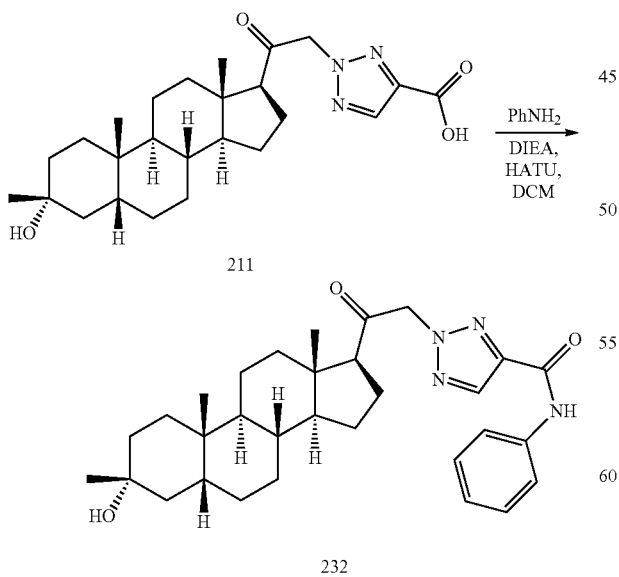

The title compound was prepared according to Example 128.

Compound 232: $^1$H NMR (DMSO-d$_6$, 400 MHz): δ10.38 (s, 1H), 8.35 (s, 1H), 7.78 (d, J=7.8 Hz, 2H), 7.36 (t, J=8.0 Hz, 2H), 7.15-7.09 (m, 1H), 5.68 (d, J=17.8 Hz, 1H), 5.47 (d, J=18.1 Hz, 1H), 4.28 (s, 1H), 2.82-2.75 (m, 1H), 2.12-1.11 (m, 25H), 0.92 (s, 3H), 0.62 (s, 3H).

LCMS R$_t$=1.474 min in 2 min chromatography, MS ESI calcd. For C$_{31}$H$_{42}$N$_4$O$_3$ [M+Na]$^+$ 541, found 541.

Example 142

Synthesis of 233 and 234

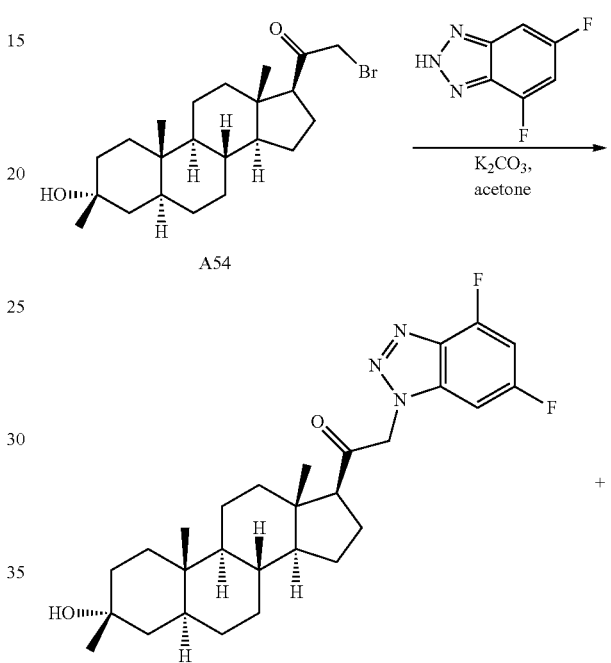

The title compounds were prepared according to Example 47, step 7.

Compound 233: $^1$H NMR (CDCl$_3$, 400 MHz): δ6.90-6.85 (m, 1H), 6.81 (t, J=6.8 Hz, 1H), 5.43-5.31 (m, 2H), 2.71 (t, J=8.8 Hz, 1H), 2.25-2.12 (m, 2H), 1.77-1.53 (m, 4H), 1.38-1.21 (m, 18H), 1.17-0.85 (m, 2H), 0.77 (s, 3H), 0.71 (s, 3H). LCMS Rt=0.974 min in 1.5 min chromatography, MS ESI calcd. for C$_{28}$H$_{37}$F$_2$N$_3$O$_2$[M+H]$^+$ 486, found 486.

Compound 234: ¹H NMR (CDCl₃, 400 MHz): δ7.30 (d, J=8 Hz, 1H), 6.93-6.89 (m, 1H), 5.56-5.46 (m, 2H), 2.66 (t, J=8.4 Hz, 1H), 2.59-2.12 (m, 2H), 1.74-1.53 (m, 4H), 1.47-1.24 (m, 18H), 1.21-0.84 (m, 2H), 0.77 (s, 3H), 0.74 (s, 3H). LCMS Rt=1.011 min in 1.5 min chromatography, MS ESI calcd. for C₂₈H₃₇F₂N₃O₂[M+H]⁺ 486, found 468.

Example 143

Synthesis of 235 and 236

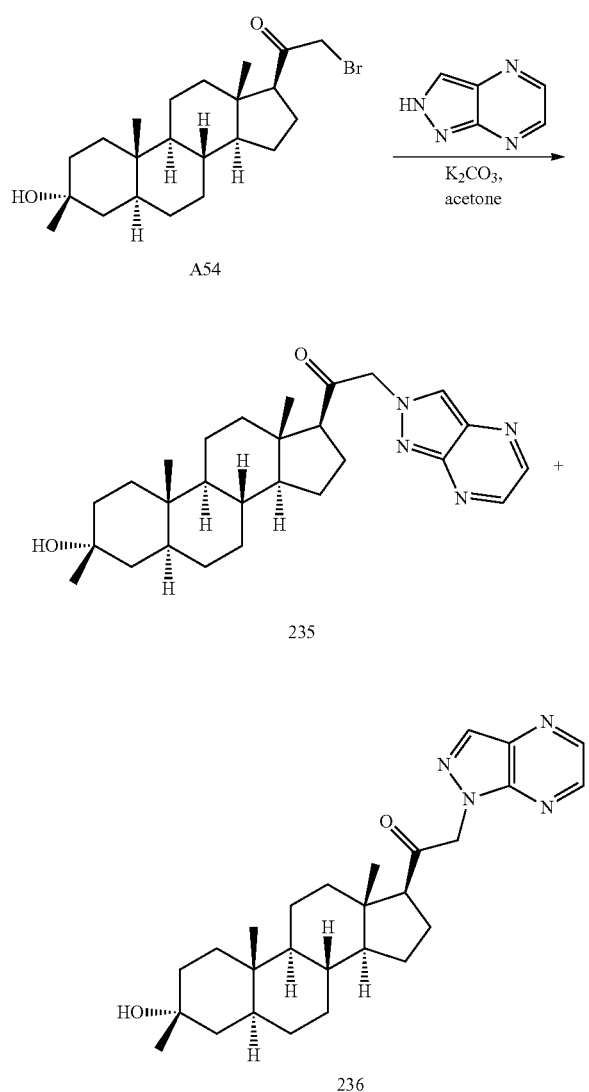

The title compounds were prepared according to Example 47, step 7.

Compound 236: ¹H NMR (CDCl₃, 400 MHz): δ8.58 (d, J=1.2 Hz, 1H), 8.43 (d, J=1.6 Hz, 1H), 8.33 (s, 1H) 5.37-5.24 (m, 2H), 2.70 (t, J=8 Hz, 1H), 2.24-2.11 (m, 2H), 1.72-1.55 (m, 7H), 1.50-1.20 (m, 16H), 0.99-0.83 (m, 3H), 0.77 (s, 3H), 0.71 (s, 3H). LCMS Rt=1.336 min in 2 min chromatography, MS ESI calcd. for C₂₇H₃₈N₄O₂ [M+H]⁺ 451, found 451.

Example 144

Synthesis of 237 and 238

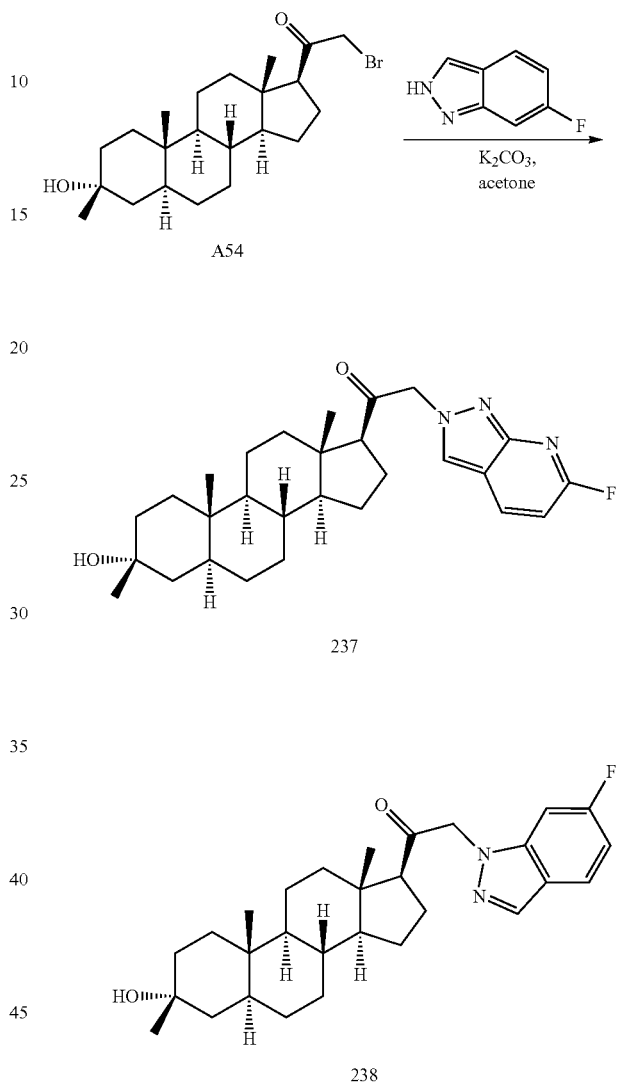

The title compounds were prepared according to Example 47, step 7.

Compound 237: ¹H NMR (CDCl₃, 400 MHz): δ7.93 (s, 1H), 7.65-7.61 (m, 1H), 7.28 (s, 1H), 6.91-6.87 (m, 1H), 5.22-5.10 (m, 2H), 2.64 (t, J=8.4 Hz, 1H), 2.12-2.02 (m, 2H), 1.73-1.54 (m, 7H), 1.37-1.20 (m, 16H), 0.81-0.78 (m, 3H), 0.76 (s, 3H), 0.69 (s, 3H). LCMS Rt=1.389 min in 2 min chromatography, MS ESI calcd. for C₂₉H₃₉FN₂O₂[M+H]⁺ 467, found 467.

Compound 238: ¹H NMR (CDCl₃, 400 MHz): δ8.00 (s, 1H), 7.69-7.66 (m, 1H), 6.95-6.91 (m, 1H), 6.84 (d, J=8.8 Hz, 1H), 5.13-5.03 (m, 2H), 2.64 (t, J=9.2 Hz, 1H), 2.12-2.09 (m, 2H), 1.71-1.52 (m, 8H), 1.37-1.22 (m, 16H), 1.20-0.82 (m, 3H), 0.76 (s, 3H), 0.70 (s, 3H).

LCMS Rt=1.436 min in 2 min chromatography, MS ESI calcd. for C₂₉H₃₉FN₂O₂[M+H]⁺ 467, found 467.

Example 145

Synthesis of 239 and 240

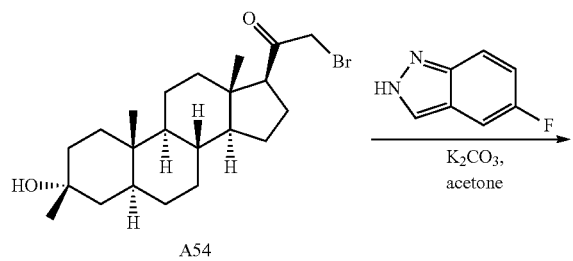

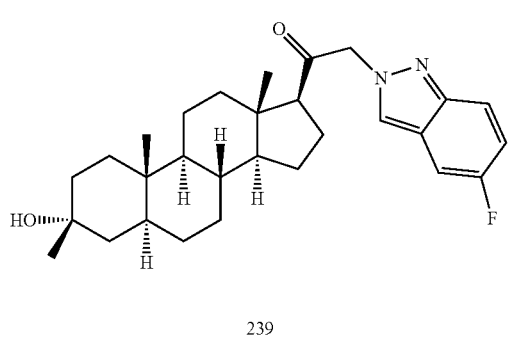

239

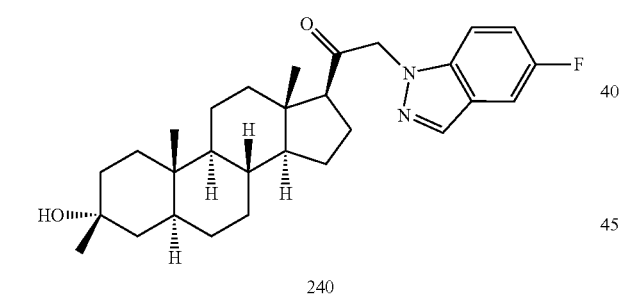

240

The title compounds were prepared according to Example 47, step 7.

Compound 239: $^1$H NMR (CDCl$_3$, 400 MHz): δ7.99 (s, 1H), 7.36 (d, J=8.4 Hz, 1H), 7.15 (d, J=6 Hz, 2H), 5.18-5.08 (m, 2H), 2.64 (d, J=8.8 Hz, 1H), 2.19-2.09 (m, 2H), 1.72-1.52 (m, 8H), 1.37-1.21 (m, 16H), 1.18-0.82 (m, 3H), 0.76 (s, 3H), 0.70 (s, 3H). LCMS Rt=0.963 min in 1.5 min chromatography, MS ESI calcd. for C$_{29}$H$_{39}$FN$_2$O$_2$[M+H]$^+$ 467, found 467.

Compound 240: $^1$H NMR (CDCl$_3$, 400 MHz): δ7.89 (s, 1H), 7.66 (t, J=8.4 Hz, 1H), 7.24 (t, J=2 Hz, 1H), 7.08 (d, J=2.4 Hz, 1H), 5.24-5.12 (m, 2H), 2.64 (t, J=8.4 Hz, 1H), 2.12-2.17 (m, 2H), 1.73-1.51 (m, 4H), 1.47-1.23 (m, 18H), 1.20-0.82 (m, 3H), 0.76 (s, 3H), 0.70 (s, 3H).

LCMS Rt=0.986 min in 1.5 min chromatography, MS ESI calcd. for C$_{29}$H$_{39}$FN$_2$O$_2$[M+H]$^+$ 467, found 467.

Example 147

Synthesis of 242

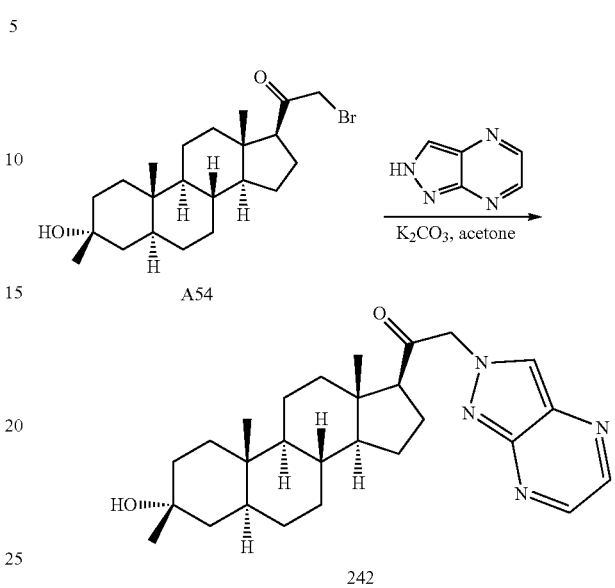

242

The title compounds were prepared according to Example 47, step 7.

Compound 242: $^1$H NMR (CDCl$_3$, 400 MHz): δ8.63 (s, 1H), 8.55 (s, 1H), 8.26 (s, 1H) 5.37-5.20 (m, 2H), 2.69 (t, J=8.4 Hz, 1H), 2.26-2.17 (m, 2H), 1.75-1.52 (m, 7H), 1.37-1.20 (m, 16H), 0.86-0.83 (m, 3H), 0.77 (s, 3H), 0.74 (s, 3H). LCMS Rt=1.257 min in 2 min chromatography, MS ESI calcd. for C$_{27}$H$_{38}$N$_4$O$_2$ [M+H]$^+$ 451, found 451.

Example 148

Synthesis of 244, 245, and 246

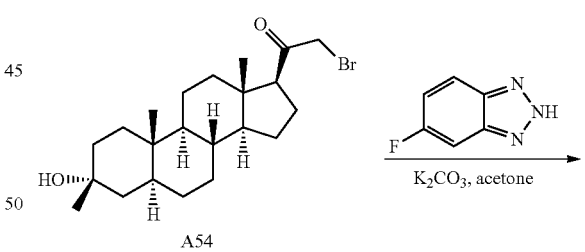

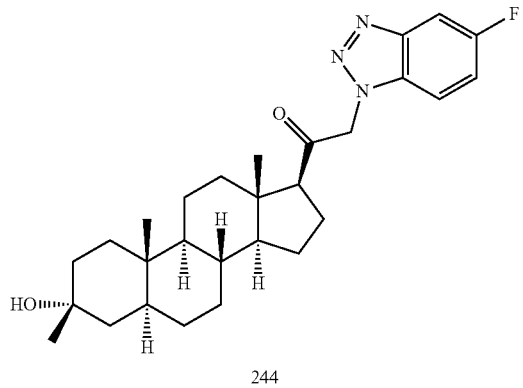

244

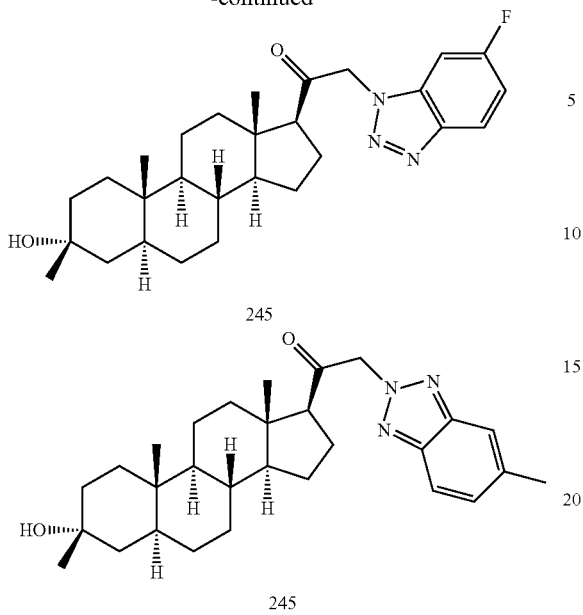

245

245

The title compounds were prepared according to Example 47, step 7.

Compound 244: $^1$H NMR (CDCl$_3$, 400 MHz): δ7.69 (d, J=7.6 Hz, 1H), 7.31-7.27 (m, 2H), 5.46-5.35 (m, 2H), 2.71 (t, J=8.8 Hz, 1H), 2.14-2.15 (m, 2H), 1.75-1.52 (m, 8H), 1.41-1.24 (m, 15H), 1.21-0.84 (m, 2H), 0.77 (s, 3H), 0.71 (s, 3H). LCMS Rt=1.373 min in 2 min chromatography, MS ESI calcd. for $C_{28}H_{38}FN_3O_2[M+H]^+$ 468, found 468.

Compound 245: $^1$H NMR (CDCl$_3$, 400 MHz): δ8.05-8.01 (m, 1H), 7.17-7.12 (m, 1H), 6.97 (t, J=8.8 Hz, 1H), 5.43-5.31 (m, 2H), 2.71 (t, J=8.8 Hz, 1H), 2.12-2.11 (m, 2H), 1.76-1.52 (m, 6H), 1.41-1.25 (m, 16H), 1.21-0.84 (m, 2H), 0.77 (s, 3H), 0.72 (s, 3H). LCMS Rt=1.392 min in 2 min chromatography, MS ESI calcd. for $C_{28}H_{38}FN_3O_2[M+H]^+$ 468, found 468.

Compound 246: $^1$H NMR (CDCl$_3$, 400 MHz): δ7.87-7.84 (m, 1H), 7.47-7.44 (m, 1H), 7.20 (t, J=2 Hz, 1H), 5.54-5.44 (m, 2H), 2.65 (t, J=8.8 Hz, 1H), 2.18-2.12 (m, 2H), 1.73-1.52 (m, 6H), 1.46-1.24 (m, 16H), 1.20-0.82 (m, 2H), 0.77 (s, 3H), 0.73 (s, 3H). LCMS Rt=0.999 min in 1.5 min chromatography, MS ESI calcd. for $C_{28}H_{38}FN_3O_2[M+H]^+$ 468, found 468.

Example 149

Synthesis of 247, 248, and 249

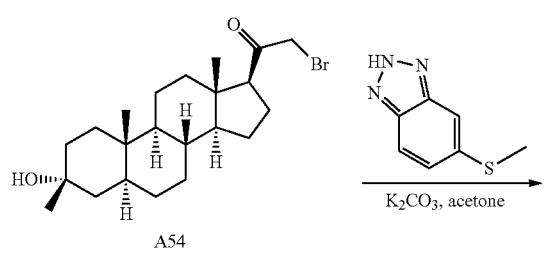

A54

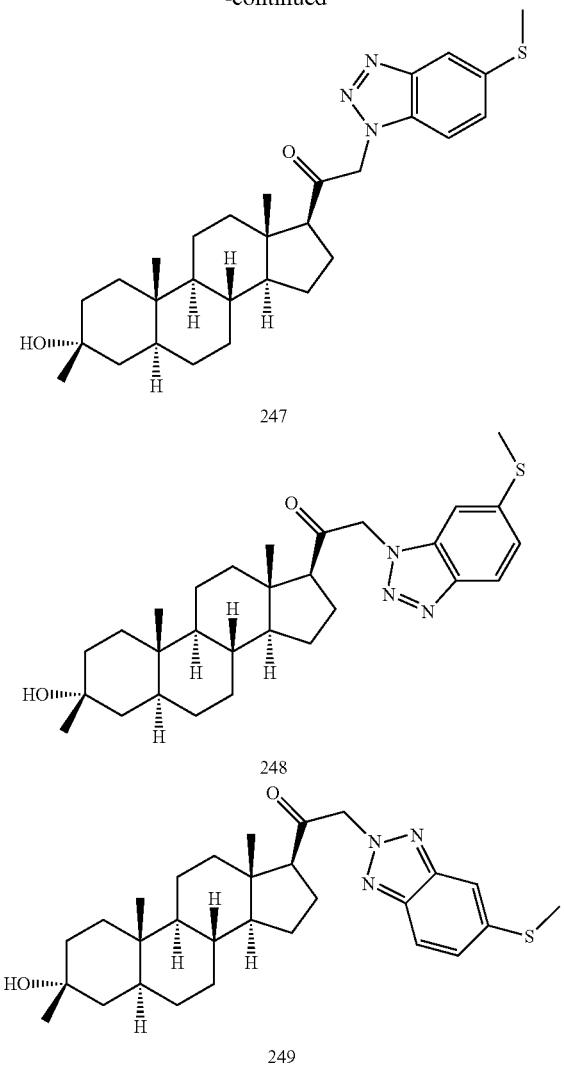

247

248

249

The title compounds were prepared according to Example 47, step 7.

Compound 247: $^1$H NMR (CDCl$_3$, 400 MHz): δ 7.88 (s, 1H), 7.40 (d, J=9.2 Hz, 1H), 7.23 (d, J=8.8 Hz, 1H), 5.43-5.30 (m, 2H), 2.69 (t, J=9.2 Hz, 1H), 2.21 (s, 3H), 2.19-2.15 (m, 2H), 1.74-1.51 (m, 5H), 1.41-1.21 (m, 17H), 0.85-0.83 (m, 4H), 0.77 (s, 3H), 0.71 (s, 3H). LCMS Rt=1.002 min in 1.5 min chromatography, MS ESI calcd. for $C_{29}H_{41}N_3O_2S$ $[M+H]^+$ 496, found 496.

Compound 248: $^1$H NMR (CDCl$_3$, 400 MHz): δ7.93 (t, J=8.4 Hz, 1H), 7.26 (d, J=3.6 Hz, 1H), 7.05 (m, 1H), 5.40-5.30 (m, 2H), 2.70 (t, J=8.4 Hz, 1H), 2.53 (s, 3H), 2.17-2.13 (m, 2H), 1.78-1.52 (m, 6H), 1.41-1.21 (m, 16H), 0.85-0.83 (m, 3H), 0.77 (s, 3H), 0.72 (s, 3H). LCMS Rt=0.970 min in 1.5 min chromatography, MS ESI calcd. for $C_{29}H_{41}N_3O_2S$ $[M+H]^+$ 496, found 496.

Compound 249: $^1$H NMR (CDCl$_3$, 400 MHz): δ7.74 (d, J=8.8 Hz, 1H), 7.55 (s, 1H), 7.28 (s, 1H), 5.51-5.41 (m, 2H), 2.63 (t, J=8.4 Hz, 1H), 2.55 (s, 3H), 2.52-2.11 (m, 2H), 1.74-1.51 (m, 5H), 1.40-1.23 (m, 17H), 1.20-0.81 (m, 3H), 0.76 (s, 3H), 0.73 (s, 3H). LCMS Rt=0.959 min in 1.5 min chromatography, MS ESI calcd. for $C_{29}H_{41}N_3O_2S$ $[M+H]^+$ 496, found 496.

Example 150

Synthesis of 250 and 251

Example 151

Synthesis of 252 and 253

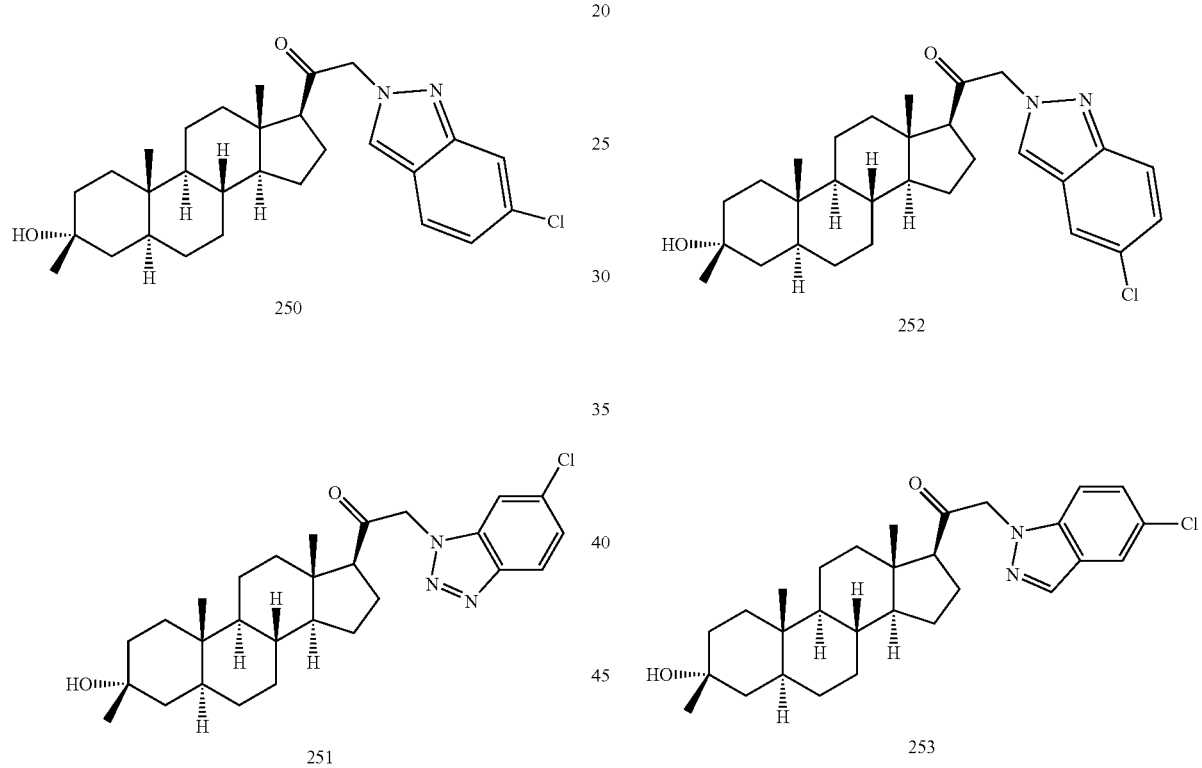

The title compounds were prepared according to Example 47, step 7.

Compound 250: $^1$H NMR (CDCl$_3$, 400 MHz): δ7.92 (s, 1H), 7.68 (s, 1H), 7.60 (d, J=8.84 Hz, 1H), 7.04-7.02 (m, 1H), 5.24-5.11 (m, 2H), 2.64 (t, J=8.8 Hz, 1H), 2.20-2.12 (m, 2H), 1.76-1.51 (m, 4H), 1.28-1.21 (m, 20H), 1.18-0.82 (m, 3H), 0.76 (s, 3H), 0.74 (s, 3H). LCMS Rt=0.993 min in 2 min chromatography, MS ESI calcd. for C$_{29}$H$_{39}$ClN$_2$O$_2$[M+H]$^+$ 483, found 483.

Compound 251: $^1$H NMR (CDCl$_3$, 400 MHz): δ8.00 (s, 1H), 7.65 (d, J=8.4 Hz, 1H), 7.20 (s, 1H), 7.13 (d, J=8.4 Hz, 1H), 5.15-5.04 (m, 2H), 2.64 (t, J=8.8 Hz, 1H), 2.20-2.11 (m, 2H), 1.72-1.53 (m, 4H), 1.38-1.21 (m, 22H), 1.18-0.83 (m, 3H), 0.77 (s, 3H), 0.71 (s, 3H)

LCMS Rt=1.019 min in 2 min chromatography, MS ESI calcd. for C$_{29}$H$_{39}$ClN$_2$O$_2$[M+H]$^+$ 483, found 483.

The title compounds were prepared according to Example 47, step 7.

Compound 252: $^1$H NMR (CDCl$_3$, 400 MHz): δ7.88 (s, 1H), 7.62 (d, J=9.6 Hz, 2H), 7.22-7.19 (m, 1H), 5.30-5.12 (m, 2H), 2.64 (d, J=8 Hz, 1H), 2.20-2.09 (m, 2H), 1.73-1.51 (m, 4H), 1.37-1.21 (m, 19H), 1.18-0.98 (m, 3H), 0.76 (s, 3H), 0.70 (s, 3H). LCMS Rt=1.016 min in 1.5 min chromatography, MS ESI calcd. for C$_{29}$H$_{39}$ClN$_2$O$_2$[M+H]$^+$ 483, found 483.

Compound 253: $^1$H NMR (CDCl$_3$, 400 MHz): δ7.98 (s, 1H), 7.71 (s, 1H), 7.33-7.31 (m, 1H), 7.13 (d, J=9.2 Hz, 1H), 5.17-5.07 (m, 2H), 2.64 (d, J=8.8 Hz, 1H), 2.19-2.09 (m, 2H), 1.72-1.55 (m, 4H), 1.37-1.21 (m, 21H), 1.18-0.82 (m, 3H), 0.76 (s, 3H), 0.70 (s, 3H). LCMS Rt=1.013 min in 1.5 min chromatography, MS ESI calcd. for C$_{29}$H$_{39}$ClN$_2$O$_2$[M+H]$^+$ 483, found 483.

Example 152

Synthesis of 254

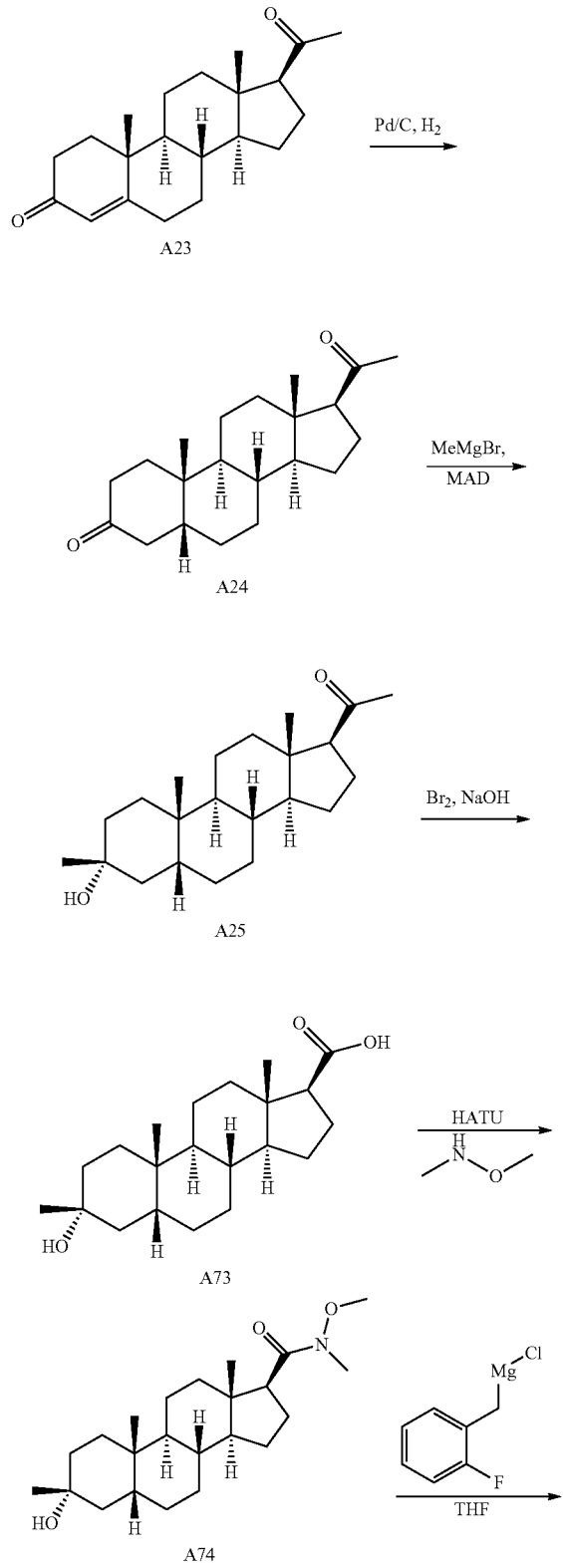

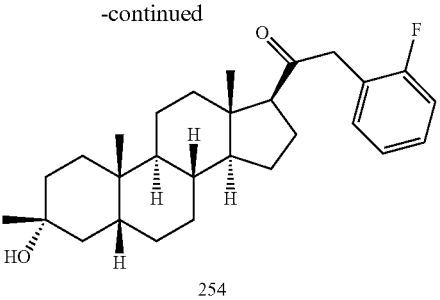

254

Synthesis of A24. A mixture of A23 (40 g, 127 mmol) and Pd/C (4 g) in ethyl acetate (200 mL) and THF (200 mL) was stirred at 25° C. under H (15 psi) for 4 hours, at which point TLC analysis (PE:EA=5:1) showed the starting material was consumed completely. The reaction mixture was filtered, and the filtered cake was washed with ethyl acetate (40 mL×5). The combined organic phase was concentrated under vacuum to give A24 (41 g, crude) as a white solid. $^1$H NMR (CDCl$_3$, 400 MHz): δ2.69 (t, J=14.1 Hz, 1H), 2.61-2.48 (m, 1H), 2.43-2.25 (m, 1H), 2.24-1.96 (m, 8H), 1.95-1.78 (m, 2H), 1.75-1.07 (m, 15H), 1.03 (s, 3H), 0.64 (s, 3H).

Synthesis of A25. To a solution of 2,6-di-tert-butyl-4-methylphenol (170 g, 774 mmol) in toluene (150 mL) was added trimethylaluminum (193 mL, 387 mmol, 2.0 M in toluene) dropwise at 25° C. under N$_2$ atmosphere. The resulting mixture was stirred at 25° C. for 1 hour, after A24 (41 g, 129 mmol) in toluene (50 mL) was added at −78° C. and stirred for one hour. Methylmagnesium bromide (129 mL, 387 mmol, 3.0 M in diethyl ether) was then added, and the reaction mixture was stirred at −78° C. for 4 hours, at which point TLC analysis (PE:EA=2:1) showed the starting material was consumed completely. The mixture was quenched by saturated aqueous NH$_4$Cl (20 mL), extracted with ethyl acetate (150 mL*2), and the combined organic phase was washed with brine (150 mL), dried over anhydrous Na$_2$SO$_4$, concentrated, and purified by chromatography on silica gel (PE/EtOAc=7/1) to afford desired product A25 (36 g, impure) as a light yellow solid. $^1$H NMR (CDCl$_3$, 400 MHz): δ 2.58-2.46 (m, 1H), 2.22-2.09 (m, 4H), 2.06-1.79 (m, 3H), 1.78-0.99 (m, 25H), 0.94 (s, 3H), 0.59 (s, 3H).

Synthesis of A73. Liquid bromine (5.76 g, 36.0 mmol) was added slowly to a vigorously stirred sodium hydroxide aqueous (48.0 mL, 3 M, 144 mmol) at 0° C. When all the bromine was dissolved, the mixture was diluted with cold dioxane (10 mL) and was added slowly to a stirred solution of A25 (4 g, 12.0 mmol) in dioxane (15 mL) and water (10 mL). The homogeneous yellow solution became colorless slowly and a white precipitate was formed, and the reaction mixture was stirred at 25° C. for 16 hours. The remaining oxidizing reagent was quenched by Na$_2$S$_2$O$_3$ aqueous (30 mL) and the mixture was then heated at 80° C. until the solid material was dissolved. Acidification of the solution with hydrochloride acid (3 N) furnished a white precipitate. The solid was filtered and washed with water (100 mL×3) to give a white solid, which was dried under vacuum to afford A73 (4.01 g, 100%) as a white solid. $^1$H NmR (CDCl$_3$, 400 MHz): δ 11.90 (br. s., 1H), 4.24 (s, 1H), 2.28 (t, J=9.0 Hz, 1H), 2.01-1.54 (m, 8H), 1.50-1.28 (m, 6H), 1.26-0.92 (m, 13H), 0.91 (s, 3H), 0.61 (s, 3H).

Synthesis of A74. To a suspension of A73 (4.01 g, 11.9 mmol) and N,O-dimethylhydroxylamine hydrochloride (4.64 g, 47.6 mmol) in DMF (40 mL) was added HATU (9.04 g, 23.8 mmol) at 25° C. DIPEA (15.3 g, 119 mmol) was added to the resulting mixture. The reaction mixture was stirred at 25° C. for 2 hours, at which point TLC analysis (PE:EA=2:1) showed the starting material was consumed completely. The reaction mixture was diluted with H$_2$O (500 mL) and a precipitate in the mixture was formed and subsequently filtered, washed with water (40 mL×3), and dried under vacuum to afford A74 (4.31 g, 95.9%) as a light yellow solid. $^1$H NmR (CDCl$_3$, 400 MHz): δ 11.90 (br. s., 1H), 4.24 (s, 1H), 2.28 (t, J=9.0 Hz, 1H), 2.01-1.54 (m, 8H), 1.50-1.28 (m, 6H), 1.26-0.92 (m, 13H), 0.91 (s, 3H), 0.61 (s, 3H).

Synthesis of 254. To a solution of A74 (100 mg, 264 μmol) in anhydrous THF (2 mL) was added (2-fluorobenzyl) magnesium chloride (5.26 mL, 0.5 M, 2.63 mmol) at 25° C., and the reaction mixture was stirred at 25° C. for 2 hours at which point LCMS showed the starting material was consumed completely. The reaction was quenched with saturated NH$_4$Cl aqueous (1 mL) and concentrated under vacuum to give a residue, which was purified by prep-HPLC (0.05% HCl-ACN) to afford 254 (22.5 mg, 20.0%) as a white solid. $^1$H NMR (CDCl$_3$, 400 MHz): δ 3.80-3.60 (m, 4H), 3.28-3.17 (m, 1H), 2.81-2.48 (m, 4H), 2.18-1.83 (m, 2H), 1.79-1.13 (m, 22H), 1.11-0.77 (m, 7H), 0.75-0.58 (m, 3H). LCMS R$_t$=1.383 min in 2 min chromatography, MS ESI calcd, for C$_{28}$H$_{39}$FO$_2$ [M+H]$^+$ 427, found 409.3 ([M−H$_2$O+H]$^+$).

Example 153

Synthesis of 255

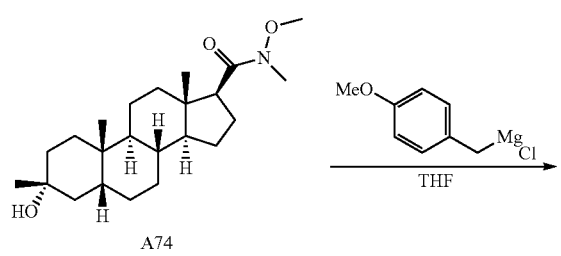

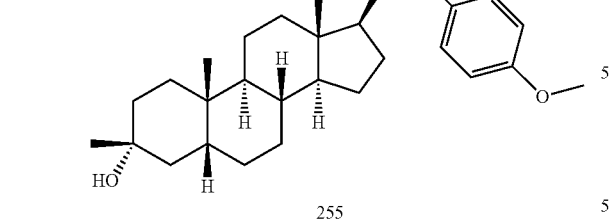

The title compound was prepared according to Example 152, step 4.

Compound 255: $^1$H NMR (CDCl$_3$, 400 MHz): δ 7.11 (d, J=8.3 Hz, 2H), 6.88 (d, J=8.5 Hz, 2H), 3.82 (s, 3H), 3.69-3.56 (m, 2H), 2.66 (t, J=8.8 Hz, 1H), 2.22-1.72 (m, 5H), 1.65 (d, J=7.8 Hz, 3H), 1.59-1.58 (m, 1H), 1.53-1.40 (m, 8H), 1.35-1.04 (m, 11H), 0.97 (s, 3H), 0.65 (s, 3H).

LCMS Rt=1.224 min in 2 min chromatography, MS ESI calcd, for C$_{29}$H$_{42}$O$_3$[M−18+H]$^+$ 421, found 421.

Example 154

Synthesis of 256

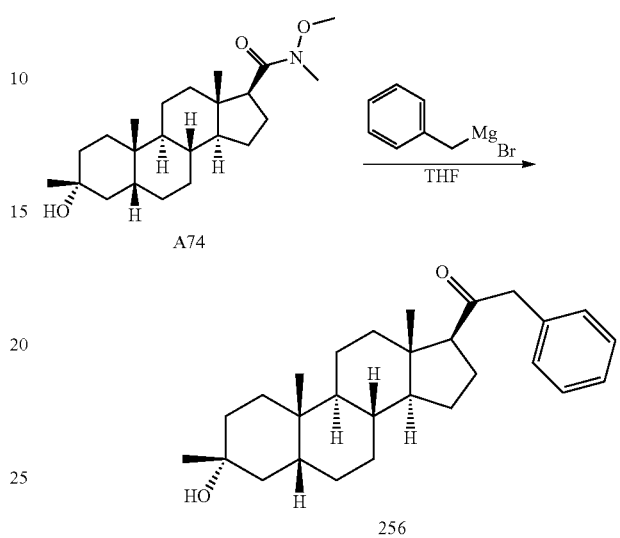

The title compound was prepared according to Example 152, step 4.

Compound 256: $^1$H NMR (CDCl$_3$, 400 MHz): δ 7.38-7.31 (m, 2H), 7.28-7.24 (m, 1H), 7.22-7.16 (m, 2H), 3.76-3.63 (m, 2H), 2.67 (t, J=8.9 Hz, 1H), 2.25-2.02 (m, 2H), 1.97 (t, J=13.2 Hz, 1H), 1.92-1.72 (m, 2H), 1.71-1.58 (m, 3H), 1.55-1.39 (m, 9H), 1.36-1.26 (m, 5H), 1.25-1.18 (m, 3H), 1.16-1.02 (m, 2H), 0.97 (s, 3H), 0.67 (s, 3H). LCMS Rt=1.240 min in 2 min chromatography, MS ESI calcd, for C$_{28}$H$_{40}$O$_2$[M−18+H]$^+$ 391, found 391.

Example 156

Synthesis of 258

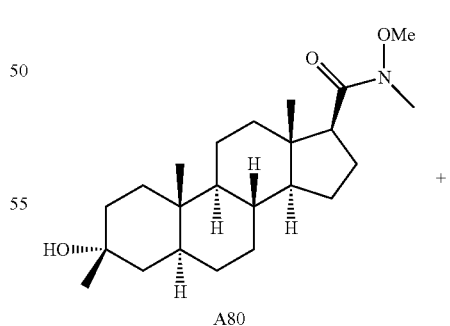

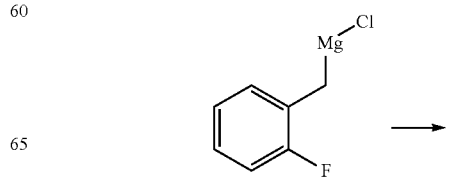

259

-continued

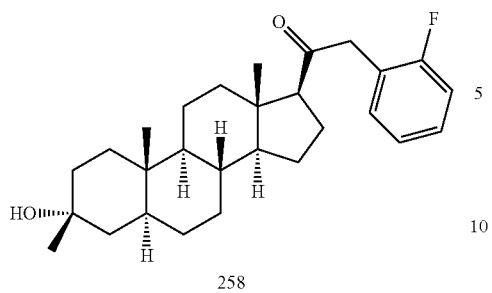
258

The title compound was prepared according to Example 155, step 8.

Compound 258: $^1$H NMR (CDCl$_3$, 400 MHz): δ 7.25-7.00 (m, 4H), 3.78-3.64 (m, 2H), 2.71-2.60 (m, 1H), 2.24-2.05 (m, 2H), 1.74-1.11 (m, 22H), 1.01-0.89 (m, 1H), 0.76 (s, 4H), 0.66 (s, 3H). LCMS 1.484 min in 2 min chromatography, MS ESI calcd. for C$_{28}$F$_{40}$FO$_2$ [M+H]$^+$ 427, found 409[M−18]$^+$.

Example 157

Synthesis of 259

A26

259

The title compound was prepared according to Example 5, step 4.

Compound 259: $^1$H NMR (CDCl$_3$, 400 MHz): δ7.01 (s, 1H), 6.38 (dd, J=8.2, 1.5 Hz, 1H), 4.55-4.66 (m, 2H), 2.57 (t, J=8.8 Hz, 1H), 2.14-2.26 (m, 1H), 1.85-2.00 (m, 3H), 1.75 (t, J=7.4 Hz, 3H), 1.41-1.55 (m, 9H), 1.22-1.29 (m, 8H), 1.03-1.19 (m, 2H), 0.96 (s, 3H), 0.65 (s, 3H). LCMS Rt=2.747 min in 4.0 min chromatography, MS ESI calcd. for C25H37FN2O2 [M+H]+ 417.28, found 417.0 ([M+H]+.

260

Example 158

Synthesis of 260

211

260

To a solution of compound 211 (50 mg, 112 μmol) in DCM (2 mL) was added DIEA (36.1 mg, 280 μmol) and HATU (85.1 mg, 224 μmol) at 25° C. The mixture was stirred at 25° C. for 30 minutes. N-methylpropan-1-amine (16.3 mg, 224 μmol) was added. The mixture was stirred at 25° C. for 30 minutes. LCMS showed the reaction was completed. The mixture was poured into water (10 mL) and extracted with EtOAc (20 mL×2). The combined organic layer was washed with brine (10 mL), dried over Na$_2$SO$_4$, filtered and concentrated under reduced pressure to give the crude product, which was purified by HPLC separation (column: Phenomenex Synergi C18 250*21.2 mm*4 um, gradient: 50-80% condition: (0.05% HCl-ACN), flow rate: 25 mL/min) to give 260 (16 mg) as a white solid.

$^1$H NMR (260): (400 MHz, CDCl$_3$) δ 8.04-8.03 (m, 1H), 5.27-5.17 (m, 2H), 3.65-3.48 (m, 2H), 3.29-3.09 (m, 3H), 2.59-2.57 (m, 1H), 2.21-2.20 (m, 1H), 2.06-2.05 (m, 3H), 1.95-1.67 (m, 2H), 1.66-1.60 (m, 5H), 1.57-1.45 (m, 8H), 1.42-1.27 (m, 9H), 1.23-1.05 (m, 2H), 0.96-0.87 (m, 4H), 0.85-0.83 (m, 2H), 0.69 (s, 3H). LCMS tR=1.238 min in 2 min chromatography, 30-90 AB, MS ESI calcd. for C$_{29}$H$_{46}$N$_4$O$_3$ [M+Na]$^+$ 521, found 521.

Example 159

Synthesis of 261

211

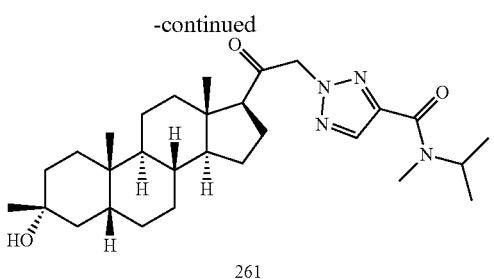

261

To a solution of compound 211 (50 mg, 112 µmol) in DCM (2 mL) was added DIEA (36.1 mg, 280 µmol) and HATU (85.1 mg, 224 µmol) at 25° C. The mixture was stirred at 25° C. for 30 minutes. N-methylpropan-2-amine (16.3 mg, 224 µmol) was added in the mixture at 25° C. The mixture was stirred at 25° C. for 30 minutes. LCMS showed the reaction was completed. The mixture was poured into water (10 mL) and extracted with EtOAc (20 mL×2). The combined organic layer was washed with brine (10 mL), dried over $Na_2SO_4$, filtered and concentrated under reduced pressure to give the crude product, which was purified by HPLC separation (column: Phenomenex Synergi C18 250*21.2 mm*4 um, gradient: 50-80% condition: (0.05% HCl-ACN), flow rate: 25 mL/min) to give 261 (16.4 mg) as a white solid.

$^1$H NMR (261): (400 MHz, CDCl3) δ 8.03-7.98 (m, 1H), 5.27-5.21 (m, 2H), 4.98-4.68 (m, 1H), 3.11-2.95 (m, 3H), 2.61-2.59 (m, 1H), 2.19-2.15 (m, 1H), 2.07-2.05 (m, 1H), 1.96-1.76 (m, 2H), 1.73-1.70 (m, 3H), 1.52-1.47 (m, 9H), 1.43-1.07 (m, 16H), 0.96 (s, 3H), 0.69 (s, 3H). LCMS Rt=1.213 min in 2 min chromatography, 30-90 AB, MS ESI calcd. for $C_{29}H_{46}N_4O_3$ [M+Na]$^+$ 521, found 521.

Example 160

Synthesis of 262

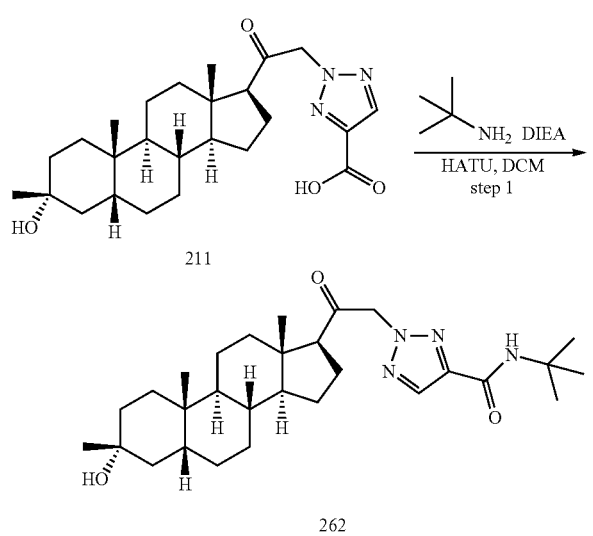

To a solution of compound 211 (50 mg, 0.112 mmol) in DCM (2 mL) was added HATU (85.1 mg, 0.224 mmol) and triethylamine (22.6 mg, 0.224 mmol) at 25° C. The reaction was stirred at 25° C. for 1 h. 2-methylpropan-2-amine (16.3 mg, 0.224 mmol) was added. The reaction was stirred at 25° C. for 16 h. LCMS showed that desired MS was found. The reaction mixture was filtered and the filtrate was concentrated in vacuum to give crude product, which was purified by prep. HPLC (column: Phenomenex Synergi C18 150*25*10 um, gradient: 52-77% B (A=0.05% HCl-ACN, B=acetonitrile), flow rate: 30 mL/min) to give 262 (14 mg, 25%) as white solid.

$^1$H NMR (262): (400 MHz, DMSO-d$_6$) δ 8.15 (s, 1H), 7.51 (s, 1H), 5.63-5.36 (m, 2H), 4.26 (s, 1H), 2.78-2.73 (m, 1H), 2.14-1.00 (m, 34H), 0.92 (s, 3H), 0.60 (m, 3H). LCMS $t_R$=1.472 min in 2 min chromatography, 10-80AB, MS ESI calcd. For $C_{29}H_{46}N_4O_3$ [M–H$_2$O+H]$^+$ 481, found 481.

Example 161

Synthesis of 263

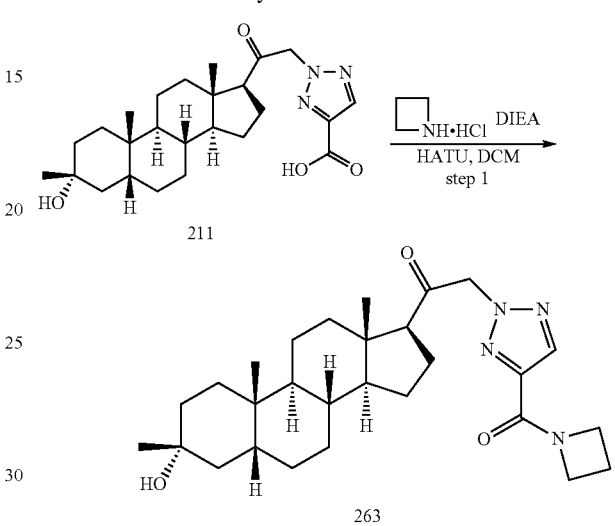

To a solution of compound 211 (50 mg, 0.112 mmol) in DCM (2 mL) was added diisopropylethylamine (43.4 mg, 0.336 mmol) and HATU (85.1 mg, 0.224 mmol). The mixture was stirred at 25° C. for 1 h. Azetidine hydrochloride (26.1 mg, 0.28 mmol) was added and stirred for 16 h. LCMS showed that desired MS was observed. The reaction mixture was filtered and the filtrate was concentrated in vacuum to give crude product, which was purified by prep. HPLC (column: Phenomenex Synergi C18 150*30 mm*4 um, gradient: 0-68% B (A=water (0.05% HCl)-ACN, B=acetonitrile), flow rate: 30 mL/min) to give the product (4 mg) as a white solid.

$^1$H NMR (263): (400 MHz, CDCl$_3$) δ 8.09 (s, 1H), 5.26-5.15 (m, 2H), 4.55-4.50 (m, 2H), 4.23-4.19 (m, 2H), 2.57-2.37 (m, 1H), 2.36-1.06 (m, 28H), 0.95 (s, 3H), 0.68 (m, 3H). LCMS $t_R$=1.333 min in 2 min chromatography, 10-80AB, MS ESI calcd. For $C_{28}H_{42}N_4O_3$ [M–H$_2$O+H]$^+$ 453, found 453.

Assay Methods

Compounds provided herein can be evaluated using various assays; examples of which are described below.

Steroid Inhibition of TBPS Binding

TBPS binding assays using rat brain cortical membranes in the presence of 5 µM GABA has been described (Gee et al, *J. Pharmacol. Exp. Ther.* 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-c eflon32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 µL) of the membrane suspensions are incubated with 3 nM [$^{35}$S]-TBPS and 5 µL aliquots of test drug dissolved in dimethyl sulfoxide (DMSO) (final 0.5%) in the presence of 5 µM GABA. The incubation is brought to a final volume of 1.0 mL with buffer. Nonspecific binding is determined in the presence of 2 µM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (I$_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures.

For Table 1, "A" indicates an IC$_{50}$<10 nM, "B" indicates an IC$_{50}$ of 10 nM to 50 nM, "C" indicates an IC$_{50}$>50 nM to 100 nM, "D" indicates an IC$_{50}$>100 nM to 500 nM, and "E" indicates IC$_{50}$>500 nM.

TABLE 1

| Compound | 35S-TBPS Radioligand Displacement (IC50) |
|---|---|
| 1 | D |
| 2 | B |
| 3 | D |
| 4 | C |
| 5 | D |
| 6 | D |
| 7 | E |
| 8 | E |
| 9 | E |
| 10 | A |
| 11 | A |
| 12 | A |
| 13 | B |
| 14 | A |
| 15 | A |
| 16 | A |
| 17 | B |
| 18 | A |
| 19 | A |
| 21 | A |
| 22 | A |
| 23 | A |
| 24 | A |
| 26 | A |
| 27 | B |
| 28 | A |
| 29 | A |
| 30 | B |
| 31 | B |
| 32 | A |
| 33 | B |
| 34 | B |
| 35 | A |
| 36 | A |
| 37 | B |
| 38 | B |
| 39 | B |
| 40 | A |
| 42 | B |
| 43 | D |
| 44 | B |
| 45 | A |
| 46 | B |
| 47 | B |
| 48 | B |
| 49 | B |
| 50 | A |
| 51 | B |
| 52 | B |
| 53 | A |
| 54 | A |
| 55 | B |
| 56 | C |
| 57 | D |
| 58 | E |
| 59 | D |
| 60 | B |
| 61 | D |
| 62 | D |
| 63 | B |
| 64 | C |
| 65 | B |
| 66 | B |
| 67 | B |
| 68 | B |
| 69 | B |
| 70 | B |
| 71 | B |
| 72 | B |
| 73 | B |
| 74 | A |
| 75 | B |
| 76 | B |
| 77 | B |
| 78 | A |
| 80 | D |
| 81 | B |
| 86 | A |
| 90 | E |
| 91 | C |
| 92 | E |
| 93 | D |
| 98 | C |
| 99 | B |
| 100 | E |
| 101 | C |
| 102 | E |
| 103 | A |
| 104 | A |
| 105 | B |
| 106 | C |
| 107 | B |
| 108 | B |
| 109 | C |
| 110 | B |
| 111 | C |
| 112 | B |
| 113 | B |
| 114 | B |
| 115 | B |
| 116 | B |
| 117 | A |
| 118 | B |
| 119 | B |
| 120 | B |
| 121 | B |
| 124 | A |
| 125 | B |

TABLE 1-continued

| Compound | 35S-TBPS Radioligand Displacement (IC50) |
|---|---|
| 126 | B |
| 127 | B |
| 128 | A |
| 129 | C |
| 130 | D |
| 131 | C |
| 133 | A |
| 134 | B |
| 135 | C |
| 136 | D |
| 137 | B |
| 138 | D |
| 139 | B |
| 140 | B |
| 141 | C |
| 142 | B |
| 143 | B |
| 145 | B |
| 146 | A |
| 147 | B |
| 148 | B |
| 149 | D |
| 150 | D |
| 151 | B |
| 152 | D |
| 153 | D |
| 154 | B |
| 155 | E |
| 156 | E |
| 157 | E |
| 158 | B |
| 159 | B |
| 160 | E |
| 161 | D |
| 162 | B |
| 163 | D |
| 164 | C |
| 165 | A |
| 166 | B |
| 167 | B |
| 168 | B |
| 169 | C |
| 170 | B |
| 171 | C |
| 172 | B |
| 173 | B |
| 174 | D |
| 176 | D |
| 177 | D |
| 178 | C |
| 179 | D |
| 180 | C |
| 181 | D |
| 182 | E |
| 183 | C |
| 184 | D |
| 185 | A |
| 186 | B |
| 187 | B |
| 188 | C |
| 189 | D |
| 190 | D |
| 191 | A |
| 193 | C |
| 194 | B |
| 195 | D |
| 196 | D |
| 197 | E |
| 198 | D |
| 199 | B |
| 200 | C |
| 202 | B |
| 203 | B |
| 204 | A |
| 205 | D |
| 206 | B |
| 207 | B |
| 208 | C |
| 209 | B |
| 210 | C |
| 211 | E |
| 212 | E |
| 213 | E |
| 214 | D |
| 215 | D |
| 216 | C |
| 217 | C |
| 218 | D |
| 219 | C |
| 220 | C |
| 221 | D |
| 222 | B |
| 223 | C |
| 224 | B |
| 225 | D |
| 226 | D |
| 227 | D |
| 228 | B |
| 229 | C |
| 230 | B |
| 231 | B |
| 232 | B |
| 233 | B |
| 234 | B |
| 236 | B |
| 237 | B |
| 238 | C |
| 239 | B |
| 240 | B |
| 242 | C |
| 244 | B |
| 245 | B |
| 246 | A |
| 247 | B |
| 248 | A |
| 249 | A |
| 250 | B |
| 251 | B |
| 252 | B |
| 253 | B |
| 254 | C |
| 255 | B |
| 256 | B |
| 257 | D |
| 258 | C |
| 259 | A |
| 260 | A |
| 261 | B |
| 262 | B |
| 263 | B |

Patch Clamp Electrophysiology of Recombinant $\alpha_1\beta_2\gamma_2$ and $\alpha_4\beta_3\delta$ GABA$_A$ Receptors Cellular electrophysiology is used to measure the pharmacological properties of our GABA$_A$ receptor modulators in heterologous cell systems. Each compound is tested for its ability to affect GABA mediated currents at a submaximal agonist dose (GABA EC$_{20}$=2 µM). LTK cells are stably transfected with the $\alpha_1\beta_2\gamma_2$ subunits of the GABA receptor and CHO cells are transiently transfected with the $\alpha_4\beta_3\delta$ subunits via the Lipofecatamine method. Cells were passaged at a confluence of about 50-80% and then seeded onto 35 mm sterile culture dishes containing 2 ml culture complete medium without antibiotics or antimycotics. Confluent clusters of cells are electrically coupled (Pritchett et al., Science, 1988, 242, 1306-1308). Because responses in distant cells are not adequately voltage clamped and because of uncertainties about the extent of coupling (Verdoorn et al., Neuron 1990, 4, 919-928), cells were cultivated at a density that enables the recording of single cells (without visible connections to other cells).

Whole cell currents were measured with HEKA EPC-10 amplifiers using PatchMaster software or by using the high throughput QPatch platform (Sophion). Bath solution for all experiments contained (in mM): NaCl 137 mM, KCl 4 mM, $CaCl_2$ 1.8 mM, $MgCl_2$ 1 mM, HEPES 10 mM, D-Glucose 10 mM, pH (NaOH) 7.4. In some cases 0.005% cremophor was also added. Intracellular (pipette) solution contained: KCl 130 mM, $MgCl_2$ 1 mM, Mg-ATP 5 mM, HEPES 10 mM, EGTA 5 mM, pH 7.2. During experiments, cells and solutions were main-ained at room temperature (19° C.-30° C.). For manual patch clamp recordings, cell culture dishes were placed on the dish holder of the microscope and continuously perfused (1 ml/min) with bath solution. After formation of a Gigaohm seal between the patch electrodes and the cell (-ipette resistance range: 2.5 MΩ-6.0 MΩ; seal resistance range: >1 GΩ) the cell membrane across the pipette tip was ruptured to assure electrical access to the cell interior (whole-cell patch-configuration). For experiments using the QPatch system, cells were transferred as suspension to the QPatch system in the bath solution and automated whole cell recordings were performed.

Cells were voltage clamped at a holding potential of −80 mV. For the analysis of test articles, GABA receptors were stimulated by 2 µM GABA after sequential pre-incubation of increasing concentrations of the test article. Pre-incubation duration was 30 s and the duration of the GABA stimulus was 2 s. Test articles were dissolved in DMSO to form stock solutions (10 mM). Test articles were diluted to 0.01, 0.1, 1, and 10 µM in bath solution. All concentrations of test articles were tested on each cell. The relative percentage potentiation was defined as the peak amplitude in response to GABA $EC_{20}$ in the presence of the test article divided by the peak amplitude in response to GABA $EC_{20}$ alone, multiplied by 100. For Table 2. $GABA_A$ receptors α1β2γ2 and α4β3δ % efficacy: "A" 10-100, "B">100-500, "C">500; D indicates the data is not available or has not been determined.

TABLE 2

Electrophysiological evaluation of the exemplary compounds at $GABA_A$-R.

| Name | GABA (α1β2γ2) Qpatch in Ltk, % efficacy at 10 µM | GABA (α4β3δ) Manual patch in CHO, % efficacy at 10 µM |
| --- | --- | --- |
| 1 | B | D |
| 2 | B | B |
| 3 | B | D |
| 42 | B | D |
| 106 | B | D |
| 108 | B | D |
| 112 | B | D |
| 113 | B | D |
| 116 | B | D |
| 117 | B | D |
| 118 | B | C |
| 121 | C | C |
| 124 | B | C |
| 125 | B | D |
| 126 | B | D |
| 127 | B | D |
| 128 | B | D |
| 129 | B | D |
| 130 | B | D |
| 131 | B | D |
| 133 | B | C |
| 134 | C | C |
| 135 | B | D |
| 136 | B | D |
| 137 | B | D |

TABLE 2-continued

Electrophysiological evaluation of the exemplary compounds at $GABA_A$-R.

| Name | GABA (α1β2γ2) Qpatch in Ltk, % efficacy at 10 µM | GABA (α4β3δ) Manual patch in CHO, % efficacy at 10 µM |
| --- | --- | --- |
| 138 | C | D |
| 140 | B | D |
| 141 | C | D |
| 142 | C | C |
| 143 | C | C |
| 145 | C | D |
| 147 | C | D |
| 148 | B | D |
| 152 | B | D |
| 153 | B | D |
| 154 | B | D |
| 158 | B | D |
| 159 | C | D |
| 161 | A | D |
| 162 | C | D |
| 165 | B | D |
| 166 | B | D |
| 167 | B | D |
| 168 | B | D |
| 169 | B | D |
| 171 | B | D |
| 172 | B | D |
| 173 | B | D |
| 174 | B | D |
| 178 | C | D |
| 193 | C | C |
| 194 | D | C |
| 196 | B | D |
| 206 | D | C |
| 207 | D | C |
| 234 | D | B |

Acute PTZ Method

The anticonvulsant effect of test compounds were assessed in a pentylenetetazol-induced seizure assay in mice similar to methods described in Giardina & Gasior (Curr Protoc Pharmacol. 2009). Male CD-1 mice were housed in groups of five under controlled conditions (temperature of 22±2° C. and 12:12 light-dark cycle, lights on at 8:00 am) and water and food were available ad libitum. The mice were housed for 1 week prior to behavioral testing, at which time they weighed 25-35 g. Pentylenetetrazol (PTZ, Sigma) was dissolved in sterile 0.9% saline at a concentration of 12 mg/mL concentration for subcutaneous administration. Test compounds were formulated and administered via oral gavage or intraperitoneal injection at a predetermined timepoint (typically 30 or 60 minutes) prior to PTZ injection. All solutions were made fresh and given in a volume corresponding to 10 ml/kg body weight.

Mice were acclimated to the test room for at least 30 min before compound administration. Mice were randomized into at least four test groups (vehicle and at least three doses of the test compound) with 10 mice per group. After compound administration, mice were observed for qualitative assessment of sedation for a pre-determined time point (30 or 60 minutes). Following the drug pretreatment time the mice were injected s.c. with PTZ (120 mg/kg). Immediately following the PTZ injection, mice were individually placed into observation chambers (25×15×15 cm) and a three-channel timer was started. Each mouse was continuously observed for 30 min and the following behaviors were recorded by observers blinded to the treatments: 1) latency to clonic convulsions that persist for 3 sec and followed by an absence of righting reflex 2) latency to tonic convulsions, characterized by the rigid extension of all four limbs that exceeded a 90 degree angle with the body 3) latency to death 4) number of clonic and tonic convulsions. Data are presented as mean±S.E.M and one-way 'nalysis of vari'nce with Dunnett's or Bonferroni's post-hoc test was used to detect significant differences in latency and number between the vehicle and dose group. p values <0.05 were regarded as statistically significant.

TABLE 3

Minimal effective anticonvulsant doses are defined as the lowest dose which significantly reduces the latency to tonic seizures in PTZ-treated mice

| Compound | Anticonvulsive Effect Dose |
|---|---|
| 32 | A |
| 19 | A |
| 24 | B |
| 28 | A |
| 31 | C |
| 54 | B |
| 206 | A |
| 132 | B |
| 194 | A |
| 193 | B |
| 207 | C |

A ≤ 1 mpk; B > 1-5 mpk; C ≥ 5 mpk; PO - oral administration.

What is claimed is:

1. A compound of the formula:

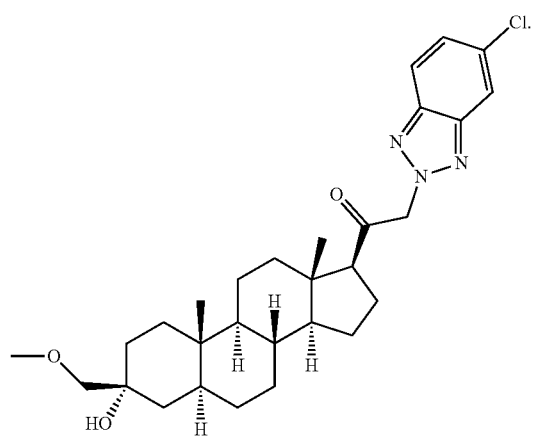

2. A pharmaceutically acceptable salt of a compound of the formula:

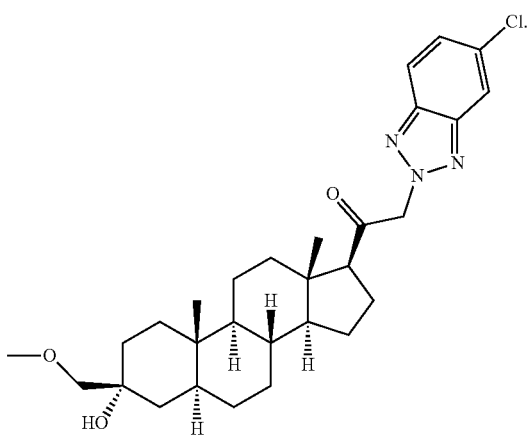

3. A pharmaceutical composition comprising a compound of the formula:

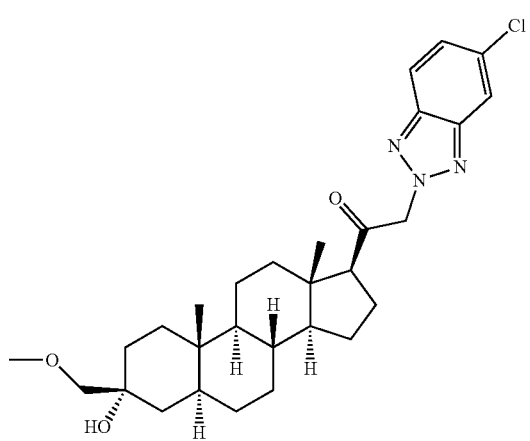

and a pharmaceutically acceptable excipient.

* * * * *